(12) United States Patent
Tweardy et al.

(10) Patent No.: US 8,779,001 B2
(45) Date of Patent: Jul. 15, 2014

(54) STAT3 INHIBITORS

(75) Inventors: David J. Tweardy, Houston, TX (US);
Xuejun Xu, Missouri City, TX (US);
Moses M. Kasembeli, Houston, TX (US)

(73) Assignees: The United States of America National Institute of Health (NIH), Washington, DC (US); The United States of America Dept. of Health and Human Services (DHHS), Washington, DC (US)

( * ) Notice: Subject to any disclaimer, the term of this patent is extended or adjusted under 35 U.S.C. 154(b) by 431 days.

(21) Appl. No.: 12/477,583

(22) Filed: Jun. 3, 2009

(65) Prior Publication Data

US 2010/0041685 A1 Feb. 18, 2010

Related U.S. Application Data

(60) Provisional application No. 61/058,742, filed on Jun. 4, 2008.

(51) Int. Cl.
*A61K 31/18* (2006.01)

(52) U.S. Cl.
USPC .......................................... 514/604

(58) Field of Classification Search
None
See application file for complete search history.

(56) References Cited

U.S. PATENT DOCUMENTS

| | | | |
|---|---|---|---|
| 6,608,101 B1 | 8/2003 | Ni et al. | |
| 2004/0198824 A1 | 10/2004 | Tsukamoto et al. | |
| 2005/0287664 A1 | 12/2005 | Fann | |
| 2006/0148715 A1 | 7/2006 | Tweardy | |
| 2007/0004704 A1 | 1/2007 | Damon et al. | |
| 2007/0203236 A1* | 8/2007 | Smith et al. | |

FOREIGN PATENT DOCUMENTS

| | | |
|---|---|---|
| WO | WO 2006/069001 | 6/2006 |
| WO | 2007136858 A2 | 11/2007 |
| WO | WO-2008/035904 A1 | 3/2008 |

OTHER PUBLICATIONS

Merriam-Webster's Online Dictionary, (downloaded from "www.merriam-webster.com/dictionary/prevent"), downloaded on Apr. 7, 2008, p. 1 of 1.*

Xu et al; Chemical Probes that Competitively and Selectively Inhibit Stat3 Activiation; PLoS One; Mar. 2009, v4, p. e4783, entire doc, 12 pages.
International Search Report issued on Nov. 5, 2009 during the prosecution of International Application No. PCT/US2009/46143.
Written Opinion issued during the prosecution of International Application No. PCT/US2009/046143.
Extended European Search Report issued in European Application No. 09759351.1, mailed Dec. 29, 2011.
Tautz et al., "Inhibition of *Yersinia* tyrosine phosphatase by furanyl salicylate compounds," *The Journal of Biological Chemistry*, 280(10):9400-9408, 2006.
Desrivieres, Sylvane, et. al; "The Biological Functions of the Versatile Transcription Factors STAT3 and STAT5 and New Strategies for their Targeted Inhibition"; J. Mammary Gland Biol. Neoplasia, 2006; vol. 11; pp. 75-87.
Chan, Timothy A.; "Nonsteroidal Anti-Inflammatory Drugs, Apoptosis, and Colon-Cancer Chemoprevention"; The Lancet Oncology, vol. 3; Mar. 2002; pp. 166-174.
Johnson, Trista W., et. al.; "Association of Aspirin and Nonsteroidal Anti-Inflammatory Drug Use with Breast Cancer"; Cancer Epidemiology, Biomarkers & Prevention; Dec. 2002; vol. 11, pp. 1586-1591.
Jiang, Wen G.; "Expression of Peroxisome-Proliferator Activated Receptor-Gamma (PPAR$\gamma$) and the PPAR$\gamma$ Co-Activator, PGC-1, in Human Breast Cancer Correlates with Clinical Outcomes"; Int. J. Cancer: 106; 2003; pp. 752-757.
Klampfer, Lidija; "Signal Transducers and Activators of Transcription (STATs): Novel Targets of Chemopreventive and Chemotherapeutic Drugs"; Current Cancer Drug Targets, 2006; vol. 6, pp. 561-571.
Johnson, Jeremy James, et. al.; "Curcumin for Chemoprevention of Colon Cancer"; Cancer Letters 255, 2007; pp. 170-181.
Bharti, Alok C., et. al.; "Curcumin (Diferuloylmethane) Inhibits Constitutive and IL-6-Inducible STAT3 Phosphorylation in Human Multiple Myeloma Cells"; The Journal of Immunology, 2003; 171:3863-3871.

* cited by examiner

*Primary Examiner* — Savitha Rao
*Assistant Examiner* — Gregg Polansky
(74) *Attorney, Agent, or Firm* — Fulbright & Jaworski LLP

(57) ABSTRACT

Small molecule inhibitors of Stat3 and their derivatives are disclosed. Also described are methods to inhibit cell growth by use of Stat3 inhibitors, and the use of Stat3 inhibitors for the prevention and/or treatment of cancer. Further, inhibitors of Stat3 that also do not inhibit Stat1 are described as well as their derivatives. Methods of screening additional compounds for Stat3 inhibition activity and/or non-inhibition of Stat1 activity are also described herein.

16 Claims, 43 Drawing Sheets

C.

D.

A. Cpd3

4-[3-(2,3-dihydro-1,4-benzodioxin-6-yl)-3-oxo-1-propen-1-yl]benzoic acid

B. Cpd30

4{5-[(3-ethyl-4-oxo-2-thioxo-1,3-thiazolidin-5-ylidene)methyl]-2-furyl}benzoic acid C. Cpd188

4-[((3-[(carboxymethyl)thio]-4-hydroxy-1-naphthyl]amino)sulfonyl]
benzoic acid

D. Cpd3-2

3-({2-chloro-4-[(1,3-dioxo-1,3-dihydro-2H-inden-2-ylidene)methyl]-6-
ethoxyphenoxy}methyl)benzoic acid E. Cpd3-7 methyl 4-({[3-(2-methoxy-2-oxoethyl)-4,8-dimethyl-2-oxo-2H-chromen-7-yl]oxy}methyl)benzoate F. Cpd30-12

4-chloro-3-{5-[(1,3-diethyl-4,6-dioxo-2-thioxotetrahydro-5(2H)-pyrimidinylidene)methyl]-2-furyl}benzoic acid Cpd3

- pMSCV-neo
- pMSCV-puro
- pMSCV-puro-PML-RARα
- pMSCV-puro-PLZF-RARα
- pMSCV-neo-Stat5b-RARα
- pMSCV-puro-R1A-RARα
- pMSCV-puro-R1A-RARa- RII
- pMSCV-neo AML1-ETO
- pMSCV-neo-AML1-MTG16
- pMSCV-neo-AML1-EVI1
- pMSCV-puro M2-CBFβ -MYH11
- pMSCV-puro-HIF1α-AML1
- pMSCV-puroTEL-AML1

SEQUENCE LISTING

```
<160> NUMBER OF SEQ ID NOS: 1

<210> SEQ ID NO 1
<211> LENGTH: 68
<212> TYPE: PRT
<213> ORGANISM: Artificial Sequence
<220> FEATURE:
<223> OTHER INFORMATION: Anything; SH2 domain

<400> SEQUENCE: 1

Met Val Asn Arg Glu Val Leu Asp Gln Val Glu Arg Gly Tyr Arg Met
1               5                   10                  15
```

```
Pro Cys Pro Pro Glu Cys Pro Glu Ser Leu His Asp Leu Met Cys Gln
            20              25                  30

Cys Trp Arg Lys Glu Pro Glu Arg Pro Thr Phe Glu Tyr Leu Gln
        35              40              45

Ala Phe Leu Glu Asp Tyr Phe Thr Ser Thr Glu Pro Gln Tyr Gln Pro
    50              55                  60

Gly Glu Asn Leu
65
```

STAT3 INHIBITORS

The present invention claims priority to U.S. Provisional Patent Application Ser. No. 61/058,742, filed Jun. 4, 2008, which is incorporated by reference herein in its entirety.

STATEMENT REGARDING FEDERALLY SPONSORED RESEARCH OR DEVELOPMENT

This invention was made with government support under National Institutes of Health Grants R01 CA072261 and R01 CA86430. The United States Government has certain rights in the invention.

TECHNICAL FIELD

The present invention generally concerns at least the fields of computational biology, cell biology, molecular biology, cancer biology, and medicine.

BACKGROUND OF THE INVENTION

Signal transducer and activator of transcription 3 (Stat3) is an oncogene (Bromberg et al., 1999) and one of seven members of the STAT protein family, which are signaling intermediates that mediate the actions of many cytokines and growth factors. Stat3 is constitutively active in many different cancers including prostate, breast, lung, squamous cell carcinoma of the head and neck, multiple myeloma, colon cancer, hepatocellular carcinomas and large granular lymphocytic leukemia (Turkson and Jove 2000; Dong et al., 2003; Kortylewski et al., 2005; Lin et al., 2005; Tweardy and Redell 2005; Redell and Tweardy 2006). Furthermore, human tumor xenograft studies in mice have repeatedly demonstrated that inhibiting Stat3 results in decreased tumor growth and improved animal survival (Redell and Tweardy 2006) by inducing apoptosis in tumor cells, inhibiting angiogenesis (Kato et al., 2004) and enhancing anti-tumor immune-mediated cytotoxicity (Dunn et al., 2002; Kortylewski et al., 2005). Thus, Stat3 has been identified as a potentially high-yield target for drug development to treat many cancers (Yu and Jove 2004; Darnell 2005).

In contrast to Stat3, Stat1 is anti-oncogenic; it is a potent inhibitor of tumor growth and promoter of apoptosis (Bromberg et al., 1999). Also, because tumors from carcinogen-treated wild-type animals grow more rapidly when transplanted into the Stat1-deficient animals than they do in a wild-type host, Stat1 contributes to tumor surveillance (Kaplan et al., 1998). Consequently, a highly desirable goal in the development of drugs that target Stat3 is selectivity for Stat3 vs. Stat1, for example.

Drugs have been developed that selectively target Stat3 vs. Stat1 (Bhasin et al., 207; Jing et al., 2004; Coleman et al., 2005; Song et al., 2005; Schust et al., 2006; Siddiquee et al., 2007). However, determination of their selectivity was established empirically after their identification as Stat3 inhibitors and was not built into the screening process. There is a need in the art to provide novel compounds and methods for inhibiting Stat3 selectively.

SUMMARY OF THE INVENTION

Stat3 is an oncogene constitutively activated in many cancer systems where it contributes to carcinogenesis. In one embodiment of the invention, there is a small-molecule, virtual ligand screening approach that targets the pY-peptide binding pocket of the Stat3 SH2 domain at three sites including, for example, a hydrophobic pocket, which served as a selectivity filter. This approach identified for the first time novel lead compounds that competitively inhibit Stat3 binding to its pY-peptide ligand, that are selective for Stat3 vs. Stat1, and that also induce apoptosis preferentially of exemplary breast cancer cells lines with constitutively activated Stat3. One compound (Cpd188) was active in the nanomolar range. In addition to yielding compounds that selectively target Stat3 by design, the invention is useful for identifying selective, chemical probes of other members of the STAT protein family, notably Stat5A/B, for example, which also has been implicated in carcinogenesis. In addition to yielding compounds that selectively target Stat3 by design, the inventive approach is useful for identifying selective, chemical probes of other members of the STAT protein family.

The present invention is particularly useful given the number of tumor systems in which Stat3 contributes to oncogenesis, as well as recent demonstrations that multiple receptor-associated and non-receptor associated tyrosine kinases are activated in a single tumor. Agents that target Stat3, a point of signaling convergence for multiple oncogenic kinases, is more broadly useful in cancer treatment than agents targeting individual oncogenic kinases, in certain embodiments.

To develop chemical probes that selectively target Stat3, 920,000 small drug-like compounds were screened by docking each into the peptide-binding pocket of the Stat3 SH2 domain, which consisted of three sites—the pY-residue binding site, the +3 residue binding site and a hydrophobic binding site, which served as a selectivity filter. Three exemplary and illustrative compounds satisfied criteria of interaction analysis, competitively inhibited recombinant Stat3 binding to its immobilized pY-peptide ligand and inhibited IL-6-mediated tyrosine phosphorylation of Stat3. These compounds were used in a similarity screen of 2.47 million compounds, which identified 3 more active compounds with similar activities. Examination of the 6 active compounds for the ability to inhibit IFN-γ-mediated Stat1 phosphorylation revealed that 5 of 6 were selective for Stat3. Sequence and 3-D structural comparison of the SH2 domains of Stat3 and Stat1 bound to compound revealed that compound interaction with the hydrophobic binding site was the basis for selectivity. All 5 selective compounds inhibited nuclear-to-cytoplasmic translocation of Stat3, while 3 of 5 compounds induced apoptosis preferentially of breast cancer cell lines with constitutive Stat3 activation. Thus, virtual ligand screening of compound libraries that targeted the Stat3 pY-peptide binding pocket identified for the first time 3 lead compounds that competitively inhibit Stat3 binding to its pY-peptide ligand; these compounds were selective for Stat3 vs. Stat1 and induced apoptosis preferentially of breast cancer cells lines with constitutively activated Stat3.

In some embodiments of the invention, the methods and/or compositions of the invention are useful for inhibiting Stat3 activity. In specific cases, the methods and/or compositions of the invention are employed to induce apoptosis in a cancer cell, inhibit angiogenesis in a tumor, enhance anti-tumor immune-mediated cytotoxicity, decrease tumor growth, improve animal survival, inhibit Stat3 phosphorylation and/or nuclear-to-cytoplasmic translocation of Stat3. In certain embodiments, Stat3 inhibitors inhibit Stat3 but fail to inhibit Stat1. In some embodiments, Stat3 inhibitors of the invention interact with the Stat3 SH2 domain, competitively inhibit recombinant Stat3 binding to its immobilized pY-peptide ligand, and/or inhibit IL-6-mediated tyrosine phosphorylation of Stat3, for example. In particular, the Stat3 inhibitor of the invention fulfills the criteria of interaction analysis (CIA): 1) global minimum energy score≤−30; 2) formation of a salt-bridge and/or H-bond network within the pY-residue binding site of Stat3; and/or 3) formation of a H-bond with or blocking access to the amide hydrogen of E638 of Stat3, for example. In some embodiments, the Stat3 inhibitor interacts with a hydrophobic binding pocket with the Stat3 SH2 domain.

In a specific embodiment of the invention, there is a method of inhibiting Stat3 in a cell comprises delivering to the cell a compound selected from the group consisting of 4-[3-(2,3-dihydro-1,4-benzodioxin-6-yl)-3-oxo-1-propen-1-yl]benzoic acid; 4{5-[(3-ethyl-4-oxo-2-thioxo-1,3-thiazolidin-5-ylidene)methyl]-2-furyl}benzoic acid; 4-[({3-[(carboxymethyl)thio]-4-hydroxy-1-naphthyl}amino) sulfonyl]benzoic acid; 3-({2-chloro-4-[(1,3-dioxo-1,3-dihydro-2H-inden-2-ylidene)methyl]-6-ethoxyphenoxy}methyl)benzoic acid; methyl 4-({[3-(2-methyoxy-2-oxoethyl)-4,8-dimethyl-2-oxo-2H-chromen-7-yl]oxy}methyl)benzoate; 4-chloro-3-{5-[(1,3-diethyl-4,6-dioxo-2-thioxotetrahydro-5(2H)-pyrimidinylidene)methyl]-2-furyl}benzoic acid; a functionally active derivative thereof; and a mixture thereof. In a specific embodiment, any of the compounds disclosed herein are suitable to inhibit Stat3 in a cancer stem cell, such as a leukemic stem cell or a breast cancer stem cell, for example.

In another embodiment, the inhibitor comprises the general formula:

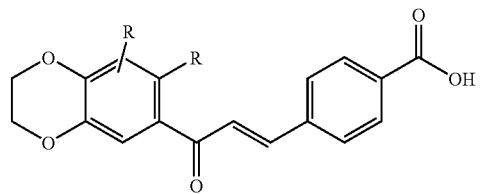

wherein $R_1$ and $R_2$ may be the same or different and are selected from the group consisting of hydrogen, carbon, sulfur, nitrogen, oxygen, flourine, chlorine, bromine, iodine, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives.

In another embodiment of the invention, the inhibitor comprises the general formula:

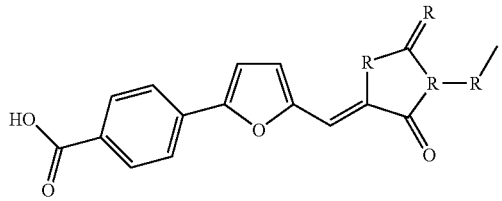

wherein $R_1$, and $R_3$ may be the same or different and are selected from the group consisting of hydrogen, carbon, nitrogen, sulfur, oxygen, flouring, chlorine, bromine, iodine, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives; and $R_2$ and $R_4$ may be the same or different and are selected from the group consisting of hydrogen, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives.

In another embodiment of the invention, the inhibitor comprises the general formula:

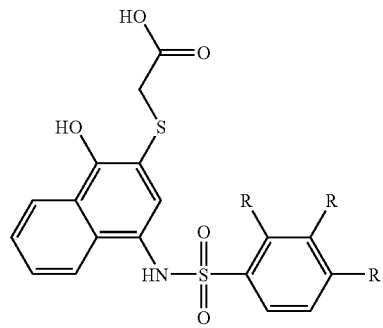

wherein $R_1$, $R_2$, and $R_3$ may be the same or different and are selected from the group consisting of hydrogen, carbon, nitrogen, sulfur, oxygen, flourine, chlorine, bromine, iodine, carboxyl, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives.

In specific embodiments, the cancer treated by the invention may be any type of cancer, although in specific embodiments the cancer comprises cells having constitutively phosphorylated Stat3 or increased Stat3 protein expression. In some cases, the cancer may be of the lung, breast, skin, liver, kidney, testes, ovary, cervix, bone, spleen, gall bladder, brain, pancreas, stomach, anus, prostate, colon or blood, for example; the inhibitor may inhibit Stat3 in a cancer stem cell of any of these cancers. Mammals may be treated with the methods and/or compositions of the invention, including humans, dogs, cats, horses, cows, pigs, sheep, and goats, for example. In other embodiments, a hyperproliferative disease such as post-transplant lymphoproliferative disease or restenosis is treated. In alternative embodiments, a chronic viral infection, such as hepatitis c or epstein-barr virus, is treated by the invention. In another embodiment, pulmonary fibrosis, myelofibrosis, myelodysplastic syndrome, or acute myelogenous leukemia (AML) is treated. In other embodiments, asthma, psoriasis or inflammatory bowel disease is treated. In specific embodiments, psoriasis, inflammatory bowel disease, uveitis, scleritis, multiple sclerosis, graft-versus-host diseases, pancreatitis, pulmonary lymphangioleiomyomatosis, age-related macular degeneration or amyloidosis are treated with the present invention.

In other embodiments of the invention, there are methods of identifying inhibitors of other members of the STAT protein family, including STAT1, STAT2, STAT3, STAT4, STAT5 (STAT5A and STAT5B), and STAT6, for example.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DESCRIPTION OF THE DRAWINGS

In FIG. 6A the negatively charged benzoic acid moiety of Cpd3 has electrostatic interactions with the positively-charge pY residue binding site consisting mainly of the guanidinium cation group of R609 and the basic ammonium group of K591. The benzoic acid group also forms a hydrogen-bond network consisting of double H-bonds between the carboxylic oxygen and the ammonium hydrogen of R609 and the amide hydrogen of E612. H-bond formation also occurs between the benzoic acid carbonyl oxygen and the side chain hydroxyl hydrogen of Serine 611. Within the +3 residue-binding site, the oxygen atom of 1,4-benzodioxin forms a hydrogen bond with the amide hydrogen of E638. In addition, the 2,3-dihydro-1,4-benzodioxin of Cpd3 interacts with the loops forming the hydrophobic binding site. In FIG. 6B the carboxylic terminus of the benzoic acid moiety of Cpd30, which is negatively charged under physiological conditions, forms a salt bridge with the guanidinium group of R609 within the pY residue binding site. Within the +3 residue-binding site, the oxygen of the thiazolidin group forms a H-bond with the peptide backbone amide hydrogen of E638. In addition, the thiazolidin moiety plunges into the hydrophobic binding site. In FIG. 6C there is an electrostatic interaction between the (carboxymethyl) thio moiety of Cpd188 carrying a negative charge and the pY-residue binding site consisting of R609 and K591 carrying positive charge under physiological conditions. There are H-bonds between the hydroxyloxygen of the (carboxymethyl) thio group of Cpd188 and the guanidinium hydrogen of R609, between the hydroxyl-oxygen of the (carboxymethyl) thio group and the backbone amide hydrogen of E612, and between the carboxyl-oxygen of the (carboxymethyl) thio group of Cpd188 and the hydroxyl-hydrogen of S611. Within the +3 residue-binding site, there is a H-bond between the hydroxyl-oxygen of benzoic acid group of Cpd188 and the amide-hydrogen of E638. In addition, the benzoic acid group extends and interacts with the hydrophobic binding site. In FIG. 6D the benzoic acid group of Cpd3-2 has significant electrostatic interactions with the pY-residue binding site pocket, mainly contributed by R609 and K591, and forms two H bonds; the carboxylic oxygen of the benzoic acid group binds the guanidinium hydrogen of R609, and the carbonyl oxygen of the benzoic acid group binds to the carbonyl hydrogen of S611. Within the +3 residue-binding site, oxygen within the 1,3-dihydro-2H-inden-2-ylidene group forms an H bond to the backbone amide-hydrogen of E638. In addition, the 1,3-dihydro-2H-inden-2-ylidene group plunges into the hydrophobic binding site. In FIG. 6E H-bonds are formed between the carbonyl-oxygen of the methyl 4-benzoate moiety of Cpd 3-7 and the side chain guanidinium of R609 and between the methoxy-oxygen and the hydrogen of the ammonium terminus of K591. The (2-methoxy-2-oxoethyl)-4,8-dimethyl-2-oxo-2H-chromen group of Cpd3-7 blocks access to the amide hydrogen of E638 within the +3 residue-binding site. In addition, this group plunges into the hydrophobic binding site. In FIG. 6F there are electrostatic interactions between the benzoic acid derivative group of Cpd30-12 and R609 and 591 within the pY-residue binding site. Also, H-bonds are formed between the hydroxyl-oxygen of Cpd30-12 and the guanidinium-hydrogen of R609, between the carboxyl-oxygen of Cpd30-12 and the hydroxyl-hydrogen of S611 and between the furyl group of Cpd30-12 and the hydrogen of ammonium of K591. The 1,3-diethyl-4,6-dioxo-2-thioxotetrahydro-5 (2H)-pyrimidinylidene groups blocks access to the +3 residue binding site; however, it extends into the groove between the pY-residue binding site and LoopβC-βD, while sparing the hydrophobic binding site.

FIG. 21 provides illustration of exemplary pMSCV-neo/puro constructs.

DETAILED DESCRIPTION OF THE INVENTION

Figure 1:
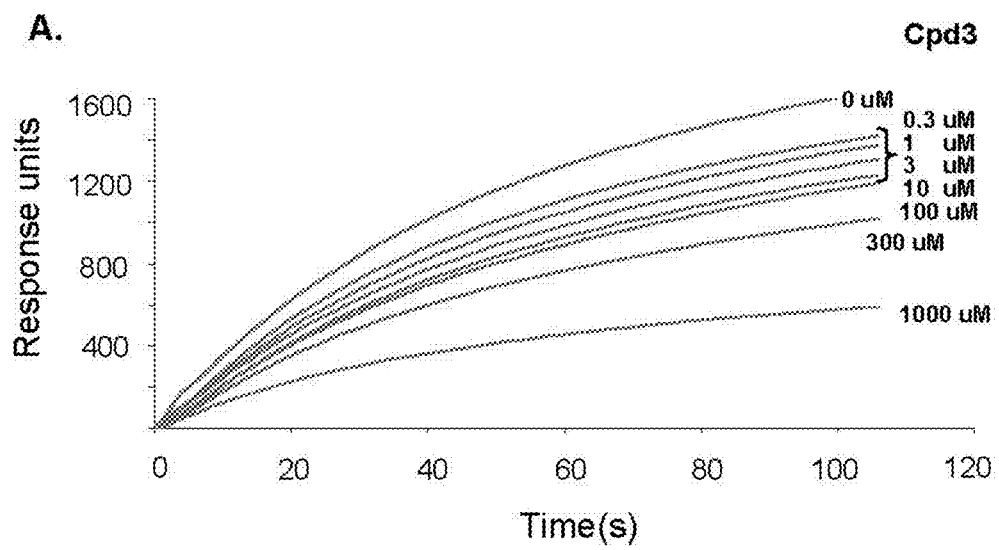
FIG. 1 demonstrates inhibition of Stat3 binding to immobilized phosphopeptide ligand by compounds. Binding of recombinant Stat3 (500 nM) to a BiaCore sensor chip coated with a phosphododecapeptide based on the amino acid sequence surrounding Y1068 within the EGFR was measured in real time by SPR (Response Units) in the absence (0 μM) or presence of increasing concentrations (0.1 to 1,000 μM) of Cpd3 (panel A), Cpd30 (panel B), Cpd188 (panel C), Cpd3-2 (panel D), Cpd3-7 (panel E) and Cpd30-12 (panel F). Data shown are representative of 2 or more experiments. The equilibrium binding levels obtained in the absence or presence of compounds were normalized (response obtained in the presence of compound÷the response obtained in the absence of compound×100), plotted against the log concentration (nM) of the compounds (panel G). The experimental points fit to a competitive binding curve that uses a four-parameter logistic equation (see exemplary methods for details). These curves were used to calculate $IC_{50}$ (Table 1).
Figure 1:
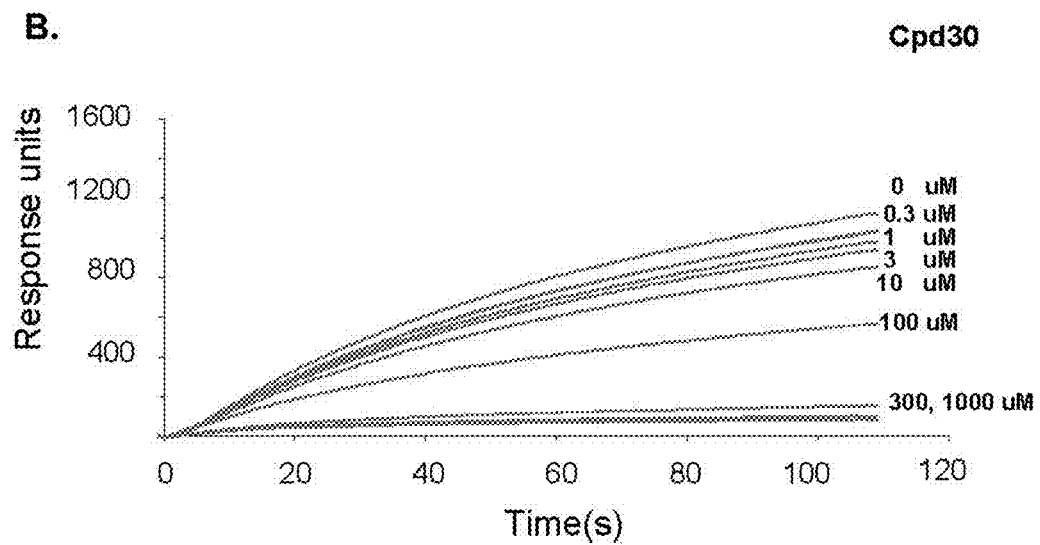
Figure 1:
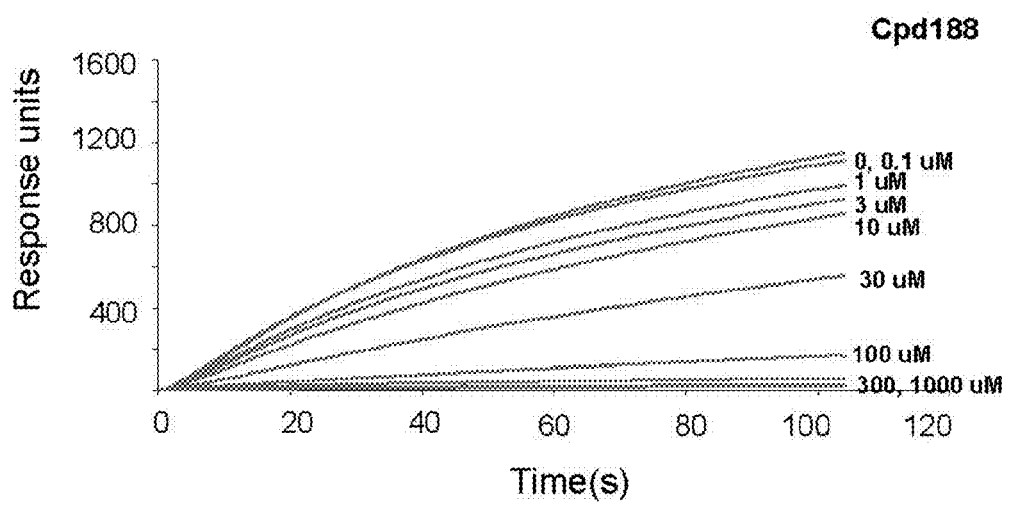
Figure 1:
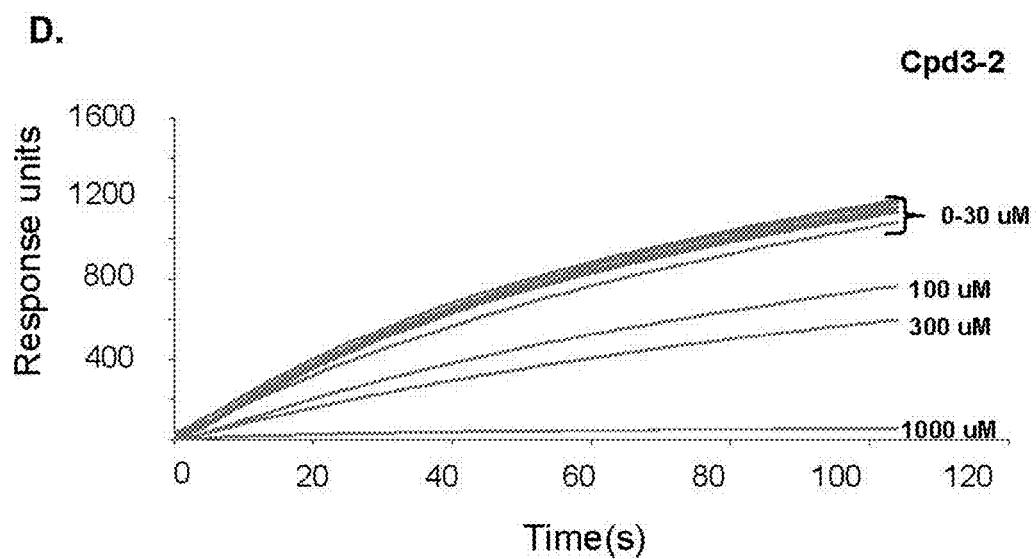
Figure 1:
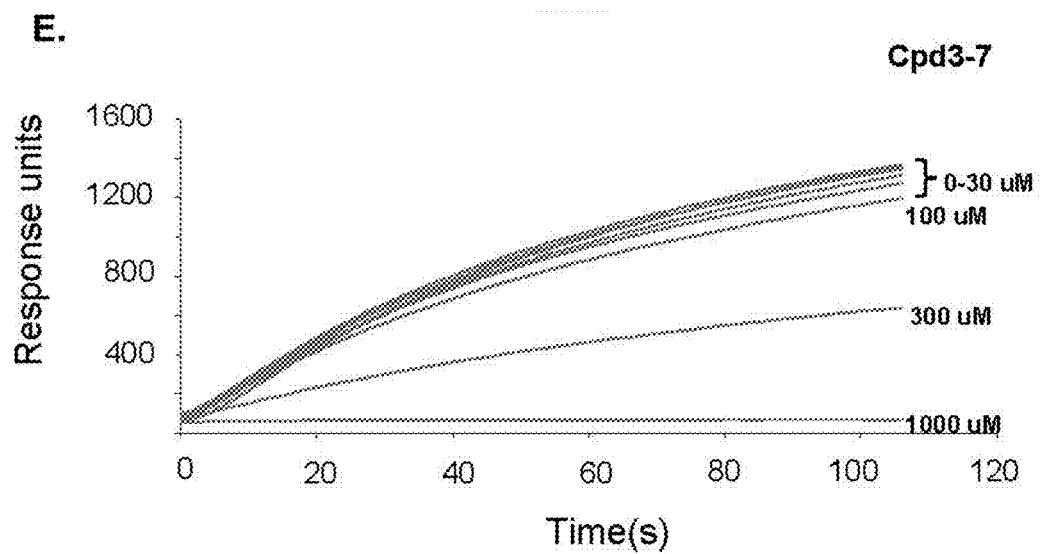
Figure 1:
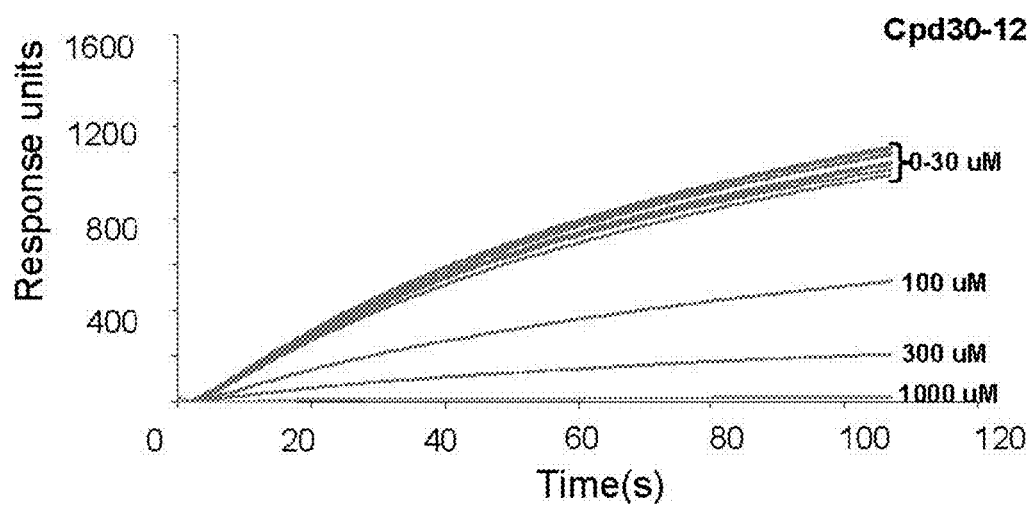
Figure 1:
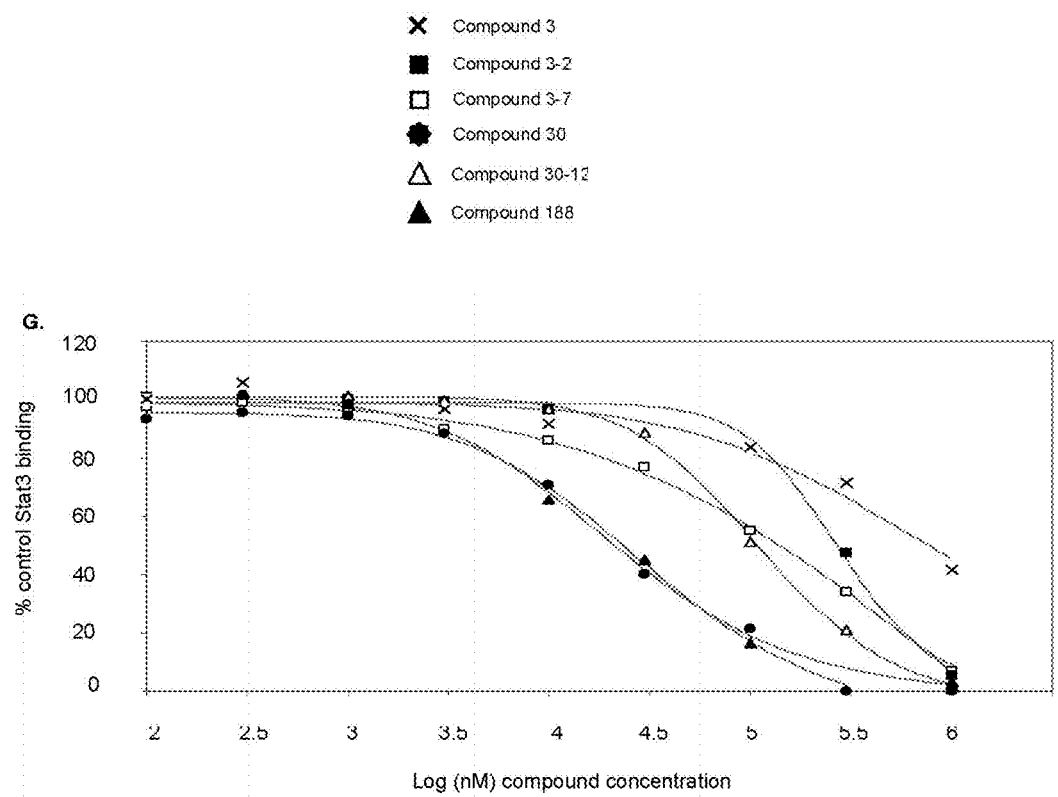

The present application incorporates by reference herein in their entirety U.S. Ser. No. 60/637,489, filed Dec. 20, 2004, and U.S. Ser. No. 11/313,104, filed Dec. 20, 2005.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

Stat3 inhibitors are described herein, both by structure, and by the method of development. At least some of these were developed from a screen of 920,000 small drug like compounds against the phosphotyrosine (pY) peptide binding pocket of the Stat3 SH2 domain. The binding-pocket consists of the pY-residue binding site, the +3 residue-binding site and a hydrophobic binding site, which served as a selectivity filter. Three compounds originally satisfied the criteria of the docking analysis by inhibiting recombinant Stat3 and inhibiting IL-6-mediated tyrosine phosphorylation of Stat3. Three more Stat3 inhibiting compounds were identified from a similarity screen of 2.47 million compounds. In addition, five of the six compounds were also found not to be inhibitory to Stat1. The hydrophobic binding site within Stat3 was revealed to be the basis for selectivity between Stat3 and Stat1. All of the five compounds that were selective of Stat3 over Stat1 also inhibited nuclear-to-cytoplasmic translocation of Stat3, while 3 of the five induced apoptosis of breast cancer cell lines with constitutive Stat3 activation. GeneID numbers, which correspond to the National Center for Biotechnology Information's database, provided as follows identify human Stat1 as GeneID 6772 and the GeneID of Stat3 as 6774, and the sequences provided therein are incorporated herein by reference in their entirety.

One embodiment of the invention is a method of inhibiting Stat3 comprising delivering to the cell a compound selected from the group consisting of 4-[3-(2,3-dihydro-1,4-benzodioxin-6-yl)-3-oxo-1-propen-1-yl]benzoic acid; 4{5-[(3-ethyl-4-oxo-2-thioxo-1,3-thiazolidin-5-ylidene)methyl]-2-furyl}benzoic acid; 4-[({3-[(carboxymethyl)thio]-4-hydroxy-1-naphthyl}amino)sulfonyl]benzoic acid; 3-({2-chloro-4-[(1,3-dioxo-1,3-dihydro-2H-inden-2-ylidene)methyl]-6-ethoxyphenoxy}methyl)benzoic acid; methyl 4-({[3-(2-methyoxy-2-oxoethyl)-4,8-dimethyl-2-oxo-2H-chromen-7-yl]oxy}methyl)benzoate; 4-chloro-3-{5-[(1,3-diethyl-4,6-dioxo-2-thioxotetrahydro-5(2H)-pyrimidinylidene)methyl]-2-furyl}benzoic acid; a functionally active derivative and a mixture thereof. In a specific embodiment of the invention, the Stat3 inhibitor does not inhibit Stat1.

In a specific embodiment of the invention, the cell to which the Stat3 inhibitor is delivered is in vivo in a mammal. In another embodiment the mammal is a human. In another specific embodiment the human is known to have cancer, is suspected of having cancer, or is at risk for developing cancer. In another embodiment, the human is known to have cancer and is receiving an additional therapy. In a specific embodiment, the cancer therapy is chemotherapy, surgery, radiation, or a combination thereof. In alternative embodiments, the mammal is known to have, suspected of having, or at risk for developing cancer, a hyperproliferative disease, or a chronic viral infection.

I. Definitions

As used herein the specification, "a" or "an" may mean one or more. As used herein in the claim(s), when used in conjunction with the word "comprising", the words "a" or "an" may mean one or more than one. As used herein "another" may mean at least a second or more. Still further, the terms "having", "including", "containing" and "comprising" are interchangeable and one of skill in the art is cognizant that these terms are open ended terms. Some embodiments of the invention may consist of or consist essentially of one or more elements, method steps, and/or methods of the invention. It is contemplated that any method or composition described herein can be implemented with respect to any other method or composition described herein.

The term "inhibitor" as used herein refers to one or more molecules that interfere at least in part with the activity of Stat3 to perform one or more activities, including the ability of Stat3 to bind to a molecule and/or the ability to be phosphorylated.

The phrase "therapeutically effective amount" as used herein means that amount of a compound, material, or composition comprising a compound of the present invention that is effective for producing some desired therapeutic effect, e.g., treating (i.e., preventing and/or ameliorating) cancer in a subject, or inhibiting protein-protein interactions mediated by an SH2 domain in a subject, at a reasonable benefit/risk ratio applicable to any medical treatment. In one embodiment, the therapeutically effective amount is enough to reduce or eliminate at least one symptom. One of skill in the art recognizes that an amount may be considered therapeutically effective even if the cancer is not totally eradicated but improved partially. For example, the spread of the cancer may be halted or reduced, a side effect from the cancer may be partially reduced or completed eliminated, life span of the subject may be increased, the subject may experience less pain, and so forth.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "at risk for having cancer" is used herein to refer to patients that have a chance to have cancer because of past, present, or future factors. These factors can include but are not limited to: patient history, family history, identification of markers of generic or tissue-specific cancer such as BRACA-1 or CEA, age, race, diet, being a smoker, or certain exposures such as chemical or radiation exposure.

As used herein, "binding affinity" refers to the strength of an interaction between two entities, such as a protein-protein interaction. Binding affinity is sometimes referred to as the $K_a$, or association constant, which describes the likelihood of the two separate entities to be in the bound state. Generally, the association constant is determined by a variety of methods in which two separate entities are mixed together, the unbound portion is separated from the bound portion, and concentrations of unbound and bound are measured. One of skill in the art realizes that there are a variety of methods for measuring association constants. For example, the unbound and bound portions may be separated from one another through adsorption, precipitation, gel filtration, dialysis, or centrifugation, for example. The measurement of the concentrations of bound and unbound portions may be accomplished, for example, by measuring radioactivity or fluorescence, for example. In certain embodiments of the invention, the binding affinity of a Stat3 inhibitor for the SH2 domain of Stat3 is similar to or greater than the affinity of the compounds listed herein.

The term "chemotherapy-resistant cancer" as used herein refers to cancer that is suspected of being unable to be treated with one or more particular chemotherapies or that is known to be unable to be treated with one or more particular chemotherapies. In particular, cells of the chemotherapy-resistant cancer are not killed or rendered quiescent with the therapy or even continue to multiply during or soon after the therapy. The cancer may be at first sensitive to a treatment and then develop resistance over time, for example, in some embodiments.

The term "domain" as used herein refers to a subsection of a polypeptide that possesses a unique structural and/or functional characteristic; typically, this characteristic is similar across diverse polypeptides. The subsection typically comprises contiguous amino acids, although it may also comprise amino acids that act in concert or that are in close proximity due to folding or other configurations. An example of a protein domain is the Src homology 2 (SH2) domain of Stat3. The term "SH2 domain" is art-recognized, and, as used herein, refers to a protein domain involved in protein-protein interactions, such as a domain within the Src tyrosine kinase that regulates kinase activity. The invention contemplates modulation of activity, such as activity dependent upon protein-protein interactions, mediated by SH2 domains of proteins (e.g., tyrosine kinases such as Src) or proteins involved with transmission of a tyrosine kinase signal in organisms including mammals, such as humans. The amino-acid sequence of the Stat3 SH2 domain is:

(SEQ ID NO: 1)
MVNREVLDQVERGYRMPCPPECPESLHDLMCQCWRKEPEERPTFEYLQAF
LEDYFTSTEPQYQPGENL.

As used herein, a "mammal" is an appropriate subject for the method of the present invention. A mammal may be any member of the higher vertebrate class Mammalia, including humans; characterized by live birth, body hair, and mammary glands in the female that secrete milk for feeding the young. Additionally, mammals are characterized by their ability to maintain a constant body temperature despite changing climatic conditions. Examples of mammals are humans, cats, dogs, cows, mice, rats, and chimpanzees. Mammals may be referred to as "patients" or "subjects" or "individuals".

The language "modulating an activity mediated by an SH2 domain" as used herein, refers to inhibiting, abolishing, or increasing the activity of a cell-signaling pathway mediated by a protein including an SH2 domain, e.g., by disrupting protein-protein interactions mediated by SH2 domains. In a preferred embodiment, an activity mediated by an SH2 domain is inhibited, for example, an interaction of Stat3 and EGFR is inhibited. In another preferred embodiment, an interaction of Stat3 and G-CSFR is inhibited. In another preferred embodiment, an interaction of one molecule of Stat3 with another molecule of Stat3 to form a homodimer.

II. Derivatives

The term "derivative" as used herein is a compound that is formed from a similar compound or a compound that can be considered to arise from another compound, if one atom is replaced with another atom or group of atoms. Derivative can also refer to compounds that at least theoretically can be formed from the precursor compound.

The term "functionally active derivative" or "functional derivative" is a derivative as previously defined that retains the function of the compound from which it is derived. In one embodiment of the invention, a derivative of 4-[3-(2,3-dihydro-1,4-benzodioxin-6-yl)-3-oxo-1-propen-1-yl]benzoic acid, 4{5-[(3-ethyl-4-oxo-2-thioxo-1,3-thiazolidin-5-ylidene)methyl]-2-furyl}benzoic acid, 4-[({3-[(carboxymethyl)thio]-4-hydroxy-1-naphthyl}amino)sulfonyl]benzoic acid, 3-({2-chloro-4-[(1,3-dioxo-1,3-dihydro-2H-inden-2-ylidene)methyl]-6-ethoxyphenoxy}methyl)benzoic acid, methyl 4-({[3-(2-methyoxy-2-oxoethyl)-4,8-dimethyl-2-oxo-2H-chromen-7-yl]oxy}methyl)benzoate, or 4-chloro-3-{5-[(1,3-diethyl-4,6-dioxo-2-thioxotetrahydro-5(2H)-pyrimidinylidene)methyl]-2-furyl}benzoic acid retains Stat3 inhibitory activity. In another embodiment of the invention, a derivative of 4-[3-(2,3-dihydro-1,4-benzodioxin-6-yl)-3-oxo-1-propen-1-yl]benzoic acid, 4{5-[(3-ethyl-4-oxo-2-thioxo-1,3-thiazolidin-5-ylidene)methyl]-2-furyl}benzoic acid, 4-[({3-[(carboxymethyl)thio]-4-hydroxy-1-naphthyl}amino)sulfonyl]benzoic acid, 3-({2-chloro-4-[(1,3-dioxo-1,3-dihydro-2H-inden-2-ylidene)methyl]-6-ethoxyphenoxy}methyl)benzoic acid, methyl 4-({[3-(2-methyoxy-2-oxoethyl)-4,8-dimethyl-2-oxo-2H-chromen-7-yl]oxy}methyl)benzoate, or 4-chloro-3-{5-[(1,3-diethyl-4,6-dioxo-2-thioxotetrahydro-5(2H)-pyrimidinylidene)methyl]-2-furyl}benzoic acid retains Stat3 inhibitory activity and, in specific embodiments, also retains non-inhibition of Stat1.

In a specific embodiment of the invention, the method of inhibiting Stat3 in a cell comprises delivering to the cell a compound selected from the group consisting of 4-[3-(2,3-dihydro-1,4-benzodioxin-6-yl)-3-oxo-1-propen-1-yl]benzoic acid 4{5-[(3-ethyl-4-oxo-2-thioxo-1,3-thiazolidin-5-ylidene)methyl]-2-furyl}benzoic acid; 4-[({3-[(carboxymethyl)thio]-4-hydroxy-1-naphthyl}amino)sulfonyl]benzoic acid; 3-({2-chloro-4-[(1,3-dioxo-1,3-dihydro-2H-inden-2-ylidene)methyl]-6-ethoxyphenoxy}methyl)benzoic acid; methyl 4-({[3-(2-methyoxy-2-oxoethyl)-4,8-dimethyl-2-oxo-2H-chromen-7-yl]oxy}methyl)benzoate; 4-chloro-3-{5-[(1,3-diethyl-4,6-dioxo-2-thioxotetrahydro-5(2H)-pyrimidinylidene)methyl]-2-furyl}benzoic acid; and a mixture thereof.

In another embodiment, the inhibitor comprises the general formula:

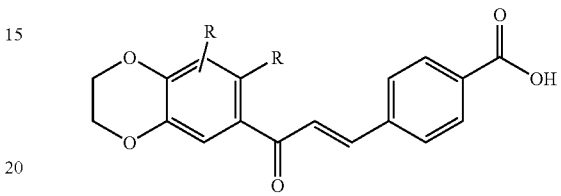

wherein $R_1$ and $R_2$ may be the same or different and are selected from the group consisting of hydrogen, carbon, sulfur, nitrogen, oxygen, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives.

In another embodiment of the invention, the inhibitor comprises the general formula:

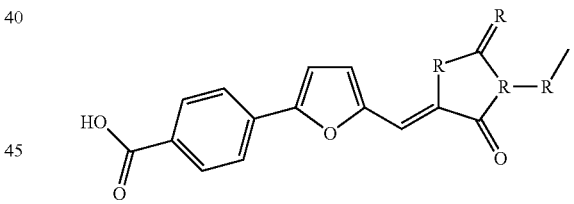

wherein $R_1$, and $R_3$ may be the same or different and are selected from the group consisting of hydrogen, carbon, nitrogen, sulfur, oxygen, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives, and $R_2$ and $R_4$ may be the same or different and are selected from the group consisting of hydrogen, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives.

In another embodiment of the invention, the inhibitor comprises the general formula:

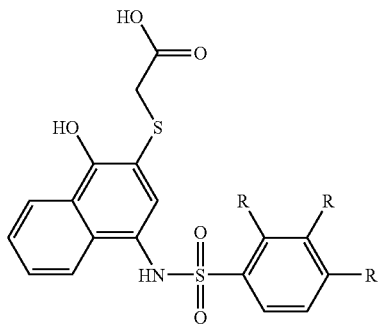

wherein $R_1$, $R_2$, and $R_3$ may be the same or different and are selected from the group consisting of hydrogen, carboxyl, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives.

An exemplary and illustrative list of alkanes, cyclic alkanes, and alkane-based derivates are found in Table 1. Non-limiting examples of ketones, ketone-based derivatives, aldehydes, aldehyde-based derivatives; carboxylic acids, carboxylic acid-based derivatives, ethers, ether-based derivatives, esters, ester-based derivatives, amines, amino-based derivatives, amides, and amide-based derivatives are listed in Table 2. Exemplary monocyclic or polycyclic arene, heteroarenes, arene-based or heteroarene-based derivatives, phenols, phenol-based derivatives, benzoic acid and benzoic acid-based derivatives are described in Table 3.

TABLE 1

| Chemical names | Formulas |
| --- | --- |
| Methyl | $CH_3$ |
| Ethyl | $C_2H_5$ |
| Vinyl (ethenyl) | $C_2H_3$ |
| Ethynyl | $C_2H$ |
| Cyclopropyl | $C_3H_5$ |
| Cyclobutyl | $C_4H_7$ |
| Cyclopentyl | $C_5H_9$ |
| Cyclohexyl | $C_6H_{11}$ |

TABLE 2

| Chemical names | Chemical formulas |
| --- | --- |
| Acetonyl | $C_3H_5O$ |
| Methanal (formaldehyde) | $CH_2O$ |
| Paraldehyde | $C_6H_{12}O_3$ |

TABLE 2-continued

| Chemical names | Chemical formulas |
| --- | --- |
| Ethanoic acid | $CH_3COOH$ |
| Diethyl ether | $C_4H_{10}O$ |
| Trimethylamine | $C_3H_9N$ |
| Acetamide | $C_2H_5NO$ |
| Ethanol | $C_2H_5OH$ |
| Methanol | $CH_3OH$ |

TABLE 3

| Chemical names | Chemical formulas |
| --- | --- |
| Benzol | $C_6H_6$ |
| Phenol | $C_6H_6O$ |
| Benzoic acid | $C_7H_6O_2$ |
| Aniline | $C_6H_7N$ |
| Toluene | $C_7H_8$ |
| Pyridazine | $C_4H_4N_2$ |
| Pyrimidine | $C_4H_4N_2$ |
| Pyrazine | $C_4H_4N_2$ |
| Biphenyl | $C_{12}H_{10}$ |

The compositions of the present invention and any functionally active derivatives thereof may be obtained by any suitable means. In specific embodiments, the derivatives of the invention are provided commercially, although in alternate embodiments the derivatives are synthesized. The chemical synthesis of the derivatives may employ well known techniques from readily available starting materials. Such synthetic transformations may include, but are not limited to protection, de-protection, oxidation, reduction, metal catalyzed C—C cross coupling, Heck coupling or Suzuki coupling steps (see for example, March's Advanced Organic Chemistry: Reactions, Mechanisms, and Structures, 5$^{th}$ Edition John Wiley and Sons by Michael B. Smith and Jerry March, incorporated here in full by reference).

III. Embodiments for Targeting STAT3

STAT proteins, of which there are seven (1, 2, 3, 4, 5A, 5B and 6), transmit peptide hormone signals from the cell surface to the nucleus. Detailed structural information of STAT proteins currently is limited to Stat1 and Stat3. Stat1 (FIG. 14) was the first STAT to be discovered (Fu et al., 1992) and is required for signaling by the Type I and II IFNs (Meraz et al., 1996; Wiederkehr-Adam et al., 2003; Durbin et al., 1996; Haan et al., 1999). Studies in Stat1-deficient mice (Meraz et al., 1996; Durbin et al., 1996; Ryan et al., 1998) support an essential role for Stat1 in innate immunity, notably against viral pathogens. In addition, Stat1 is a potent inhibitor of growth and promoter of apoptosis (Bromberg and Darnell, 2000). Also, because tumors from carcinogen-treated wild-type animals grow more rapidly when transplanted into the Stat1-deficient animals than they do in a wild-type host, Stat1 contributes to tumor surveillance (Kaplan et al., 1998).

Stat3 was originally termed acute-phase response factor (APRF) because it was first identified as a transcription factor that bound to IL-6-response elements within the enhancer-promoter region of various acute-phase protein genes (Akira, 1997). In addition to receptors for the IL-6 cytokine family, other signaling pathways are linked to Stat3 activation include receptors for other type I and type II cytokine receptors, receptor tyrosine kinases, G-protein-coupled receptors and Src kinases (Schindler and Darnell, 1995; Turkson et al., 1998). Targeted disruption of the mouse Stat3 gene leads to embryonic lethality at 6.5 to 7.5 days (Takeda et al., 1997)

indicating that Stat3 is essential for early embryonic development possibly gastrulation or visceral endoderm function (Akira, 2000). Tissue-specific deletion of Stat3 using Cre-lox technology has revealed decreased mammary epithelial cell apoptosis resulting in delayed breast involution during weaning (Chapman et al., 1999). Recent findings indicate that switching of the predominant STAT protein activated by a given receptor can occur when a STAT downstream of that receptor is genetically deleted (Costa-Pereira et al., 2002; Qing and Stark, 2004). These findings suggest the possibility that the effect of Stat3 deletion in breast tissue may be mediated indirectly by increased activation of other STAT proteins, especially Stat5.

Stat1 and Stat3 Isoforms.

Figure 14:
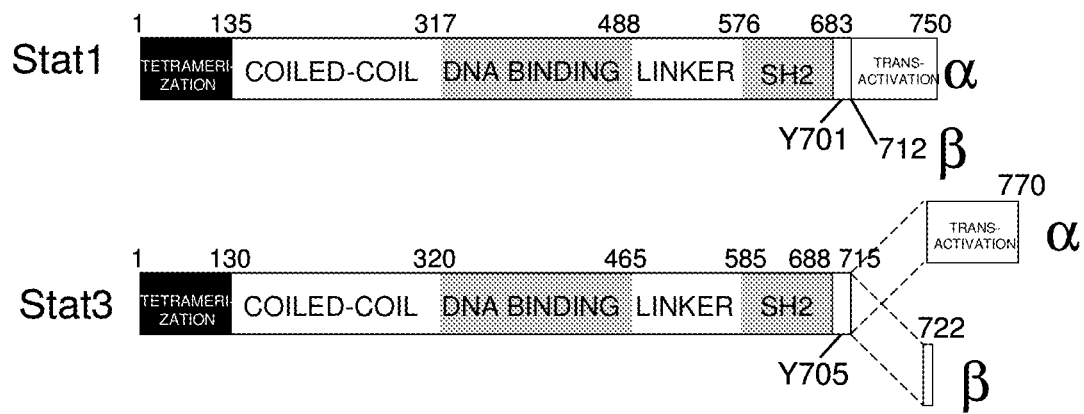
FIG. 14 illustrates schematic diagrams of Stat1 and Stat3.

Two isoforms of Stat1 and Stat3 have been identified—α (p91 and p92, respectively) and β (p84 and p83, respectively) (Schindler et al., 1992; Schaefer et al., 1995; Caldenhoven et al., 1996; Chakraborty et al., 1996)—that arise due to alternative mRNA splicing (FIG. 14). In contrast to Stat1β (712 aa), in which the C-terminal transactivation is simply deleted, the 55 amino acid residues of Stat3α are replaced in Stat3 β by 7 unique amino acid residues at its C-terminus. Unlike Stat1 β, Stat3 β is not simply a dominant-negative of Stat3α □ (Maritano et al., 2004) and regulates gene targets in a manner distinct from Stat3 β (Maritano et al., 2004; Yoo et al., 2002). Stat3α has been demonstrated to contribute to transformation in cell models and many human cancers including breast cancer. Stat3α was shown to be constitutively activated in fibroblasts transformed by oncoproteins such as v-Src (Yu et al., 1995; Garcia and Jove, 1998) and to be essential for v-Src-mediated transformation (Turkson et al., 1998; Costa-Pereira et al., 2002). In contrast to Stat3α, Stat3β antagonized v-Src transformation mediated through Stat3α (Turkson et al., 1998). Overexpression of a constitutively active form of Stat3α in immortalized rat or mouse fibroblasts induced their transformation and conferred the ability to form tumors in nude mice (Bromberg et al., 1999). Stat3 has been shown to be constitutively activated in a variety of hematological and solid tumors including breast cancer (Dong et al., 2003; Redell and Tweardy, 2003) as a result of either autocrine growth factor production or dysregulation of protein tyrosine kinases. In virtually all cases, the isoform demonstrating increased activity is Stat3α.

Targeting Stat3α while Sparing Stat1.

Given its multiple contributory roles to oncogenesis, Stat3 has recently gained attention as a potential target for cancer therapy (Bromberg, 2002; Turkson, 2004). While several methods of Stat3 inhibition have been employed successfully and have established proof-of-principle that targeting Stat3 is potentially beneficial in a variety of tumor systems including breast cancer in which Stat3 is constitutively activated (Epling-Burnette et al., 2001; Yoshikawa et al., 2001; Li and Shaw, 2002; Catlett-Falcone et al., 1999; Mora et al., 2002; Grandis et al., 2000; Leong et al., 2003; Jing et al., 2003; Jing et al., 2004; Turkson et al., 2001; Ren et al., 2003; Shao et al., 2003; Turkson et al., 2004; Uddin et al., 2005); all have potential limitations for translation to clinical use for cancer therapy related to issues regarding delivery, specificity or toxicity.

Specific strategies that target Stat3 by identifying inhibitors of Stat3 recruitment and/or dimerization have been pursued by several groups (Turkson et al., 2001; Ren et al., 2003; Shao et al., 2003; Uddin et al., 2005; Song et al., 2005; Schust et al., 2006). As outlined below, this strategy has the potential to achieve specificity based on the observation that the preferred pY peptide motif of each STAT protein is distinct. When coupled to a small molecule approach, this strategy has the potential to overcome issues of delivery and toxicity.

Targeting Stat3α while Sparing Stat3β.

Some of the distinct biochemical features of Stat3β vs. Stat3α, notably constitutive activation and a 10-to-20 fold increased DNA binding affinity, have been attributed to the absence of the C-terminal transactivation domain (TAD) resulting in increased Stat3β dimer stability (Park et al., 1996; Park et al., 2000). Increased dimer stability likely results from higher binding affinity of the SH2 domain to pY peptide motifs when in the context of Stat3β compared to Stat3α because of reduced steric hindrance conferred by removal of the TAD. These differential biochemical features between Stat3 α and Stat3β are exploited to develop a chemical compound that selectively targets Stat3 α, in some embodiments. This selectivity enhances the anti-tumor effect of such compounds, in certain cases, because they would spare Stat3β, which functions to antagonize the oncogenic functions of Stat3α.

In certain embodiments of the invention, specific therapies targeting Stat3 signaling in the unique chemoresistant subpopulation of cancer cells improves efficacy of current treatments. As outlined in the Examples below, the inventors have identified competitive and selective lead small-molecule inhibitors of Stat3 that target the Stat3 SH2-pY peptide interactions using a virtual ligand screening approach that was based on a structural model of this interaction developed by the inventors. The most active of these lead compounds was used in 3-D pharmacophore analysis to identify 2nd generation compounds. In initial studies, some have 1-2 log greater activity than the parent lead compound. Herein the inventors employ a structure-activity relationship (SAR)-based approach to develop novel 3rd generation Stat3 inhibitors. Ultimately, these studies lead to the development of new small-molecule Stat3 inhibitors for suppressing cancer stem cell self-renewal pathways to improve existing breast cancer therapies in patients, for example.

IV. Targeting Cancer Stem Cells

The ability to chemically probe both normal and cancer stem cells is essential to understand and control their function, especially to treat patients with a deficiency in mature cell number or function, or to cure patients with cancer. In particular, curing cancer will require development of drugs that target cancer stem cells while sparing normal stem cells. Our understanding of the signals required for maintenance and expansion of normal and cancer stem cells is incomplete and is limited by the paucity of probes for stem-cell specific targets.

Recent evidence has accumulated that Stat3 is required for maintenance of some normal stem cells (embryonic stem cells) but not others (normal hematopoietic stem cells), for example. In contrast, evidence is accumulating for a critical role for Stat3 in survival of stem cells in multiple cancer systems including acute myeloid leukemia (AML) and breast cancer. Development of highly effective probes that target Stat3 is useful for understanding of normal and cancer stem cells and is useful for treatment of cancer through targeting of cancer stem cells and sparing normal hematopoietic stem cells.

In specific embodiments of the invention, particular Stat3 inhibitors selectively target cancer stem cells. In certain embodiments of the invention, the Stat3 inhibitors spare normal hematopoietic stem cells while targeting leukemic stem cells, as well as other cancer stem cells such as breast cancer stem cells.

To begin to develop chemical probes that selectively target Stat3, the inventors virtually screened 920,000 small drug-like compounds by docking each into the peptide-binding pocket of the Stat3 SH2 domain, which consists of three sites—the pY-residue binding site, the +3 residue-binding site and a hydrophobic binding site, which served as a selectivity filter (Alten, 2006). Three compounds (Cpd3, Cpd30 and Cpd188) satisfied criteria of interaction analysis, competitively inhibited recombinant Stat3 binding to its immobilized pY-peptide ligand and inhibited IL-6-mediated tyrosine phosphorylation of Stat3. These compounds were used in a similarity screen of 2.47 million compounds, which identified 3 more compounds (Cpd3-2, Cpd3-7 and Cpd30-12) with similar activities.

Examinations of the 6 active compounds for the ability to inhibit IFN-γ-mediated Stat1 phosphorylation revealed that all but Cpd30-12 were selective for Stat3. All 5 Stat3 selective probes inhibited nuclear-to-cytoplasmic translocation of Stat3, while 3 of 5 probes (Cpd3, Cpd30 and Cpd188) induced apoptosis preferentially of cancer cell with constitutive Stat3 activation.

Initial similarity screening did not yield any hits using the most active of the 3 lead probes, Cpd188, as the query compound. Consequently, the inventors repeated 2-D similarity screening using the scaffold of Cpd188 as the query structure and the Life Chemicals library, which yielded 207 hits. 3-D pharmacophore analysis was performed and the top 39 scoring compounds were purchased and tested for inhibition of Stat3 binding to its phosphopeptide ligand by surface plasmon resonance (SPR). All but six of these 39 compounds have measurable $IC_{50}$s, with 19 having $IC_{50}$ values equal to or less than the parent probe; two probes (Cpd188-9 and Cpd188-15) have $IC_{50}$ values in SPR and in leukemia cell apoptosis assays that are one log better than the parent Cpd 188. In particular aspects of the invention, Stat3 is dispensable for the function of normal hematopoietic stem cells but not for cancer stem cells, for example, leukemic stem cells.

The present invention addresses the following: 1) use of medicinal chemistry in synthesis of 3rd generation 188-like sulfamide Stat3 probes (the most active 2nd generation probe, Cpd188-15, serves as a scaffold for making 3rd generation probes, and in certain embodiments there are modifications pursuant to structure-activity relationship (SAR) analysis performed on 2nd generation probes that center around the straightforward synthesis of sulfamides from panels of sulfonyl chlorides and amides); 2) identification of chemical probes among the sulfamide compounds synthesized in item 1) that are the most active and selective for Stat3; each novel sulfamide compound is examined in a rapid throughput SPR assay for the ability to inhibit Stat3 binding to its phosphopeptide ligand followed by a high throughput fluorescence microscopy (HTFM) assay examining inhibition of IL-6-stimulated cytoplasmic-to-nuclear translocation; the most active probes in these assays are examined for their selectivity for Stat3 vs. Stat1 by testing for inhibition of IL-6-stimulated Stat3 phosphorylation and for failure to inhibit IFN-γ-stimulated Stat1 phosphorylation; and 3) examination of candidate 3rd generation Stat3 chemical probes for the ability to selectively target myeloid leukemic stem cells while sparing normal hematopoietic stem/progenitor cells, wherein compounds demonstrating activity greater than the most active 2nd generation 188-like probe and selectivity for Stat3 are examined for the ability to target leukemic stem cells while sparing normal hematopoietic stem cells.

V. Combination Therapy

It is an aspect of this invention that a Stat3 inhibitor of the invention is used in combination with another agent or therapy method, such as another cancer treatment. The Stat3 inhibitor of the invention may precede or follow the other agent treatment by intervals ranging from minutes to weeks, for example. In embodiments where the other agent and the composition of the invention are applied separately to a cancer cell, such as upon delivery to an individual suspected of having cancer, known to have cancer, or at risk for having cancer, one would generally ensure that a significant period of time did not expire between the time of each delivery, such that the agent and composition of the invention would still be able to exert an advantageously combined effect on the cell. For example, in such instances, it is contemplated that one may contact the cell, tissue or organism with one, two, three, four or more modalities substantially simultaneously (i.e., within less than about a minute) with the Stat3 inhibitor of the invention. In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours or more prior to and/or after administering the Stat3 inhibitor of the invention. In certain other embodiments, an agent may be administered within of from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the Stat3 inhibitor of the invention, for example. In some situations, it may be desirable to extend the time period for treatment significantly, such as where several weeks (e.g., about 1, about 2, about 3, about 4, about 5, about 6, about 7 or about 8 weeks or more) lapse between the respective administrations.

Various combinations may be employed, the Stat3 inhibitor of the invention is "A" and the secondary agent, which can be any other cancer therapeutic agent, is "B":

A/B/A B/A/B B/B/A A/A/B A/B/B B/A/A A/B/B/B

B/A/B/B

B/B/B/A B/B/A/B A/A/B/B A/B/A/B A/B/B/A B/B/A/A

B/A/B/A B/A/B/B A/A/B/B B/A/A/A A/B/A/A A/A/B/A

Administration of the therapeutic expression constructs of the present invention to a patient will follow general protocols for the administration of chemotherapeutics, taking into account the toxicity. It is expected that the treatment cycles would be repeated as necessary. It also is contemplated that various standard therapies, as well as surgical intervention, may be applied in combination with the Stat3 inhibitor of the invention. The additional therapies include but are not limited to chemotherapy, radiotherapy, immunotherapy, gene therapy and surgery, for example.

A. Chemotherapy

Cancer therapies also include a variety of combination therapies with both chemical and radiation based treatments. In specific embodiments, the additional therapy to the therapy of the invention also targets cancer stem cells. Combination chemotherapy include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, COX-2 inhibitors, cholesterol synthesis inhibitors, cisplatinum, 5-fluorouracil, vincristin, vinblastin, staurosporine, streptozocin, fludurabine, methotrexate, genistein, curcumin, resveratrol, silymarin, caffeic acid phenethyl ester, flavopiridol, emodin, green tea polyphenols, piperine, oleandrin, ursolic acid, butamic acid, actinomycin D, thalidomide or any analog or derivative variant of the foregoing. Chemotherapy can be systemic, targeted and/or hormonal based. These can be used individually or in combination. Exemplary breast cancer therapy includes herceptin, tykerb, arastin, tamoxifen, and aromatic inhibitors. Other exemplary treatments are oxaliplatin, docetaxel, imatinib, and abraxan, in addition to tyrosine kinase inhibitors such as sorefinib or sunitinib. One of skill in the art would know that siRNA types of cancer treatment may also be considered.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Radiochemotherapy

Radiochemotherapy is the combined delivery of radiation and chemotherapy to a target. This can be achieved in a single agent through conjugation of a chemotherapeutic agent to a chelating moiety, which is then subsequently radiolabeled with a therapeutic radionuclide. Combinations of radiochemotherapy include, for example, cisplatin (CDDP) with a-emitters, cyclophosphamide with b-emitters, doxorubicin with b/g-emitters and taxol with Auger-emitters, or any analog or derivative variant of the foregoing.

D. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy could thus be used as part of a combined therapy, possibly in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155, for example.

E. Gene Therapy

In yet another embodiment, the secondary treatment is a gene therapy in which a therapeutic polynucleotide is administered before, after, or at the same time a first therapeutic agent. Delivery of the therapeutic agent in conjunction with a vector encoding a gene product will have a combined anti-hyperproliferative effect on target tissues, in certain cases.

F. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically or partially removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue. Breast cancer surgery includes mastectomy or lumpectomy.

VI. Pharmaceutical Compositions

Pharmaceutical compositions of the present invention comprise an effective amount of a composition of the invention dissolved or dispersed in a pharmaceutically acceptable carrier. The phrases "pharmaceutical" or "pharmacologically acceptable" refer to molecular entities and compositions that do not produce an adverse, allergic or other untoward reaction when administered to an animal, such as, for example, a human, as appropriate. The preparation of a pharmaceutical composition that contains at least one Stat3 inhibitor of the invention, and in some cases an additional active ingredient, will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The Stat3 inhibitor of the invention may comprise different types of carriers depending on whether it is to be administered in solid, liquid or aerosol form, and whether it needs to be sterile for such routes of administration such as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a patient can be determined by physical and physiological factors such as body weight, severity of condition, the type of disease being treated, previous or concurrent therapeutic interventions, and the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a Stat3 inhibitor of the invention. In other embodiments, the active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above. In certain embodiments of the invention, various dosing mechanisms are contemplated. For example, the composition may be given one or more times a day, one or more times a week, or one or more times a month, and so forth.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The Stat3 inhibitor of the invention may be formulated into a composition in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example, liquid polyol or lipids; by the use of surfactants such as, for example, hydroxypropylcellulose; or combinations thereof such methods. In many cases, it will be preferable to include isotonic agents, such as, for example, sugars, sodium chloride or combinations thereof.

Sterile injectable solutions are prepared by incorporating the instant invention in the required amount of the appropriate solvent with various amounts of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof

VII. Kits of the Invention

Any of the Stat3 inhibitor compositions described herein may be comprised in a kit, and they are housed in a suitable container. The kits will thus comprise, in suitable container means, one or more Stat3 inhibitors and, in some cases, an additional agent of the present invention.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the Stat3 inhibitor, additional agent, and any other reagent containers in close confinement for commercial sale. Such containers may include injection or blow molded plastic containers into which the desired vials are retained.

Compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Materials and Methods

Virtual Ligand Screening.

The inventors isolated the three-dimensional structure of the Stat3 SH2 domain from the core fragment structure of phosphorylated Stat3 homodimers bound to DNA (Becker et al., 1998) deposited in the RCSB Protein Data Bank (PDB) databank (PDB code 1BG1) and converted it to be an Internal Coordinate Mechanics (ICM)-compatible system by adding hydrogen atoms, modifying unusual amino acids, making charge adjustments and performing additional cleanup steps. In addition, the inventors retrieved the coordinates of the Stat1 SH2 domain from the PDB databank (PDB code 1BF5) for use in computational selectivity analysis (Chen et al., 1998). Commercial chemical databases (Chembridge, Asinex, ChemDiv, Enamine, Keyorganics and Life Chemicals) were chosen as sources of compounds for screening in silico. Selection was of the amide hydrogen of E638 within the site that binds the +3 residue (Q, C or T) within the pY-peptide ligand (Shao et al., 2006) as the central point of the binding pocket, which consisted of a cube with dimensions 16.0×16.9×13.7 angstrom. In addition to the +3 binding site, this cube contained the pY residue binding site consisting mainly of R609 and K591 (Shao et al., 2006) and a hydrophobic binding site consisting of $Loop_{\beta C-\beta D}$ and $Loop_{\alpha B-\alpha C}$. Sequence alignment and overlay of the Stat3 and Stat1 structures revealed substantial differences in sequence of these loops; lack of their superimposition indicated that this region might serve as a selectivity filter (Cohen et al., 2005). A flexible docking calculation (Totrov and Abagyan 1997) was performed in order to determine the global minimum energy score and thereby predict the optimum conformation of the compound within the pocket. A compound was selected for purchase and biochemical testing based on fulfilling the criteria of interaction analysis (CIA): 1) global minimum energy score≤−30, 2) formation of a salt-bridge and/or H-bond network within the pY-residue binding site and 3) formation of a H-bond with or blocking access to the amide hydrogen of E638. Most, but not all, compounds also interacted with the hydrophobic binding site.

Stat3 SH2/pY-peptide binding assay. Stat3 binding assays were performed at 25° C. with a BIAcore 3000 biosensor using 20 mM Tris buffer pH 8 containing 2 mM mercaptoethanol and 5% DMSO as the running buffer (Kim et al., 2005). Phosphorylated and control non-phosphorylated biotinylated EGFR derived dodecapeptides based on the sequence surrounding Y1068 (Shao et al., 2004) were immobilized on a streptavidin coated sensor chip (BIAcore inc., Picataway N.J.). The binding of Stat3 was conducted in 20 mM Tris buffer pH 8 containing 2 mM β-mercaptoethanol at a flow rate of 10 uL/min for 1-2 minute. Aliquots of Stat3 at 500 nM were premixed with compound to achieve a final concentration of 1-1,000 uM and incubated at 4° C. prior to being injected onto the sensor chip. The chip was regenerated by injecting 10 uL of 100 mM glycine at pH 1.5 after each sample injection. A control (Stat3 with DMSO but without compound) was run at the beginning and the end of each cycle (40 sample injections) to ensure that the integrity of the sensor chip was maintained throughout the cycle run. The average of the two controls was normalized to 100% and used to evaluate the effect of each compound on Stat3 binding. Responses were normalized by dividing the value at 2 min by the response obtained in the absence of compounds at 2 min and multiplying by 100. $IC_{50}$ values were determined by plotting % maximum response as a function of log concentration of compound and fitting the experimental points to a competitive binding model using a four parameter logistic equation: $R=R_{high}-(R_{high}-R_{low})/(1+conc/A1)^{\wedge}A2$, where R=percent response at inhibitor concentration, $R_{high}$=percent response with no compound, $R_{low}$=percent response at highest compound concentration, A2=fitting parameter (slope) and A1=$IC_{50}$ (BIAevaluation Software version 4.1).

Immunoblot assay. The human hepatocellular carcinoma cell line (HepG2) was grown in 6-well plates under standard conditions. Cells were pretreated with compounds (0, 1, 3, 10, 30, 100 and 300 uM) for 1 hour then stimulated under optimal conditions with either interferon gamma (IFN-γ; 30 ng/ml for 30 min) to activate Stat1 or interleukin-6 (IL-6; 30 ng/ml for 30 min) to activate Stat3 (30-31). Cultures were then harvested and proteins extracted using high-salt buffer, as described (Shao et al., 2006). Briefly, extracts were mixed with 2× sodium dodecyl sulfate (SDS) sample buffer (125 mmol/L Tris-HCL pH 6.8; 4% SDS; 20% glycerol; 10% 2-mercaptoethanol) at a 1:1 ratio and heated for 5 minutes at 100° C. Proteins (20 μg) were separated by 7.5% SDS-PAGE and transferred to polyvinylidene fluoride (PVDF) membrane (Millipore, Waltham, Mass.) and immunoblotted. Prestained molecular weight markers (Biorad, Hercules, Calif.) were included in each gel. Membranes were probed serially with antibody against Stat1 $pY^{701}$ or Stat3 $pY^{705}$ followed by antibody against Stat1 or Stat3 (Transduction labs, Lexington, Ky.) then antibody against β-actin (Abcam, Cambridge, Mass.). Membranes were stripped between antibody probing using Restore™ Western Blot Stripping Buffer (Thermo Fisher Scientific Inc., Waltham, Mass.) per the manufacturer's instructions. Horseradish peroxidase-conjugated goat-anti-mouse IgG was used as the secondary antibody (Invitrogen Carlsbad, Calif.) and the membranes were developed with enhanced chemiluminescence (ECL) detection system (Amersham Life Sciences Inc.; Arlington Heights, Ill.).

Similarity screen. Three compounds identified in the initial virtual ligand screening (VLS)—Cpd3, Cpd30 and Cpd188—inhibited Stat3 SH2/pY-peptide binding and IL-6-mediated Stat3 phosphorylation and were chosen as reference molecules for similarity screening. A fingerprint similarity query for each reference compound was submitted to Molcart/ICM (Max Distance, 0.4). Similarity between each reference molecule and each database molecule was computed and the similarity results were ranked in decreasing order of ICM similarity score (Eckert and Bajorath 2007). The databases searched included ChemBridge, LifeChemicals, Enamine, ChemDiv, Asinex, AcbBlocks, KeyOrganics and PubChem for a total of 2.47 million compounds. All compounds identified were docked into the binding pocket of Stat3 SH2 domain in silico. Compounds that fulfilled CIA criteria were purchased and tested as described for compounds identified in the primary screen.

Electrophoretic Mobility Shift Assay (EMSA): EMSA was performed using the hSIE radiolabeled duplex oligonucleotide as a probe as described (Tweardy et al., 1995). Briefly, high salt extracts were prepared from HepG2 cells incubated without or with IL-6 (30 ng/ml) for 30 minutes. Protein concentration was determined by Bradford Assay and 20 ug of extract was incubated with compound (300 uM) for 60 minutes at 37° C. Bound and unbound hSIE probe was separated by polyacrylamide gel electrophoresis (4.5%). Gels were dried and autoradiographed.

Molecular modeling. All 3-D configurations of the Stat3 SH2 domain complexed with compounds were determined by global energy optimization that involves multiple steps: 1) location of organic molecules were adjusted as a whole in 2 A amplitude by pseudo-Brownian random translations and rotations around the molecular center of gravity, 2) the internal variables of organic molecules were randomly changed. 3) coupled groups within the Stat3 SH2 domain side-chain torsion angles were sampled with biased probability shaking while the remaining variables of the protein were fixed, 4) local energy minimizations were performed using the Empirical Conformation Energy Program for Peptides type-3 (ECEPP3) in a vacuum (Nemethy et al., 1992) with distance-dependent dielectric constant $\in=4r$, surface-based solvent energy and entropic contributions from the protein side chains evaluated added and 5) conformations of the complex, which were determined by Metropolis criteria, were selected for the next conformation-scanning circle. The initial 3-dimensional configuration of the Stat1 SH2 domain in a complex with each compound was predicted and generated by superimposing, within the computational model, the 3-dimensional features of the Stat1 SH2 onto the 3-dimensional configuration of the Stat3 SH2 domain in a complex with each compound. The final computational model of Stat1 SH2 in a complex with each compound was determined by local minimization using Internal Coordinate Force Field (ICFF)-based molecular mechanics (Totrov and Abagyan 1997). The inventors computed the van der Waals energy of the complex of Stat1 or 3-SH2 bound with each compound using Lennard-Jones potential with ECEPP/3 force field (Nemethy et al., 1992).

Confocal and high-throughput fluorescence microscopy. Confocal and highthroughput fluorescence microscopy (HTFM) of MEF/GFP-Stat3α cells were performed as described (Huang et al., 2007). Briefly, for confocal fluorescence microscopy, cells were grown in 6-well plates containing a cover slip. For HTFM, cells were seeded into 96-well CC3 plates at a density of 5,000 cells/well using an automated plating system. Cells were cultured under standard conditions until 85-90% confluent. Cells were pretreated with compound for 1 hour at 37° C. then stimulated with IL-6 (200 ng/ml) and IL-6sR (250 ng/ml) for 30 minutes. Cells were fixed with 4% formaldehyde in PEM Buffer (80 mM Potassium PIPES, pH 6.8, 5 mM EGTA pH 7.0, 2 mM $MgCl_2$) for 30 minutes at 4° C., quenched in 1 mg/ml of NaBH4 (Sigma) in PEM buffer and counterstained for 1 min in 4,6-diamidino-2-phenylindole (DAPI; Sigma; 1 mg/ml) in PEM buffer. Cover slips were examined by confocal fluorescent microscopy. Plates were analyzed by automated HTFM using the Cell Lab IC Image Cytometer (IC100) platform and CytoshopVersion 2.1 analysis software (Beckman Coulter). Nuclear translocation is quantified by using the fraction localized in the nucleus (FLIN) measurement (Sharp et al., 2006).

Breast cancer cell line apoptosis assay. Human breast carcinoma cell lines MDA-MB-468, MDA-MB-231, MBA-MD-435 and MCF7 were kindly provided by Dr. Powel H. Brown (Breast Cancer Center, Baylor College of Medicine). Breast cancer cell line, MDA-MB-453 was kindly provided by Dr. Shou Jiang (Breast Cancer Center, Baylor College of Medicine). All cell lines were grown in DMEM medium supplemented with 10% fetal bovine serum (FBS), 25,000 units penicillin G, 25,000 ug streptomycin, and 131.4 mg L-Glutamine and cultured in the incubator under the condition of 95% air, 5% $CO_2$ at 37° C. (Garcia et al., 2001). Cells were seeded at 2,500 cells/$cm^2$ into 12-well plates. At 80% confluency, cells were washed with PBS and supplemented with fresh medium containing compound or the topoisomerase 1-inhibitor, camptothecin, at 0, 0.1, 03, 1, 3, 10, 30, 100, 300 μM. At 24 hours, treatment was terminated by removing the medium from each well. Cells were lysed with cell lysis buffer (600 μl for 30 minutes at 25° C.). Cell lysate (200 μl) was centrifuged at 200×g for 10 minutes and 20 μl of each supernatant was assayed for nucleosomes using the Cell Death Detection ELISA (Roche Applied Science) as described by the manufacturer. The percent maximum nucleosome level was calculated by dividing the nucleosome level by the maximum nucleosome level achieved in the assay and multiplying by 100. This value was plotted as a function of the log compound concentration and the best-fitting curve generated using 4-Parameter Logistic Model/Dose Response/XLfit 4.2, IDBS software.

Example 2

Identification by VLS of Compounds that Blocked STAT3 Binding to its Phosphopeptide Ligand and Inhibited IL-6-Mediated Phosphorylation of STAT3

Figure 3:
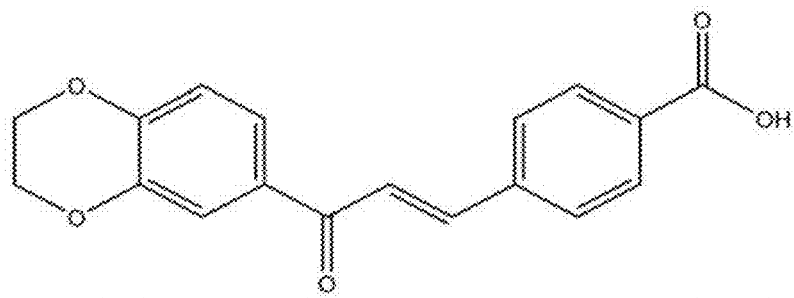
FIG. 3 provides exemplary chemical formulas and names of compounds. The chemical formulas and names are indicated for Cpd3 (panel A), Cpd30 (panel B), Cpd188 (panel C), Cpd3-2 (panel D), Cpd3-7 (panel E) and Cpd30-12 (panel F).
Figure 3:
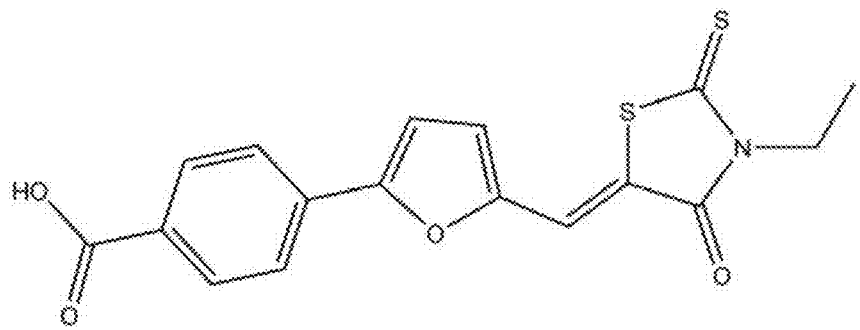
Figure 3:
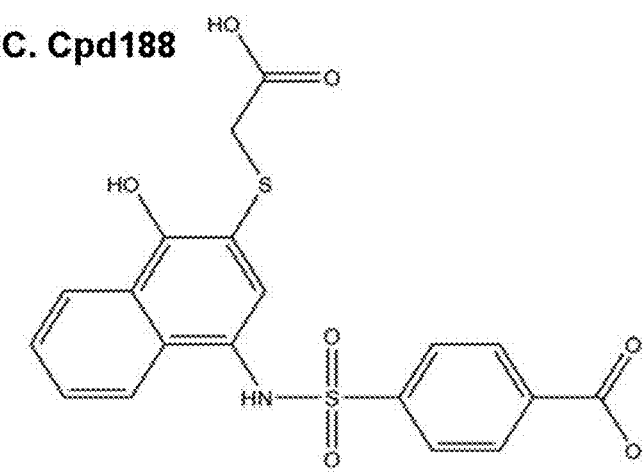
Figure 3:
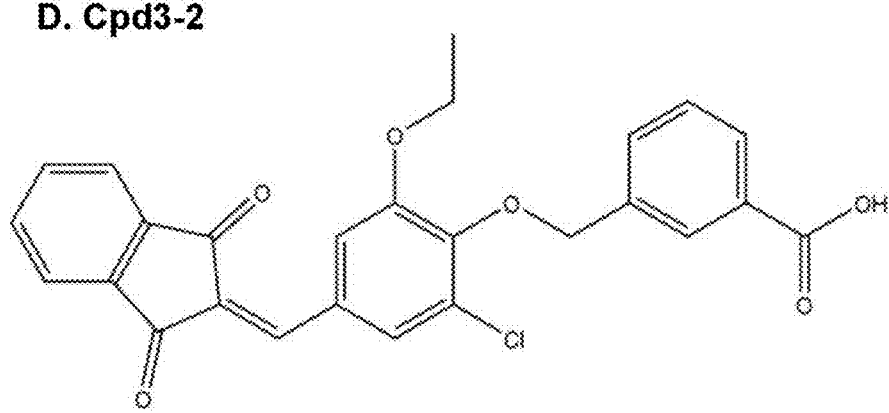
Figure 3:
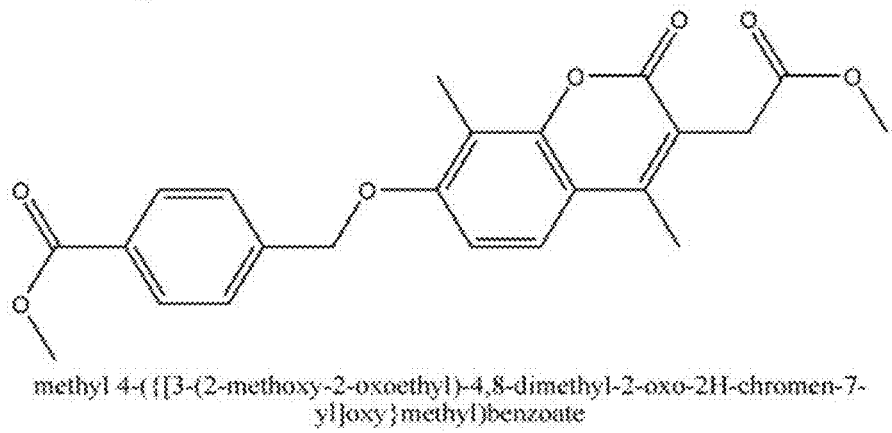
Figure 3:
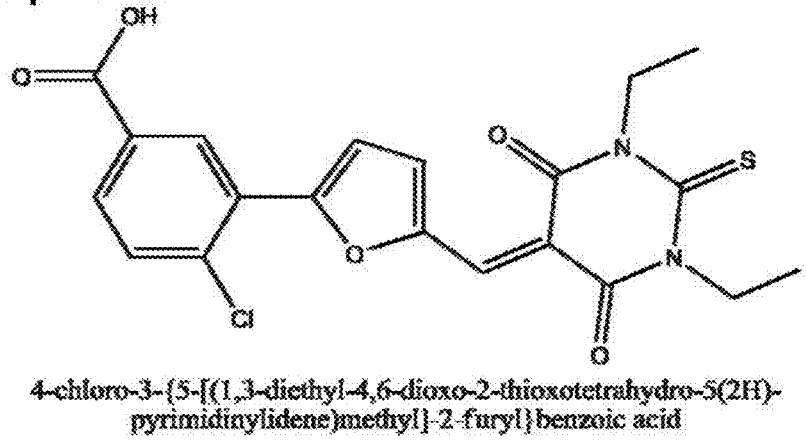

The VLS protocol was used to evaluate a total of 920,000 drug-like compounds. Of these, 142 compounds fulfilled CIA criteria. These compounds were purchased and tested for their ability to block Stat3 binding to its phosphopeptide ligand in a surface plasmon resonance (SPR)-based binding assay and to inhibit IL-6-mediated phosphorylation of Stat3. SPR competition experiments showed that of the 142 compounds tested, 3 compounds—Cpd3, Cpd30 and Cpd188—were able to directly compete with pY-peptide for binding to Stat3 with $IC_{50}$ values of 447, 30, and 20 μM, respectively (FIGS. 1 and 3; Table 4).

TABLE 4

| IC$_{50}$ values (μM) of 6 active compounds | | | | | | |
|---|---|---|---|---|---|---|
| Assay | Cpd3 | Cpd30 | Cpd188 | Cpd3-2 | Cpd3-7 | Cpd30-12 |
| SPR | 447[1] | 30 | 20 | 256 | 137 | 114 |
| pStat3 | 91 | 18 | 73 | 144 | 63 | 60 |
| HTM | 131 | 77 | 39 | 150 | 20 | >300 |

[1]Data presented are the mean or mean ± SD;
ND = not determined.

Figure 2:
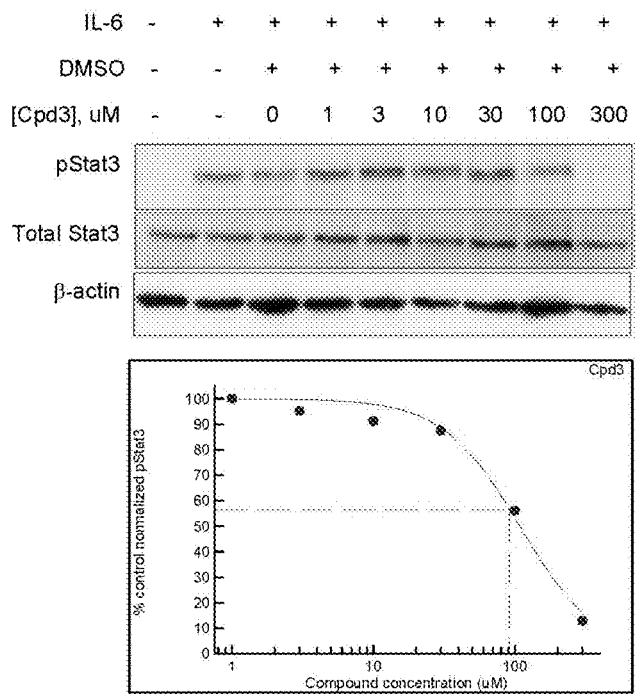
FIG. 2 demonstrates inhibition of IL-6-mediated activation of Stat3 by compounds. HepG2 cells were pretreated with DMSO alone or DMSO containing Cpd3 (panel A), Cpd188 (panel B), Cpd30 (panel C), Cpd3-2 (panel D), Cpd3-7 (panel E) or Cpd30-12 (panel F) at the indicated concentration for 60 min. Cells were then stimulated with IL-6 (30 ng/ml) for 30 min. Protein extracts of cells were separated by SDS-PAGE, blotted and developed serially with antibodies to pStat3, total Stat3 and β-actin. Blots were stripped between each antibody probing. The bands intensities of immunoblot were quantified by densitometry. The value of each pStat3 band's intensity was divided by each corresponding value of total Stat3 band intensity and the results normalized to the DMSO-treated control value and plotted as a function of the log compound concentration. The best-fit curves were generated based on 4 Parameter Logistic Model/Dose Response One Site/XLfit 4.2, IDBS. Each panel is representative of 3 or more experiments.
Figure 2:
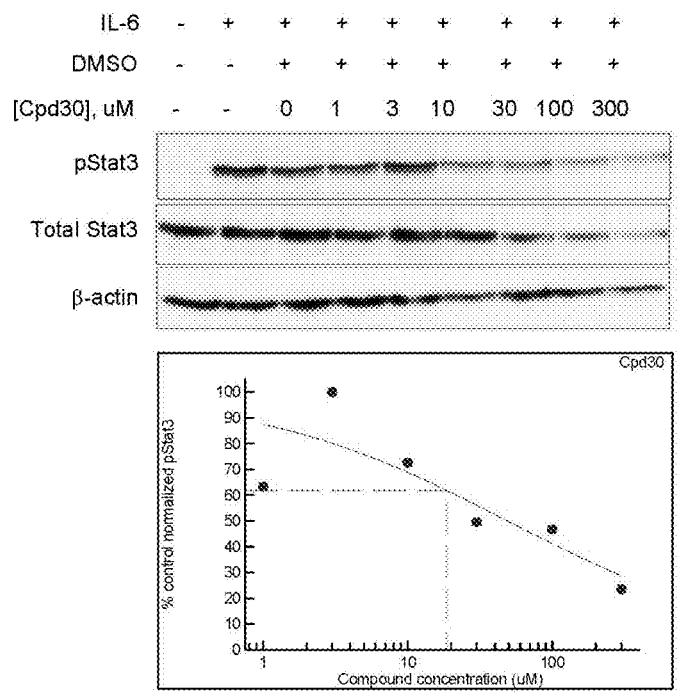
Figure 2:
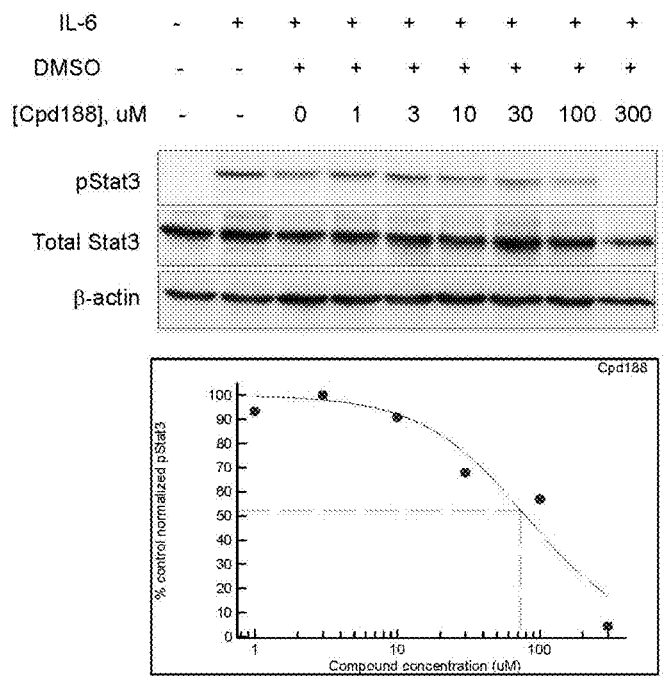
Figure 2:
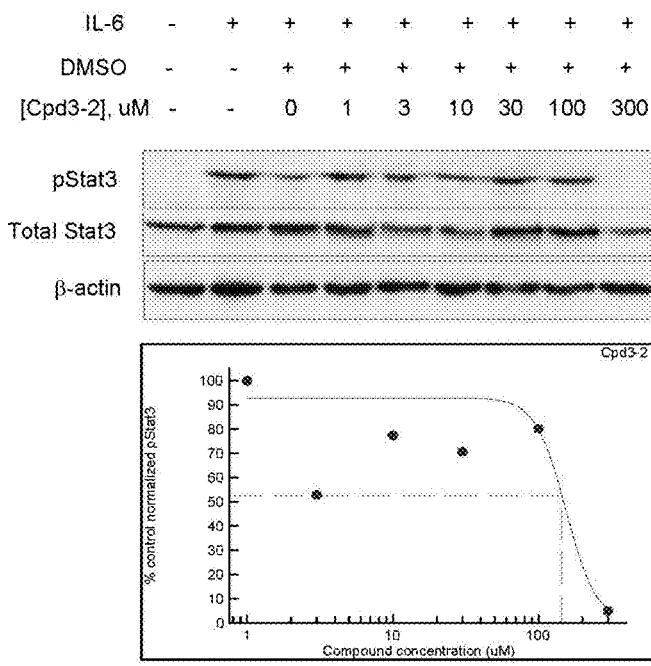
Figure 2:
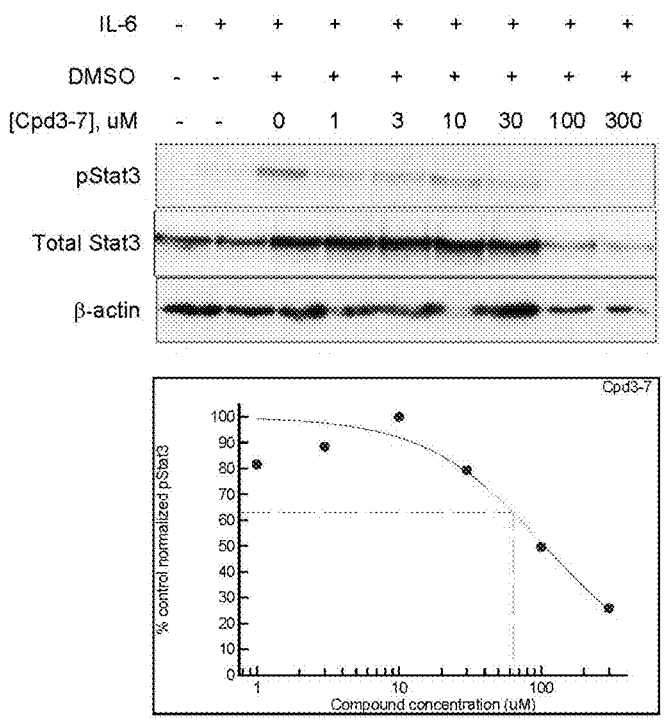
Figure 2:
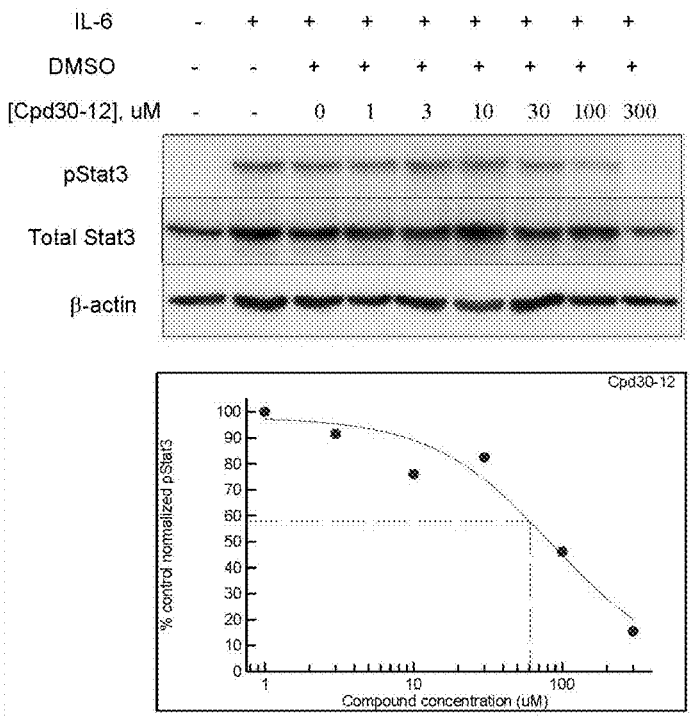

In addition, each compound inhibited IL-6-mediated phosphorylation of Stat3 with IC50 values of 91, 18 and 73 μM respectively (FIG. 2; Table 4).

Similarity screening with Cpd3, Cpd30 and Cpd188 identified 4,302 additional compounds. VLS screening was performed with each of these compounds, which identified 41 compounds that fulfilled CIA criteria; these were purchased and tested. SPR competition experiments showed that of these 41 compounds, 3 compounds—Cpd3-2, Cpd3-7 and Cpd30-12—were able to directly compete with pY-peptide for binding to Stat3 with IC$_{50}$ values of 256, 137 and 114 μM, respectively (FIGS. 1 and 3; Table 4). In addition, each compound inhibited IL-6-mediated phosphorylation of Stat3 with IC50 values of 144, 63 and 60 μM, respectively (FIG. 2; Table 4).

Example 3

Compound-Mediated Inhibition of Ligand-Stimulated Phosphorylation of STAT3 is Specific for STAT3 vs. STAT1

Figure 4:
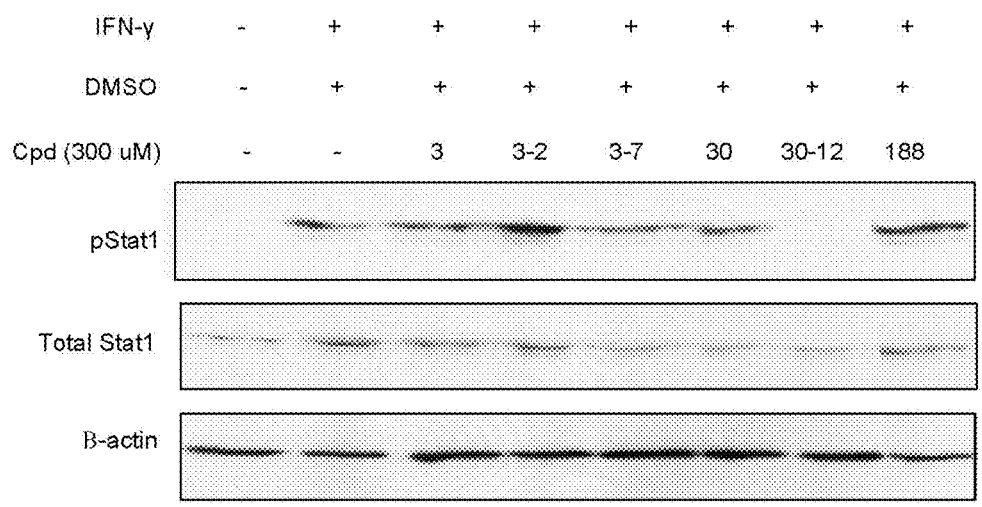
FIG. 4 shows effect of compounds on Stat1 activation. HepG2 cells were pretreated with DMSO alone or DMSO containing each of the compounds at a concentration of 300 μM for 60 min. Cells were then stimulated with IFN-γ (30 ng/ml) for 30 min. Protein extracts of cells were separated by SDS-PAGE and immunoblotted serially with antibodies to pStat1, total Stat1 and β-actin. Blots were stripped between each immunoblotting. The results shown are representative of 2 or more experiments.

While Stat3 contributes to oncogenesis, in part, through inhibition of apoptosis, Stat1 is anti-oncogenic; it mediates the apoptotic effects of interferons and contributes to tumor surveillance (Kaplan et al., 1998; Ramana et al., 2000). Consequently, compounds that target Stat3 while sparing Stat1, leaving its anti-oncogenic functions unopposed, may result in a synergistic anti-tumor effect. To assess the selectivity of the compounds for Stat3 vs. Stat1, HepG2 cells were incubated with Cpd3, Cpd30, Cpd188, Cpd3-2, Cpd3-7, and Cpd30-12 (300 μM) for 1 hour at 37° C. before IFN-γ stimulation (FIG. 4). Only treatment with Cpd30-12 blocked Stat1 phosphorylation while each of the other five compounds—Cpd3, Cpd30, Cpd188, Cpd3-2 and Cpd3-7—did not. Thus, five of the six exemplary compounds identified were selective and inhibited ligand-stimulated phosphorylation of Stat3 but not Stat1.

Example 4

Figure 5:
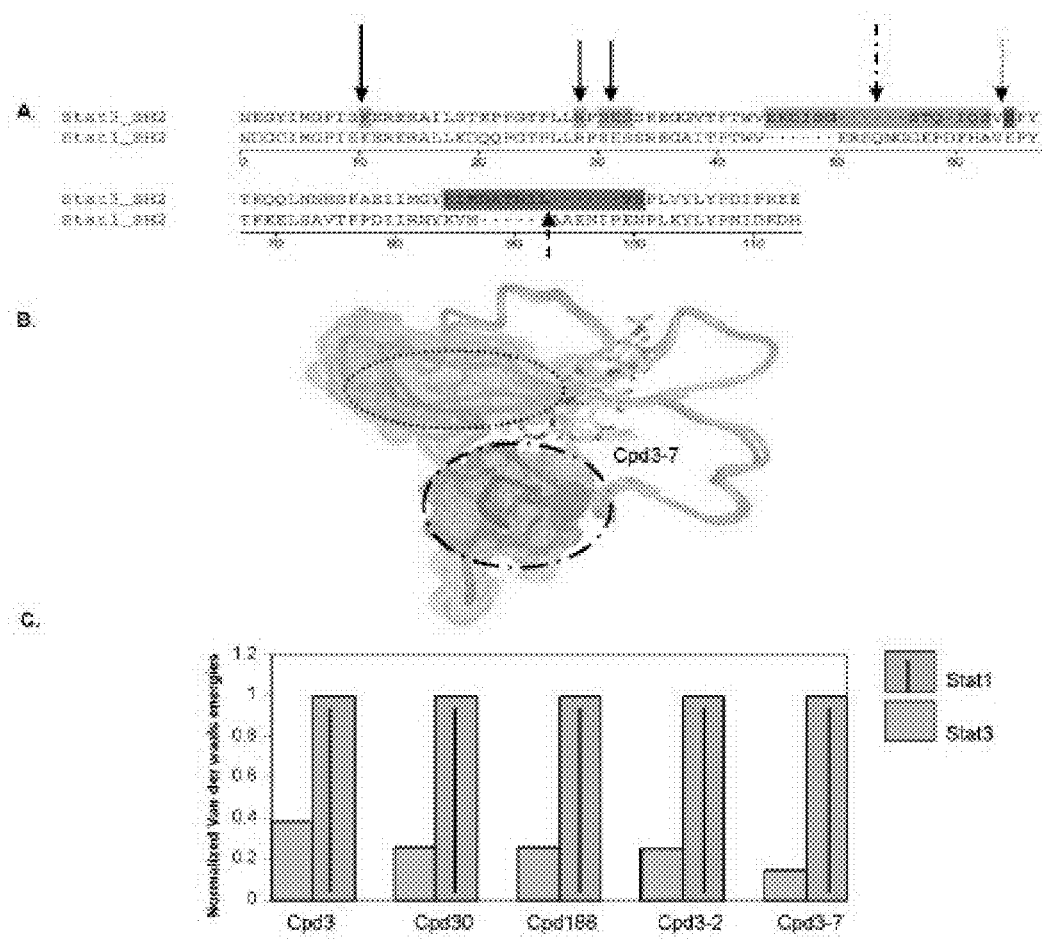
FIG. 5 provides comparisons of the Stat3 and Stat1 SH2 domain sequences, 3-D structures and van der Waals energies of compound binding. Sequence alignment of Stat3 and Stat1 SH2 domains is shown in panel A. The residues that bind the pY residue are highlighted in and pointed to by a solid arrow, the residue (E638) that binds to the +3 residue highlighted and pointed to by a dotted arrow and $Loop_{\beta C-\beta D}$ and $Loop_{\alpha B-\alpha C}$, which comprise the hydrophobic binding site consisting, are highlighted and pointed to by dot-dashed and dashed arrows, respectively. Panel B shows an overlay of a tube-and-fog van der Waals surface model of the Stat3 SH2 domain and a tube-and-fog van der Waals surface model of the Stat1 SH2. The residues of the Stat3 SH2 domain represents $Loop_{\beta C-\beta D}$ are highlighted and shown by dotted circles and the residues represent $Loop_{\alpha B-\alpha C}$ are highlighted and shown by a dotted-dashed circle; the corresponding loop residues within the Stat1 SH2 domain are shown in a light fog surrounding the circles. This overlay is shown bound by Cpd3-7 as it would bind to the Stat3 SH2 domain. The van der Waals energy of each compound bound to the Stat1 SH2 domain or the Stat3 SH2 domain was calculated, normalized to the value for Stat1 and depicted in panel C.

Sequence Analysis and Molecular Modeling of the Interaction of Each Compound with the STAT3 Vs. STAT1 SH2 Domain To understand at the molecular level the basis for the selectivity of Cpds 3, 30, 188, 3-2 and 3-7 and the absence of selectivity in the case of Cpd 30-12, the amino acid sequence and available structures of the Stat1 and Stat3 SH2 domain were compared and also it was examined how each compound interacted with both. Sequence alignment revealed identity in the residues within Stat3 and Stat1 corresponding to the binding site for the pY residue and the +3 residue (FIG. 5A). In addition, overlay of the Stat3 and Stat1 SH2 structures revealed that the loops that contained these binding sites were superimposed (FIG. 5B). In contrast, sequence alignment revealed substantial differences in the sequence of the regions of the SH2 domain corresponding to the loops forming the hydrophobic binding site (FIG. 5A). In addition, review of the overlay of Stat3 and Stat1 SH2 domains revealed that, in contrast to the close apposition of the two loops of Stat3 that form the hydrophobic binding site, the corresponding two loops of Stat1 are not closely apposed to form a pocket (FIG. 5B).

Figure 6:
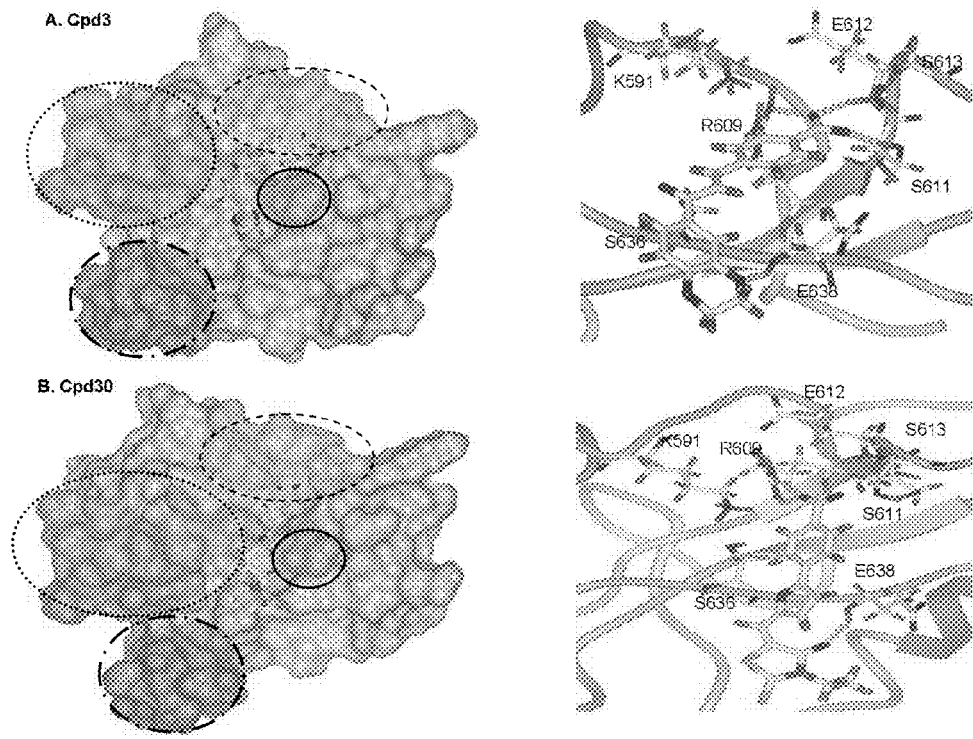
FIG. 6 shows a computer model of each compound bound by the Stat3 SH2 domain. The results of computer docking to the Stat3 SH2 domain is shown for Cpd3 (panel A), Cpd30 (panel B), Cpd188 (panel C), Cpd3-2 (panel D), Cpd3-7 (panel E) and Cpd30-12 (panel F). The image on the left of each panel shows the compound binding to a spacefilling model of the Stat3 SH2 domain. The pY-residue binding site is represented by dashed circle, the +3 residue binding site is represented by a solid circle, loop $Loop_{\beta C-\beta D}$ is represented by dotted circle and loop $Loop_{\alpha B-\alpha C}$ is represented by dot-dashed circle. Residues R609 and K591 critical for binding pY are shown within a dashed circle, residue E638 that binds the +3 residue shown within a solid circle and the hydrophobic binding site consisting of $Loop_{\beta C-\beta D}$ and $Loop_{\alpha B-\alpha C}$ is shown within a dash-dot and dotted circle, respectively. The image on the right side of each panel is a closer view of this interaction with hydrogen bonds indicated by dotted lines.
Figure 6:
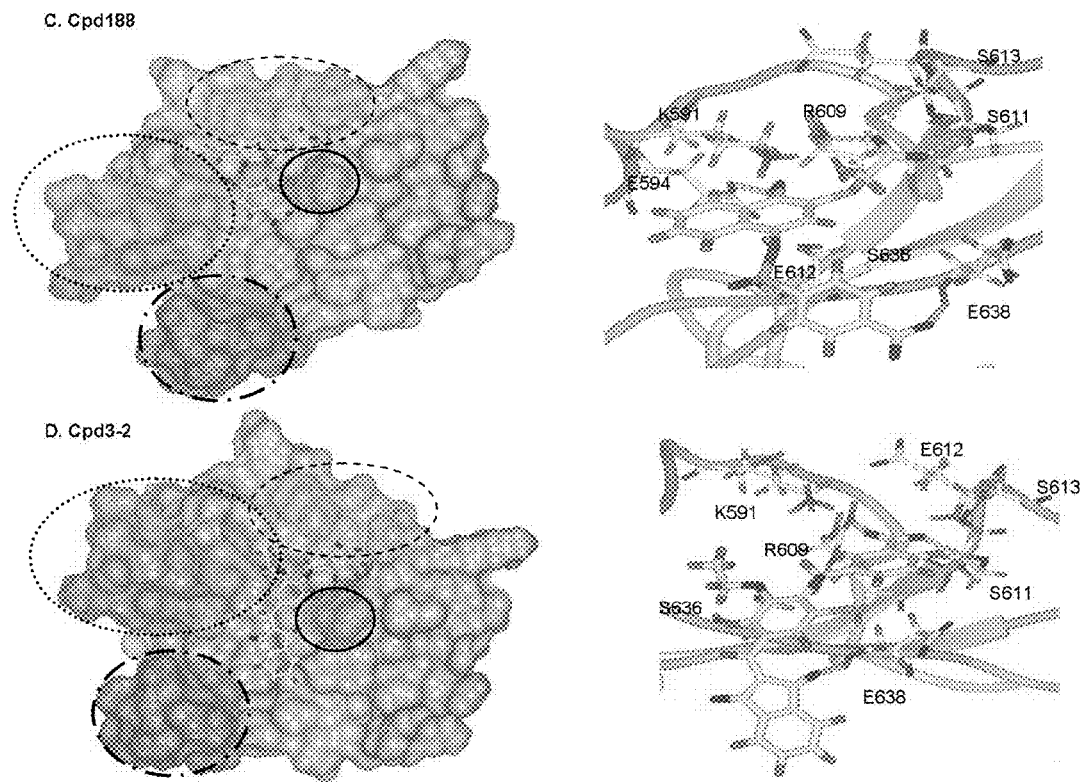
Figure 6:
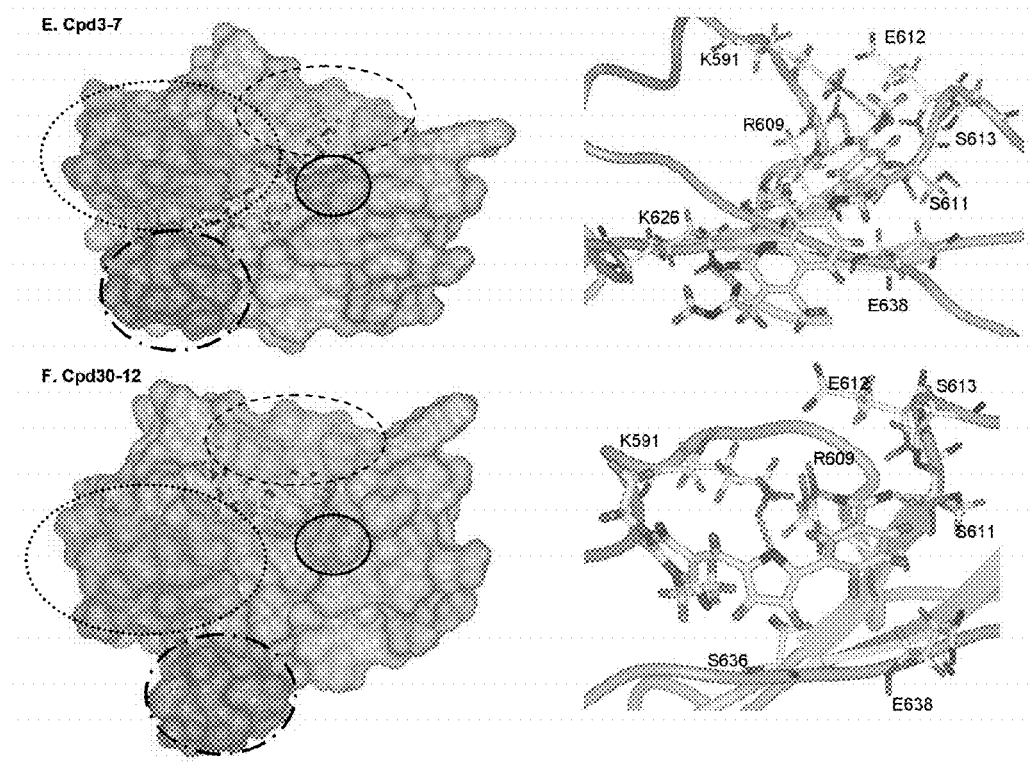

Review of computational models of Cpd3, Cpd30, Cpd188, Cpd3-2 and Cpd3-7 in a complex with the Stat3 SH2 domain revealed that each has significant interactions with the Stat3 SH2 domain binding pocket at all three binding sites, the pY-residue binding site, the +3 residue binding site and the hydrophobic binding site (FIGS. 6A, B, C, D, and E). In contrast, Cpd30-12 interacts with the pY-residue binding site and blocks access to the +3 residue-binding site but does not interact with or block access to the hydrophobic binding site (FIG. 6F). In addition, van der Waals energies of the 5 selective compounds were much more favorable for their interaction with the loops of Stat3 forming the hydrophobic binding site than with corresponding loops of Stat1 (FIG. 5C). Thus, computer modeling indicated that activity of compounds against Stat3 derives from their ability to interact with the binding sites for the pY and the +3 residues within the binding pocket, while selectivity for Stat3 vs. Stat1 derives from the ability of compounds to interact with the hydrophobic binding site within the Stat3 SH2 binding pocket, which served as a selectivity filter.

Example 5

Figure 7:
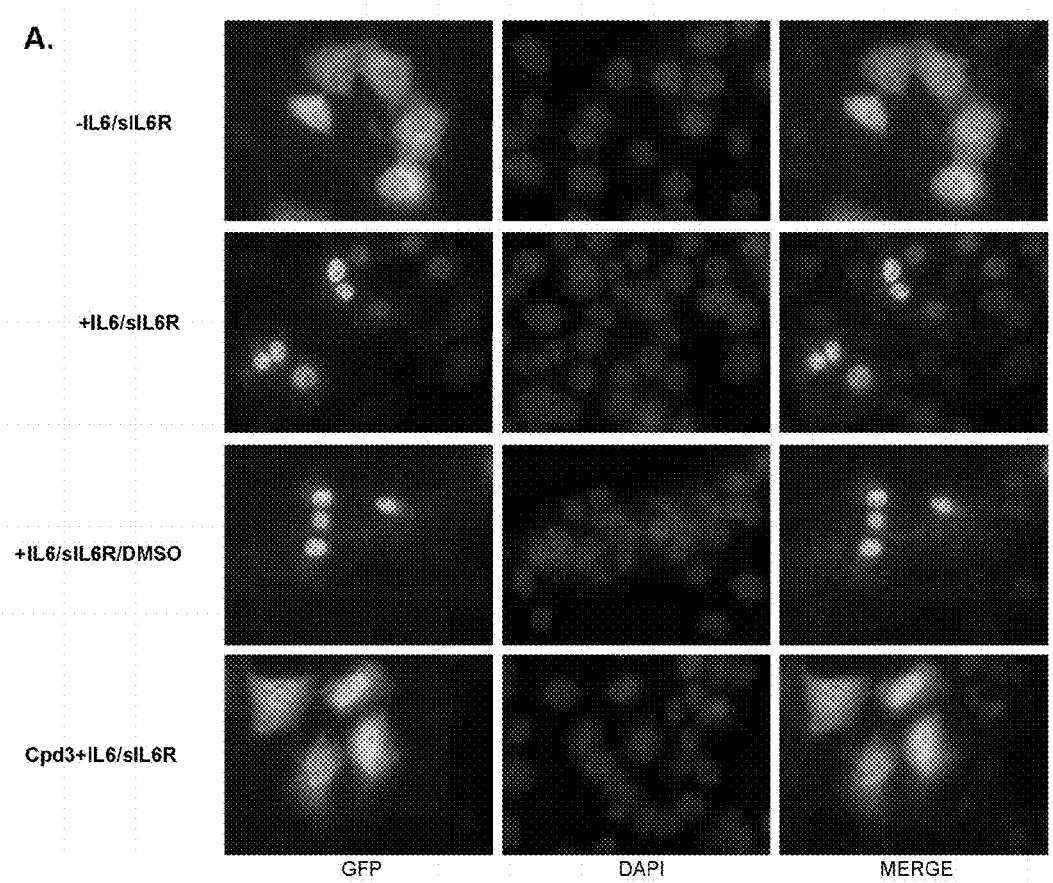
FIG. 7 shows inhibition of cytoplasmic-to-nuclear translocation of Stat3 assessed by confocal and high-throughput fluorescence microscopy. In panel A, MEF/GFP-Stat3 cells grown on coverslips were pretreated with DMSO that either contained (row four) or did not contain (row three) Cpd3 (300 μM) for 60 min before being stimulated without (row one) or with IL-6 (200 ng/ml) and IL-6sR (250 ng/ml) for 30 minutes (rows two, three and four). Coverslips were examined by confocal fluorescent microscopy using filters to detect GFP (column one), DAPI (column two) or both (merge; column three). In panel B, MEF-GFP-Stat3 cells were grown in 96-well plates with optical glass bottoms and pretreated with the indicated compound at the indicated concentrations in quadruplicate for 1 hour then stimulated with IL-6 (200 ng/ml) and IL-6sR (250 ng/ml) for 30 minutes. Cells were fixed and the plates were examined by high-throughput microscopy to determine the fluorescence intensity in the nucleus (FLIN) and the % $\Delta FLIN_{Max}$ was calculated as described in Example 1. Data shown are mean±SD and are representative of 2 or more studies. Best-fit curves were generated based on 4 Parameter Logistic Model/Dose Response One Site/XLfit 4.2, IDBS and were used to calculate $IC_{50}$ (Table 1).
Figure 7:
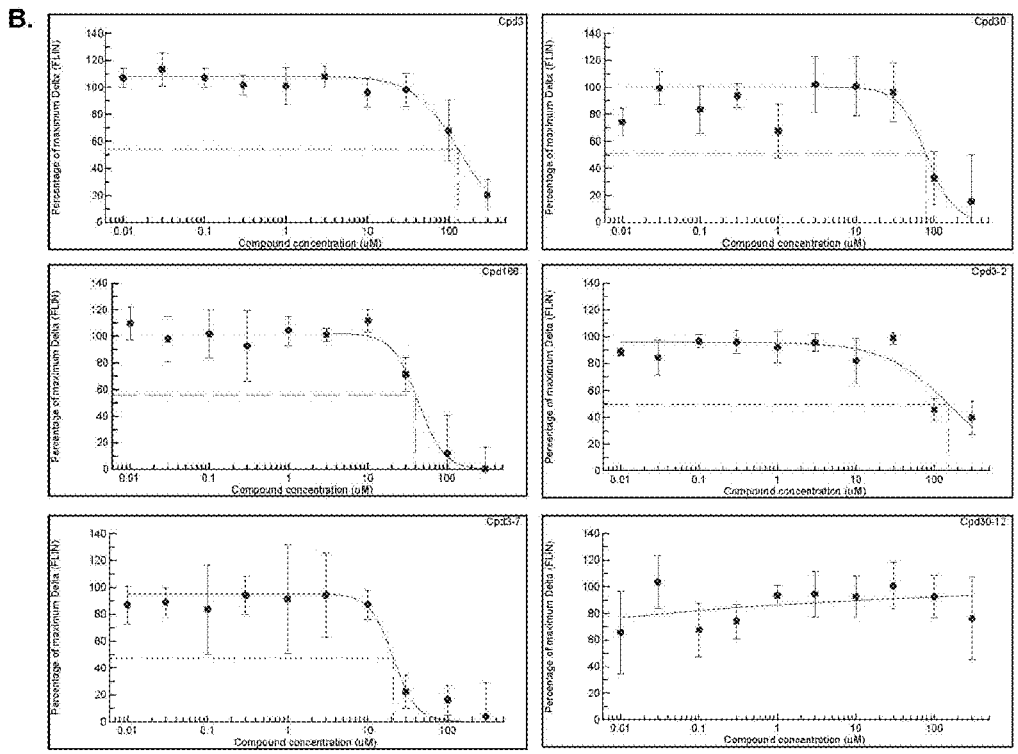

Inhibition of Nuclear Translocation of Phosphorylated STAT3 by CPD3, CPD30, CPD188, CPD3-2 AND CPD3-7 Assessed by HTFM Following its phosphorylation on Y705, Stat3 undergoes a change in conformation from head-to-head dimerization mediated through its N-terminal oligomerization domain to tail-to-tail dimerization mediated by reciprocal SH2/pY705-peptide ligand interactions. This conformational change is followed by nuclear accumulation. Compounds that targeted SH2/pY-peptide ligand interactions of Stat3 would be expected to inhibit nuclear accumulation of Stat3. To determine if this was the case with the compounds herein, a nuclear translocation assay (FIG. 7) was employed using murine embryonic fibroblast (MEF) cells that are deficient in endogenous Stat3 but constitutively express GFP-tagged Stat3α at endogenous levels, MEF/GFP-Stat3 α (Huang et al., 2007). Preincubation of MEF/GFP-Stat3 α cells with Cpd3, Cpd30, Cpd188, Cpd3-2 and Cpd3-7, but not Cpd30-12, blocked ligand-mediated nuclear translocation of GFP-Stat3 α with IC$_{50}$ values of 131, 77, 39, 150 and 20 μM (FIG. 7 and Table 4).

Example 6

Destabilization of STAT3-DNA Complexes by CPD3 and CPD3-7

Figure 8:
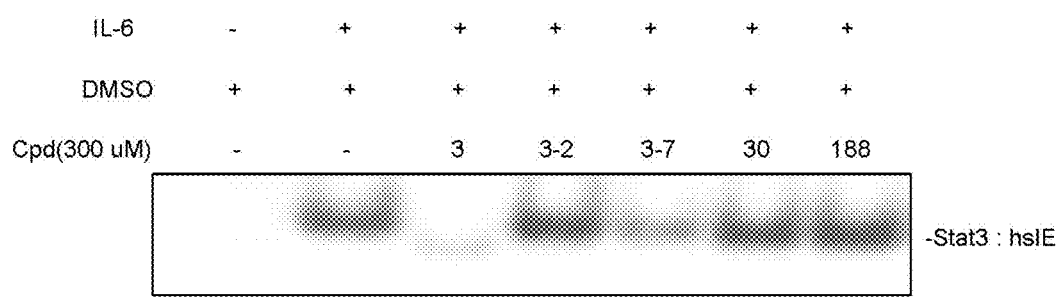
FIG. 8 demonstrates inhibition of Stat3 DNA binding by compounds. Electrophoretic mobility shift assays were performed using whole-cell extracts prepared from HepG2 cells without and with stimulation with IL-6 (30 ng/ml) for 30 min. Protein (20 μg) was incubated with radiolabeled duplex oligonucleotide (hSIE) and DMSO without or with the indicated compounds (300 uM) for 60 minutes at 37° C. then separated by PAGE. The gel was dried and autoradiographed; the portion of the gel corresponding to the Stat3-bound hSIE band is shown. Data shown are representative of 2 studies.

Once in the nucleus, Stat3 dimers bind to specific DNA elements to activate and, in some instances, repress gene transcription. Tyrosine-phosphorylated dodecapeptides based on motifs within receptors that recruit Stat3 have previously been shown to destabilize Stat3 (Chakraborty et al., 1999; Shao et al., 2003). Compounds that bind to the phosphopeptide-binding site of Stat3 might be expected to do the same. To determine if this was the case for any of the compounds we identified, extracts of IL-6-stimulated HepG2 cells were incubated in binding reactions containing radiolabeled hSIE (FIG. 8) and each of the five selective compounds (300 μM). Incubation with Cpd3 or Cpd3-7 reduced the amount of hSIE shifted by half or greater. The other compounds did not have a detectable effect on the Stat3:hSIE band intensity. Thus, 2 of the 5 selective compounds destabilized Stat3:hSIE complexes.

Example 7

Induction of Apoptosis of Breast Cancer Cell Lines by CPD3, CPD30 and CPD188; Apoptosis is Selective for Cell Lines with Constitutive STAT3 Activation Previously identified compounds that target Stat3 induce cell apoptosis (Jing et al., 2004; Song et al., 2005; Jing et al., 2006; Schust et al., 2006; Siddiquee et al., 2007). To determine if any of the selective Stat3 compounds induce apoptosis and whether or not apoptosis induction is selective for tumor cell lines with constitutive Stat3 activation, the Stat3 selective compounds herein were examined for the ability to induce apoptosis of breast cancer cell lines, MDA-MB-231 (Cailleau R 1978; Satya-Prakash K L 1981; Zhang R D 1991), MBA-MB-468 (Brinkley et al., 1980; Garcia et al., 1997; Garcia et al., 2001) and MDAMB-435 (Brinkley et al., 1980; Garcia et al., 2001) with constitutively active Stat3 and two breast cancer cell lines, MDA-MB-453 (Brinkley et al., 1980; Garcia et al., 2001; Song et al., 2005) and MCF7 (Song et al., 2005), without constitutively active Stat3.

Two compounds—Cpd3 and Cpd30—induced apoptosis of the three breast cancer cell lines with constitutive Stat3 activity—MDA-MB-468, MDA-MB-231 and MDA-MB-435 (FIGS. 9A, B and C)—with EC50 values from 2.3 to 26.9 μM and the 6.4 to 92.2 μM ranges, respectively (Table 5).

TABLE 5

$EC_{50}$ values (μM) for selective Stat3 inhibitors

| Cell line | Cpd3 | Cpd30 | Cpd188 | CAM[1] |
|---|---|---|---|---|
| MDA-MB-468 | 2.28[2] | 6.42 | 0.73 | 0.74 |
| MDA-MB-231 | 26.91 | 92.01 | 3.96 | 1.62 |
| MDA-MB-435 | 16.5 | 16.29 | 7.01 | 1.64 |
| MCF7 | >300 | >300 | 17.19 | 0.13 |
| MDA-MB-453 | >300 | >300 | 15.5 | 0.93 |

[1]CAM-camptothecin
[2]Data presented are means.

Figure 9:
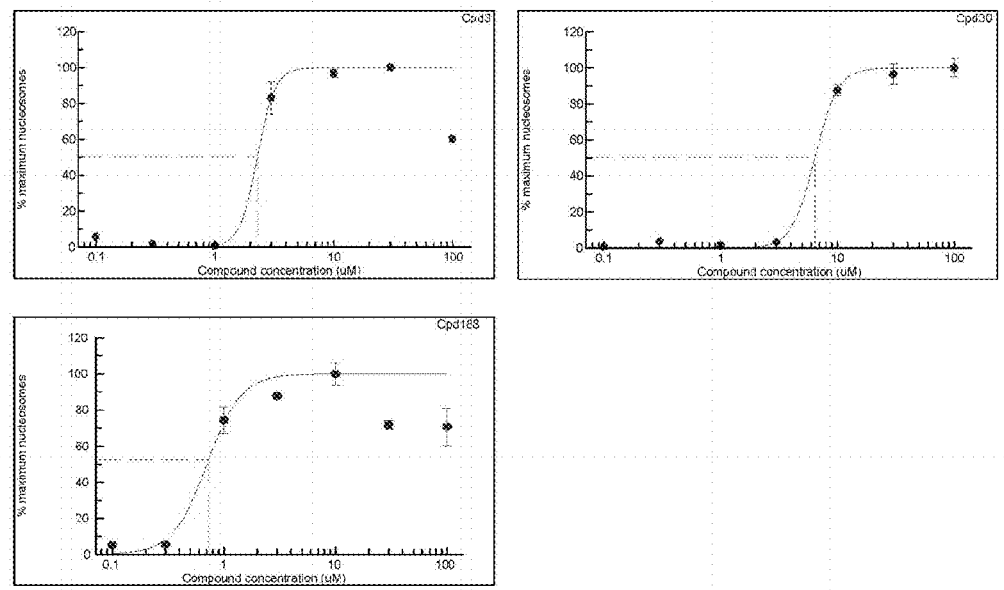
FIG. 9 demonstrates apoptosis induction of breast cancer cell lines by compounds; selective apoptosis of cell lines that are Stat3 dependent. MDA-MB-468 (panel A), MDA-MB-231 (panel B), MDA-MB-435 (panel C), MCF7 (panel D) and MDA-MB-453 (panel E) were seeded in 12-well plates, grown overnight then treated with the indicated compound for 24 hr. Cells were centrifuged and the supernatants assayed for nucleosome levels by ELISA. The percent maximum nucleosome level was calculated (nucleosome level÷maximum nucleosome level achieved in the assay× 100) and plotted as a function of the log compound concentration and the best-fitting curve generated using 4-Parameter Logistic Model/Dose Response One Site/XLfit 4.2, IDBS software. This curve was used to calculate the $EC_{50}$.
Figure 9:
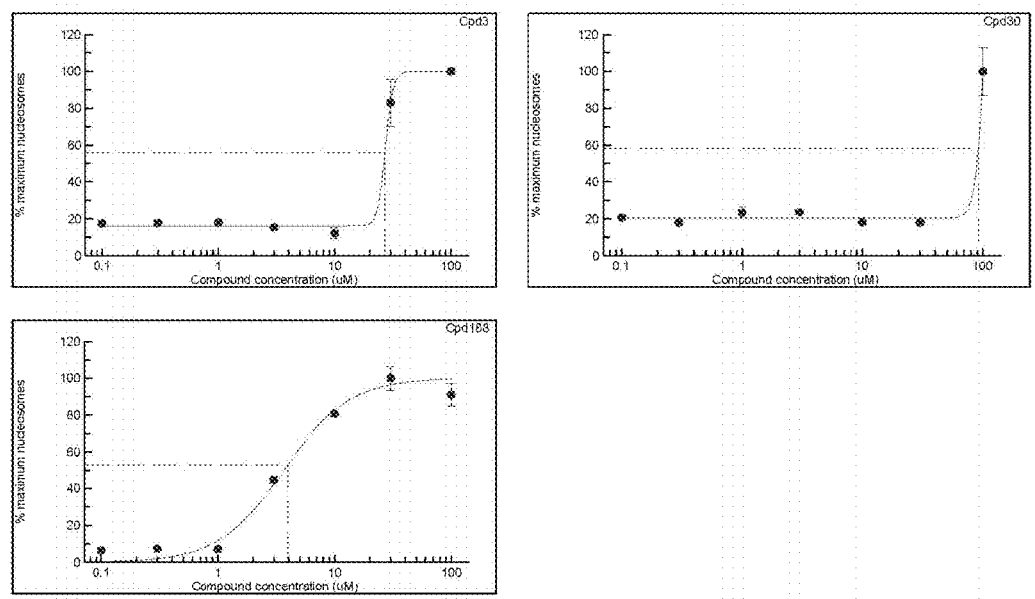
Figure 9:
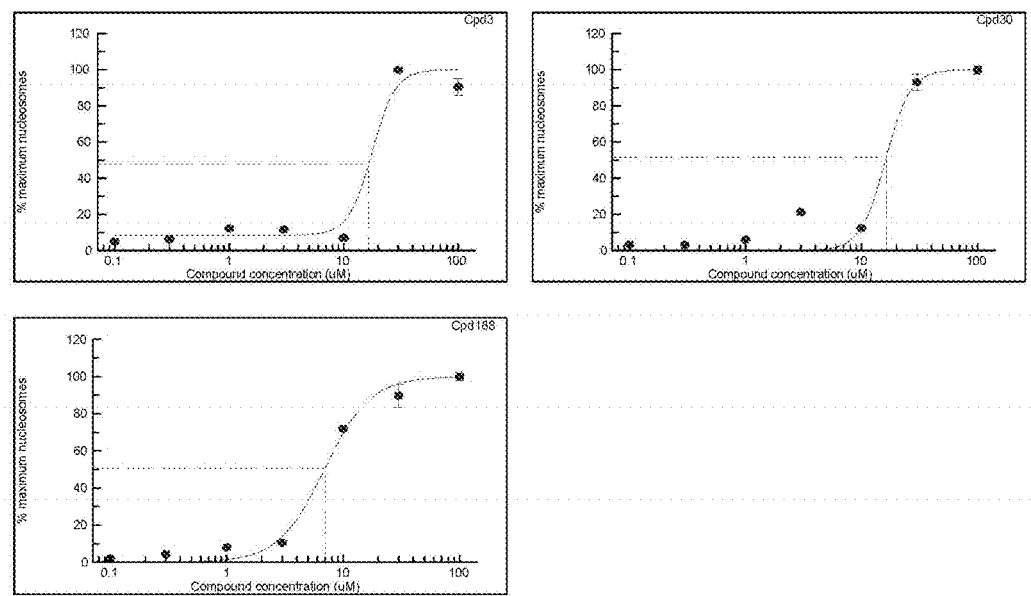
Figure 9:
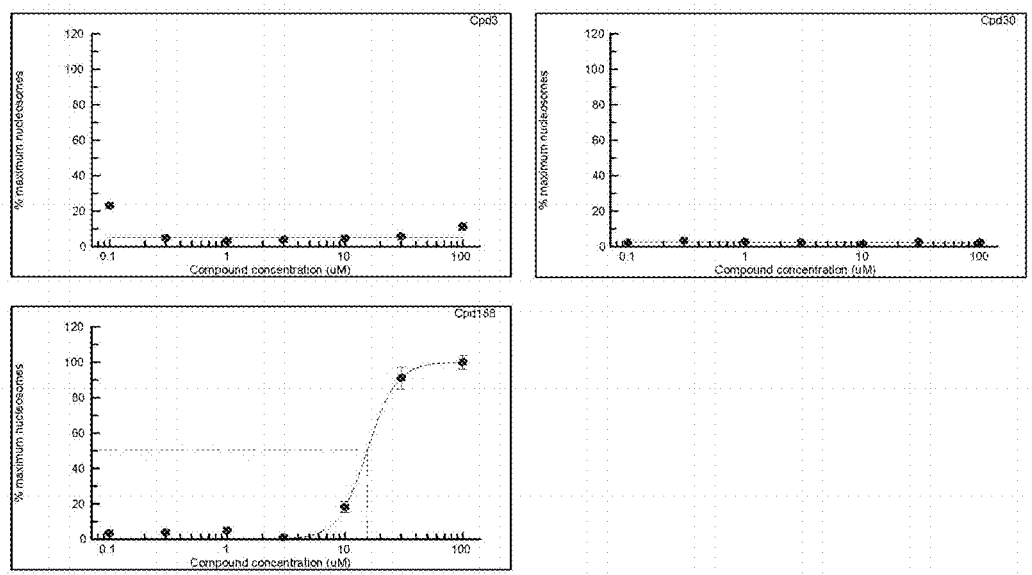
Figure 9:
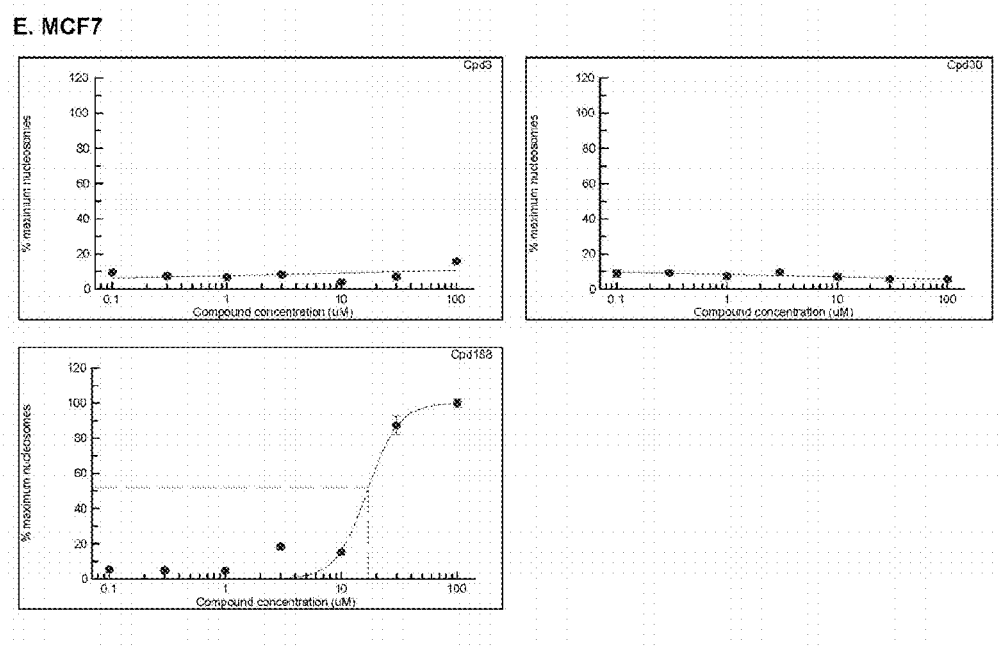
Figure 10:
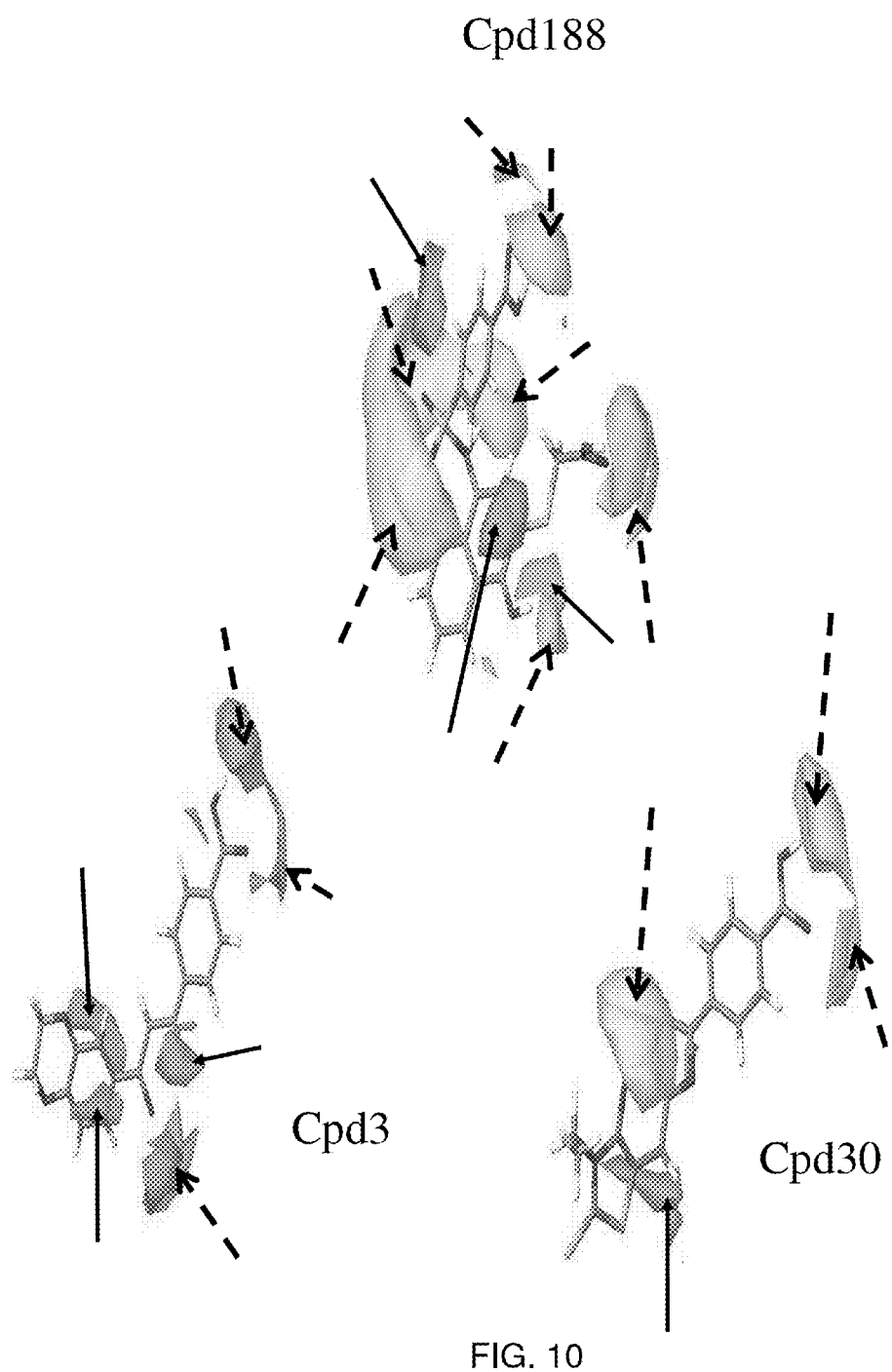
FIG. 10 shows Cpd3, Cpd30 and Cpd188 and the hydrophobicity or hydrophilicity of the surface of the molecule. The dashed arrows point to hydrophilic surfaces, and the solid arrows point to hydrophobic surfaces.
Figure 11:
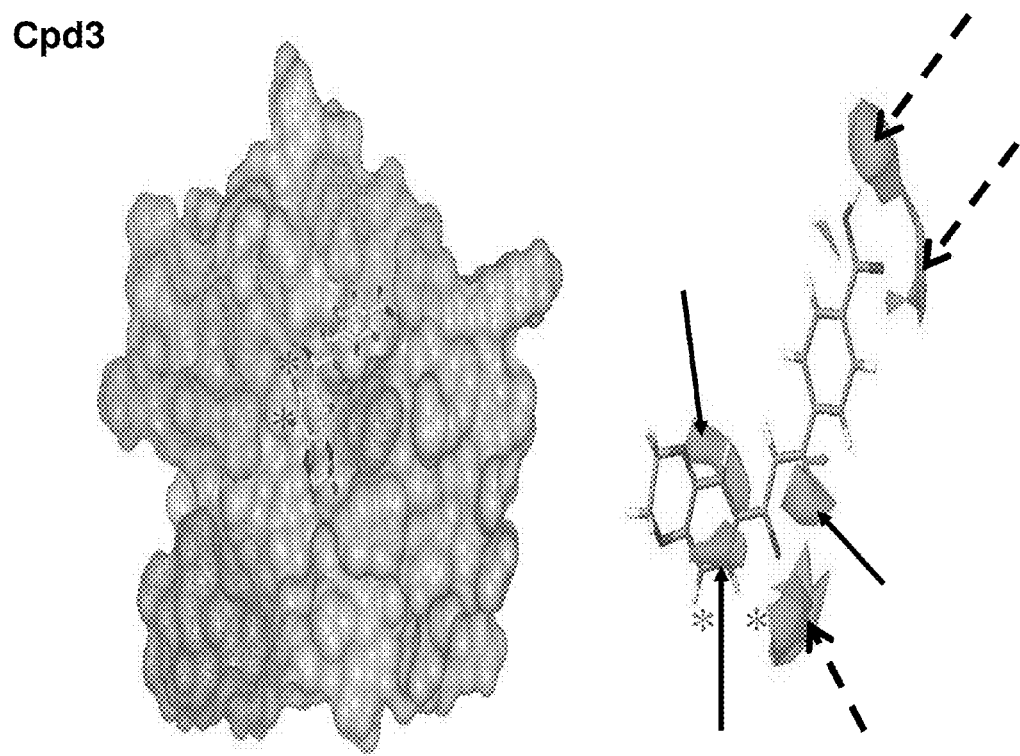
FIG. 11 illustrates exemplary compound 3 (Cpd3). The top-left picture of FIG. 11 shows Cpd3 docked into Stat3 and the interaction between Cpd3 and the surface of the protein and derivatives of Cpd3 that can fit into the surface of the protein. Stars represent atoms and chemical groups that can be replaced with other atoms or chemical groups to create one or more functional derivatives. The hydrophobic/hydrophilic surfaces of Cpd3 are also demonstrated on the top-right picture. The dashed arrows point to hydrophilic surfaces, and the solid arrows point to hydrophobic surfaces. $R_1$ and $R_2$ could be identical or different and may comprise hydrogen, carbon, sulfur, nitrogen, oxygen, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, or benzoic acid-based derivatives.
Figure 11:
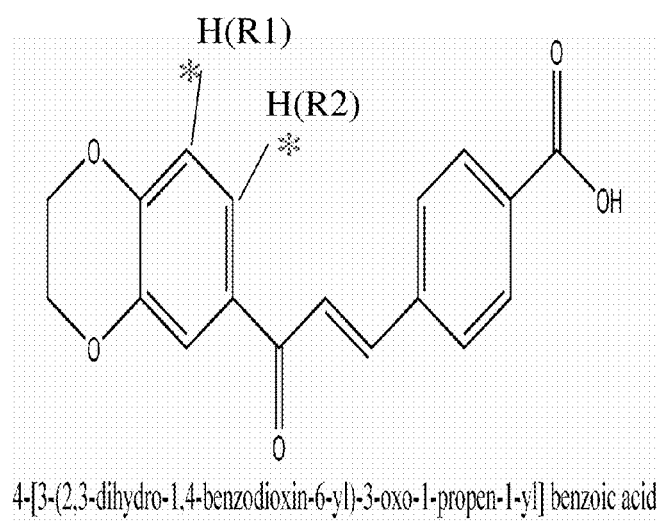
Figure 12:
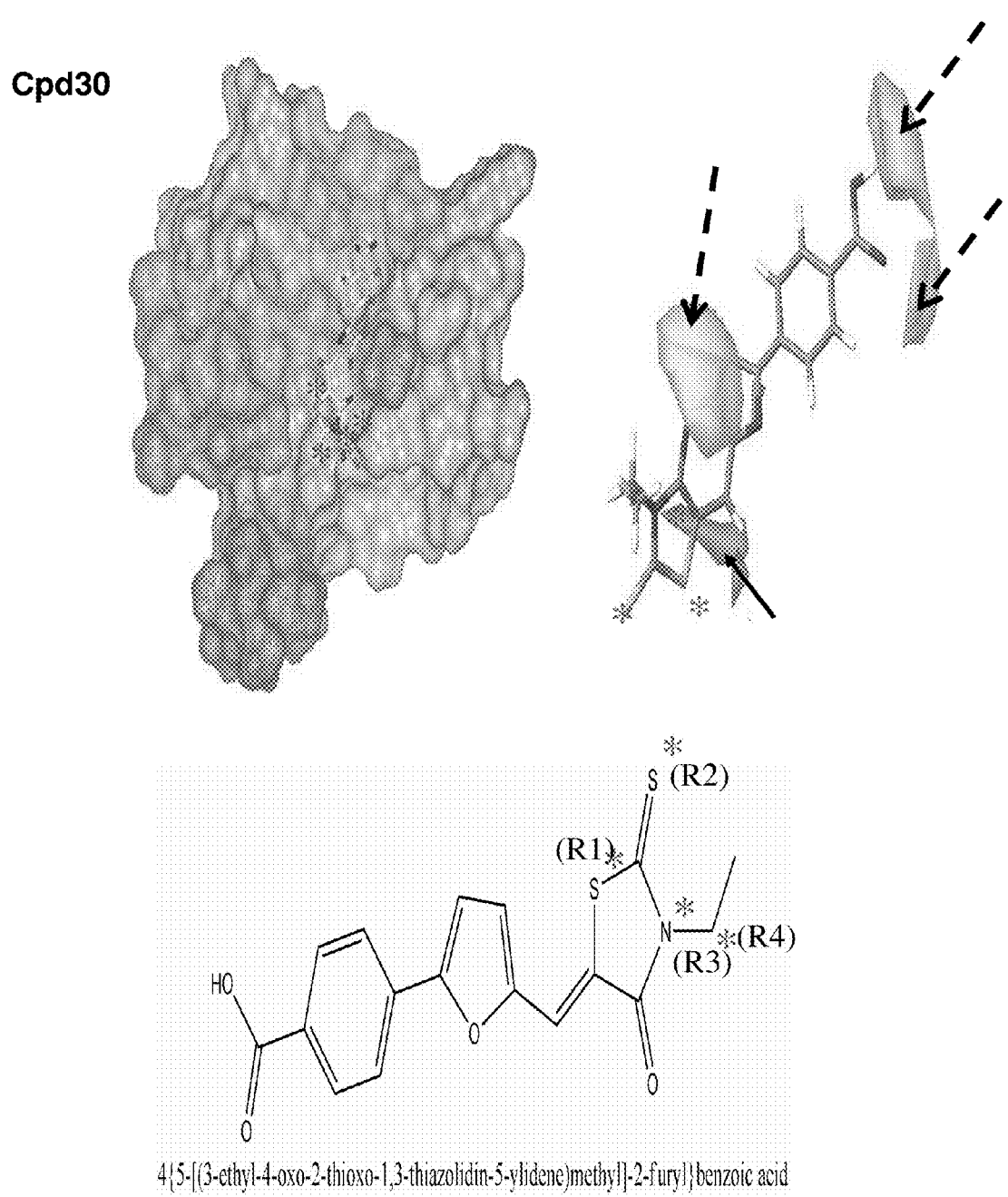
FIG. 12 illustrates exemplary compound 30 (Cpd30). The top-left picture of FIG. 12 shows Cpd30 docked into Stat3 and the interaction between Cpd30 and the surface of the protein, and derivatives of Cpd30 that fit into the surface of the protein. Stars represent atoms and chemical groups that can be replaced with other atoms or chemical groups to create one or more functional derivatives. The hydrophobic/hydrophilic surfaces of Cpd30 are also demonstrated on the top-right picture. The dashed arrows point to hydrophilic surfaces, and the solid arrows point to hydrophobic surfaces. 2-D structure of Cpd30 shown on the bottom picture, $R_1$, $R_2$ $R_3$ and $R_4$ could identical or different and may comprise be hydrogen, carbon, sulfur, nitrogen, oxygen, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, aor benzoic acid-based derivatives.
Figure 13:
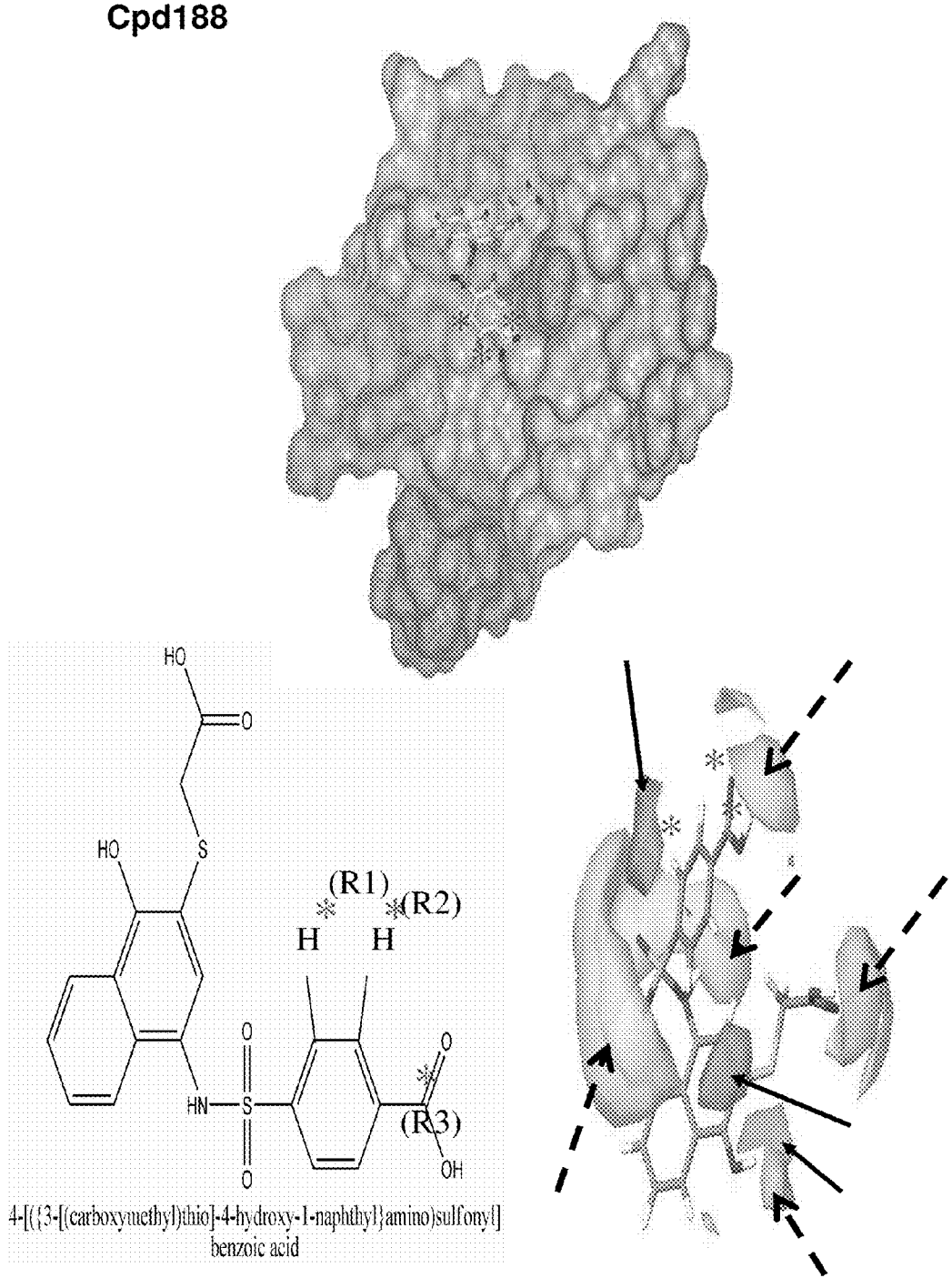
FIG. 13 illustrates exemplary compound 188 (Cpd188). The top picture of FIG. 13 shows Cpd188 docked into Stat3 SH2 domain and the interaction between Cpd188 and the surface of the protein, and derivatives of Cpd188 that fit into the surface of the protein. Stars represent atoms and chemical groups that can be replaced with other atoms or chemical groups to create one or more functional derivative. The hydrophobic/hydrophilic surfaces of Cpd188 are also demonstrated on the left picture on the bottom. The dashed arrows point to hydrophilic surfaces, and the solid arrows point to hydrophobic surfaces. Shown on the right bottom picture, $R_1$ and $R_2$ could be identical or different and may comprise hydrogen, carbon, sulfur, nitrogen, oxygen, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, or benzoic acid-based derivatives.

In contrast, neither compound induced apoptosis of cell lines MDA-MB-453 and MCF7 that do not demonstrate constitutive Stat3 activity in concentrations up to 300 μM (FIGS. 9D and E and Table 5). Cpd188 was even more effective at inducing apoptosis of cell lines with constitutive Stat3 activity (FIGS. 9A, B and C) demonstrating EC50 values in the 0.7 to 7 μM range (Table 2). Unlike Cpd3 and Cpd30, however, Cpd188 also had detectable activity against MDA-MB-453 and MCF7 (FIGS. 9D and E), demonstrating EC50 values of 17.2 and 15.5 μM, respectively. However, similar to Cpd 3 and Cpd30, Cpd188 showed preferential activity against cell lines with constitutive Stat3 activity (Table 5). In contrast to Cpd3, Cpd30 and Cpd188, neither Cpd3-2 nor Cpd3-7 induced apoptosis of any of the breast cancer cell lines tested.

Example 8

Significance of Certain Embodiments of the Present Invention

To develop chemical probes that selectively target Stat3, the inventors virtually screened 920,000 small drug-liked compounds by docking each into the pY-peptide-binding pocket of the Stat3 SH2 domain, which consisted of three sites—the pY binding site, the +3 residue binding site and a hydrophobic binding site. Three compounds satisfied criteria of interaction analysis, inhibited recombinant Stat3 binding to its immobilized pY-peptide ligand and inhibited IL-6-mediated tyrosine phosphorylation of Stat3. These compounds were used in a similarity screen of 2.47 million compounds, which identified 3 more active compounds. Examination of the 6 positive compounds for the ability to inhibit IFN-γ-mediated Stat1 phosphorylation revealed that 5 of 6 were selective for Stat3 vs. Stat1. Sequence and structural analysis of the SH2 domains of Stat3 and Stat1 revealed that the ability of the compound to interact with the hydrophobic binding site was the basis for selectivity. All 5 selective compounds inhibited nuclear-to-cytoplasmic translocation of Stat3, while 3 of 5 preferentially induced apoptosis of breast cancer cell lines with constitutive Stat3 activation with one (Cpd188) active in the sub-micromolar range. Thus, virtual ligand screening of compound libraries targeting the pY-peptide binding pocket of the Stat3 SH2 domain identified for the first time 3 lead compounds that competitively inhibit Stat3 SH2 domain binding to its pY-peptide ligand, selectively target Stat3 vs. Stat1 and induce apoptosis preferentially of breast cancer cells lines with constitutively activated Stat3.

Several molecules have been identified recently that target Stat3 (Bhasin et al., 207; Jing et al., 2004; Coleman et al., 2005; Song et al., 2005; Schust et al., 2006; Siddiquee et al., 2007). Fluorescence polarization studies indicated that a peptidomimetic, hydrocinnamoyl-Tyr(PO3H2)-Leu-cis-3,4-methanoPro-Gln-NHB, was a potent inhibitor of Stat3 binding to pY-peptide binding with an $IC_{50}$ of 125 nM (Coleman et al., 2005). Results of its ability to inhibit Stat3 phosphorylation or nuclear translocation within cells has not been reported reflecting, perhaps, the general obstacle of cell permeability posed by the peptidomimetic class of drugs.

The G-rich, quartet-forming oligodeoxynucleotide, T40214, was identified as a Stat3 inhibitor through docking studies of T40214 onto the known structure of Stat3 (Jing et al., 2003). T40214 targeted Stat3 tail-to-tail homodimers, decreased Stat3 binding to DNA and inhibited growth of prostate, breast and lung cancer cells in the nude mouse xenograft model through induction of apoptosis (Jing et al., 2003; Jing et al., 2004; Jing and Tweardy 2005; Jing et al., 2006; Zhu and Jing 2007). T40214 is administered IV or intraperitoneally in a complex with polyethyleneimine, which greatly improves intracellular uptake. To complement these efforts and develop a different class of Stat3 inhibitor for use in cancer treatment with the potential for oral administration, we determined if recent information obtained regarding the structural requirements of Stat3 SH2/pY-peptide binding (Shao et al., 2004; Shao et al., 2006) could be exploited to develop a small molecular inhibitor of Stat3.

Others groups have taken a small-molecule approach to targeting Stat3 with some success. STA-21 is a small molecule inhibitor of Stat3 identified through virtual ligand screening of compounds that bound to the interface of Stat3 SH2 homodimers (Song et al., 2005). STA-21 treatment of cells disrupted Stat3/DNA complexes, abrogated Stat3 translocation into the nucleus, inhibited expression of proteins such as Bcl-XL and Cyclin D1 and induced the apoptosis of breast cancer cell lines. No evidence was provided that STA-21 bound directly to Stat3 reflecting, perhaps, the non-availability of suitable reagents i.e. purified Stat3 homodimers. More recently, a model of STA-21 interaction with the Stat3 SH2 pY-peptide binding pocket has been proposed, which featured the 1-oxygen of STA-21 binding to the side chain ammonium hydrogen of Arg609 within the pY-residue binding site. Chemical modification of STA-21 was undertaken with the goal to generate compounds with improved interaction at this site. They synthesized 4 compounds the most potent of which demonstrated activity similar to STA-21 with an $EC_{50}$ for apoptosis induction of three Stat3-dependent prostate cancer cell lines with constitutive Stat3 activity of from 13.4 to 34.1 µM (Bhasin et al., 207).

Schust (Schust et al., 2006) identified another small molecule inhibitor of Stat3, Stattic, using a fluorescence polarization high throughput assay of Stat3 binding. This group screened 17,298 chemical compounds and identified 144 compounds with significant activity in this assay. The most active compound, Stattic, inhibited Stat3 binding to a cognate pY-peptide ligand, inhibited ligand-mediated Stat3 phosphorylation and nuclear translocation, reduced Stat3 binding to DNA and induced apoptosis of breast cancer cells with constitutively activated Stat3 in the 5-20 µM range. Similar to the compounds identified herein, inhibition of ligand-induced phosphorylation was selective for Stat3 vs. Stat1. Unlike the compounds herein, however, inhibition of Stat3 by Stattic was blocked by the presence of a reducing agent (DTT), was not reversible and may not be mediated by direct inhibition of pY-peptide binding. Rather, Stattic may alter the Stat3 SH2 pYpeptide binding site shape through alkylating the Cys687 residue on the opposite side of the SH2 domain (McMurray 2006).

Siddiquee et al., (Siddiquee et al., 2007) recently identified a small molecule Stat3 inhibitor, S31-201, using an approach similar to that described herein targeting the Stat3 SH2 pY-peptide binding site. S31-201 inhibited Stat3 homodimerization, DNA binding, induction of cyclin D1, Bcl-xL and survivin and induced apoptosis of v-Src-transformed NIH3T3 cells and breast cancer cell lines with constitutive active Stat3 in the 30 to 100 µM range. Similar to T40214, S31-201 (5 mg/kg every 2-3 days) inhibited growth of nude mice xenografts of one of these breast cancer cell lines (MDA-MB-231). Similar to STA-21, and unlike the compounds herein, no evidence of the ability of S3I-201 to directly bind Stat3 or to inhibit the binding of Stat3 to its pY-peptide ligand was presented leaving open the question of the precise mechanism of action of S3I-201.

The use of molecular modeling to delineate the structural basis for competitive inhibition of Stat3 SH2/pY-peptide binding by the compounds described herein identified the hydrophobic binding site as a selectivity filter. It also provides a rational basis for modification of the three lead compounds to identify related ones with greater potency; these studies are underway. In addition, the strategy employed here can be employed to developed selective chemical probes for other members of the STAT protein family. In addition to Stat3 and Stat1, structural information currently is available for Stat5A (Neculai et al., 2005). Overlay of the SH2 domains of Stat5A and Stat1 and Stat5A and Stat3 revealed differences within the pY-peptide binding site of Stat5A and both Stat1 and Stat3. In certain embodiments, VLS screening is employed to exploit these differences to identify selective chemical probes of Stat5 for use in chemical genomic studies and as potential therapy for cancers in which Stat5 contributes to oncogenesis.

Example 9

Overview of Targeting Cancer Stem Cells with STAT3 Inhibitors

In certain embodiments of the invention, there is development of potent and selective probes for interrogating the function of Stat3 in stem cells. In specific embodiments, Stat3 is dispensable for the function of normal hematopoietic stem/progenitor cells but not for cancer stem cells, in particular, leukemic stem cells, for example. In particular embodiments of the invention, unique probes spare normal hematopoietic stem cells while targeting leukemic stem cells, as well as other cancer stem cells.

Stem Cell Hypothesis.

The hypothesis that a minor population of cells is able to give rise to all mature parenchymal cell types within an organ system gained experimental support in the 1960's from in vitro colony-forming assays and the demonstration that bone marrow transplantation could reconstitute the hematopoietic system of lethally irradiated mice. The stem cell hypothesis became established clinically in the 1970's and 80's through the successful performance of bone marrow transplantation and was extended during the 1990's to include all organ systems thereby becoming one of the central tenets of regenerative medicine. More recently, the stem cell hypothesis has emerged within the cancer field. Current opinion holds that curative therapies for many refractory cancers will almost certainly require the successful targeting of cancer stem cells.

The ability to chemically probe both normal and cancer stem cells is essential to understanding and controlling their function to treat individuals with deficiencies in mature cell number or function or to treat or cure patients with cancer. In particular, curing cancer will require development of drugs that target cancer stem cells while sparing normal stem cells in at least certain aspects.

Stat3 and Stem Cells.

Evidence is accumulating that Stat3 is required for maintenance of some normal stem cells, e.g. embryonic stem cells, and many types of malignant stem cells including stems cells of acute myeloid leukemia (AML) and breast cancer, for example. Full understanding of the role of Stat3 in stem cell biology has been stymied by the finding that whole-animal Stat3 knockout mice are embryonic lethal at 6.5-to-7 days (Takeda et al., 1997). In addition, the results of tissue-specific knockout studies often have yielded contradictory and confusing results (Levy and Lee, 2002). Specific and highly active Stat3 chemical probes greatly clarify the understanding of the role of Stat3 in stem cells and provide tools for specifically interrogating Stat3 function in cancer stem cells.

In certain embodiments of the invention, the methods and compositions are useful in regenerative medicine, oncology, asthma, and chronic viral infections, for example. Asthma and chronic viral infections, for example, are two disease processes in which Stat3 plays a critical role.

Focus on Normal and Leukemic Myeloid Stem Cells, for Example.

In certain aspects of the invention, agents targeting cancer stem cells spare normal hematopoietic stem cells because otherwise their use would have lethal hematological and immune consequences. AML is among the top 10 most common cancers. Despite substantial advances in its treatment, 5-yr mortality exceeds 50%. Successful cure of AML, as well as other refractory cancers, will involve eliminating the leukemia stem while sparing normal stem cells within the bone marrow. Current cytoreductive therapies for AML and other cancers target cycling cells. The hematopoietic system is able to reconstitute itself after cytoreductive therapy because hematopoietic stem cells are not cycling. Like normal stem cells, cancer stem cells are quiescent and not cycling. New therapeutic regimens for cancer include agents that target non-cycling cancer stem cells, in certain aspects. However, in particular embodiments agents that target cancer stems cells spare normal hematopoietic stem cells to permit reconstitution of this organ system.

While Stat3 is essential for embryonic stem cell maintenance (Raz et al., 1999), deletion of Stat3 within the hematopoietic lineage including hematopoietic stem cells of normal mice does not result in impaired blood cell production. In fact, circulating cells within the granulocyte lineage are increased in these mice (Lee et al., 2002). In contrast to having no role, if any, in normal resting hematopoiesis, Stat3 is activated in up to 95% of leukemic blast samples and may be critical for survival of these cells (Spiekermann et al., 2001). In certain aspects, this is true of leukemic stem cells whereas in other aspects Stat3 activation within these cells is critical for their survival. In the present invention, high-affinity and selective chemical probes for Stat3 that are used to determine if Stat3 is critical for leukemic stem cell survival and if Stat3 can be targeted in hematopoietic stem/progenitor cells without deleterious effects.

Acute leukemia in humans arises from blood cell progenitors within the myeloid or lymphoid pathway. The most striking finding in acute leukemia is nonrandom, somatically acquired chromosomal translocations in up to 60% of the acute leukemia patients. These chromosomal translocations abnormally activate transcription factor genes in acute myeloid leukemia (AML) and acute lymphoblastic leukemia (ALL) and show remarkable specificity for hematopoietic cells blocked in defined stages of blood cell differentiation. AML comprises a heterogeneous group of acute leukemias derived from malignantly transformed myeloid precursors. Recently, the WHO classified AML with recurrent chromosomal translocations (60% of all AML) into four main categories, i) acute promyelocytic leukemia (APL) with t(15;17) (resulting in the PML-RARα fusion gene) and variants, ii) AML with t(8;21) (resulting in the AML1-ETO fusion gene), iii) AML-M4 with abnormal bone marrow eosinophils and inv(16) (resulting in the CBFβ-MYH11 fusion gene), and iv) AML with 11q23 (MLL fusion gene, such as MLL-AF9) abnormalities, which are characterized by distinct biological and prognostic features.

Acute promyelocytic leukemia (APL) is a distinct subtype of acute myeloid leukemia (AML) that comprises about 10% of cases of AML. In APL, fusion of the retinoic acid receptor-alpha (RARα) with the gene coding for PML protein, the PML-RARα t(15:17) translocation, is required for blocking myeloid cell differentiation. Retinoic acids, which are used to treat this cancer, bind to the retinoic acid receptor (RARα) component of the fusion product, resulting in degradation of the fusion protein by ubiquitinization (Melnick and Licht, 1999). However, relapses are frequent and are usually resistant to re-treatment with retinoic acid.

The chromosomal translocation t(8;21) is found in 15-20% of AML cases. Among the non-random chromosomal aberrations observed in AML, t(8;21) is the most common chromosomal translocation known in human leukemia and usually correlates with the AML M2-subtype of the French-American-British classification, with well-defined and specific morphological features. The translocation between chromosomes 8 and 21 is considered a cytogenetic hallmark of the M2-subtype of acute myeloid leukemia. AML1 is normally expressed in hematopoietic cells and belongs to a family of transcription factors that is defined by the runt homology domain (RHD), a DNA-binding motif. AML1 is a sequence-specific DNA-binding protein that complexes with core binding factor β (CBFβ) to activate transcription of target genes. CBFβ does not bind DNA itself, but instead increases the DNA affinity of AML1. CBFβ is commonly involved in a different translocation that involves the inversion of chromosome 16, which produces a CBFβ-SMMHC fusion gene.

To assess the impact of RARα- and AML1-containing fusion oncoproteins on primary bone marrow cells, Dr. Dong and his colleagues performed retroviral transduction and transformation assays (RTTAs) using these fusion proteins (Zeisig et al., 2007; Kwok et al., 2006; Kwok et al., 2009). These studies of primary hematopoietic cells using RTTA revealed the impact of these fusion proteins in promoting leukemic stem cell self-renewal and provided a physiologically relevant system to study the transformational properties of these fusion proteins. In the present invention the inventors expand the use the RTTA into a platform for drug discovery, in particular, to identify Stat3 chemical probes that selectively target and kill AML stem cells, for example, generated by these fusion proteins while sparing normal hematopoietic stem cells.

Example 10

Exemplary Approach for STAT3 Inhibitors for Cancer Stem Cells

In the field of Stat3 probe development the inventors have focused on small molecule Stat3 probes (Xu et al., 2009), and several features of the small molecule program are useful, including: 1) a clearly defined mode of action of these probes: they target the Stat3 Src-homology (SH) 2 domain that is involved in 2 steps in the Stat3 activation pathway; 2) their specificity of action; and 3) the potential for using lead probes identified so far to identify probes with 2-to-3 logs greater activity based on recent and exemplary SAR analysis and medicinal chemistry considerations outlined below.

In specific embodiments, compound affinity is improved upon gaining a log greater affinity upon moving from $1^{st}$ generation to 2nd generation probes using 3-D pharmacophore analysis. In addition, selectivity is improved through modeling embodiments, in particular through identification of a distinct hydrophobic binding domain in the phosphopeptide binding pocket of Stat3 SH2 vs. the Stat1 SH2 (Xu et al., 2009).

Identification of 1st Generation Stat3 Chemical Probes.

To develop chemical probes that selectively target Stat3, the inventors virtually screened 920,000 small drug-like compounds by docking each into the peptide-binding pocket of the Stat3 SH2 domain, which consists of three sites—the pY-residue binding site, the +3 residue-binding site and a hydrophobic binding site, which served as a selectivity filter (Xu et al., 2009). Three compounds (Cpd3, Cpd30 and Cpd188) satisfied criteria of interaction analysis, competitively inhibited recombinant Stat3 binding to its immobilized pY-peptide ligand and inhibited IL-6-mediated tyrosine phosphorylation of Stat3. These compounds were used in a similarity screen of 2.47 million compounds, which identified 3 more compounds (Cpd3-2, Cpd3-7 and Cpd30-12) with similar activities. Examinations of the 6 active compounds for the ability to inhibit IFN-γ-mediated Stat1 phosphorylation revealed that all but Cpd30-12 were selective for Stat3.

Molecular modeling of the SH2 domains of Stat3 and Stat1 bound to compound revealed that compound interaction with the hydrophobic binding site was the basis for selectivity. All 5 selective compounds inhibited nuclear-tocytoplasmic translocation of Stat3, while 3 of 5 compounds (Cpd3, Cpd30 and Cpd188) induced apoptosis preferentially of exemplary breast cancer cell lines with constitutive Stat3 activation.

Identification of 2nd Generation Stat3 Chemical Probes.

Figure 15:
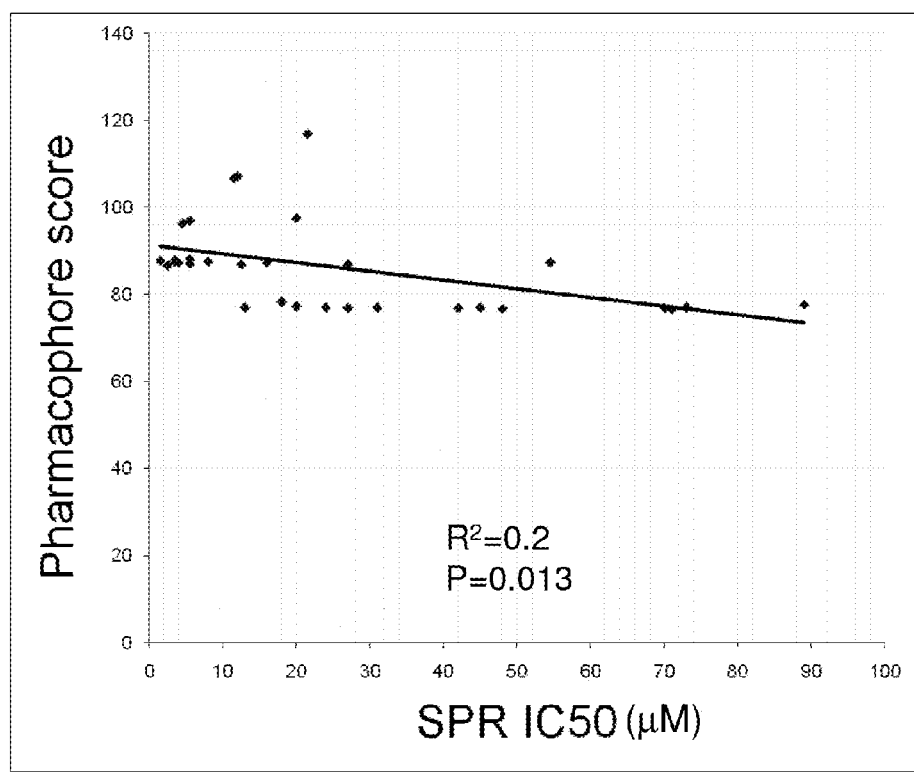
FIG. 15 demonstrates that SPR $IC_{50}$ of 2nd generation Stat3 chemical probes is inversely correlated with 3-D pharmacophore score.
Figure 16:
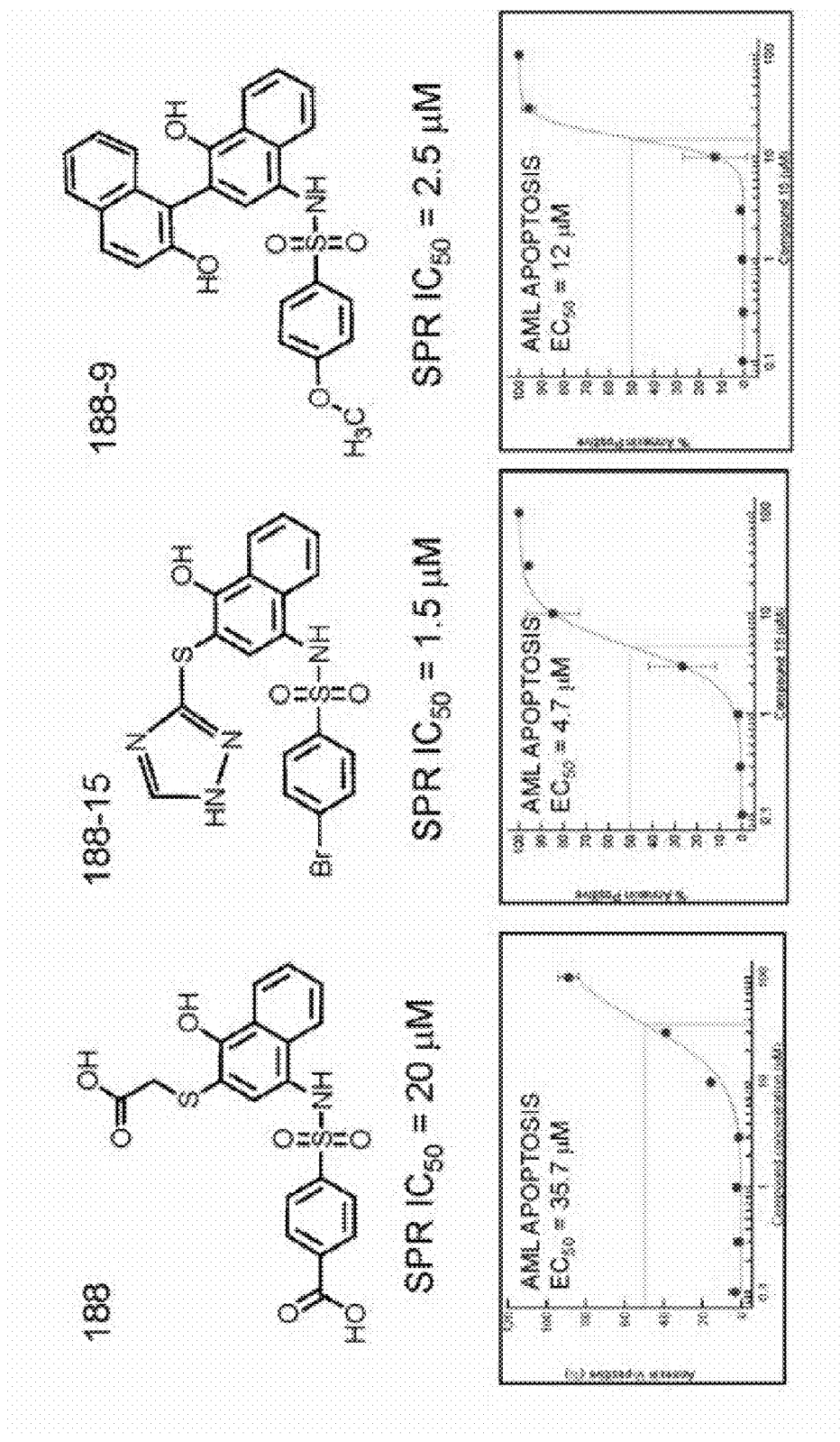
FIG. 16. shows SPR $IC_{50}$ and AML apoptosis $EC_{50}$ of parent Cpd188 and two 2nd generation 188-like Stat3 chemical probes.

The similarity screening described above did not yield any hits using Cpd188, the most active of the 3 lead compounds, as the query compound. Consequently, the inventors repeated 2-D similarity screening using the scaffold of Cpd188 as the query structure and the Life Chemicals library, which yielded 207 hits. 3-D pharmacophore analysis was performed on these 207 compounds using Ligand Scout and the top 39 scoring compounds were purchased and tested for inhibition of Stat3 binding to its phosphopeptide ligand by SPR. All but six of these 39 compounds have measurable SPR IC50s, with 19 having IC50 values equal to or less than the parent compound and 2 (Cpd188-9 and Cpd188-15) having IC50 values one log lower. Examination of these 19 compounds has revealed a statistically significant correlation between 3-D pharmacophore scores and SPR IC50s and as well as 3-D pharmacophore score and IC50s for inhibition of ligand-mediated cytoplasmic-to-nuclear translocation (FIG. 15 and data not shown). In addition, both Cpd188-9 and Cpd188-15 exhibited a log greater activity in inducing human leukemic cell line apoptosis than the parent Cpd188 (FIG. 16). In addition, Cpd188-38 exhibited a 2 logs greater activity than parent Cpd188 in inhibiting cytoplasmic-to-nuclear translocation in HTFM assay, while Cpd188-15 exhibited a 1 log greater activity than parent Cpd188 in decreasing MSFE (Table 6). Furthermore, several of the second-generation 188-like compounds represent a substantial improvement over Cpd188 from a medicinal chemistry, metabolism and bioavailability standpoint. In particular, Cpd188-9 lacked both carboxyl groups, which in particular cases improves cell permeability and/or the thioether group, which is subject to oxidation. $R^2=0.2$ $P=0.013$ ($\mu M$)

TABLE 6

Summary of Certain 2$^{nd}$ Generation 188-like Compounds

| Compound | SPR IC$_{50}$, $\mu M$* | HTFM IC$_{50}$, $\mu M$* | Mammosphere ~IC$_{50}$, $\mu M$*** |
|---|---|---|---|
| 188 | 20** | 32 ± 4 | 30-100 |
| 188-1 | 6 ± 2 | 26 ± 4 | 30 |
| 188-9 | 3 ± 2 | 47 ± 21 | 10 |
| 188-10 | 8 ± 3 | 22 ± 19 | 30 |
| 188-15 | 2 ± 1 | 49 | 3 |
| 188-16 | 4 ± 0 | 9 ± 5 | 30 |
| 188-17 | 4 ± 2 | 76 | 30 |
| 188-18 | 4 ± 1 | 27 ± 8 | 30 |
| 188-38 | 19 ± 9 | 0.4 ± 0.1 | 10-30 |

*mean ± SD
**Xu et al PLoS ONE
***SUM159PT and HS578T cells plated (6 wells per test) without or with compound at 1, 10 or 100 μM, incubated 3 d; spheres counted on day 3.

Structure-Activity Relationship (SAR) Analysis of 2nd Generation Stat3 Probes.

Figure 17:
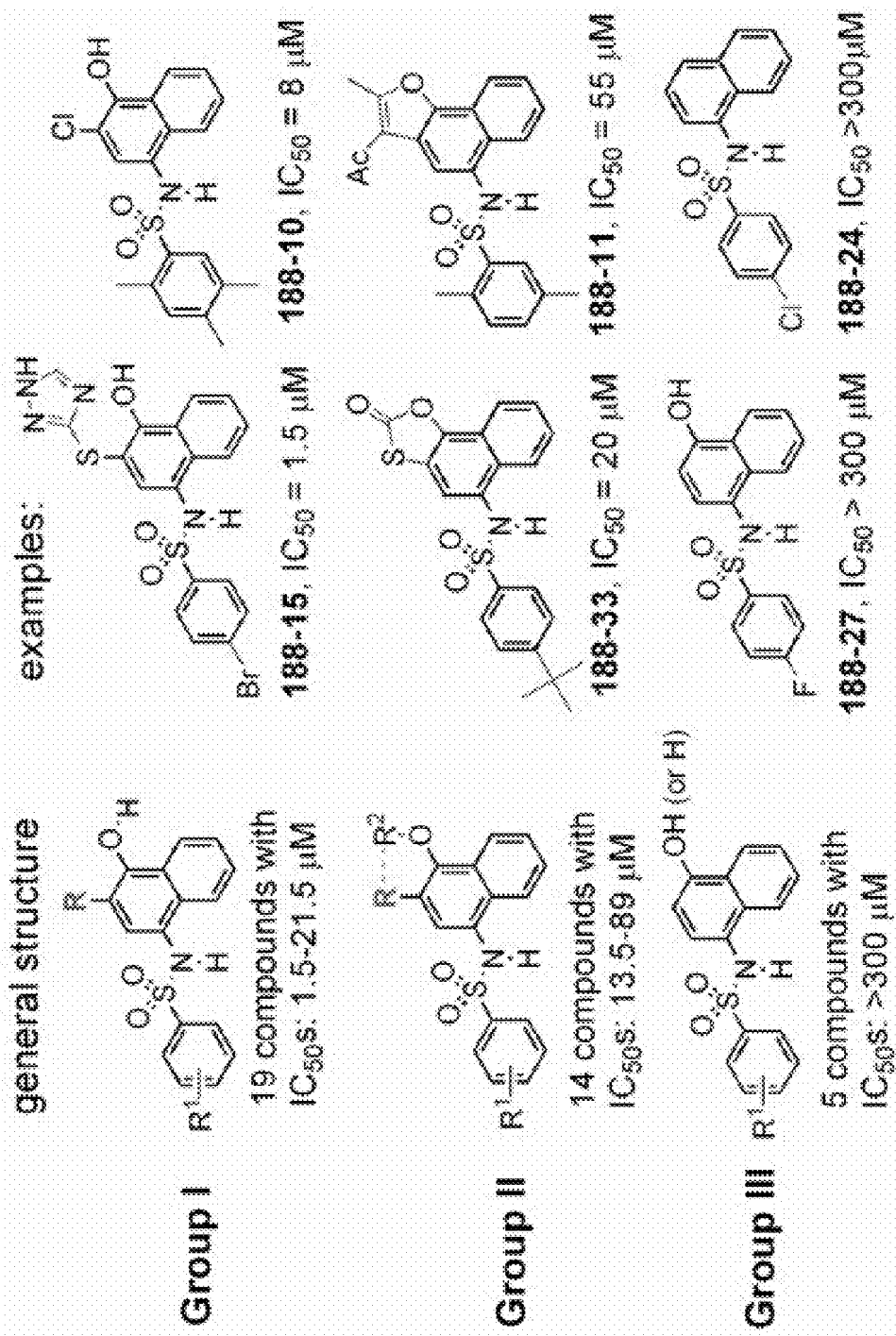
FIG. 17 provides an illustration of structure-activity relationships of 38 Cpd188-like, 2nd generation Stat3 probes wherein R is selected from the group consisting of hydrogen, phenylsulfanyl, 2-Hydroxy-naphthalen-1-yl, quinolin-8-yl-sulfanyl, triazol-3-yl sulfanyl, benzothiazol-2-ylsulfanyl, chloro, fluoro, and bromo; wherein $R^1$ is selected from the group consisting of hydrogen, methyl, chloro, bromo, ethyl, methoxy, ethoxy, tert-Butyl, nitro, methyl ester, acetamide, 1,4 dioxine, fluoro, trifluoro methoxy, acetyl, trifluoro methyl, propyl, cyclohexene, methoxy-phenoxy, chloro phenoxy, tolyloxy, and phenoxy; and wherein $R^2$ is selected from the group consisting of C=O and C—$CH_3$.

All of the 39 second generation compounds described above, plus Cpd188 itself, are derivatives of N-naphth-1-yl benzenesulfamide. Upon careful analysis of their structure-activity relationships (SAR), the inventors found that most of these Cpd188-like compounds (38 out of 40: the rest of 2 are weak and will be described below in EXP ID) can be divided into three structural groups in a general trend of decreased activity, as shown in FIG. 17. Five compounds in Group III are actually the parents of compounds in Groups I and II. Addition of a variety of groups (the —R group highlighted in red in the general structure of Group I in FIG. 17), such as a triazole-3-yl-mercapto (188-15) or a chloro (188-10) group, to the 3-position of the naphthylamine ring led to the Group I compounds, which are the most potent series of Stat3 probes. In a specific embodiment, this is the most important contributor to the inhibitory activity: a total of eight 3-substituents are found in Group I compounds, which invariably enhance the activity by several orders of magnitude.

Most Stat3 probes in Group II contain a 5-membered ring that combines the 3-R and 4-OR2 groups, such as a furan (188-11). However, the compounds in this group are, in average, ~5× less active than the Group I compounds, which indicates that in certain aspects the H atom of the 4-hydroxy group (highlighted in blue in the general structure of Group I in FIG. 17) is important, e.g., involved in a favorable H-bond with the protein. Lacking the ability to form the H-bond attributes to the weaker activities of Group II probes, in particular cases. These considerations underlie the medicinal chemistry approach outlined in Example 11.

Example 11

Figure 18:
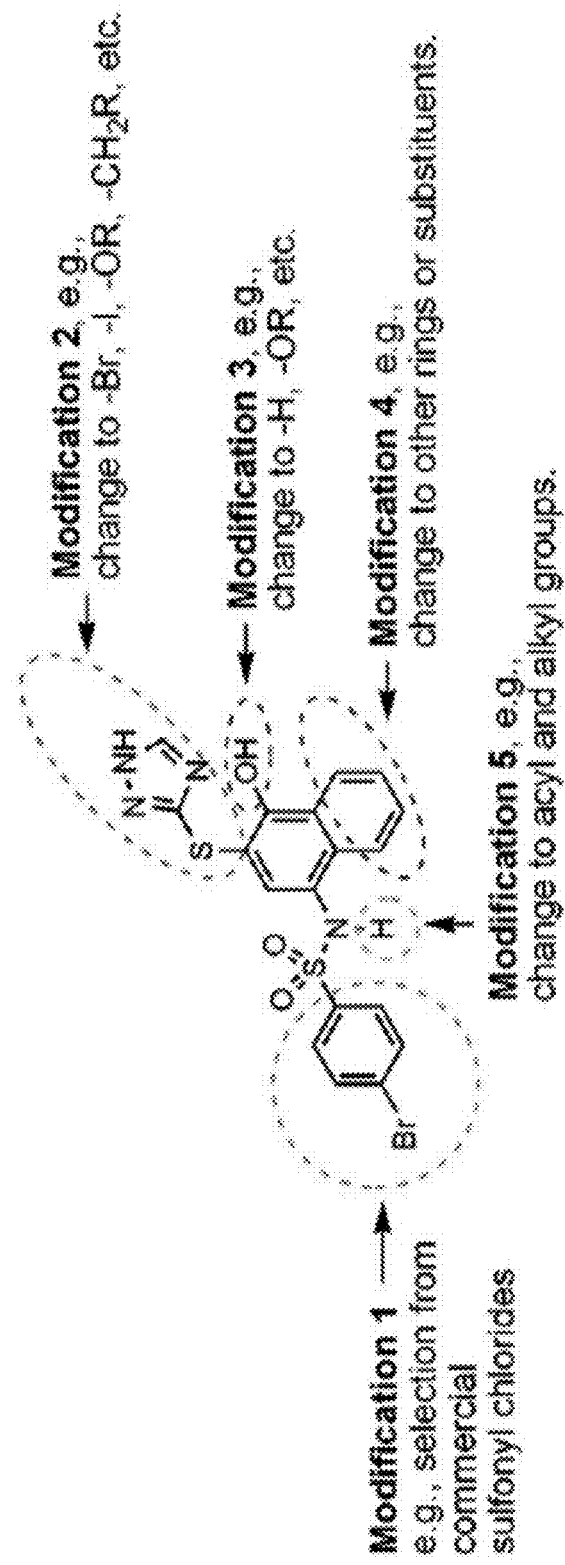
FIG. 18 shows an exemplary modification scheme for 3rd generation Stat3 probe development using Cpd188-15 as a scaffold.
Figure 19:
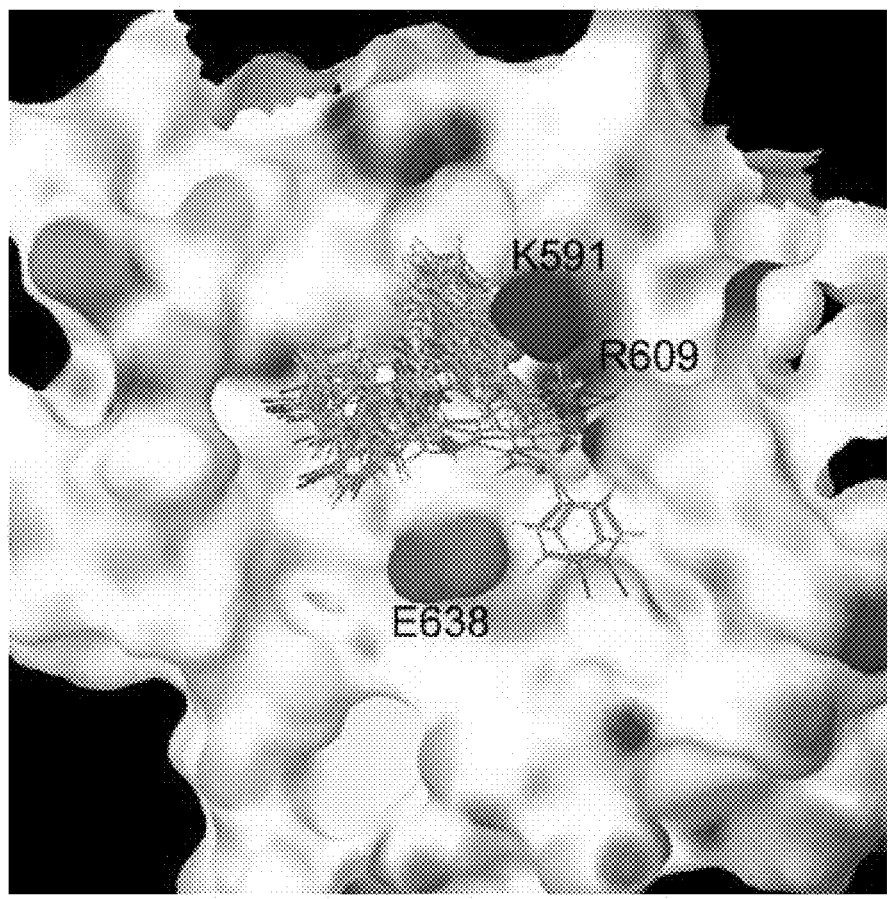
FIG. 19 provides illustration of the electrostatic surface of Stat3 SH2 domain (positive area in blue, neutral in white and negative in red in a color figure) and 20 docking poses of 5 (R=$CH_2PO_3^{2-}$), showing strong interactions between phosphonate groups (in purple and red) and K591/R609.

Medicinal Chemistry for Synthesis of 3$^{rd}$ Generation 188-Like Sulfamide STAT3 Probes The crystal structure of Stat3 shows that the SH2 domain has a large, widely dispersed and generally shallow binding area with several valleys and hills that recognize the pY-peptide ligand (FIG. 19). Structure-based molecular modeling (docking) was useful in identifying the contribution of the hydrophobic binding surface of the Stat3 SH2 domain as a selectivity filter (Xu et al., 2009). However, different docking programs gave distinct binding poses for the same probe over the binding surface with similar predicted binding affinities. The inventors therefore in particular embodiments, based on initial SAR results outlined above, use traditional medicinal chemistry to further carry out an exemplary comprehensive structure activity relationship study, to optimize the activity as well as the selectivity of this novel class of sulfamide probes of Stat3. Compound 188-15 serves as a scaffold for making the new generation compounds, as shown schematically below (FIG. 18):

In addition, chemistry for making these compounds is straightforward with a good yield, involving the reaction of a sulfonyl chloride with an aniline/amine, which can be either obtained commercially or synthesized readily.

EXP IA. Modification 1. Since almost all of the 2$^{nd}$ generation probes contain a phenylsulfonyl group, the first step towards activity optimization focuses on synthesizing a series of compounds that have a larger (e.g., bicyclic or tricyclic) or an alkyl sulfonyl group. The general synthetic route is shown as follows:

There are about 4,300 commercially available sulfonyl chlorides, among which 25, such as those shown above, are selected to make probes. Aniline 2, which is the amine component of compound 188-10 (FIG. 16), one the most active probes, is readily made in a simple two step reaction from nitro compound I. One can first make 25 (for example) compounds and test their activities in an in vitro rapid throughput SPR and in vivo HTFM assays (described below). Based on the outcomes of structure-activity relationship study, more compounds can be designed and synthesized and tested in an iterative manner until optimization of this modification.

EXP IB. Modification 2. Next, one can modify the 3-substituent of the naphthylamine ring, based on either the structure of compound 188-15 (currently the most potent probe) or that having a novel, more active sulfonyl group emerged from the above Modification 1 study. Prior SAR studies demonstrated this substituent is useful to the activity of this class of probes, in certain embodiments. However, a total of 8 groups at this position with a huge difference in size, from a single atom Cl to a large, bicyclic benzothiazole-2-ylmercapto group, showed similar activities. This feature indicates that in certain embodiments modifications at this position should be more focused on other properties, such as electrostatic interactions with the protein, as exemplified below. In addition, many of these groups are thioethers, which may be subjected to oxidation/degradation in vivo and lead to an unfavorable pharmacokinetic profile, in particular aspects. The central —S— atom is changed to a more metabolically stable isosteres, such as —CH$_2$—, —NH—, and —O—, in certain cases. In certain aspects one can synthesize the following compounds to optimize the 3-substituent:

The synthesis is also started from 1, in certain cases. Regioselective halogenation and formylation at the 3-position gives rise to two compounds, i.e., bromo- or iodo-compound 3 and aldehyde 4, which are versatile, common starting compounds for introducing a wide range of substituents at this position (e.g., those listed above).

Moreover, the crystal structure of Stat3 SH2 domain also provides strong evidence that more compounds with different electrostatic properties are useful for characterization. The electrostatic molecular surface of the protein shows two distinct features, as shown in FIG. 19. The first one is the red, negatively charged Glu638 surface stands out in the center. Next, of particular interest is a positively charged area (in blue in a color version), composed of Arg609 and Lys591 located in the edge of the domain, which is actually the pY (phosphorylated tyrosine) binding site of the receptor. The inventors also found that introducing a negatively charged group targeting the pY binding site leads to particularly active probes, in certain embodiments. For example, the docking study of the 3-phosphomethyl compound 5 (R═CH$_2$PO$_3^{2-}$) showed all of the phosphonate groups of the 20 docking poses are tightly clustered together and located in the pY binding site, indicating strong electrostatic and H-bond interactions with the residues Arg609 and Lys591 (FIG. 19).

EXP IC. Modifications 3 and 4. Collectively, Modifications 3 and 4 test the effects of changing the substituents at the 4, 5, and 6-positions. The —OH at 4-position is superior to —OR, in certain aspects. One can test whether the H atom in —OH is responsible for a better activity by synthesizing compounds 6 (acylated or alkylated 5), as schematically shown below. In addition, dehydroxy compounds 7 is also made, starting from 3-bromonaphthyl-1-amine.

Next, the general synthetic methods for modifying positions 5 and 6 are shown below. One can first synthesize about a dozen of these compounds in this category and if very active compounds emerge, one can make more compounds to optimize the activity for these two positions.

EXP ID. Modification 5. The only two compounds not included in the SAR analysis (due to a different 4-substituent) are shown here, as well as their inhibitory activities against Stat3:

Despite the weak activity, masking the polar H of the sulfamide for the second compound is favorable, in certain aspects, which provides an easy route to making more potent probes. One can therefore use the following method to make a series of N-acyl or N-alkyl sulfamides 5:

Example 12

Identification of STAT3-Selective Chemical Probes from Sulfamide Compounds Synthesized in Example 11

Each novel sulfamide compound is tested for the ability to inhibit Stat3 binding to its phosphopeptide ligand by SPR and the ability to block IL-6-stimulated cytoplasmic-to-nuclear translocation in the HTFM assay. Probes with activity in these assays equivalent to or greater than the most active 2nd generation compounds are tested for inhibition of IL-6-stimulated Stat3 phosphorylation and lack of ability to inhibit IFN-γ-stimulated Stat1 phosphorylation as outlined below.

EXP IIA. Stat3/pY-peptide SPR binding inhibition assay. Stat3 pY-peptide binding assays is performed at 25° C. using a BIAcore 3000 biosensor as described (Xu et al., 2009). Briefly, phosphorylated and control nonphosphorylated biotinylated EGFR derived dodecapeptides based on the sequence surrounding Y1068 are immobilized on a streptavidin coated sensor chip (BIAcore Inc., Piscataway N.J.). The binding of Stat3 is performed in 20 mM Tris buffer pH 8 containing 2 mM β-mercaptoethanol at a flow rate of 10 uL/min for 1-2 minute. Aliquots of Stat3 at 500 nM are premixed with compound to achieve a final concentration of 1-1,000 uM and incubated at 4° C. prior to being injected onto the sensor chip. The chip is regenerated by injecting 10 uL of 100 mM glycine at pH 1.5 after each sample injection. A control (Stat3 with DMSO but without compound) is run at the beginning and the end of each cycle (40 sample injections) to ensure that the integrity of the sensor chip is maintained throughout the cycle run. The average of the two controls is normalized to 100% and used to evaluate the effect of each compound on Stat3 binding. Responses are normalized by dividing the value at 2 min by the response obtained in the absence of compounds at 2 min and multiplying by 100. IC$_{50}$ values are determined by plotting % maximum response as a function of log concentration of compound and fitting the experimental points to a competitive binding model using a four parameter logistic equation: R=R$_{high}$−(R$_{high}$−R$_{low}$)/(1+conc/A1)$^{A2}$, where R=percent response at inhibitor concentration, R$_{high}$=percent response with no compound, R$_{low}$=percent response at highest compound concentration, A2=fitting parameter (slope) and A1=IC$_{50}$ (BIAevaluation Software version 4.1).

EXP IIB. High throughput fluorescence microscopy (HTFM), cytoplasm-to-nucleus translocation inhibition assays. HTFM of MEF/GFP-Stat3α cells is performed to assess the ability of probes to inhibit GFP-Stat3 cytoplasmic-to-nuclear translocation, as described (Xu et al., 2009), using the robotic system available as part of the John S. Dunn Gulf Coast Consortium for Chemical Genomics at the University of Texas-Houston School of Medicine. Briefly, cells are seeded into 96-well CC3 plates at a density of 5,000 cells/well and cultured under standard conditions until 85-90% confluent. Cells are pre-treated with compound for 1 hour at 37° C. then stimulated with IL-6 (100 ng/ml) and IL-6sR (150 ng/ml) for 30 minutes. Cells are fixed with 4% formaldehyde in PEM Buffer (80 mM Potassium PIPES, pH 6.8, 5 mM EGTA pH 7.0, 2 mM MgCl$_2$) for 30 minutes at 4° C., quenched in 1 mg/ml of NaBH$_4$ (Sigma) in PEM buffer and counterstained for 1 min in 4,6-diamidino-2-phenylindole (DAPI; Sigma; 1 mg/ml) in PEM buffer. Plates are analyzed by automated HTFM using the Cell Lab IC Image Cytometer (IC100) platform and CytoshopVersion 2.1 analysis software (Beckman Coulter).

Nuclear translocation is quantified by using the fraction localized in the nucleus (FLIN) measurement. FLIN values are normalized by subtracting the FLIN for unstimulated cells then dividing this difference by the maximum difference (delta, A) in FLIN (FLIN in cells stimulated with IL-6/sIL-6R in the absence of compound minus FLIN of unstimulated cells). This ratio is multiplied by 100 to obtain the percentage of maximum difference in FLIN and is plotted as a function of the log compound concentration. The best-fitting curve and $IC_{50}$ value are determined using 4-Parameter LogisticModel/Dose Response/XLfit 4.2, IDBS software.

EXP IIC. Ligand-mediated pStat3 and pStat1 inhibition assays. Newly synthesized Stat3 probes with activity equivalent to or greater than parent compound 188 in the SPR and HTFM assays will be tested for the ability to selectively inhibit ligand-mediated phosphorylation of Stat3 as described (Xu et al., 2009). Briefly, human hepatocellular carcinoma cells (HepG2) are grown in 6-well plates and pretreated with compounds (0, 0.1, 0.3, 1, 3, 10, 30, 100 µM) for 1 hour then stimulated under optimal conditions with either interleukin-6 (IL-6; 30 ng/ml for 30 min) to activate Stat3 or interferon gamma (IFN-γ, 30 ng/ml for 30 min) to activate Stat1. Cells are harvested and proteins extracted using high-salt buffer, mixed with 2× sodium dodecyl sulfate (SDS) sample buffer (125 mmol/L Tris-HCL pH 6.8; 4% SDS; 20% glycerol; 10% 2-mercaptoethanol) at a 1:1 ratio then heated for 5 minutes at 100° C. Proteins (20 µg) are separated by 7.5% SDS-PAGE and transferred to polyvinylidene fluoride (PVDF) membrane (Millipore, Waltham, Mass.) and immunoblotted. Membranes are probed serially with antibody against Stat1 pY701 or Stat3 pY705 followed by antibody against Stat1 or Stat3 (Transduction labs, Lexington, Ky.) then antibody against β-actin (Abcam, Cambridge, Mass.). Membranes are stripped between antibody probings using Restore™ Western Blot Stripping Buffer (Thermo Fisher Scientific Inc., Waltham, Mass.) per the manufacturer's instructions. Horseradish peroxidase-conjugated goat-anti-mouse IgG is used as the secondary antibody (Invitrogen Carlsbad, Calif.) and the membranes are developed with enhanced chemiluminescence (ECL) detection system (Amersham Life Sciences Inc.; Arlington Heights, Ill.). Band intensities are quantified by densitometry. The value of each pStat3 band is divided by its corresponding total Stat3 band intensity; the results are normalized to the DMSO-treated control value. This value was plotted as a function of the log compound concentration. The best-fitting curve is determined using 4-Parameter Logistic Model/Dose Response/XLfit 4.2, IDBS software and was used to calculate the $IC_{50}$ value.

EXP IID. Molecular modeling of probe-Stat3 interactions. The results of modeling of the binding of the first generation probe to the Stat3 vs. Stat1 SH2 domains suggested that the basis for experimental selectivity of probes for Stat3 vs. Stat1 rested on the ability of the probes to have greater interaction with the hydrophobic binding site within the pY-peptide binding pocket of Stat3 compared to Stat1. Thus, the hydrophobic binding site served as a selectivity filter. To test if this remains the case for newly synthesized 3rd generation probes, one can use 2 complementary docking programs GLIDE (Schrödinger) and ICM (MolSoft) to determine the lowest energy docking configuration of each probe within the pY-peptide binding domain of Stat3 and Stat1 SH2 domain. One can review the computational models of each probe in a complex with the Stat3 vs. Stat1 SH2 domain and, in particular, compare the van der Waals energies and determine if they are equivalent for their interaction with the Stat3 SH2 domain vs. the Stat1 SH2 domain. It was this calculation that determined the selectivity of 1st generation probes for Stat3 vs. Stat1. In particular, van der Waals energy calculations implicated residues that form the hydrophobic binding site (W623, Q635, V637, Y640 and Y657) as critical for this selectivity.

In specific embodiments of the invention, there is identification of probes with one log or greater activity than $2^{nd}$ generation probes in SPR, HTFM and pStat3 assays. Furthermore, in certain aspects some of the most active $3^{rd}$ generation probes that emerge from this analysis are selective for Stat3 vs. Stat1 based on their greater interaction with the hydrophobic binding site within the Stat3 vs. Stat1 SH2 pY-peptide binding pocket. The most active and selective probes are examined for their effect on the biology of normal hematopoietic stem cells and leukemic stem cells as outlined in Example 13 below and on breast cancer stem cells as outlined in Example 16.

Example 13

Examination of Candidate $3^{rd}$ Generation STAT3 Chemical Probes for Selective Targeting of Myeloid Leukemic Stem Cells while Sparing Normal Hematopoietic Stem/Progenitor Cells Third generation probes with activity greater than the most active 2nd generation probe, as well as the most active 2nd generation probes, are examined for their effects on normal and exemplary leukemia myeloid stem/progenitor cells using normal and leukemic granulocyte/macrophage colony-forming unit (CFU-GM) assays. One can identify Stat3 probes that spare normal stem/progenitor cells in this assay while targeting leukemic stem cells. The normal CFU-GM assay takes one week to perform, while the retroviral transducation/transplantation assay (RTTA) leukemic CFU-GM assay takes 3 weeks. Consequently, one can first screen each candidate Stat3 probe in the normal CFU-GM assay. Those probes without activity in the normal CFU-GM assay are then tested in the RTTA.

Figure 20:
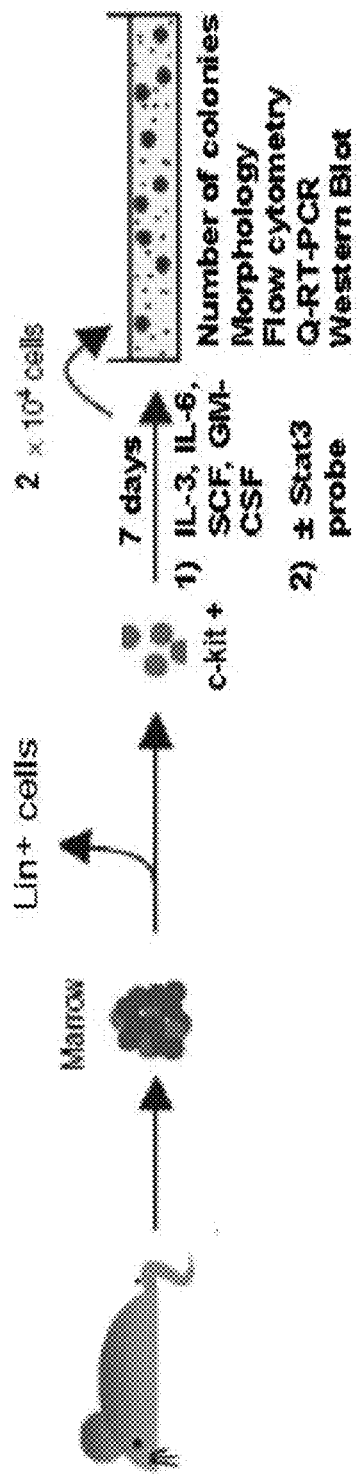
FIG. 20 shows an exemplary schema for testing of candidate Stat3 probes in normal CFU-GM assay.

EXP IIIA. Screening of probes for activity against normal hematopoietic stem/progenitor cells in the CFU-GM assay. Murine bone marrow cells are collected and processed, as described previously (Tweardy et al., 1991) with the following modifications (FIG. 20). Briefly, c-kit selected hematopoietic stem cells (HSC) are plated at $2-5 \times 10^4$ cells per plate in methylcellulose containing stem cell factor (SCF), IL-3, IL-6 and GM-CSF. These HSC are treated with or without Stat3 probes. At 7 days, the plates are evaluated to see if these compounds have any effects on normal hematopoiesis as assessed by colony number, morphology, cell surface antigens examined by FACS using antibodies such as CD11b, Gr-1 and B220, Q-RT-PCR and Western blot.

EXP IIIB. Testing of Stat3 probes for activity against leukemic stem cells in the RTTA assay. The inventors have constructed pMSCV-based vectors each containing a member of one of the major groups of chimeric fusion proteins occurring in AML including those involving RARα genes and AML1 genes (FIG. 21). Members of the first group, in particular, have been demonstrated to be involved in cross talk with the Stat3 signaling pathway (Dong and Tweardy, 2002; Dong et al., 2003).

Figure 22:
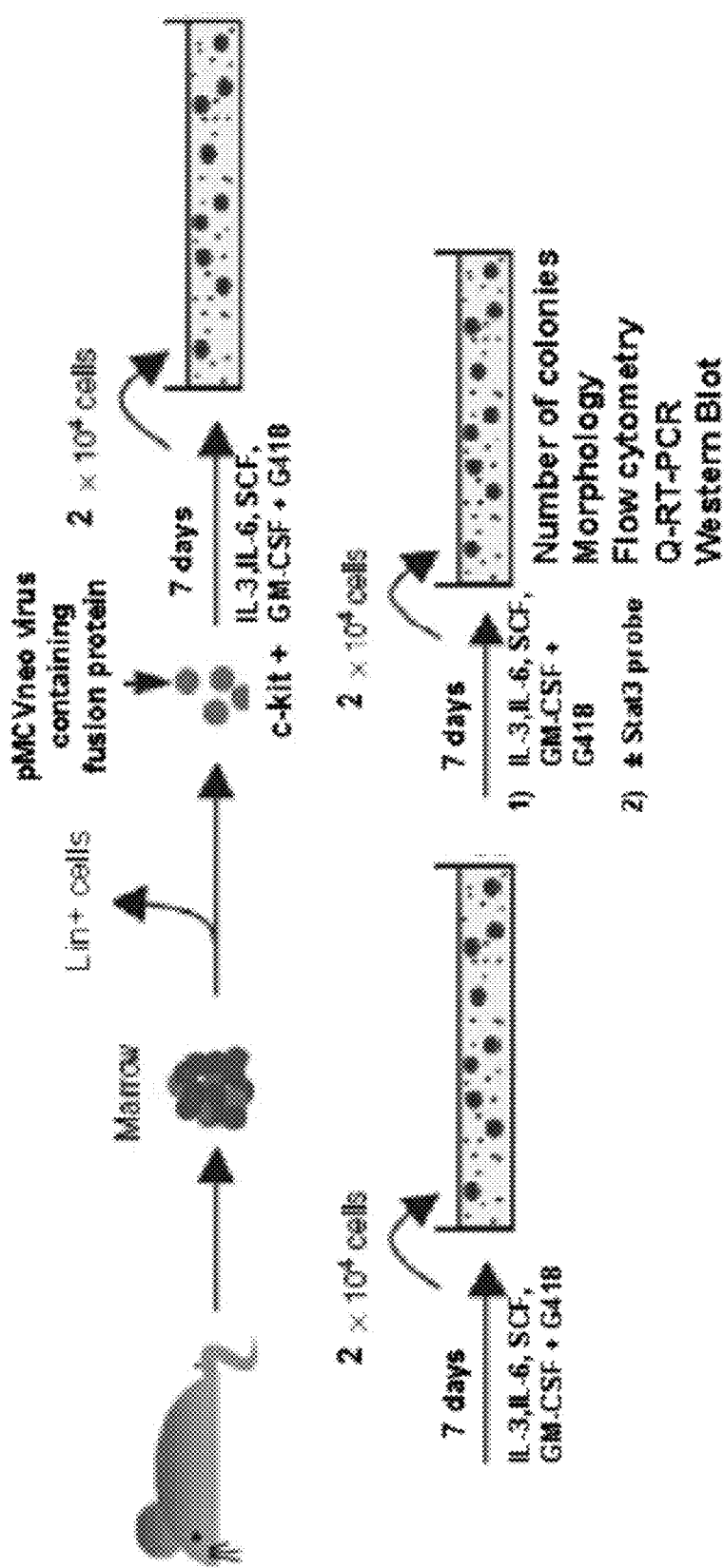
FIG. 22 provides an exemplary schema of testing Stat3 probes in the RTTA assay.

Each construct is examined for its ability to transform normal bone marrow stem/progenitor cells in the RTTA (FIG. 22). Briefly, pseudotyped retroviral supernatants are produced by transient transfection of Phoenix packaging cells with Murine Stem Cell Virus (MSCV) retroviral constructs containing a leukemia fusion protein. Viral supernatants will be used to infect purified 4-to-10-week-old wild-type C57BL/6 mice murine hematopoietic progenitors that have been positively selected for c-kit expression by magnetic-activated cell sorting (MACS). After spinoculation, transduced cells are plated in 1% methylcellulose supplemented with stem cell factor (SCF), IL-3, IL-6 and GM-CSF in the presence or absence of G418 or puromycin. G418 or puromycin resistant colonies will be replated twice in the same conditioned methylcellulose media after 7 days culture.

Figure 23:
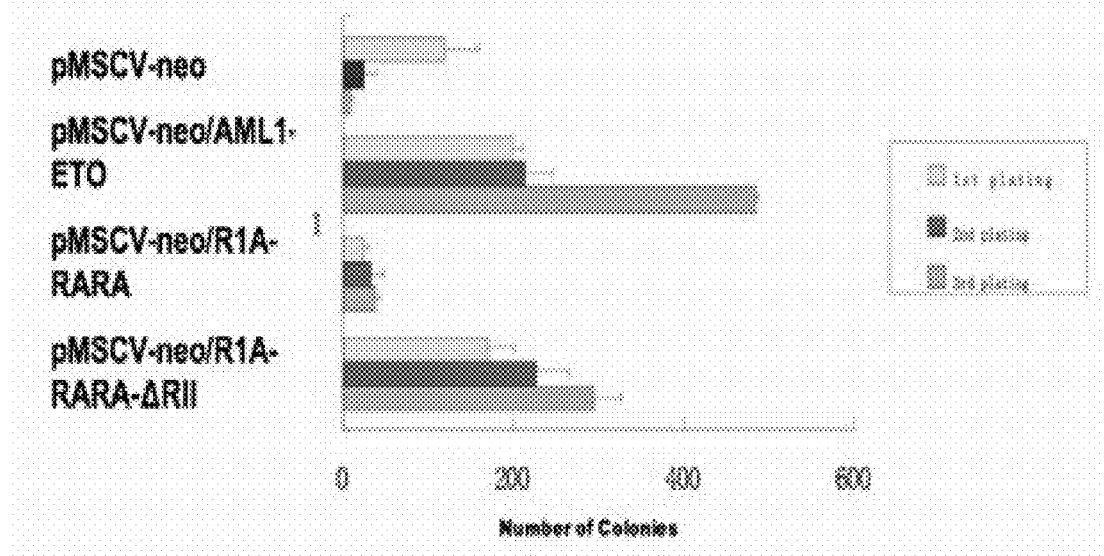
FIG. 23 shows RTTA assay results using representative fusion proteins.

Cells transduced with control vector exhaust their proliferative capability in the second round of plating while cells immortalized by leukemia oncoproteins maintain their replanting ability and are able to expand in liquid culture (see FIG. 23). Replating is repeated every 7 days. For drug screening studies, transduced cells are harvested after the second plating and split evenly into a sufficient number of plates for testing of Stat3 probe over a concentration range of 0.1-10 μM in half-log concentration increments. After 7 days incubation, one can examine plates for the effect of the probes on colony number, morphology and for expression of relevant surface antigens, mRNA and protein.

For constructs in which Stat3 probes inhibit leukemic colony formation, one can confirm that the effect of the Stat3 probe is due to the effect on Stat3 and not an off target effect by testing the effect leukemic stem cell colonies formation of co-transfection of c-kit+ cells with the pMSCV-neo/fusion protein construct and pSuperpuro/shRNA-mStat3. Murine (m) Stat3 shRNA constructs are designed, as described (Ling and Arlinghaus, 2005), and used in RTTA cotransfection experiments, as described (Zeisig et al., 2007).

Figure 24:
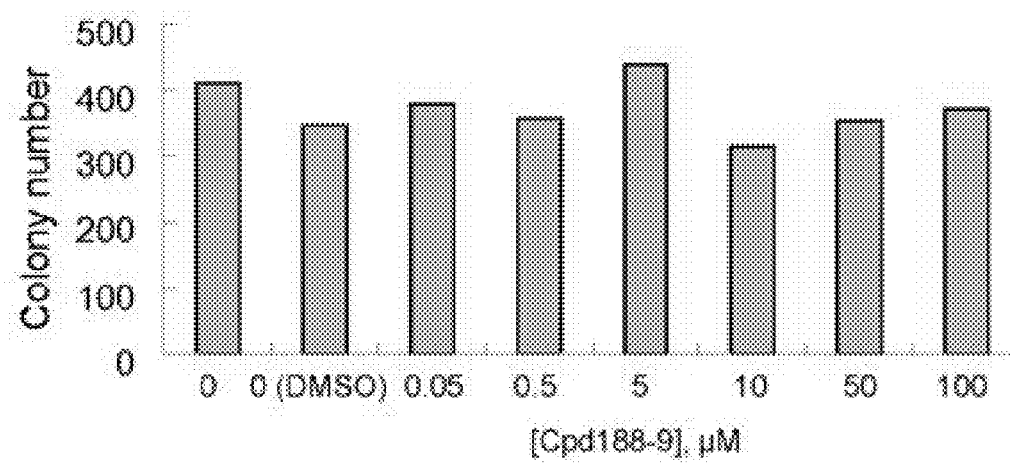
FIG. 24 demonstrates that Cpd188-9 did not effect normal CFUGM colony formation.
Figure 25:
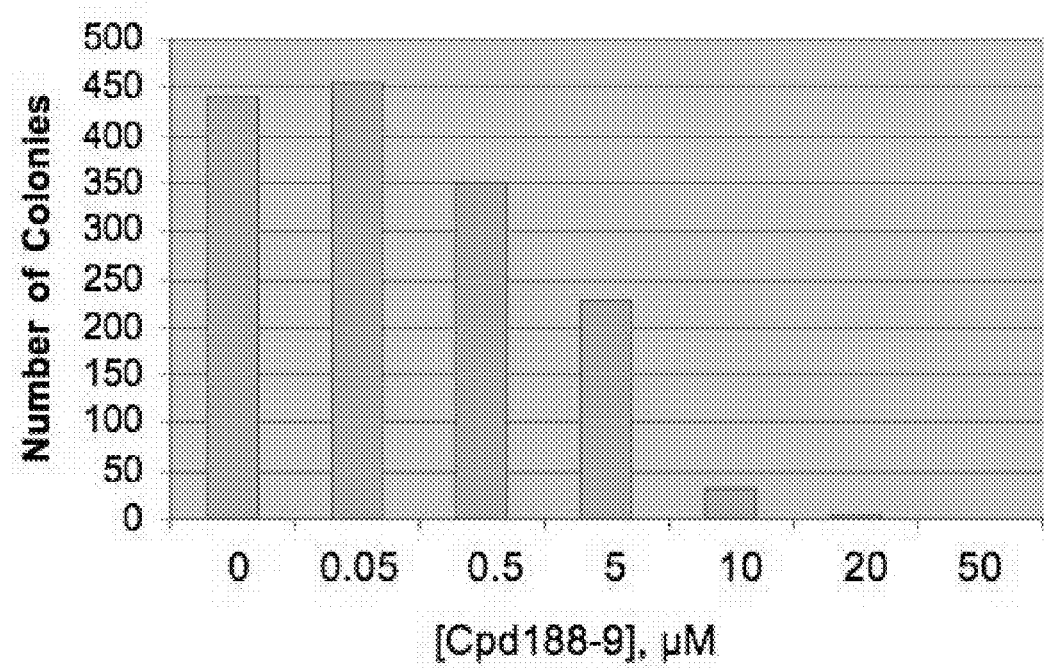
FIG. 25 shows an effect of Cpd188-9 on leukemic CFU-GM induced by pMSCV-neo/R1ARAR α-ΔRII. Provided are photographs of representative plates (upper panel) and the total number of colonies within plates (lower panel).

The inventors obtained useful results testing the first of the 2nd generation Stat3 chemical probes, Cpd188-9, for the ability to inhibit the number of normal and leukemic CFU-GM colonies. Cpd 188-9 showed no inhibitory effect on growth of normal CFU-GM colonies up to a concentration of 100 μM (FIG. 24). In contrast, it inhibited leukemic stem cell colony formation in the RTTA with an EC50 of ~5 μM (FIG. 25).

Example 14

Overview of Breast Cancer Embodiments of the Invention

Breast cancer is the most common female cancer in the United States, the second most common cause of cancer death in women (after lung cancer), and the main cause of death in women ages 45 to 55. Data from the Surveillance, Epidemiology, and End Results (SEER) program of the National Cancer Institute indicate that the lifetime probability of developing breast cancer is one in six; for invasive breast cancer, the probability is one in nine. While recent data from the SEER program suggest that the incidence of estrogen (ER) and/or progesterone (PgR) receptor-negative breast cancer is declining relative to ER/PgR-positive disease (Li et al., 2003), treatment options for ER/PgR-negative disease have greater toxicity and outcomes are much poorer than for ER/PgR-positive disease underscoring an urgent need for new therapies for this subset of cancers. In addition, every year, ~40,000 women in the US alone will suffer a breast cancer relapse, and most of these will die of their disease (Jemal et al., 2006). There has been little change in the overall survival for women with metastatic breast cancer over the last several decades (Minino et al., 2007), despite all of the significant advances in breast cancer biology and the multitude of clinical trials that have been conducted.

Breast Cancer Stem Cells.

Conventional chemotherapies are initially effective in controlling growth of many tumors. Yet, many patients relapse over time despite initially responding. A possible explanation is that a rare sub-population of cells with tumorigenic potential is intrinsically resistant to therapy. This hypothesis provides a unified explanation for the success and failures of cytotoxic chemotherapy—namely, although the majority of cells in the original tumor may be killed, the most important target, a small population of therapy-resistant cancer cells possessing tumor-initiating capacity (cancer stem cells) is spared, thereby allowing tumor re-growth. Recent research by the inventors and others has provided strong support for the "cancer stem cell (CSC) hypothesis", which provides a mechanism for the resistance to conventional treatments, as well as a possible explanation of relapse and metastases. The CSC hypothesis is a fundamentally different model in which tumors contain a sub-population that retains key stem cell properties including self-renewal which initiates and drives carcinogenesis and differentiation that contributes to cellular heterogeneity. Although the concept that cancers arise from both germ cells or stem cells was first proposed over 150 years ago (Fiala, 1968), it is only recently that advances in stem cell biology have allowed for direct testing of the CSC hypothesis. Recently, these concepts were extended to solid tumors by some groups demonstrating that human breast cancers were driven by a "cancer stem cell component" characterized by the phenotype $CD44^+/CD24^{-/low}$ (Al-Hajj et al., 2003). The inventors have recently completed a neoadjuvant breast cancer clinical trial, which provides strong clinical evidence for the resistance of CSCs to chemotherapy. They demonstrated a three-fold increase in the proportion of $CD44^+/CD24^{-/low}$ CSCs following chemotherapy in women with locally advanced breast cancer. Interestingly, the EGFR/HER2 tyrosine kinase inhibitor lapatinib led to a decrease in the proportion of CSCs (Strecker et al., 2009). This study indicated that CSCs are relatively resistant the chemotherapy, but are affected by the EGFR/HER2 inhibitor lapatinib (Strecker et al., 2009). Consistent with this, it has been shown for the first time clinically in human breast cancer patients that residual tumors after chemotherapy are 1) enriched for the tumorigenic $CD44^+/CD24^{-/low}$ population, 2) show enhanced mammosphere-forming efficiency (MSFE), and 3) display an increase in outgrowths in xenograft transplants in immunocompromised SCID/Beige mice, thus suggesting their increased tumorigenicity (Li et al., 2008; Dave and Chang, 2009).

Targeting Cancer Stem Cells.

Both preclinical and clinical studies support the hypothesis that CSCs contribute to treatment resistance and relapse. More effective therapies will thus require the selective targeting of this crucial cell population. From biopsies obtained from women with primary breast cancer, the inventors have identified a "cancer stem cell signature", with key regulatory pathways, like Notch, PI3-AKT and Stat3 and others, that may be responsible for cancer stem cell self-renewal, and therefore, treatment resistance and relapse.

Breast Cancer and Stat3.

Recent reports indicate there is increased activation of Stat3 in ER-negative, invasive breast cancer samples and in ER-negative, metastatic cell lines. Increased Stat3 activation within these cancer tissues and cells results in increased levels of anti-apoptotic proteins including Bcl-2 and Survivin (Diaz et al., 2006; Gritsko et al., 2006; Real et al., 2002). In addition to upregulation of anti-apoptotic proteins, increased Stat3 activity contributes to oncogenesis in breast cancer and other cancer systems through several additional pathways including enhancement of cell proliferation, induction of angiogenesis and suppression of immune responses (Yu and Jove, 2004) making Stat3 a potentially high-yield target for drug development to treat many cancers, but, in particular, for treatment of ER-negative and HER2/Neu-negative breast cancer for which there currently are few effective and virtually no non-toxic therapies. Furthermore, the inventors have determined from the largest data set of gene expression analysis of the $CD44^+/CD24^{-/low}$-MS population that the top canonical pathways involved in stem cell self-renewal includes Stat3 signaling.

In certain aspects of the invention, Stat3 is indispensable for the function of breast cancer stem cells and can be inhibited with small molecules that target its SH2 domain thereby effectively targeting breast cancer stem cells.

In a certain embodiment of the invention, third (3rd) generation Stat3 probes are developed with increased inhibitory activity by performing medicinal chemistry. Third generation probes are developed with increased activity against Stat3 based on structural modifications of the most active 2nd generation probe, for example. In one embodiment, one can use the most active 2nd generation probe, Cpd188-15, for example, as a scaffold for making 3rd generation probes. Modifications may be based on the results of an exemplary structure-activity relationship (SAR) analysis performed on 2nd generation probes and center around the straightforward synthesis of sulfamides from panels of sulfonyl chlorides and amides. Each novel sulfamide compound is examined in a rapid throughput SPR assay for the ability to inhibit Stat3 binding to its phosphopeptide ligand followed by high throughput fluorescence microscopy (HTFM) examining inhibition of IL-6-stimulated cytoplasmic-to-nuclear translocation. The most active probes in these assays are examined for their selectivity for Stat3 vs. Stat1 by testing for inhibition of IL-6-stimulated Stat3 phosphorylation and for failure to inhibit IFN-γ-stimulated Stat1 phosphorylation.

In another embodiment, it is determined whether suppression of the Stat3 pathway can improve existing cancer therapies in preclinical mammosphere forming efficiently (MSFE) and human xenograft models. In a specific embodiment, breast cancer stem cells are eliminated with specific probes that target Stat3. Using the most active probe developed as described above, one can determine whether Stat3 inhibition by these 3rd generation compounds improves efficacy of conventional therapy in vitro and in vivo, using MSFE and human breast cancer xenograft models.

Example 15

STAT3 Inhibitors for Human Breast Cancer

Enrichment of cancer stem cells in residual tumors following neoadjuvant therapy. The inventors isolated CSCs, marked by $CD44^+/CD24^{-/low}$ from paired breast cancer core biopsies obtained from primary breast cancer patients before and after chemotherapy (n=31). Chemotherapy led to an increased percentage of $CD44^+/CD24^{-/low}$ cells (mean at baseline vs. 12 weeks, 4.7% vs. 13.6%, P<0.001) and increased self-renewal capacity on MSFE assays (P<0.001) (Li et al., 2008; Dave and Chang, 2009). Hence, residual tumors after conventional therapy are enriched for cancer stem cells (CSCs).

Preclinical Models.

There are robust preclinical models utilizing both in vitro systems (MSFE), as well as tumor xenografts (Strecker et al., 2009; Li et al., 2008) to elucidate the molecular regulatory pathways of cancer stem cells that have led to the development of novel agents to target these cells. From biopsies of primary breast cancers, the inventors have established thirteen primary xenografts. Of these, the inventors have successfully transplanted ten different human breast cancers into tertiary xenografts. The gene expression patterns of the primary and tertiary xenografts were similar, thus providing a renewable source of human breast cancers each of which is genotypically stable.

Gene Transcription Patterns in Breast Cancer Cells with Tumorigenic Potential.

The inventors reasoned that expression profile features in common between $CD44^+/CD24^{-/low}$ vs. all other cell subpopulations, and cancer-derived MS vs. bulk tumor would be most likely to represent the tumor-initiating or "cancer stem cells". Between the two gene sets, 477 genes were in common, with 185 of these more highly expressed in $CD44^+/CD24^{-/low}$ cells and in MS, a highly significant overlap (p<1.0E-9, one-sided Fisher's exact). In addition, there were 292 genes whose expression was lower in $CD44^+/CD24^{-/low}$ cells and cancer-derived MS vs. all other cells and bulk tumors, respectively. Again, this degree of overlap was highly statistically significant (p<5.0E-5, one-sided Fisher's exact). In Ingenuity pathway analysis, the signature shared by the chemoresistant CD44+/CD24−/low cells and cancer-derived MSs showed differential expression of genes related to Notch, PI3-AKT, and Stat3 pathways. From initial studies, Stat3 is the top candidate target responsible for cancer stem cell self-renewal.

Development of First Generation Stat3 Probes.

To develop chemical probes that selectively target Stat3, the inventors virtually screened 920,000 small drug-like compounds by docking each into the peptide-binding pocket of the Stat3 SH2 domain, which consists of three sites: 1) the pY-residue binding site, conserved within all SH2 domains (general binding site, GBS), 2) the +3 residue-binding site specific for Stat3 binding its pY-peptide domain (specific binding site, SBS) and 3) a hydrophobic binding site (HBS), which served as a selectivity filter. Three compounds (Cpd3, Cpd30 and Cpd188) satisfied criteria of interaction analysis, competitively inhibited recombinant Stat3 binding to its immobilized pY-peptide ligand and inhibited IL-6-mediated tyrosine phosphorylation of Stat3. These compounds were used in a similarity screen of 2.47 million compounds, which identified 3 more compounds (Cpd3-2, Cpd3-7 and Cpd30-12) with similar activities. Examination of the six active compounds for the ability to inhibit IFN-γ-mediated Stat1 phosphorylation revealed that all but Cpd30-12 was selective for Stat3. Molecular modeling of the SH2 domains of Stat3 and Stat1 bound to compound revealed that compound interaction with the hydrophobic binding site was the basis for selectivity. All 5 selective compounds inhibited nuclear-to-cytoplasmic translocation of Stat3, while 3 of 5 compounds (Cpd3, Cpd30 and Cpd188) induced apoptosis preferentially of breast cancer cell lines with constitutive Stat3 activation. Thus, virtual ligand screening of compound libraries that targeted the Stat3 pY-peptide binding pocket identified for the first time three lead compounds that competitively inhibited Stat3 binding to its pY-peptide ligand; these compounds were selective for Stat3 vs. Stat1 and induced apoptosis preferentially of breast cancer cells lines with constitutively activated Stat3 (Xu et 2009).

Figure 26:
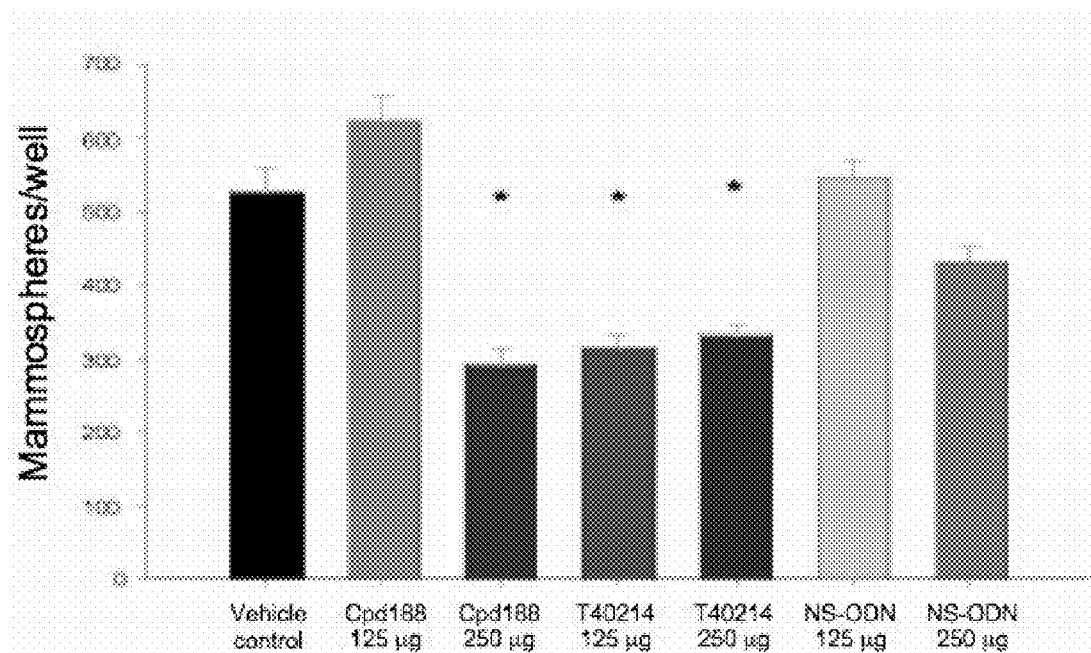
FIG. 26 illustrates a two-day pilot, triple-negative xenograft experiment (n=3) with vehicle control or Stat3 inhibitors: Cpd188), GQ-ODN T40214, and non-specific (NS) ODN at two doses (125 and 250 µg). The mice were sacrificed after two days and MSFE measured.

First generation Stat3 inhibitor (Cpd188) in human breast cancer xenograft significantly reduces MSFE. An initial pilot study was conducted to determine if Cpd188 would decrease MSFE. A tumor line derived from a "triple negative" (ER-negative, PgR-negative, and HER-2 negative) human breast cancer biopsy specimen was transplanted into immunocompromised SCID Beige mice. The animals (n=3) received two doses of vehicle control, 2 different doses of Cpd 188 (125 or 250 mcg), a G-quartet oligodeoxynucleotide (GQ-ODN, T40214; GQ-I) previously determined to target Stat3 (Jing et al., 2004) and a control non-specific ODN (GQ-II) each at two doses (125 or 250 mcg). The animals were sacrificed after only two days of treatment, and MSFE determined. From these short-term studies, Cpd 188 (250 mcg) and T40214 (GQ-1; 125 and 250 mcg) showed significant reduction in MSFE compared to control (P<0.05; FIG. 26). Based on these initial results, the inventors have undertaken full scale experiments using at least two xenograft tumor models, to demonstrate that Cpd188 and the leading 2nd generation inhibitor (Cpd188-15, see below) improve existing cancer therapies by decreasing tumor volume and decreasing MSFE.

Example 16

Suppression of the STAT3 Pathway and Cancer Therapies

In one embodiment of the invention, it is determined that suppression of the Stat3 pathway improves existing cancer therapies in preclinical MSFE and human breast cancer xenograft models, for example.

One can determine Stat3 inhibition improves efficacy of conventional therapy using MSFE and human breast cancer xenograft models. In a specific embodiment, CSCs can be eliminated with specific inhibitors that target Stat3. In initial studies, a second generation Stat3 inhibitor (CMP188-15) affects self-renewal as measured by MSFE. Based on initial studies, one can determine if these 2nd and 3rd generation Stat3 inhibitors improves efficacy of conventional chemotherapy. These studies involve in vitro analyses of pathway activation as well as tumor xenograft stem cell models developed by the inventors. One can characterize the role of Stat3 in regulating breast cancer stem cell self-renewal and survival.

In certain embodiments, the activity of lead 3rd generation Stat3 probes are determined in MSFE inhibition and xenograft inhibition assays.

MS Treatment Assays.

Using the secondary MSs created from human breast cancer specimens, one can test a range of ~fifty 3rd generation Stat3 inhibitors vs. no-treatment controls. Secondary MSs created from human breast cancer biopsies, as described elsewhere herein are used. These secondary MSs are grown to a diameter of 50-100 μm and treated with control or inhibitor. Residual cancer cells following treatment are dissociated to single cells by brief trypsinization and the cells re-plated. Formation of tertiary MSs reflects the proportion of MS-initiating cells that survived treatment, which might therefore be left alive to re-initiate tumor growth. MSFE values are log-transformed and compared using a t-test. From these MSFE assays, the top 5 inhibitors (for example) are tested in xenograft studies, as described below.

Xenograft Assays.

One can use two xenografts developed from human breast cancer biopsies that express activated p-Stat3 by IHC. From these established xenograft lines, for each of the top 5 inhibitors, the following studies may be undertaken: a) short term experiments with stem cell inhibitors at two doses vs. vehicle control and b) the optimal dose of the combination of chemotherapy with each of the five stem cell inhibitors.

a) Short term (2-day) experiments: One can test the five inhibitors at 2 doses. In these initial studies, one can analyze selected xenografts (3 mice per xenograft×2 xenografts×5 self-renewal inhibitors at two doses+1 untreated control group) to: 1) confirm that the target pathway has been inhibited, and 2) measure any change in markers of stem cell populations by MSFE.

b) Long-term (2-week studies) experiments: One can assess the effect of the self-renewal inhibitor on tumor growth and stem cell behavior. Eight mice for each of the two xenograft lines per treatment are tested. Animals receive two transplants, one in each #4 mammary fat pad (8 mice/xenograft/treatment with 5 treatment groups+one untreated control=32 mice per xenograft). When the xenograft tumors reach an average of 5 mm in diameter, one tumor from one side of the animal (randomly selected) is removed surgically to serve as a pre-treatment control. After one week recovery, the mouse is randomly assigned to a docetaxel, inhibitor, inhibitor+docetaxel vs. control. The animals is sacrificed after two weeks, yielding sets of paired samples before and after treatment for each drug and dose. Size of the xenografts is monitored longitudinally by caliper measurement using the RECIST criteria for assessment of tumor response. Outcomes from the study include tumor size at harvest/sacrifice, pre- vs. post-treatment % CD44+/CD24−, and pre- vs. post-treatment MSFE. This experiment allows one to pick, for each xenograft, a drug and dose that shrinks tumors and increases putative self-renewing cells, but does not cure the mouse. This is combined with the signaling inhibitors in subsequent studies. These studies require 8 mice/xenograft/treatment with 6 treatment groups+one untreated control=56 mice per xenograft, for example. For each inhibitor one can select the smallest dose that results in a substantial decrease in self-renewing cells (i.e. % CD44+/CD24− or MSFE).

Statistical Considerations

For each xenograft in the chemotherapy study, one can study 8 mice/drug/dose, and in specific embodiments this provides at least 80% power to detect a dose-response effect for each drug and in each xenograft tissue line. This estimate is based on review of initial studies, where treatment resulted in roughly a 1 standard deviation (SD) increase in % CD44+/CD24− (log transformed) (9-fold increase untransformed). In a specific embodiment, variability within a xenograft line is less than variability between xenografts from different tumors, so that a similar absolute change represents at least 1.5 SD's. In specific embodiments, the untreated group demonstrates no change (i.e. pre and post-treatment % CD44+/CD24− are the same), the low dose demonstrates about half the change (0.75 SD's), and the high dose demonstrates the full change (1.5 SD's). In this scenario, using a linear mixed model with contrasts to test for the presence of a linear trend at the 5% level has 80% power. Changes in mammosphere-forming efficiency are similarly detectable. Short term growth curves (by drug and xenograft tissue line) are compared using mixed models with repeated measures.

In a specific embodiment for MS treatment assays, residual MS after Stat3 show a significant decrease in the number of surviving MS-initiating cells upon replating. The most efficacious inhibitors are then tested in human cancer xenografts. In certain aspects, Stat3 inhibitors have little effect on breast tumor xenograft growth. In contrast, chemotherapy alone may cause rapid tumor regression, but the tumors will eventually re-grow. In certain embodiments, the combination of therapies causes similar shrinkage compared to chemotherapy, but the tumors do not re-grow. Total eradication of the tumors is confirmed by stopping therapy to allow re-growth if any tumor remains, and confirmation by pathologic assessment.

Example 17
Exemplary STAT 3 Inhibitors
Exemplary Stat3 inhibitors are provided in Tables 7-12 below.
TABLE 7
| IDNUMBER | Structure | Formula structure | MW | LogP |
|---|---|---|---|---|
| F1566-0306 | 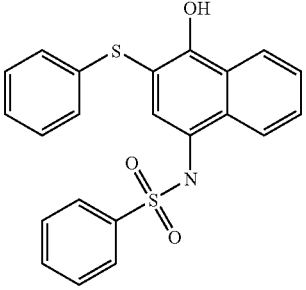 [SMILES: O=S(=O)(Nc1cc(Sc2ccccc2)c(O)c2ccccc12)c1ccccc1] | C22H17NO3S2 | 407.5137 | 5.846 |
| F1566-0318 | 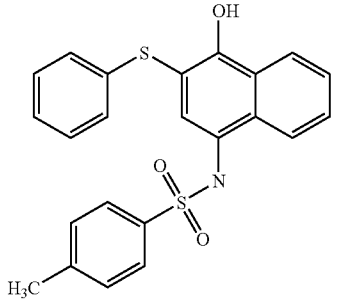 [SMILES: Cc1ccc(S(=O)(=O)Nc2cc(Sc3ccccc3)c(O)c3ccccc23)cc1] | C23H19NO3S2 | 421.5408 | 6.144 |
| F1566-0330 | 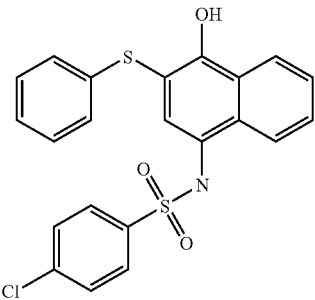 | C22H16ClNO3S2 | 441.9587 | 6.438 |
| F1566-0342 | 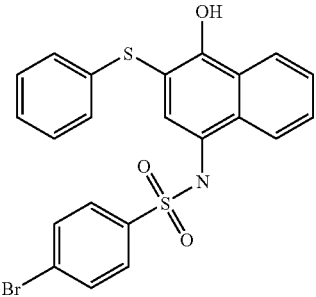 [SMILES: O=S(=O)(Nc1cc(Sc2ccccc2)c(O)c2ccccc12)c1ccc(Cl)cc1] | C22H16BrNO3S2 | 486.4097 | 6.644 |

TABLE 7-continued

| IDNUMBER | Structure | Formula structure | MW | LogP |
| --- | --- | --- | --- | --- |
| F1566-0366 | 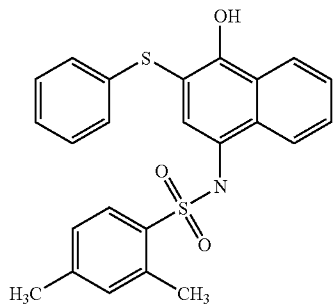 [SMILES: Cc1ccc(S(=O)(=O)Nc2cc(Sc3ccccc3)c(O)c3ccccc23)c(C)c1] | C24H21NO3S2 | 435.5679 | 6.477 |
| F1566-0414 | 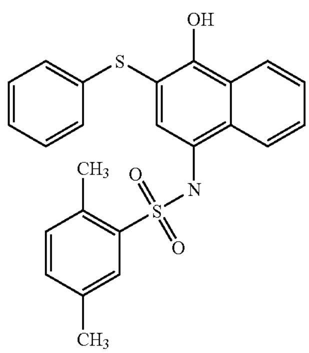 [SMILES: Cc1ccc(C)c(S(=O)(=O)Nc2cc(Sc3ccccc3)c(O)c3ccccc23)c1] | C24H21NO3S2 | 435.5679 | 6.477 |
| F1566-0438 | 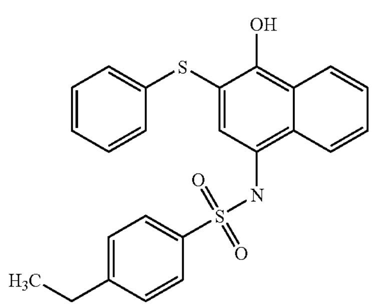 [SMILES: CCc1ccc(S(=O)(=O)Nc2cc(Sc3ccccc3)c(O)c3ccccc23)cc1] | C24H21NO3S2 | 435.5679 | 6.619 |
| F1566-0450 | 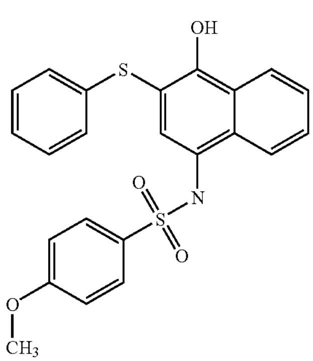 [SMILES: COc1ccc(S(=O)(=O)Nc2cc(Sc3ccccc3)c(O)c3ccccc23)cc1] | C23H19NO4S2 | 437.5402 | 5.802 |

TABLE 7-continued
| IDNUMBER | Structure | Formula structure | MW | LogP |
|---|---|---|---|---|
| F1566-0462 | 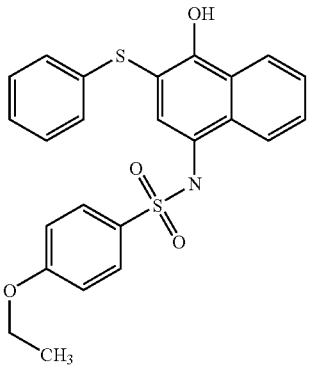 [SMILES: CCOc1ccc(S(=O)(=O)Nc2cc(Sc3ccccc3)c(O)c3ccccc23)cc1] | C24H21NO4S2 | 451.5673 | 6.143 |
| F1566-0486 | 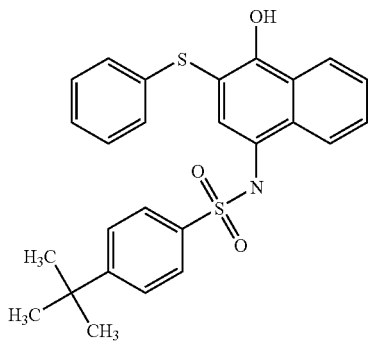 [SMILES: CC(C)(C)c1ccc(S(=O)(=O)Nc2cc(Sc3ccccc3)c(O)c3ccccc23)cc1] | C26H25NO3S2 | 463.6221 | 7.345 |
| F1566-0510 | 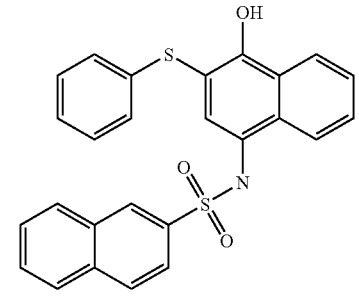 [SMILES: O=S(=O)(Nc1cc(Sc2ccccc2)c(O)c2ccccc12)c1ccc2ccccc2c1] | C26H19NO3S2 | 457.5742 | 7.105 |
| F1566-0546 | 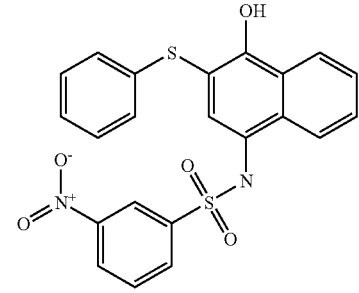 [SMILES: O=[N+]([O-])c1cccc(S(=O)(=O)Nc2cc(Sc3ccccc3)c(O)c3ccccc23)c1] | C22H16N2O5S2 | 452.5112 | 5.818 |

TABLE 7-continued
| IDNUMBER | Structure | Formula structure | MW | LogP |
|---|---|---|---|---|
| F1566-0558 | 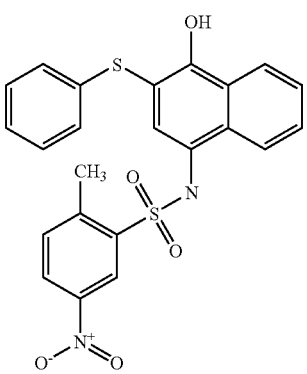 [SMILES: Cc1ccc([N+](=O)[O-])cc1S(=O)(=O)Nc1cc(Sc2ccccc2)c(O)c2ccccc12] | C23H18N2O5S2 | 466.5383 | 6.114 |
| F1566-0618 | 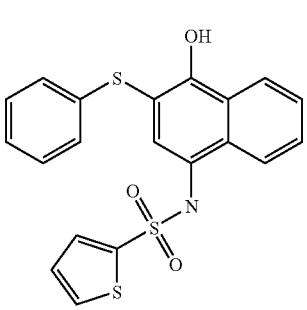 [SMILES: O=S(=O)(Nc1cc(Sc2ccccc2)c(O)c2ccccc12)c1cccs1] | C20H15NO3S3 | 413.5395 | 5.359 |
| F1566-1606 | 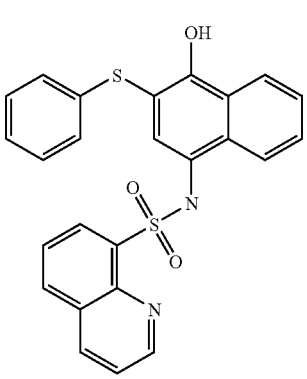 [SMILES: O=S(=O)(Nc1cc(Sc2ccccc2)c(O)c2ccccc12)c1cccc2cccnc12] | C25H18N2O3S2 | 458.5618 | 6.046 |
| F1566-1818 | 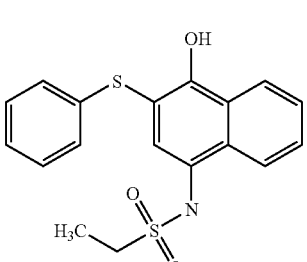 | C18H17NO3S2 | 359.4691 | 4.705 |
| F1566-1832 | 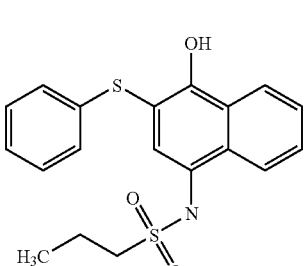 | C19H19NO3S2 | 373.4962 | 5.147 |

TABLE 7-continued

| IDNUMBER | Structure | Formula structure | MW | LogP |
|---|---|---|---|---|
| F1566-1846 | 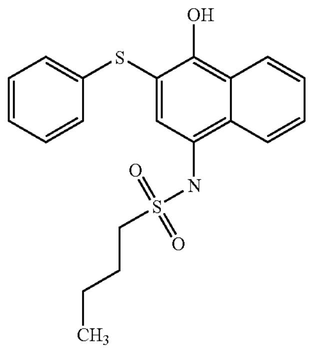 [SMILES: CCCCS(=O)(=O)Nc1cc(Sc2ccccc2)c(O)c2ccccc12] | C20H21NO3S2 | 387.5233 | 5.589 |
| F1566-1860 | 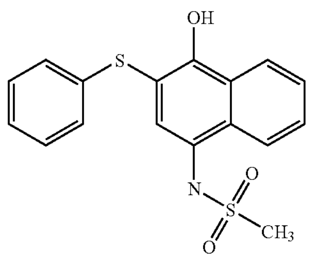 [SMILES: CS(=O)(=O)Nc1cc(Sc2ccccc2)c(O)c2ccccc12] | C17H15NO3S2 | 345.442 | 4.192 |
| F5749-0371 | 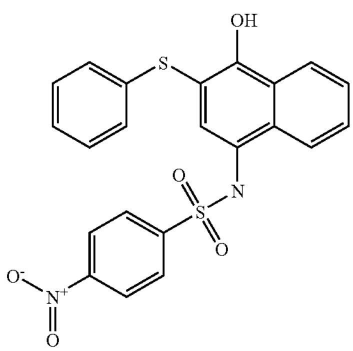 [SMILES: O=[N+]([O-])c1ccc(S(=O)(=O)Nc2cc(Sc3ccccc3)c(O)c3ccccc23)cc1] | C22H16N2O5S2 | 452.5112 | 5.781 |
| F5749-0372 | 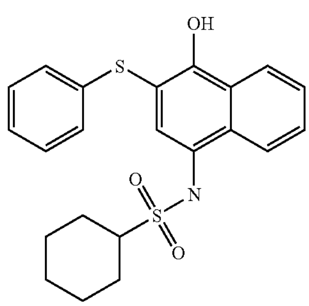 [SMILES: O=S(=O)(Nc1cc(Sc2ccccc2)c(O)c2ccccc12)C1CCCCC1] | C22H23NO3S2 | 413.5615 | 6.171 |
| F5749-0373 | 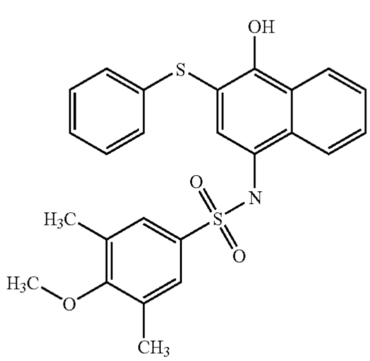 [SMILES: COc1c(C)cc(S(=O)(=O)Nc2cc(Sc3ccccc3)c(O)c3ccccc23)cc1C] | C25H23NO4S2 | 465.5944 | 6.468 |

TABLE 7-continued
| IDNUMBER | Structure | Formula structure | MW | LogP |
|---|---|---|---|---|
| F5749-0374 | 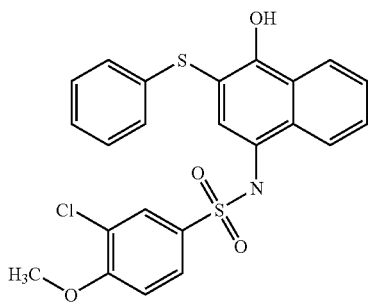 [SMILES: COc1ccc(S(=O)(=O)Nc2cc(Sc3ccccc3)c(O)c3ccccc23)cc1Cl] | C23H18ClNO4S2 | 471.9852 | 6.429 |
| F5749-0375 | 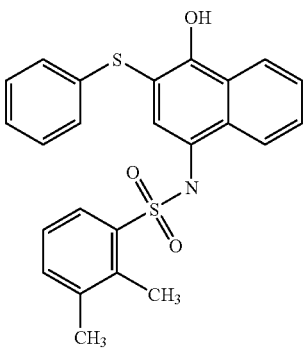 [SMILES: Cc1cccc(S(=O)(=O)Nc2cc(Sc3ccccc3)c(O)c3ccccc23)c1C] | C24H21NO3S2 | 435.5679 | 6.438 |
| F5749-0376 | 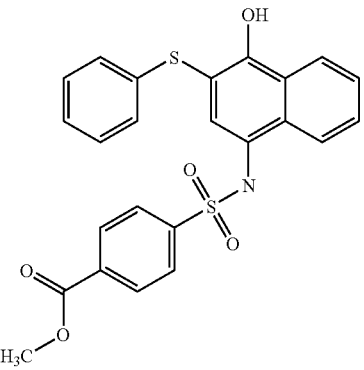 [SMILES: COC(=O)c1ccc(S(=O)(=O)Nc2cc(Sc3ccccc3)c(O)c3ccccc23)cc1] | C24H19NO5S2 | 465.5507 | 5.787 |
| F5749-0377 | 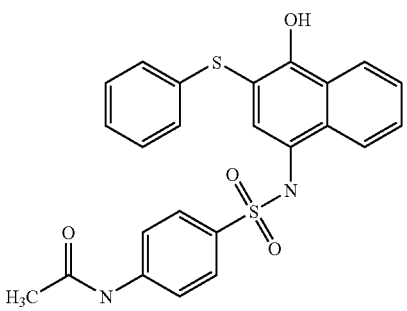 [SMILES: CC(=O)Nc1ccc(S(=O)(=O)Nc2cc(Sc3ccccc3)c(O)c3ccccc23)cc1] | C24H20N2O4S2 | 464.566 | 5.137 |

TABLE 7-continued

| IDNUMBER | Structure | Formula structure | MW | LogP |
|---|---|---|---|---|
| F5749-0378 | 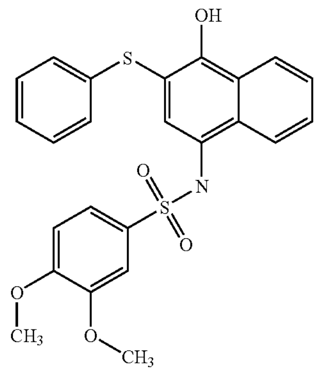 [SMILES: COc1ccc(S(=O)(=O)Nc2cc(Sc3ccccc3)c(O)c3ccccc23)cc1OC] | C24H21NO5S2 | 467.5667 | 5.54474 |
| F5749-0379 | 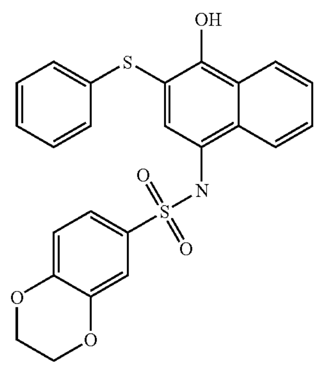 [SMILES: O=S(=O)(Nc1cc(Sc2ccccc2)c(O)c2ccccc12)c1ccc2c(c1)OCCO2] | C24H19NO5S2 | 465.5507 | 5.441 |
| F5749-0380 | 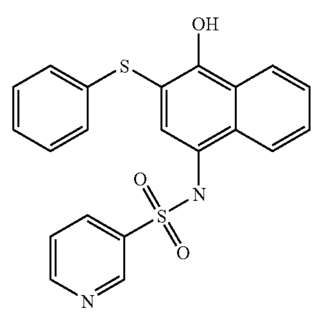 [SMILES: O=S(=O)(Nc1cc(Sc2ccccc2)c(O)c2ccccc12)c1cccnc1] | C21H16N2O3S2 | 408.5013 | 4.613 |
| F5749-0381 | 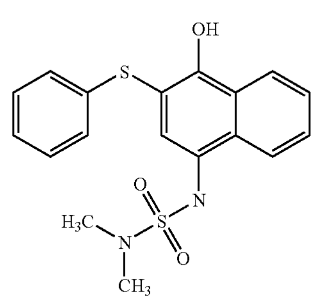 | C18H18N2O3S2 | 374.4838 | 3.74 |

TABLE 7-continued

| IDNUMBER | Structure | Formula structure | MW | LogP |
|---|---|---|---|---|
| F5749-0382 | 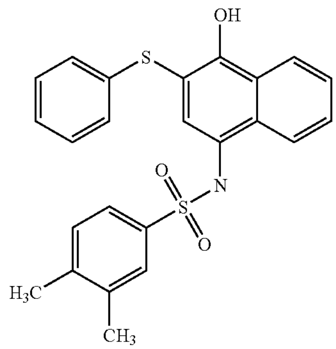 [SMILES: Cc1ccc(S(=O)(=O)Nc2cc(Sc3ccccc3)c(O)c3ccccc23)cc1C] | C24H21NO3S2 | 435.5679 | 6.477 |
| F5749-0383 | 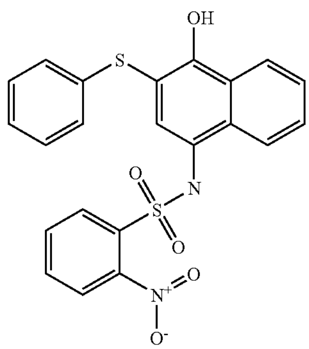 [SMILES: O=[N+]([O-])c1ccccc1S(=O)(=O)Nc1cc(Sc2ccccc2)c(O)c2ccccc12] | C22H16N2O5S2 | 452.5112 | 5.779 |
| F5749-0384 | 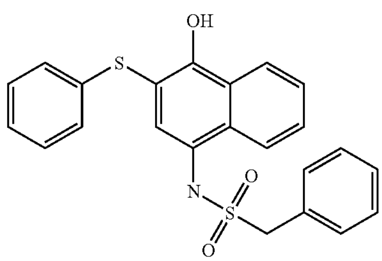 [SMILES: O=S(=O)(Cc1ccccc1)Nc1cc(Sc2ccccc2)c(O)c2ccccc12] | C23H19NO3S2 | 421.5408 | 5.98 |
| F5749-0385 | 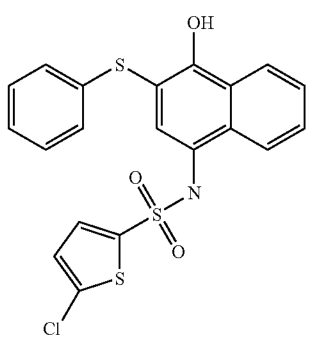 [SMILES: O=S(=O)(Nc1cc(Sc2ccccc2)c(O)c2ccccc12)c1ccc(Cl)s1] | C20H14ClNO3S3 | 447.9845 | 6.649 |
| F5749-0386 | 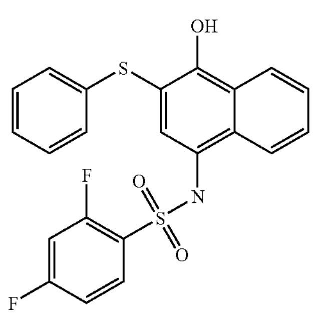 [SMILES: O=S(=O)(Nc1cc(Sc2ccccc2)c(O)c2ccccc12)c1ccc(F)cc1F] | C22H15F2NO3S2 | 443.4946 | 6.187 |

TABLE 7-continued

| IDNUMBER | Structure | Formula structure | MW | LogP |
|---|---|---|---|---|
| F5749-0387 | 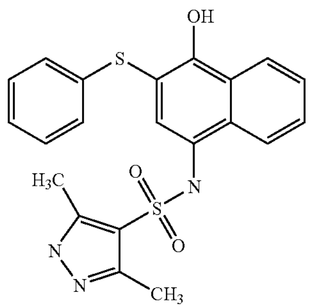 | C21H19N3O3S2 | 425.5319 | 4.956 |
| F5749-0388 | 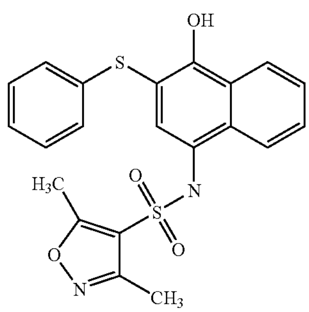 [SMILES: Cc1n[nH]c(C)c1S(=O)(=O)Nc1cc(Sc2ccccc2)c(O)c2ccccc12] | C21H18N2O4S2 | 426.5166 | 4.99 |
| F5749-0389 | 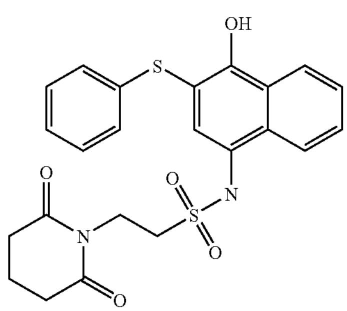 [SMILES: O=C1CCCC(=O)N1CCS(=O)(=O)Nc1cc(Sc2ccccc2)c(O)c2ccccc12] | C23H22N2O5S2 | 470.5702 | 3.633 |
| F5749-0390 | 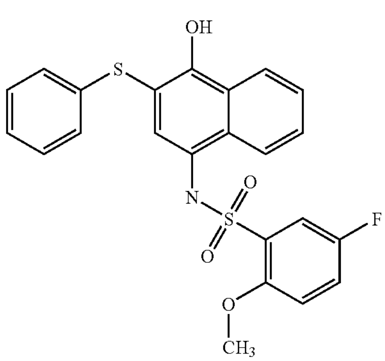 [SMILES: COc1ccc(F)cc1S(=O)(=O)Nc1cc(Sc2ccccc2)c(O)c2ccccc12] | C23H18FNO4S2 | 455.5306 | 5.99 |

TABLE 7-continued

| IDNUMBER | Structure | Formula structure | MW | LogP |
| --- | --- | --- | --- | --- |
| F5749-0391 | 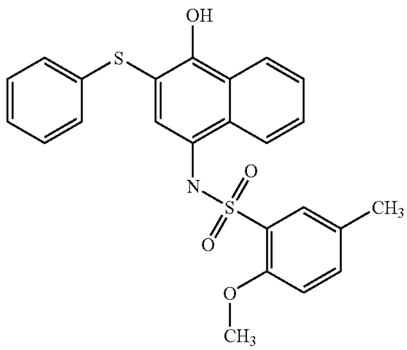 [SMILES: COc1ccc(C)cc1S(=O)(=O)Nc1cc(Sc2ccccc2)c(O)c2ccccc12] | C24H21NO4S2 | 451.5673 | 6.135 |
| F5749-0392 | 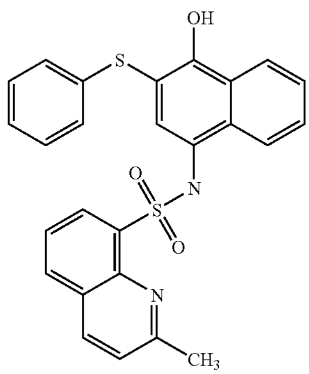 [SMILES: Cc1ccc2cccc(S(=O)(=O)Nc3cc(Sc4ccccc4)c(O)c4ccccc34)c2n1] | C26H20N2O3S2 | 472.5889 | 6.305 |
| F5749-0393 | 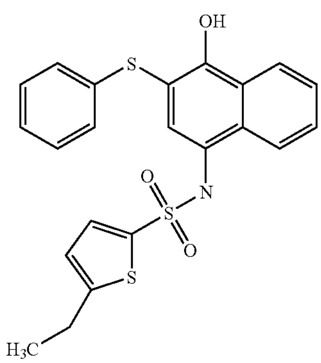 [SMILES: CCc1ccc(S(=O)(=O)Nc2cc(Sc3ccccc3)c(O)c3ccccc23)s1] | C22H19NO3S3 | 441.5936 | 6.497 |
| F5749-0394 | 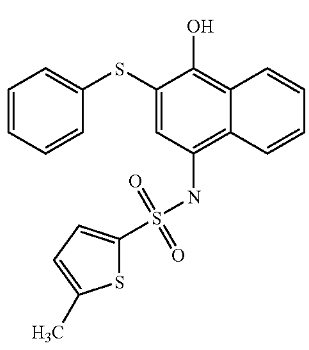 [SMILES: Cc1ccc(S(=O)(=O)Nc2cc(Sc3ccccc3)c(O)c3ccccc23)s1] | C21H17NO3S3 | 427.5665 | 6.022 |

TABLE 7-continued
| IDNUMBER | Structure | Formula structure | MW | LogP |
|---|---|---|---|---|
| F5749-0395 | 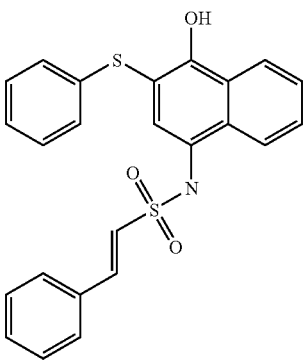 [SMILES: O=S(=O)(/C=C/c1ccccc1)Nc1cc(Sc2ccccc2)c(O)c2ccccc12] | C24H19NO3S2 | 433.5519 | 6.204 |
| F5749-0396 | 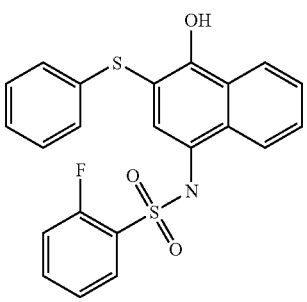 [SMILES: O=S(=O)(Nc1cc(Sc2ccccc2)c(O)c2ccccc12)c1ccccc1F] | C22H16FNO3S2 | 425.5041 | 5.997 |
| F5749-0397 | 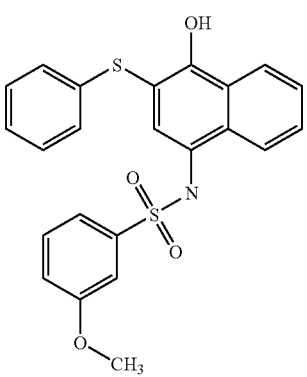 [SMILES: COc1cccc(S(=O)(=O)Nc2cc(Sc3ccccc3)c(O)c3ccccc23)c1] | C23H19NO4S2 | 437.5402 | 5.839 |
| F5749-0398 | 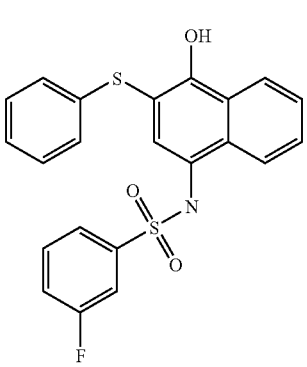 [SMILES: O=S(=O)(Nc1cc(Sc2ccccc2)c(O)c2ccccc12)c1cccc(F)c1] | C22H16FNO3S2 | 425.5041 | 6.036 |

TABLE 7-continued
| IDNUMBER | Structure | Formula structure | MW | LogP |
|---|---|---|---|---|
| F5749-0399 | 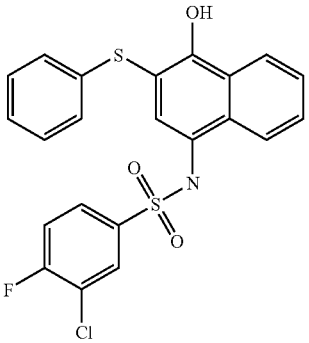 [SMILES: O=S(=O)(Nc1cc(Sc2ccccc2)c(O)c2ccccc12)c1ccc(F)c(Cl)c1] | C22H15ClFNO3S2 | 459.9492 | 6.626 |
| F5749-0400 | 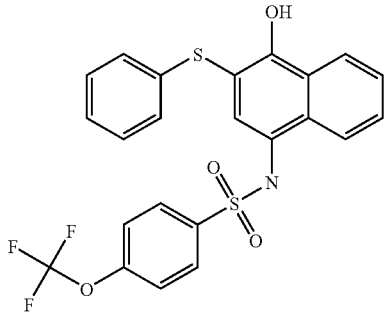 [SMILES: O=S(=O)(Nc1cc(Sc2ccccc2)c(O)c2ccccc12)c1ccc(OC(F)(F)F)cc1] | C23H16F3NO4S2 | 491.5115 | 7.24476 |
| F5749-0401 | 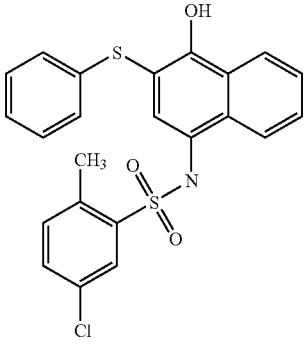 [SMILES: Cc1ccc(Cl)cc1S(=O)(=O)Nc1cc(Sc2ccccc2)c(O)c2ccccc12] | C23H18ClNO3S2 | 455.9858 | 6.771 |
| F5749-0402 | 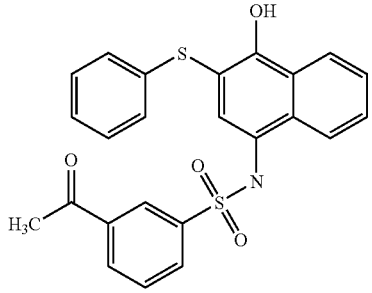 [SMILES: CC(=O)c1cccc(S(=O)(=O)Nc2cc(Sc3ccccc3)c(O)c3ccccc23)c1] | C24H19NO4S2 | 449.5513 | 5.736 |

TABLE 7-continued

| IDNUMBER | Structure | Formula structure | MW | LogP |
|---|---|---|---|---|
| F5749-0403 | 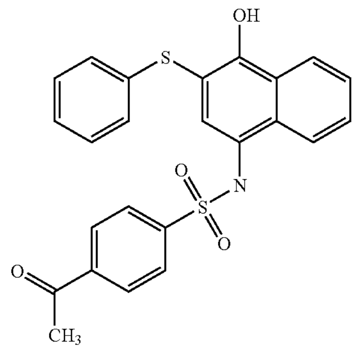 [SMILES: CC(=O)c1ccc(S(=O)(=O)Nc2cc(Sc3ccccc3)c(O)c3ccccc23)cc1] | C24H19NO4S2 | 449.5513 | 5.699 |
| F5749-0404 | 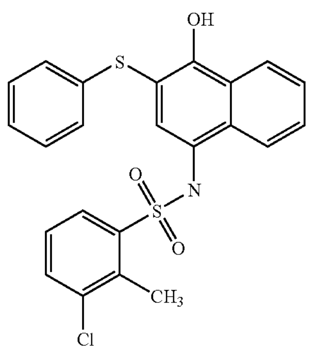 [SMILES: Cc1c(Cl)cccc1S(=O)(=O)Nc1cc(Sc2ccccc2)c(O)c2ccccc12] | C23H18ClNO3S2 | 455.9858 | 6.732 |
| F5749-0405 | 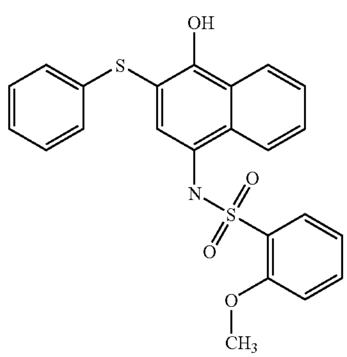 [SMILES: COc1ccccc1S(=O)(=O)Nc1cc(Sc2ccccc2)c(O)c2ccccc12] | C23H19NO4S2 | 437.5402 | 5.8 |
| F5749-0406 | 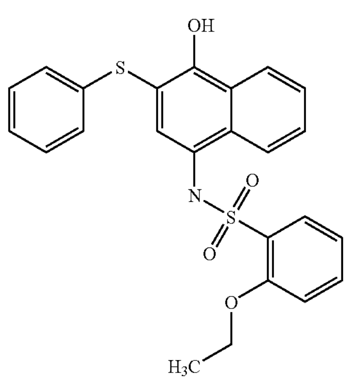 [SMILES: CCOc1ccccc1S(=O)(=O)Nc1cc(Sc2ccccc2)c(O)c2ccccc12] | C24H21NO4S2 | 451.5673 | 6.141 |

TABLE 7-continued

| IDNUMBER | Structure | Formula structure | MW | LogP |
| --- | --- | --- | --- | --- |
| F5749-0407 | 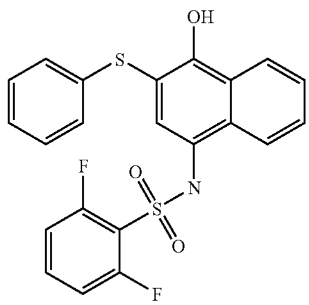 [SMILES: O=S(=O)(Nc1cc(Sc2ccccc2)c(O)c2ccccc12)c1c(F)cccc1F] | C22H15F2NO3S2 | 443.4946 | 6.148 |
| F5749-0408 | 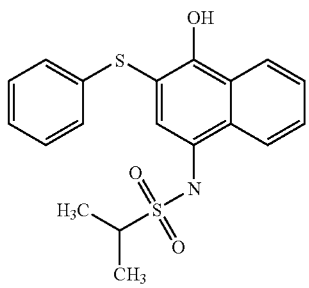 [SMILES: CC(C)S(=O)(=O)Nc1cc(Sc2ccccc2)c(O)c2ccccc12] | C19H19NO3S2 | 373.4962 | 5.339 |
| F5749-0409 | 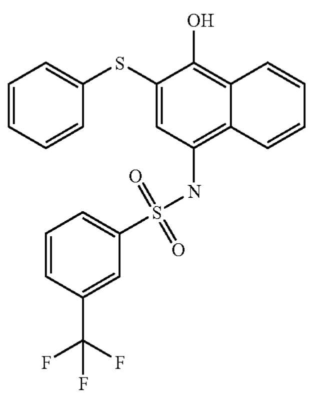 [SMILES: O=S(=O)(Nc1cc(Sc2ccccc2)c(O)c2ccccc12)c1cccc(C(F)(F)F)c1] | C23H16F3NO3S2 | 475.5121 | 6.81776 |
| F5749-0410 | 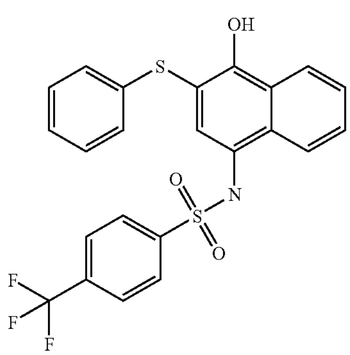 [SMILES: O=S(=O)(Nc1cc(Sc2ccccc2)c(O)c2ccccc12)c1ccc(C(F)(F)F)cc1] | C23H16F3NO3S2 | 475.5121 | 6.78076 |
| F5749-0411 | 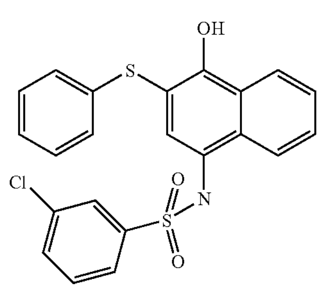 [SMILES: O=S(=O)(Nc1cc(Sc2ccccc2)c(O)c2ccccc12)c1cccc(Cl)c1] | C22H16ClNO3S2 | 441.9587 | 6.475 |

TABLE 7-continued

| IDNUMBER | Structure | Formula structure | MW | LogP |
|---|---|---|---|---|
| F5749-0412 | 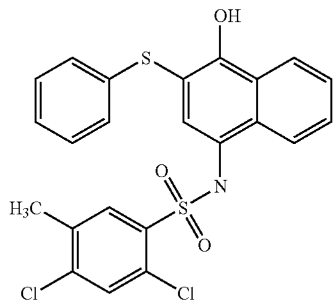 [SMILES: Cc1cc(S(=O)(=O)Nc2cc(Sc3ccccc3)c(O)c3ccccc23)c(Cl)cc1Cl] | C23H17Cl2NO3S2 | 490.4308 | 7.398 |
| F5749-0413 | 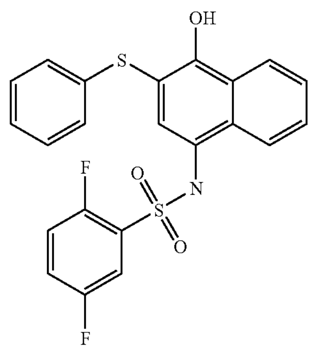 [SMILES: O=S(=O)(Nc1cc(Sc2ccccc2)c(O)c2ccccc12)c1cc(F)ccc1F] | C22H15F2NO3S2 | 443.4946 | 6.187 |
| F5749-0414 | 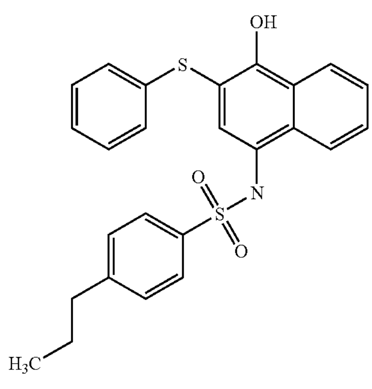 [SMILES: CCCc1ccc(S(=O)(=O)Nc2cc(Sc3ccccc3)c(O)c3ccccc23)cc1] | C25H23NO3S2 | 449.595 | 7.061 |
| F5749-0415 | 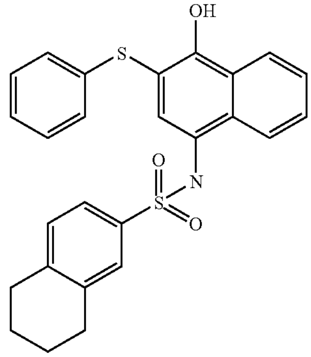 [SMILES: O=S(=O)(Nc1cc(Sc2ccccc2)c(O)c2ccccc12)c1ccc2c(c1)CCCC2] | C26H23NO3S2 | 461.6061 | 6.933 |

//

TABLE 7-continued

| IDNUMBER | Structure | Formula structure | MW | LogP |
|---|---|---|---|---|
| F5749-0416 | 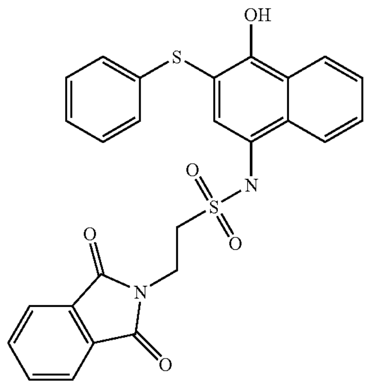 [SMILES: O=C1c2ccccc2C(=O)N1CCS(=O)(=O)Nc1cc(Sc2ccccc2)c(O)c2ccccc12] | C26H20N2O5S2 | 504.5877 | 4.973 |
| F5749-0417 | 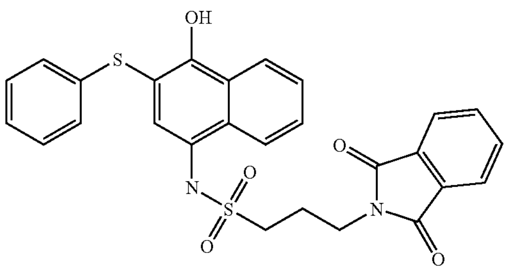 [SMILES: O=C1c2ccccc2C(=O)N1CCCS(=O)(=O)Nc1cc(Sc2ccccc2)c(O)c2ccccc12] | C27H22N2O5S2 | 518.6148 | 5.415 |
| F5749-0418 | 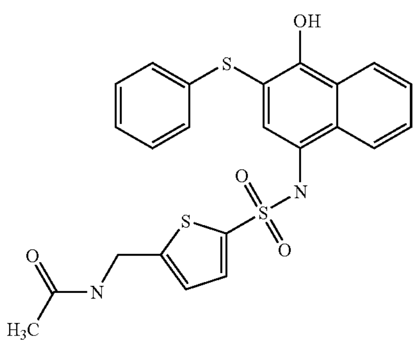 [SMILES: CC(=O)NCc1ccc(S(=O)(=O)Nc2cc(Sc3ccccc3)c(O)c3ccccc23)s1] | C23H20N2O4S3 | 484.6189 | 5.149 |
| F5749-0419 | 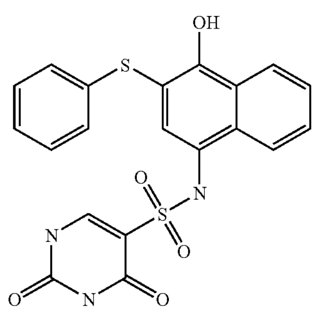 [SMILES: O=c1[nH]cc(S(=O)(=O)Nc2cc(Sc3ccccc3)c(O)c3ccccc23)c(=O)[nH]1] | C20H15N3O5S2 | 441.4877 | 2.891 |
| F5749-0420 | 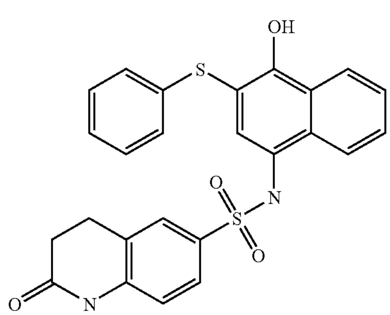 [SMILES: O=C1CCc2cc(S(=O)(=O)Nc3cc(Sc4ccccc4)c(O)c4ccccc34)ccc2N1] | C25H20N2O4S2 | 476.5772 | 5.042 |

TABLE 7-continued
| IDNUMBER | Structure | Formula structure | MW | LogP |
|---|---|---|---|---|
| F5749-0421 | 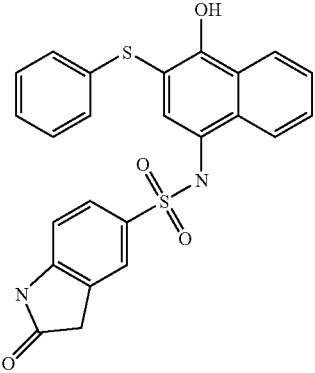 [SMILES: O=C1Cc2cc(S(=O)(=O)Nc3cc(Sc4ccccc4)c(O)c4ccccc34)ccc2N1] | C24H18N2O4S2 | 462.5501 | 4.954 |
| F5749-0422 | 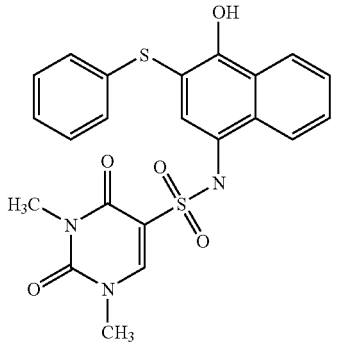 [SMILES: Cn1cc(S(=O)(=O)Nc2cc(Sc3ccccc3)c(O)c3ccccc23)c(=O)n(C)c1=O] | C22H19N3O5S2 | 469.5418 | 2.955 |
| F5749-0423 | 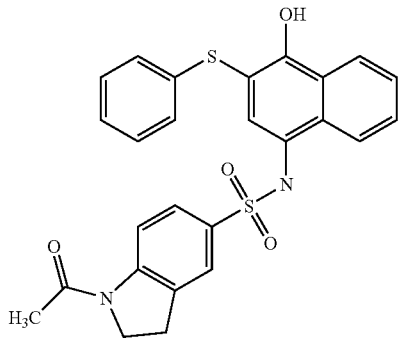 [SMILES: CC(=O)N1CCc2cc(S(=O)(=O)Nc3cc(Sc4ccccc4)c(O)c4ccccc34)ccc21] | C26H22N2O4S2 | 490.6042 | 5.277 |
| F5749-0424 | 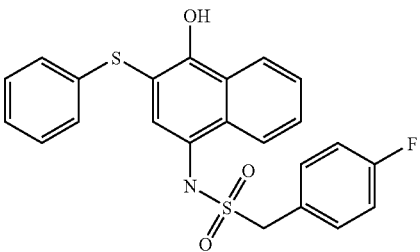 [SMILES: O=S(=O)(Cc1ccc(F)cc1)Nc1cc(Sc2ccccc2)c(O)c2ccccc12] | C23H18FNO3S2 | 439.5312 | 6.133 |

TABLE 7-continued

| IDNUMBER | Structure | Formula structure | MW | LogP |
|---|---|---|---|---|
| F5749-0425 | 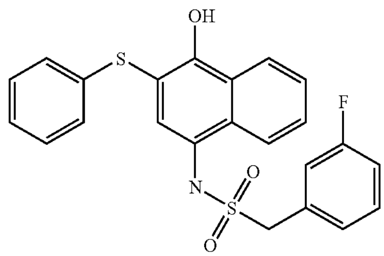 [SMILES: O=S(=O)(Cc1cccc(F)c1)Nc1cc(Sc2ccccc2)c(O)c2ccccc12] | C23H18FNO3S2 | 439.5312 | 6.17 |
| F5749-0426 | 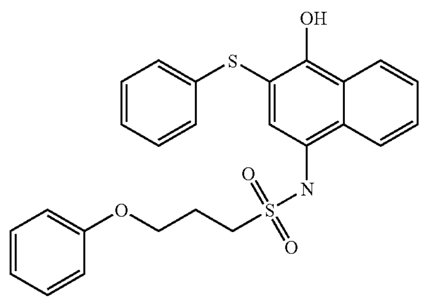 [SMILES: O=S(=O)(CCCOc1ccccc1)Nc1cc(Sc2ccccc2)c(O)c2ccccc12] | C25H23NO4S2 | 465.5944 | 6.206 |
| F5749-0427 | 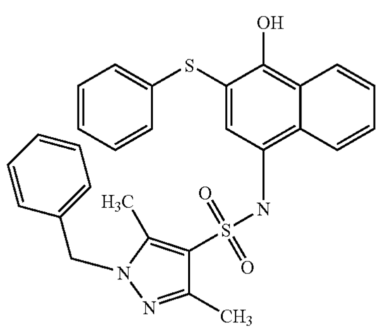 [SMILES: Cc1nn(Cc2ccccc2)c(C)c1S(=O)(=O)Nc1cc(Sc2ccccc2)c(O)c2ccccc12] | C28H25N3O3S2 | 515.6578 | 6.125 |
| F5749-0428 | 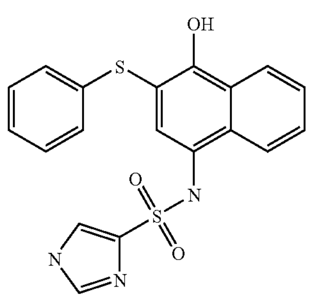 [SMILES: O=S(=O)(Nc1cc(Sc2ccccc2)c(O)c2ccccc12)c1c[nH]cn1] | C19H15N3O3S2 | 397.4777 | 3.986 |
| F5749-0429 | 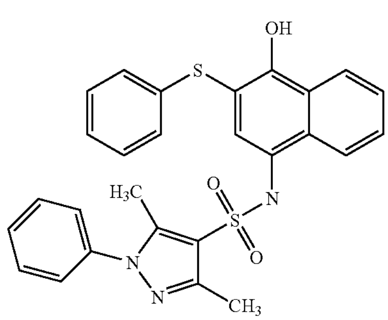 [SMILES: Cc1nn(-c2ccccc2)c(C)c1S(=O)(=O)Nc1cc(Sc2ccccc2)c(O)c2ccccc12] | C27H23N3O3S2 | 501.6307 | 5.991 |

TABLE 7-continued

| IDNUMBER | Structure | Formula structure | MW | LogP |
|---|---|---|---|---|
| F5749-0430 | 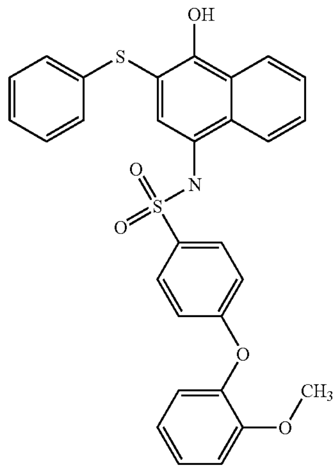 [SMILES: COc1ccccc1Oc1ccc(S(=O)(=O)Nc2cc(Sc3ccccc3)c(O)c3ccccc23)cc1] | C29H23NO5S2 | 529.6384 | 7.16174 |
| F5749-0431 | 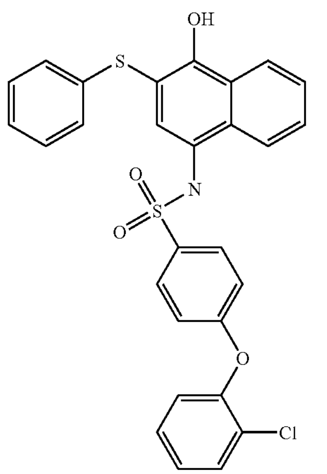 [SMILES: O=S(=O)(Nc1cc(Sc2ccccc2)c(O)c2ccccc12)c1ccc(Oc2ccccc2Cl)cc1] | C28H20ClNO4S2 | 534.0569 | 8.046 |
| F5749-0432 | 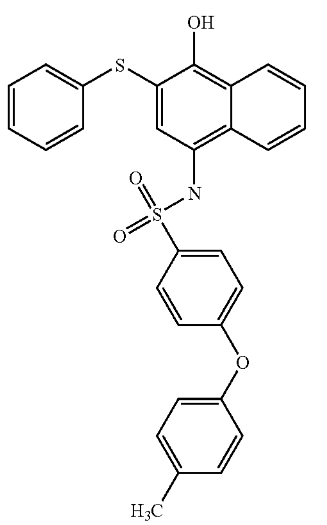 [SMILES: Cc1ccc(Oc2ccc(S(=O)(=O)Nc3cc(Sc4ccccc4)c(O)c4ccccc34)cc2)cc1] | C29H23NO4S2 | 513.639 | 7.754 |

TABLE 7-continued

| IDNUMBER | Structure | Formula structure | MW | LogP |
|---|---|---|---|---|
| F5749-0433 | 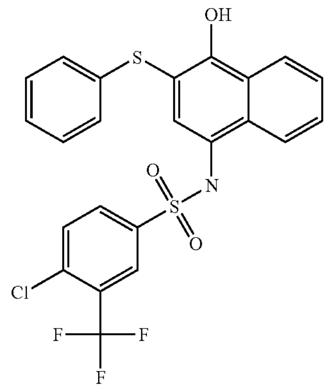 [SMILES: O=S(=O)(Nc1cc(Sc2ccccc2)c(O)c2ccccc12)c1ccc(Cl)c(C(F)(F)F)c1] | C23H15ClF3NO3S2 | 509.9571 | 7.40776 |
| F5749-0434 | 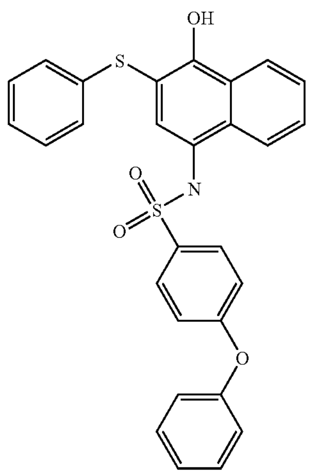 [SMILES: O=S(=O)(Nc1cc(Sc2ccccc2)c(O)c2ccccc12)c1ccc(Oc2ccccc2)cc1] | C28H21NO4S2 | 499.6119 | 7.456 |
| F5749-0435 | 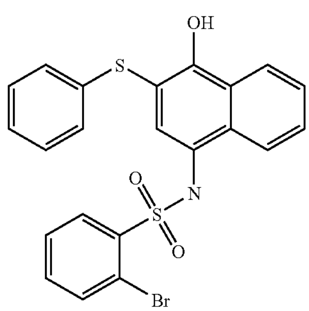 [SMILES: O=S(=O)(Nc1cc(Sc2ccccc2)c(O)c2ccccc12)c1ccccc1Br] | C22H16BrNO3S2 | 486.4097 | 6.642 |
| F5749-0436 | 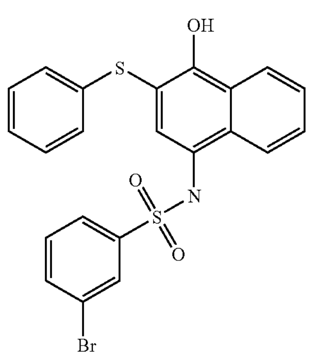 [SMILES: O=S(=O)(Nc1cc(Sc2ccccc2)c(O)c2ccccc12)c1cccc(Br)c1] | C22H16BrNO3S2 | 486.4097 | 6.681 |

TABLE 7-continued
| IDNUMBER | Structure | Formula structure | MW | LogP |
|---|---|---|---|---|
| F5749-0437 | 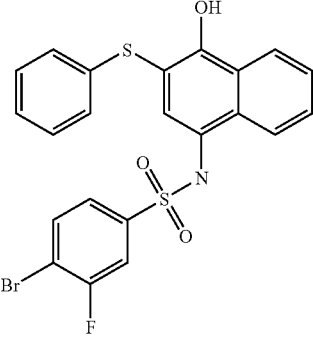 [SMILES: O=S(=O)(Nc1cc(Sc2ccccc2)c(O)c2ccccc12)c1ccc(Br)c(F)c1] | C22H15BrFNO3S2 | 504.4002 | 6.832 |
| F5749-0438 | 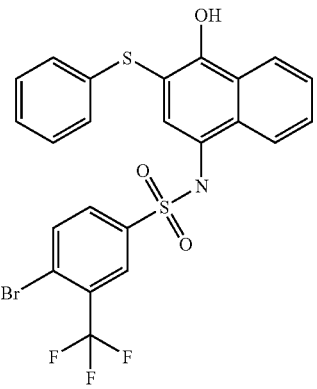 [SMILES: O=S(=O)(Nc1cc(Sc2ccccc2)c(O)c2ccccc12)c1ccc(Br)c(C(F)(F)F)c1] | C23H15BrF3NO3S2 | 554.4081 | 7.61376 |
| F5749-0439 | 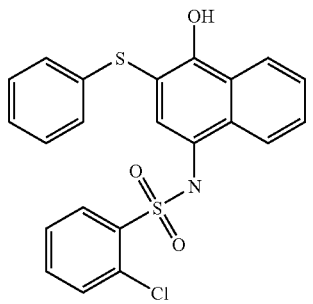 | C22H16ClNO3S2 | 441.9587 | 6.436 |
| F5749-0440 | 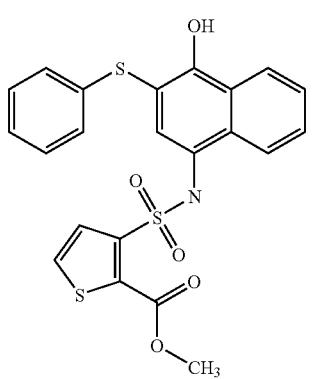 [SMILES: COC(=O)c1sccc1S(=O)(=O)Nc1cc(Sc2ccccc2)c(O)c2ccccc12] | C22H17NO5S3 | 471.5765 | 5.046 |

TABLE 7-continued
| IDNUMBER | Structure | Formula structure | MW | LogP |
|---|---|---|---|---|
| F5749-0441 | 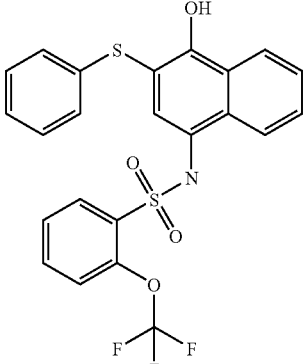 | C23H16F3NO4S2 | 491.5115 | 7.24276 |
TABLE 8
| IDNUMBER | Structure | Formula structure | MW | LogP |
|---|---|---|---|---|
| F0808-0081 | 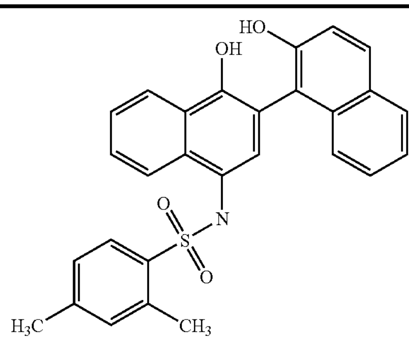 | C28H23NO4S | 469.5638 | 7.101 |
| F0808-0084 | 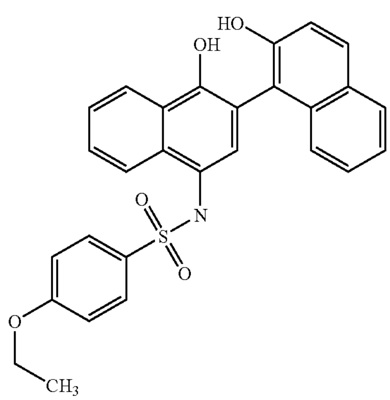 [SMILES: CCOc1ccc(S(=O)(=O)Nc2cc(-c3c(O)ccc4ccccc34)c(O)c3ccccc23)cc1] | C28H23NO5S | 485.5632 | 6.767 |
| F0808-0085 | 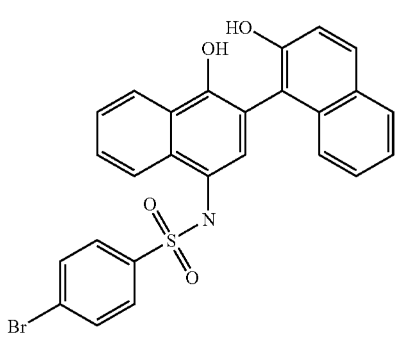 | C26H18BrNO4S | 520.4057 | 7.268 |

TABLE 8-continued
| IDNUMBER | Structure | Formula structure | MW | LogP |
|---|---|---|---|---|
| F0808-0086 | 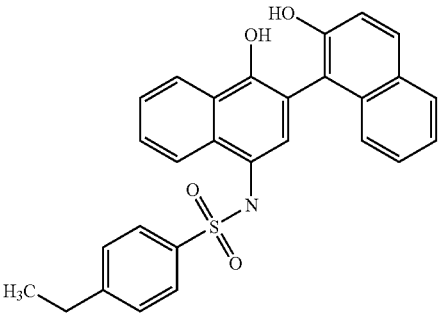 [SMILES: CCc1ccc(S(=O)(=O)Nc2cc(-c3c(O)ccc4ccccc34)c(O)c3ccccc23)cc1] | C28H23NO4S | 469.5638 | 7.243 |
| F0808-0089 | 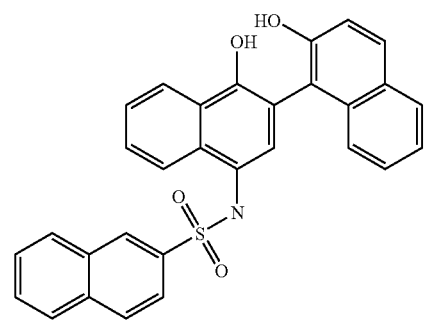 [SMILES: O=S(=O)(Nc1cc(-c2c(O)ccc3ccccc23)c(O)c2ccccc12)c1ccc2ccccc2c1] | C30H21NO4S | 491.5702 | 7.729 |
| F0808-0091 | 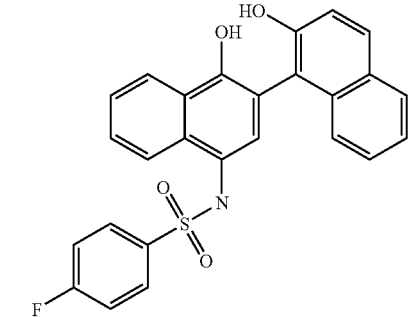 [SMILES: O=S(=O)(Nc1cc(-c2c(O)ccc3ccccc23)c(O)c2ccccc12)c1ccc(F)cc1] | C26H18FNO4S | 459.5001 | 6.623 |
| F0808-0092 | 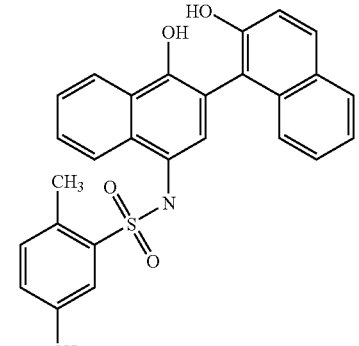 | C28H23NO4S | 469.5638 | 7.101 |

TABLE 8-continued
| IDNUMBER | Structure | Formula structure | MW | LogP |
| --- | --- | --- | --- | --- |
| F0808-0094 | 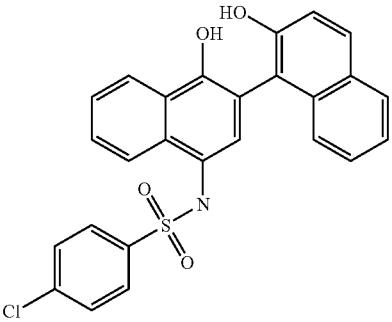 [SMILES: O=S(=O)(Nc1cc(-c2c(O)ccc3ccccc23)c(O)c2ccccc12)c1ccc(Cl)cc1] | C26H18ClNO4S | 475.9547 | 7.062 |
| F1269-0222 | 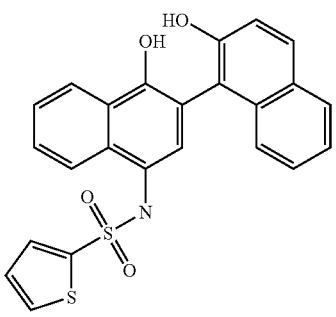 [SMILES: O=S(=O)(Nc1cc(-c2c(O)ccc3ccccc23)c(O)c2ccccc12)c1cccs1] | C24H17NO4S2 | 447.5354 | 5.983 |
| F1269-2003 | 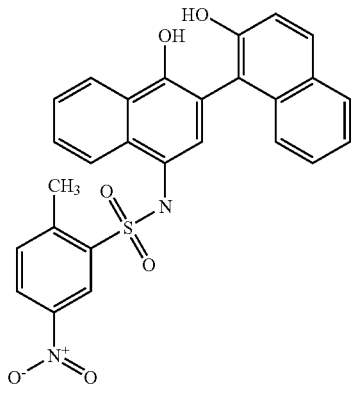 [SMILES: Cc1ccc([N+](=O)[O-])cc1S(=O)(=O)Nc1cc(-c2c(O)ccc3ccccc23)c(O)c2ccccc12] | C27H20N2O6S | 500.5343 | 6.738 |
| F1566-1138 | 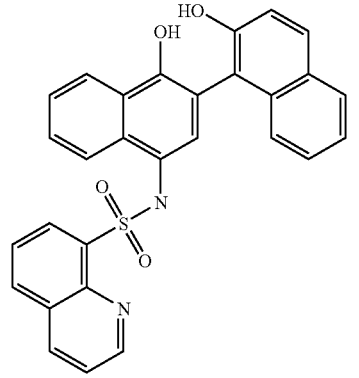 [SMILES: O=S(=O)(Nc1cc(-c2c(O)ccc3ccccc23)c(O)c2ccccc12)c1cccc2cccnc12] | C29H20N2O4S | 492.5578 | 6.67 |

TABLE 8-continued

| IDNUMBER | Structure | Formula structure | MW | LogP |
|---|---|---|---|---|
| F5749-0001 | 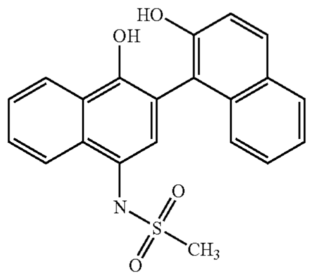 [SMILES: CS(=O)(=O)Nc1cc(-c2c(O)ccc3ccccc23)c(O)c2ccccc12] | C21H17NO4S | 379.4379 | 4.816 |
| F5749-0002 | 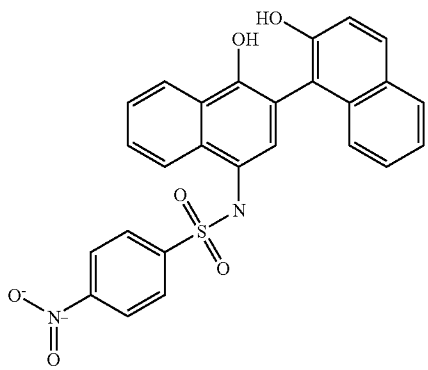 | C26H18N2O6S | 486.5072 | 6.405 |
| F5749-0003 | 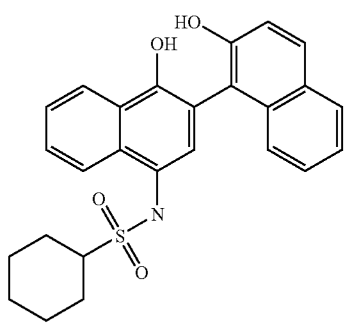 [SMILES: O=S(=O)(Nc1cc(-c2c(O)ccc3ccccc23)c(O)c2ccccc12)C1CCCCC1] | C26H25NO4S | 447.5575 | 6.795 |
| F5749-0004 | 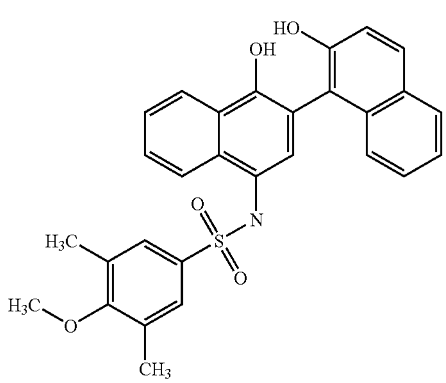 [SMILES: COc1c(C)cc(S(=O)(=O)Nc2cc(-c3c(O)ccc4ccccc34)c(O)c3ccccc23)cc1C] | C29H25NO5S | 499.5903 | 7.092 |

TABLE 8-continued
| IDNUMBER | Structure | Formula structure | MW | LogP |
|---|---|---|---|---|
| F5749-0005 | 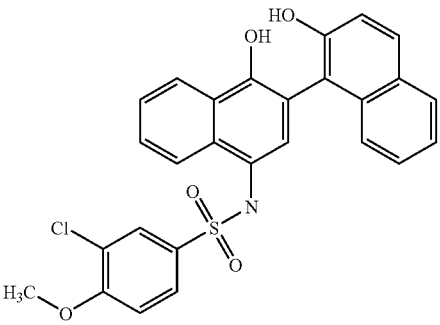 [SMILES: COc1ccc(S(=O)(=O)Nc2cc(-c3c(O)ccc4ccccc34)c(O)c3ccccc23)cc1Cl] | C27H20ClNO5S | 505.9812 | 7.053 |
| F5749-0006 | 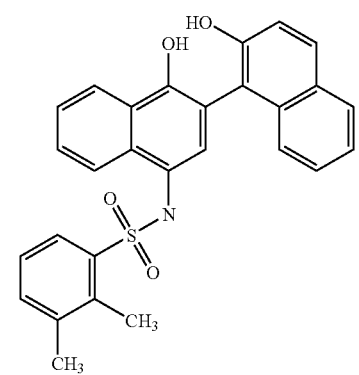 [SMILES: Cc1cccc(S(=O)(=O)Nc2cc(-c3c(O)ccc4ccccc34)c(O)c3ccccc23)c1C] | C28H23NO4S | 469.5638 | 7.062 |
| F5749-0007 | 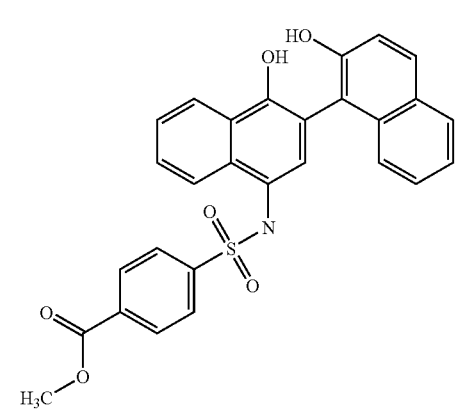 [SMILES: COC(=O)c1ccc(S(=O)(=O)Nc2cc(-c3c(O)ccc4ccccc34)c(O)c3ccccc23)cc1] | C28H21NO6S | 499.5467 | 6.411 |
| F5749-0008 | 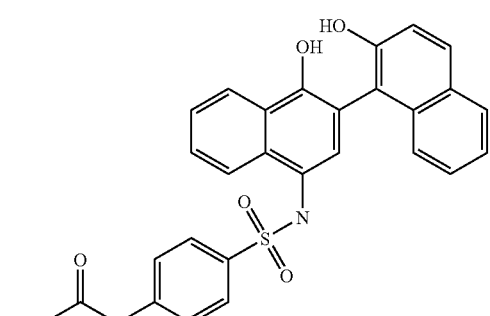 | C28H22N2O5S | 498.5619 | 5.761 |

TABLE 8-continued

| IDNUMBER | Structure | Formula structure | MW | LogP |
|---|---|---|---|---|
| F5749-0009 | 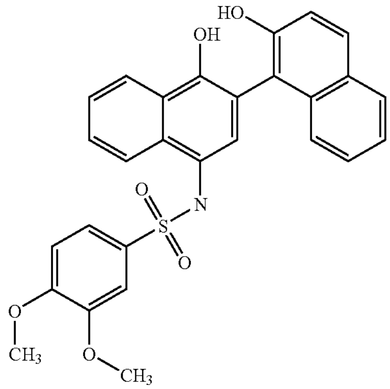 [SMILES: COc1ccc(S(=O)(=O)Nc2cc(-c3c(O)ccc4ccccc34)c(O)c3ccccc23)cc1OC] | C28H23NO6S | 501.5626 | 6.16874 |
| F5749-0010 | 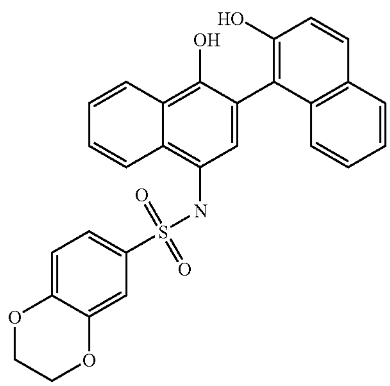 [SMILES: O=S(=O)(Nc1cc(-c2c(O)ccc3ccccc23)c(O)c2ccccc12)c1ccc2c(c1)OCCO2] | C28H21NO6S | 499.5467 | 6.065 |
| F5749-0011 | 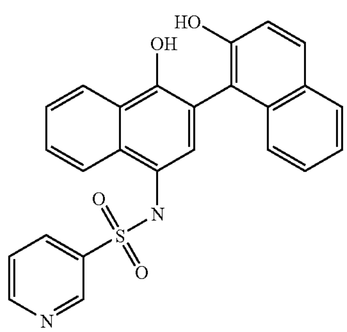 [SMILES: O=S(=O)(Nc1cc(-c2c(O)ccc3ccccc23)c(O)c2ccccc12)c1cccnc1] | C25H18N2O4S | 442.4972 | 5.237 |
| F5749-0012 | 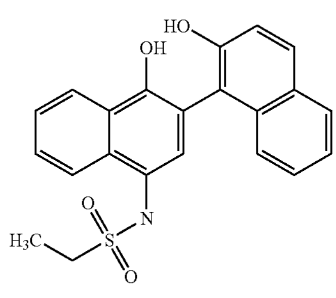 [SMILES: CCS(=O)(=O)Nc1cc(-c2c(O)ccc3ccccc23)c(O)c2ccccc12] | C22H19NO4S | 393.465 | 5.329 |

TABLE 8-continued

| IDNUMBER | Structure | Formula structure | MW | LogP |
| --- | --- | --- | --- | --- |
| F5749-0013 | 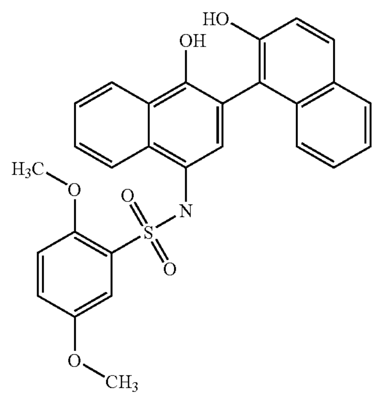 [SMILES: COc1ccc(OC)c(S(=O)(=O)Nc2cc(-c3c(O)ccc4ccccc34)c(O)c3ccccc23)c1] | C28H23NO6S | 501.5626 | 6.417 |
| F5749-0014 | 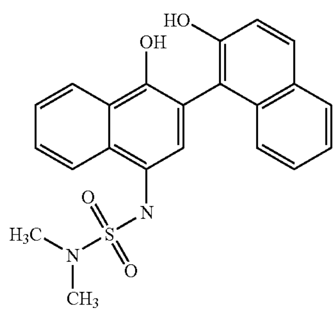 [SMILES: CN(C)S(=O)(=O)Nc1cc(-c2c(O)ccc3ccccc23)c(O)c2ccccc12] | C22H20N2O4S | 408.4797 | 4.364 |
| F5749-0015 | 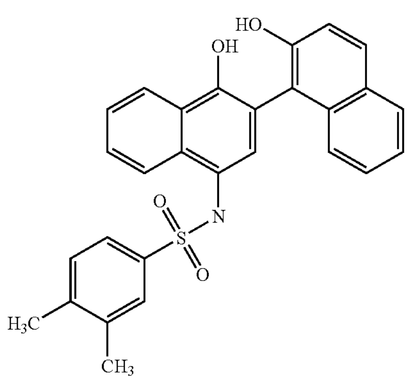 [SMILES: Cc1ccc(S(=O)(=O)Nc2cc(-c3c(O)ccc4ccccc34)c(O)c3ccccc23)cc1C] | C28H23NO4S | 469.5638 | 7.101 |
| F5749-0016 | 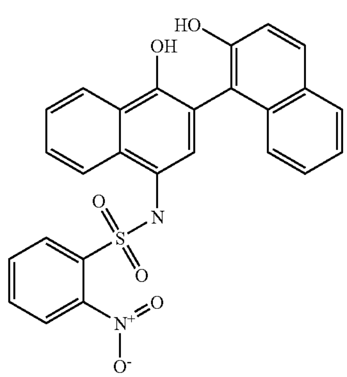 [SMILES: O=[N+]([O-])c1ccccc1S(=O)(=O)Nc1cc(-c2c(O)ccc3ccccc23)c(O)c2ccccc12] | C26H18N2O6S | 486.5072 | 6.403 |

TABLE 8-continued

| IDNUMBER | Structure | Formula structure | MW | LogP |
|---|---|---|---|---|
| F5749-0017 | 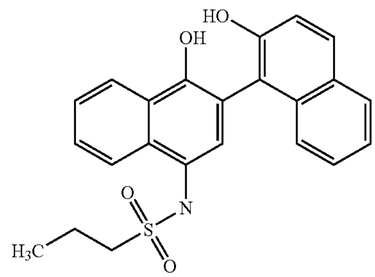 [SMILES: CCCS(=O)(=O)Nc1cc(-c2c(O)ccc3ccccc23)c(O)c2ccccc12] | C23H21NO4S | 407.4921 | 5.771 |
| F5749-0018 | 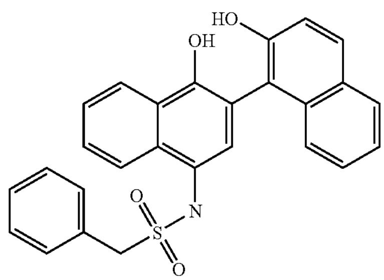 [SMILES: O=S(=O)(Cc1ccccc1)Nc1cc(-c2c(O)ccc3ccccc23)c(O)c2ccccc12] | C27H21NO4S | 455.5367 | 6.604 |
| F5749-0019 | 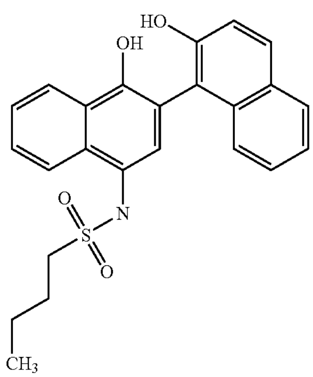 [SMILES: CCCCS(=O)(=O)Nc1cc(-c2c(O)ccc3ccccc23)c(O)c2ccccc12] | C24H23NO4S | 421.5192 | 6.213 |
| F5749-0020 | 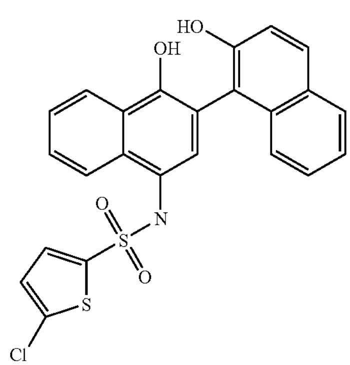 [SMILES: O=S(=O)(Nc1cc(-c2c(O)ccc3ccccc23)c(O)c2ccccc12)c1ccc(Cl)s1] | C24H16ClNO4S2 | 481.9804 | 7.273 |

TABLE 8-continued
| IDNUMBER | Structure | Formula structure | MW | LogP |
| --- | --- | --- | --- | --- |
| F5749-0021 | 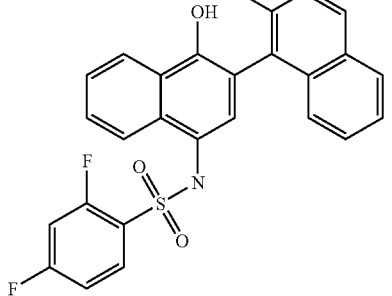 | C26H17F2NO4S | 477.4905 | 6.811 |
| F5749-0022 | 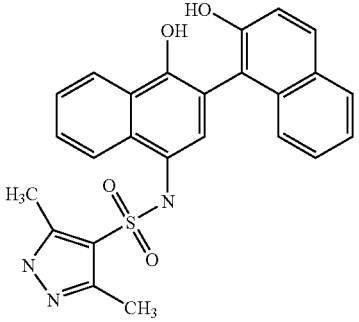 | C25H21N3O4S | 459.5278 | 5.58 |
| F5749-0023 | 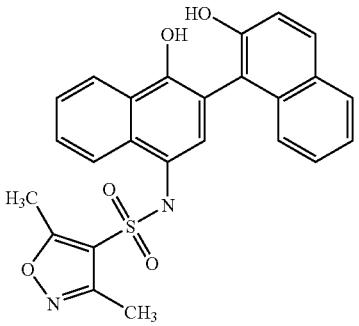 [SMILES: Cc1n[nH]c(C)c1S(=O)(=O)Nc1cc(-c2c(O)ccc3ccccc23)c(O)c2ccccc12] | C25H20N2O5S | 460.5126 | 5.614 |
| F5749-0024 | 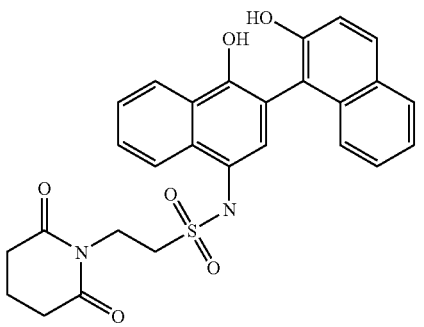 [SMILES: O=C1CCCC(=O)N1CCS(=O)(=O)Nc1cc(-c2c(O)ccc3ccccc23)c(O)c2ccccc12] | C27H24N2O6S | 504.5661 | 4.257 |

TABLE 8-continued

| IDNUMBER | Structure | Formula structure | MW | LogP |
|---|---|---|---|---|
| F5749-0025 | 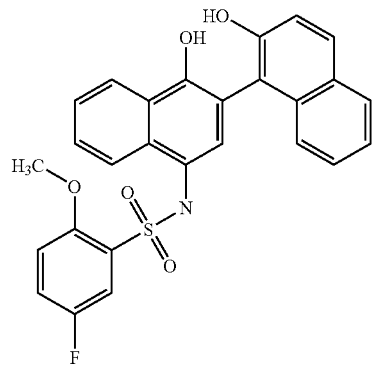 [SMILES: COc1ccc(F)cc1S(=O)(=O)Nc1cc(-c2c(O)ccc3ccccc23)c(O)c2ccccc12] | C27H20FNO5S | 489.5266 | 6.614 |
| F5749-0026 | 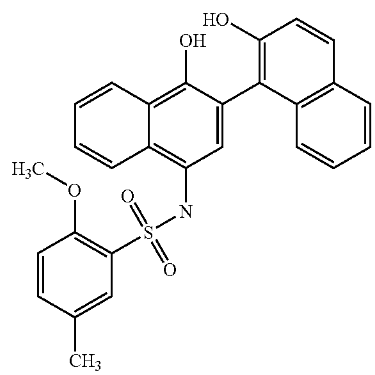 [SMILES: COc1ccc(C)cc1S(=O)(=O)Nc1cc(-c2c(O)ccc3ccccc23)c(O)c2ccccc12] | C28H23NO5S | 485.5632 | 6.759 |
| F5749-0027 | 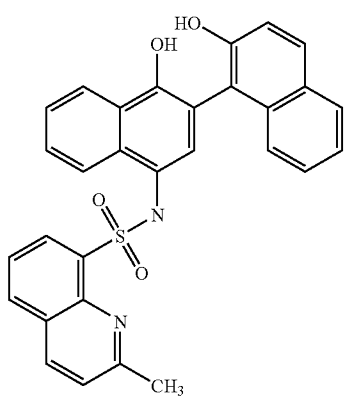 [SMILES: Cc1ccc2cccc(S(=O)(=O)Nc3cc(-c4c(O)ccc5ccccc45)c(O)c4ccccc34)c2n1] | C30H22N2O4S | 506.5848 | 6.929 |
| F5749-0028 | 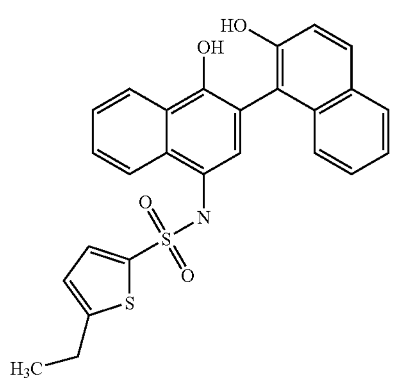 [SMILES: CCc1ccc(S(=O)(=O)Nc2cc(-c3c(O)ccc4ccccc34)c(O)c3ccccc23)s1] | C26H21NO4S2 | 475.5896 | 7.121 |

TABLE 8-continued

| IDNUMBER | Structure | Formula structure | MW | LogP |
|---|---|---|---|---|
| F5749-0029 | 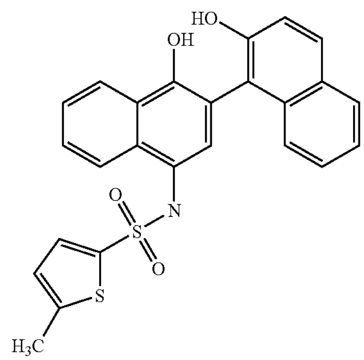 [SMILES: Cc1ccc(S(=O)(=O)Nc2cc(-c3c(O)ccc4ccccc34)c(O)c3ccccc23)s1] | C25H19NO4S2 | 461.5625 | 6.646 |
| F5749-0030 | 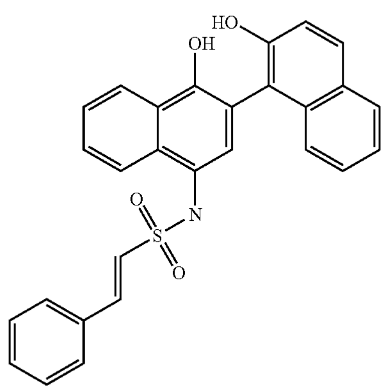 [SMILES: O=S(=O)(/C=C/c1ccccc1)Nc1cc(-c2c(O)ccc3ccccc23)c(O)c2ccccc12] | C28H21NO4S | 467.5479 | 6.828 |
| F5749-0031 | 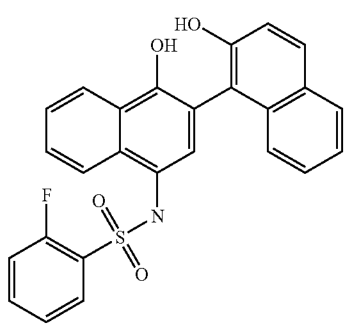 [SMILES: O=S(=O)(Nc1cc(-c2c(O)ccc3ccccc23)c(O)c2ccccc12)c1ccccc1F] | C26H18FNO4S | 459.5001 | 6.621 |
| F5749-0032 | 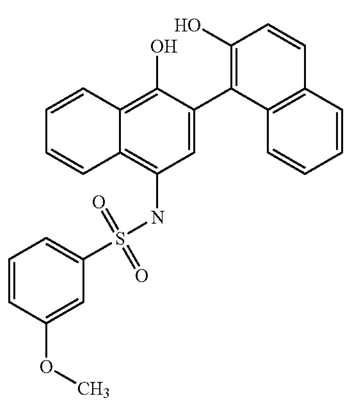 [SMILES: COc1cccc(S(=O)(=O)Nc2cc(-c3c(O)ccc4ccccc34)c(O)c3ccccc23)c1] | C27H21NO5S | 471.5361 | 6.463 |

TABLE 8-continued

| IDNUMBER | Structure | Formula structure | MW | LogP |
|---|---|---|---|---|
| F5749-0033 | 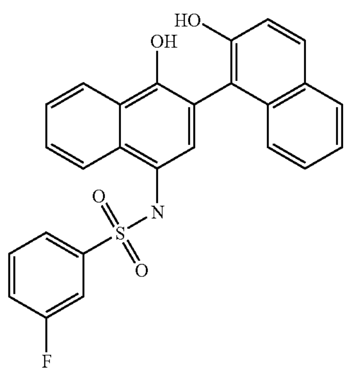 | C26H18FNO4S | 459.5001 | 6.66 |
| F5749-0034 | 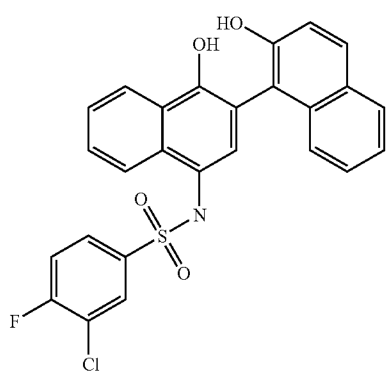 [SMILES: O=S(=O)(Nc1cc(-c2c(O)ccc3ccccc23)c(O)c2ccccc12)c1ccc(F)c(Cl)c1] | C26H17ClFNO4S | 493.9451 | 7.25 |
| F5749-0035 | 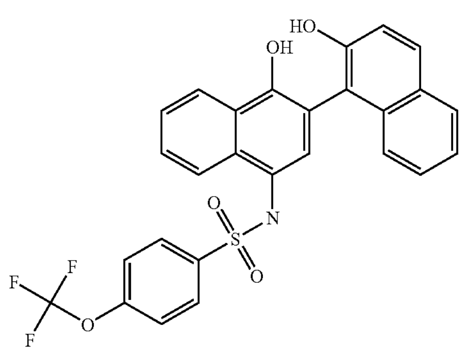 [SMILES: O=S(=O)(Nc1cc(-c2c(O)ccc3ccccc23)c(O)c2ccccc12)c1ccc(OC(F)(F)F)cc1] | C27H18F3NO5S | 525.5074 | 7.86876 |
| F5749-0036 | 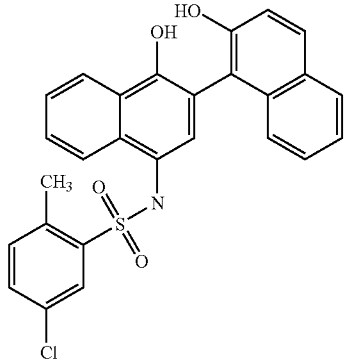 [SMILES: Cc1ccc(Cl)cc1S(=O)(=O)Nc1cc(-c2c(O)ccc3ccccc23)c(O)c2ccccc12] | C27H20ClNO4S | 489.9818 | 7.395 |

TABLE 8-continued
| IDNUMBER | Structure | Formula structure | MW | LogP |
|---|---|---|---|---|
| F5749-0037 | 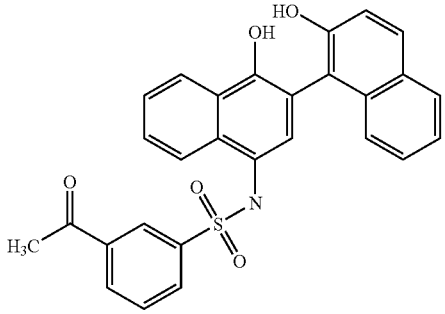 [SMILES: CC(=O)c1cccc(S(=O)(=O)Nc2cc(-c3c(O)ccc4ccccc34)c(O)c3ccccc23)c1] | C28H21NO5S | 483.5473 | 6.36 |
| F5749-0038 | 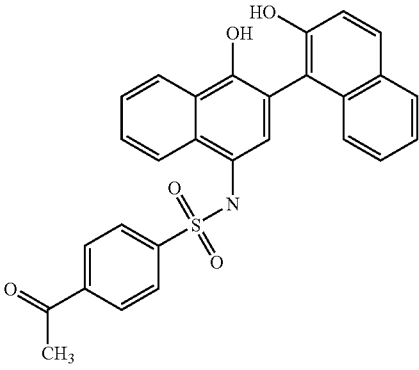 [SMILES: CC(=O)c1ccc(S(=O)(=O)Nc2cc(-c3c(O)ccc4ccccc34)c(O)c3ccccc23)cc1] | C28H21NO5S | 483.5473 | 6.323 |
| F5749-0039 | 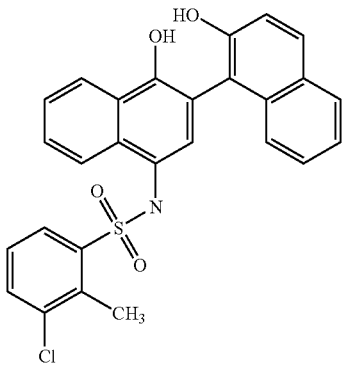 [SMILES: Cc1c(Cl)cccc1S(=O)(=O)Nc1cc(-c2c(O)ccc3ccccc23)c(O)c2ccccc12] | C27H20ClNO4S | 489.9818 | 7.356 |
| F5749-0040 | 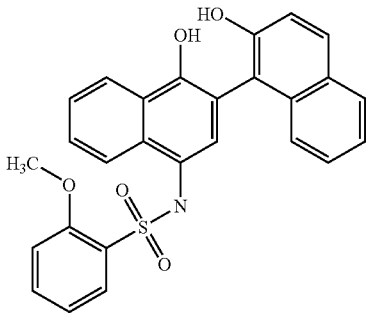 [SMILES: COc1ccccc1S(=O)(=O)Nc1cc(-c2c(O)ccc3ccccc23)c(O)c2ccccc12] | C27H21NO5S | 471.5361 | 6.424 |

TABLE 8-continued

| IDNUMBER | Structure | Formula structure | MW | LogP |
|---|---|---|---|---|
| F5749-0041 | 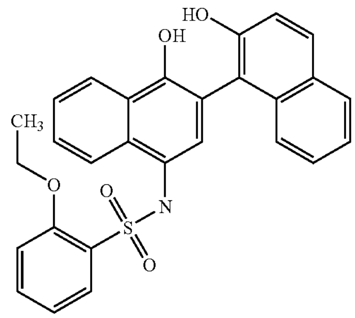 [SMILES: CCOc1ccccc1S(=O)(=O)Nc1cc(-c2c(O)ccc3ccccc23)c(O)c2ccccc12] | C28H23NO5S | 485.5632 | 6.765 |
| F5749-0042 | 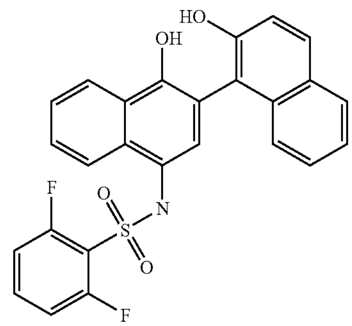 [SMILES: O=S(=O)(Nc1cc(-c2c(O)ccc3ccccc23)c(O)c2ccccc12)c1c(F)cccc1F] | C26H17F2NO4S | 477.4905 | 6.772 |
| F5749-0043 | 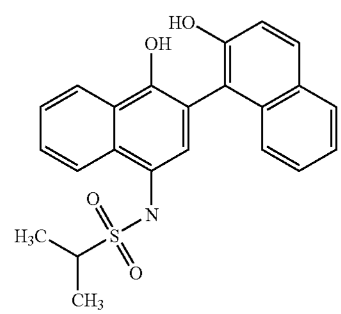 | C23H21NO4S | 407.4921 | 5.963 |
| F5749-0044 | 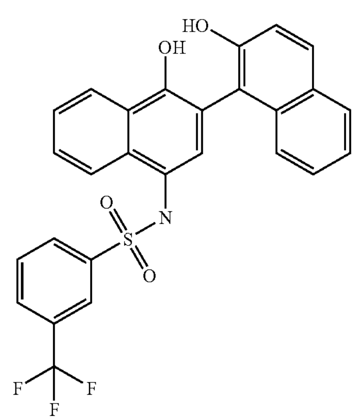 [SMILES: O=S(=O)(Nc1cc(-c2c(O)ccc3ccccc23)c(O)c2ccccc12)c1cccc(C(F)(F)F)c1] | C27H18F3NO4S | 509.508 | 7.44176 |

TABLE 8-continued
| IDNUMBER | Structure | Formula structure | MW | LogP |
|---|---|---|---|---|
| F5749-0045 | 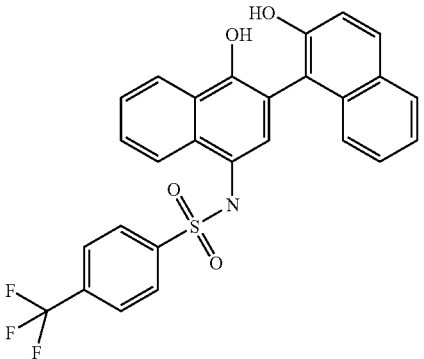 [SMILES: O=S(=O)(Nc1cc(-c2c(O)ccc3ccccc23)c(O)c2ccccc12)c1ccc(C(F)(F)F)cc1] | C27H18F3NO4S | 509.508 | 7.40476 |
| F5749-0046 | 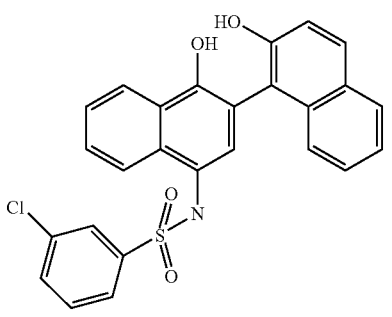 [SMILES: O=S(=O)(Nc1cc(-c2c(O)ccc3ccccc23)c(O)c2ccccc12)c1cccc(Cl)c1] | C26H18ClNO4S | 475.9547 | 7.099 |
| F5749-0047 | 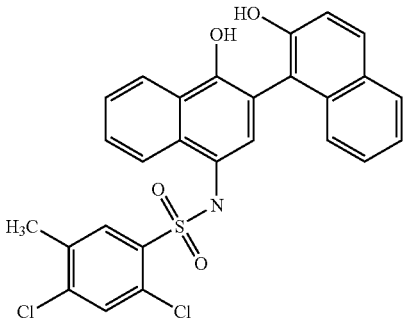 [SMILES: Cc1cc(S(=O)(=O)Nc2cc(-c3c(O)ccc4ccccc34)c(O)c3ccccc23)c(Cl)cc1Cl] | C27H19Cl2NO4S | 524.4268 | 8.022 |
| F5749-0048 | 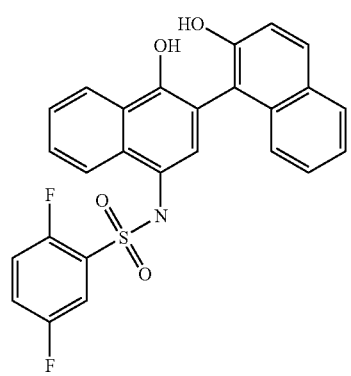 [SMILES: O=S(=O)(Nc1cc(-c2c(O)ccc3ccccc23)c(O)c2ccccc12)c1cc(F)ccc1F] | C26H17F2NO4S | 477.4905 | 6.811 |

TABLE 8-continued

| IDNUMBER | Structure | Formula structure | MW | LogP |
|---|---|---|---|---|
| F5749-0049 | 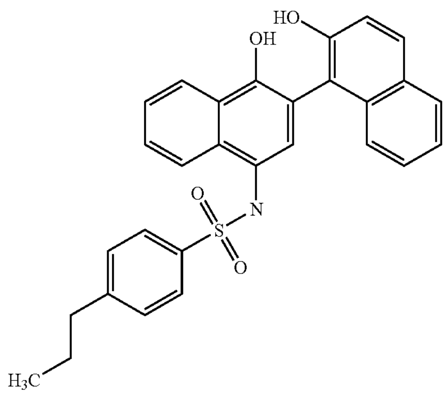 [SMILES: CCCc1ccc(S(=O)(=O)Nc2cc(-c3c(O)ccc4ccccc34)c(O)c3ccccc23)cc1] | C29H25NO4S | 483.5909 | 7.685 |
| F5749-0050 | 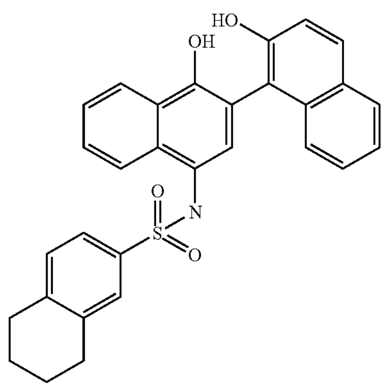 [SMILES: O=S(=O)(Nc1cc(-c2c(O)ccc3ccccc23)c(O)c2ccccc12)c1ccc2c(c1)CCCC2] | C30H25NO4S | 495.6021 | 7.557 |
| F5749-0051 | 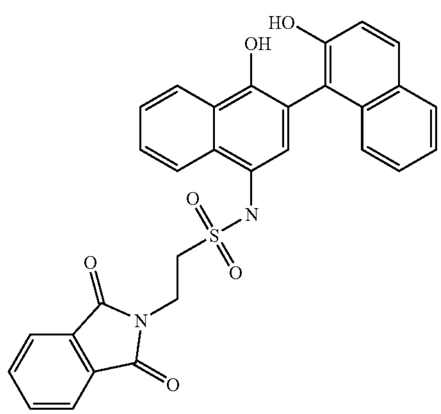 [SMILES: O=C1c2ccccc2C(=O)N1CCS(=O)(=O)Nc1cc(-c2c(O)ccc3ccccc23)c(O)c2ccccc12] | C30H22N2O6S | 538.5836 | 5.597 |
| F5749-0052 | 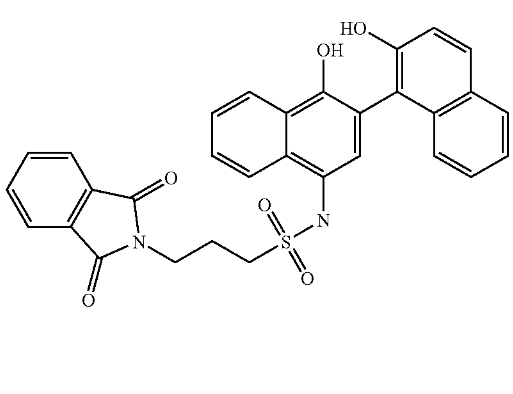 [SMILES: O=C1c2ccccc2C(=O)N1CCCS(=O)(=O)Nc1cc(-c2c(O)ccc3ccccc23)c(O)c2ccccc12] | C31H24N2O6S | 552.6107 | 6.039 |

TABLE 8-continued

| IDNUMBER | Structure | Formula structure | MW | LogP |
| --- | --- | --- | --- | --- |
| F5749-0053 | 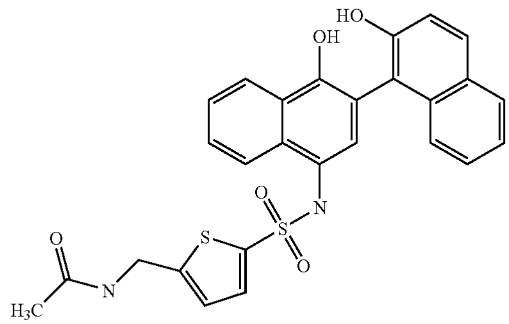 [SMILES: CC(=O)NCc1ccc(S(=O)(=O)Nc2cc(-c3c(O)ccc4ccccc34)c(O)c3ccccc23)s1] | C27H22N2O5S2 | 518.6148 | 5.773 |
| F5749-0054 | 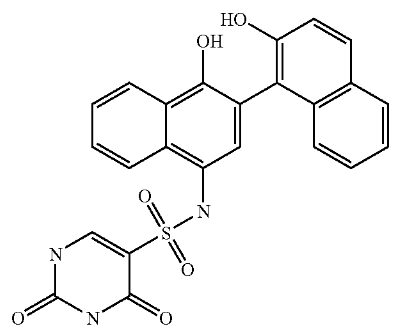 [SMILES: O=c1[nH]cc(S(=O)(=O)Nc2cc(-c3c(O)ccc4ccccc34)c(O)c3ccccc23)c(=O)[nH]1] | C24H17N3O6S | 475.4836 | 3.515 |
| F5749-0055 | 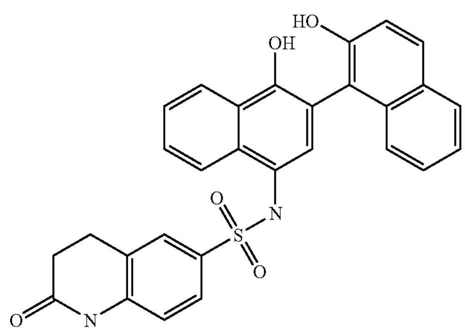 [SMILES: O=C1CCc2cc(S(=O)(=O)Nc3cc(-c4c(O)ccc5ccccc45)c(O)c4ccccc34)ccc2N1] | C29H22N2O5S | 510.5731 | 5.666 |
| F5749-0056 | 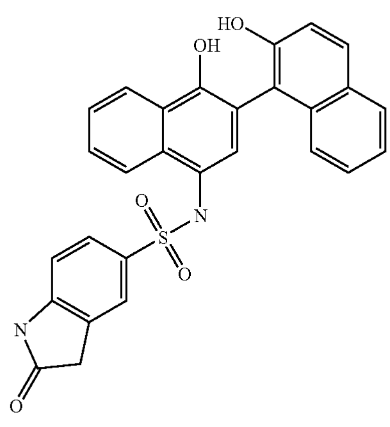 [SMILES: O=C1Cc2cc(S(=O)(=O)Nc3cc(-c4c(O)ccc5ccccc45)c(O)c4ccccc34)ccc2N1] | C28H20N2O5S | 496.546 | 5.578 |

TABLE 8-continued

| IDNUMBER | Structure | Formula structure | MW | LogP |
|---|---|---|---|---|
| F5749-0057 | 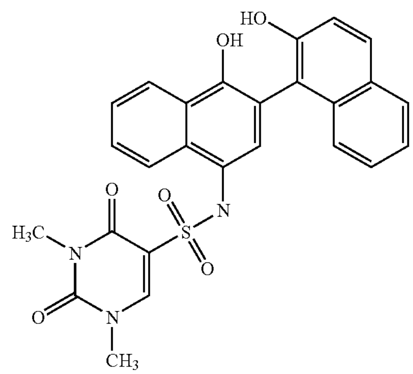 [SMILES: Cn1cc(S(=O)(=O)Nc2cc(-c3c(O)ccc4ccccc34)c(O)c3ccccc23)c(=O)n(C)c1=O] | C26H21N3O6S | 503.5378 | 3.579 |
| F5749-0058 | 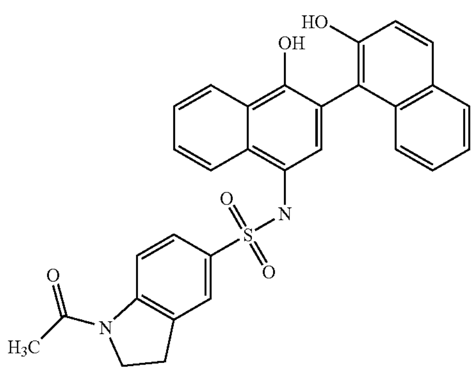 [SMILES: CC(=O)N1CCc2cc(S(=O)(=O)Nc3cc(-c4c(O)ccc5ccccc45)c(O)c4ccccc34)ccc21] | C30H24N2O5S | 524.6002 | 5.901 |
| F5749-0059 | 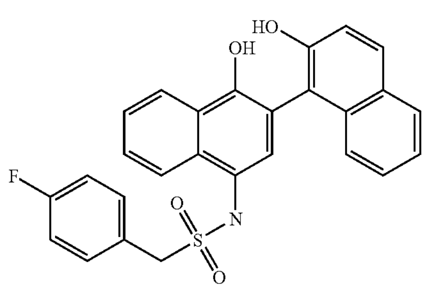 [SMILES: O=S(=O)(Cc1ccc(F)cc1)Nc1cc(-c2c(O)ccc3ccccc23)c(O)c2ccccc12] | C27H20FNO4S | 473.5272 | 6.757 |
| F5749-0060 | 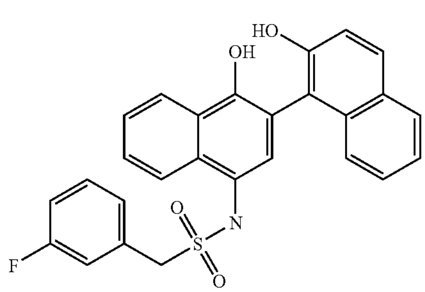 [SMILES: O=S(=O)(Cc1cccc(F)c1)Nc1cc(-c2c(O)ccc3ccccc23)c(O)c2ccccc12] | C27H20FNO4S | 473.5272 | 6.794 |

| IDNUMBER | Structure | Formula structure | MW | LogP |
|---|---|---|---|---|
| F5749-0061 | 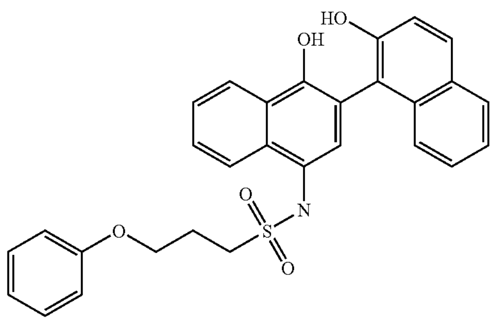 [SMILES: O=S(=O)(CCCOc1ccccc1)Nc1cc(-c2c(O)ccc3ccccc23)c(O)c2ccccc12] | C29H25NO5S | 499.5903 | 6.83 |
| F5749-0062 | 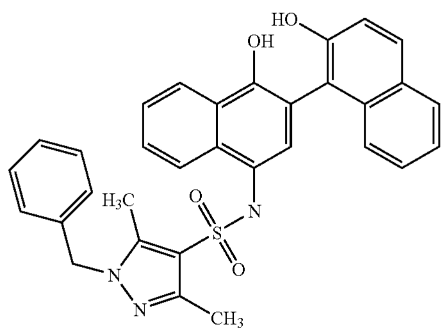 [SMILES: Cc1nn(Cc2ccccc2)c(C)c1S(=O)(=O)Nc1cc(-c2c(O)ccc3ccccc23)c(O)c2ccccc12] | C32H27N3O4S | 549.6537 | 6.749 |
| F5749-0063 | 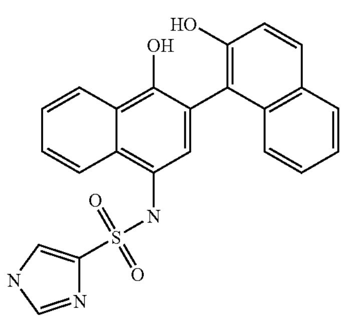 [SMILES: O=S(=O)(Nc1cc(-c2c(O)ccc3ccccc23)c(O)c2ccccc12)c1c[nH]cn1] | C23H17N3O4S | 431.4736 | 4.61 |
| F5749-0064 | 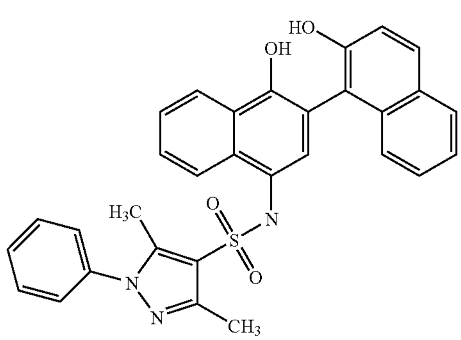 [SMILES: Cc1nn(-c2ccccc2)c(C)c1S(=O)(=O)Nc1cc(-c2c(O)ccc3ccccc23)c(O)c2ccccc12] | C31H25N3O4S | 535.6266 | 6.615 |

TABLE 8-continued

| IDNUMBER | Structure | Formula structure | MW | LogP |
|---|---|---|---|---|
| F5749-0065 | 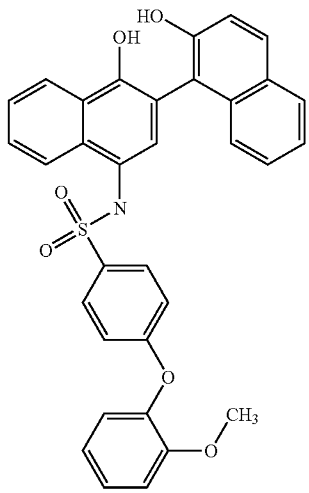 [SMILES: COc1ccccc1Oc1ccc(S(=O)(=O)Nc2cc(-c3c(O)ccc4ccccc34)c(O)c3ccccc23)cc1] | C33H25NO6S | 563.6343 | 7.78574 |
| F5749-0066 | 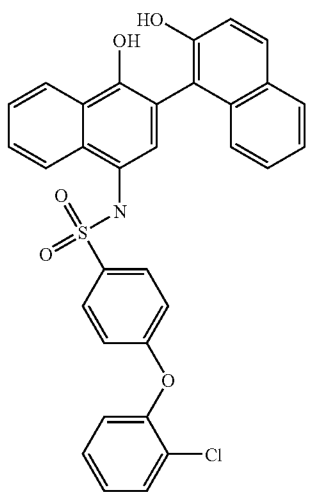 [SMILES: O=S(=O)(Nc1cc(-c2c(O)ccc3ccccc23)c(O)c2ccccc12)c1ccc(Oc2ccccc2Cl)cc1] | C32H22ClNO5S | 568.0528 | 8.67 |
| F5749-0067 | 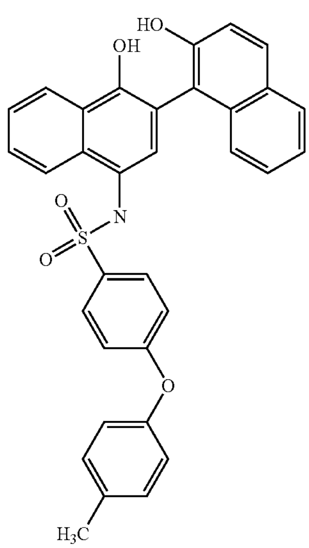 [SMILES: Cc1ccc(Oc2ccc(S(=O)(=O)Nc3cc(-c4c(O)ccc5ccccc45)c(O)c4ccccc34)cc2)cc1] | C33H25NO5S | 547.6349 | 8.378 |

TABLE 8-continued
| IDNUMBER | Structure | Formula structure | MW | LogP |
|---|---|---|---|---|
| F5749-0068 | 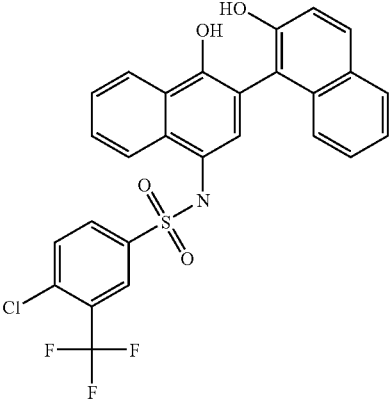 [SMILES: O=S(=O)(Nc1cc(-c2c(O)ccc3ccccc23)c(O)c2ccccc12)c1ccc(Cl)c(C(F)(F)F)c1] | C27H17ClF3NO4S | 543.953 | 8.03176 |
| F5749-0069 | 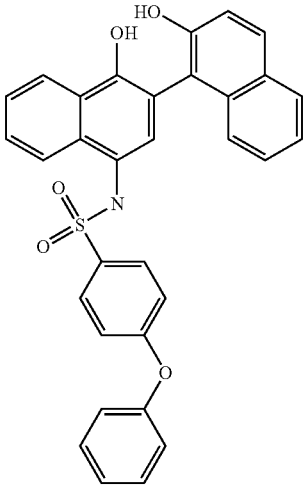 [SMILES: O=S(=O)(Nc1cc(-c2c(O)ccc3ccccc23)c(O)c2ccccc12)c1ccc(Oc2ccccc2)cc1] | C32H23NO5S | 533.6078 | 8.08 |
| F5749-0070 | 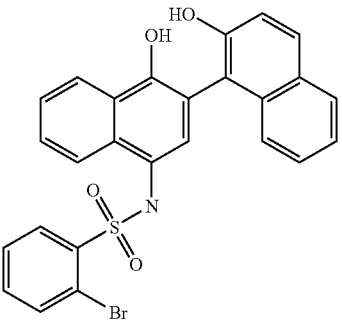 [SMILES: O=S(=O)(Nc1cc(-c2c(O)ccc3ccccc23)c(O)c2ccccc12)c1ccccc1Br] | C26H18BrNO4S | 520.4057 | 7.266 |
| F5749-0071 | 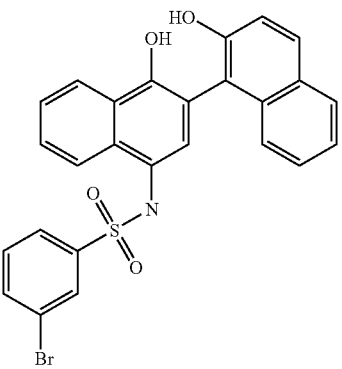 | C26H18BrNO4S | 520.4057 | 7.305 |

TABLE 8-continued
| IDNUMBER | Structure | Formula structure | MW | LogP |
|---|---|---|---|---|
| F5749-0072 | 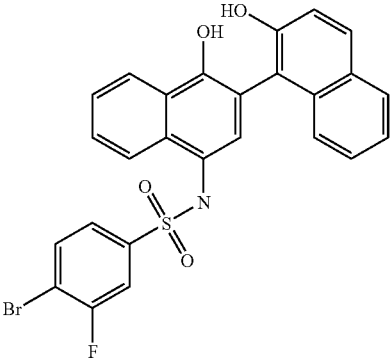 [SMILES: O=S(=O)(Nc1cc(-c2c(O)ccc3ccccc23)c(O)c2ccccc12)c1ccc(Br)c(F)c1] | C26H17BrFNO4S | 538.3961 | 7.456 |
| F5749-0073 | 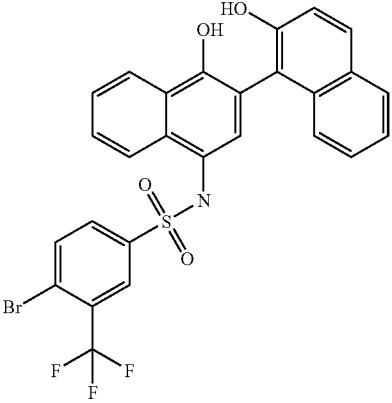 [SMILES: O=S(=O)(Nc1cc(-c2c(O)ccc3ccccc23)c(O)c2ccccc12)c1ccc(Br)c(C(F)(F)F)c1] | C27H17BrF3NO4S | 588.404 | 8.23776 |
| F5749-0074 | 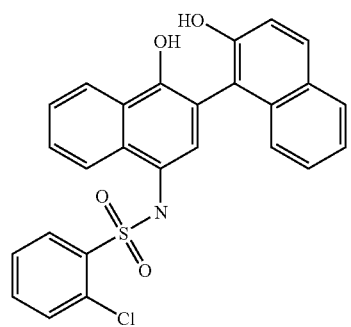 [SMILES: O=S(=O)(Nc1cc(-c2c(O)ccc3ccccc23)c(O)c2ccccc12)c1ccccc1Cl] | C26H18ClNO4S | 475.9547 | 7.06 |
| F5749-0075 | 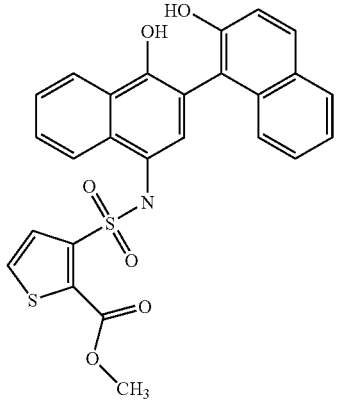 [SMILES: COC(=O)c1sccc1S(=O)(=O)Nc1cc(-c2c(O)ccc3ccccc23)c(O)c2ccccc12] | C26H19NO6S2 | 505.5724 | 5.67 |

TABLE 8-continued
| IDNUMBER | Structure | Formula structure | MW | LogP |
|---|---|---|---|---|
| F5749-0076 | 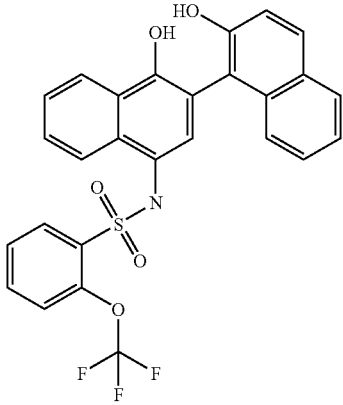 [SMILES: O=S(=O)(Nc1cc(-c2c(O)ccc3ccccc23)c(O)c2ccccc12)c1ccccc1OC(F)(F)F] | C27H18F3NO5S | 525.5074 | 7.86676 |
TABLE 9
| IDNUMBER | Structure | Formula structure | MW | LogP |
|---|---|---|---|---|
| F1566-0329 | 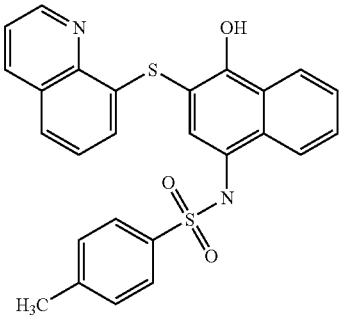 | C26H20N2O3S2 | 472.5889 | 6.344 |
| F1566-0341 | 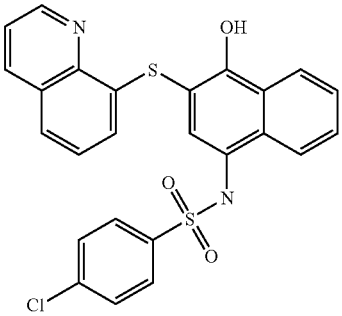 [SMILES: O=S(=O)(Nc1cc(Sc2cccc3cccnc23)c(O)c2ccccc12)c1ccc(Cl)cc1] | C25H17ClN2O3S2 | 493.0068 | 6.638 |
| F1566-0353 | 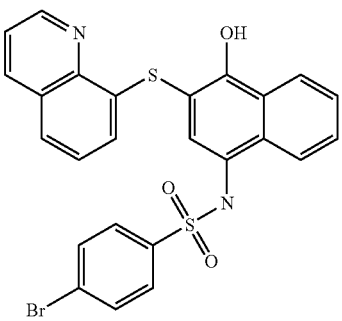 [SMILES: O=S(=O)(Nc1cc(Sc2cccc3cccnc23)c(O)c2ccccc12)c1ccc(Br)cc1] | C25H17BrN2O3S2 | 537.4578 | 6.844 |

TABLE 9-continued

| IDNUMBER | Structure | Formula structure | MW | LogP |
|---|---|---|---|---|
| F1566-0377 | 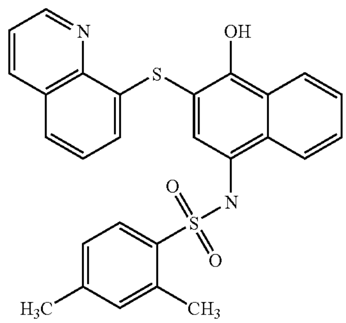 [SMILES: Cc1ccc(S(=O)(=O)Nc2cc(Sc3cccc4cccnc34)c(O)c3ccccc23)c(C)c1] | C27H22N2O3S2 | 486.616 | 6.677 |
| F1566-0425 | 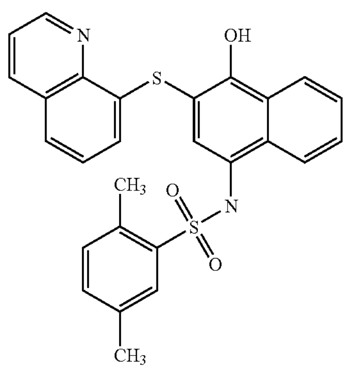 [SMILES: Cc1ccc(C)c(S(=O)(=O)Nc2cc(Sc3cccc4cccnc34)c(O)c3ccccc23)c1] | C27H22N2O3S2 | 486.616 | 6.677 |
| F1566-0449 | 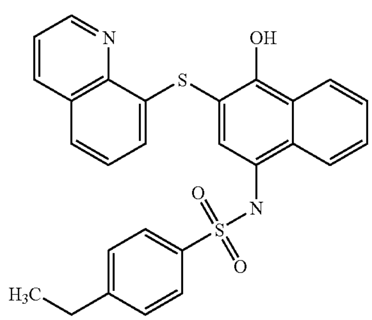 [SMILES: CCc1ccc(S(=O)(=O)Nc2cc(Sc3cccc4cccnc34)c(O)c3ccccc23)cc1] | C27H22N2O3S2 | 486.616 | 6.819 |
| F1566-0473 | 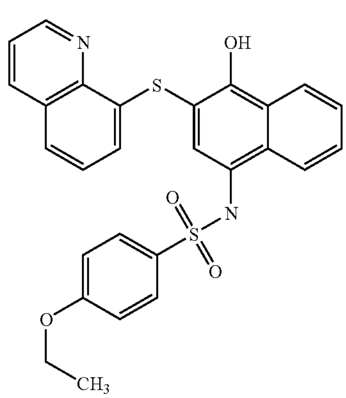 [SMILES: CCOc1ccc(S(=O)(=O)Nc2cc(Sc3cccc4cccnc34)c(O)c3ccccc23)cc1] | C27H22N2O4S2 | 502.6154 | 6.343 |

TABLE 9-continued
| IDNUMBER | Structure | Formula structure | MW | LogP |
|---|---|---|---|---|
| F1566-0497 | 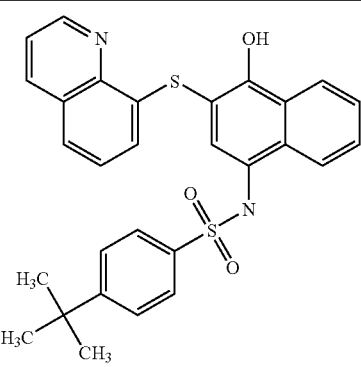 | C29H26N2O3S2 | 514.6702 | 7.545 |
| F1566-0521 | 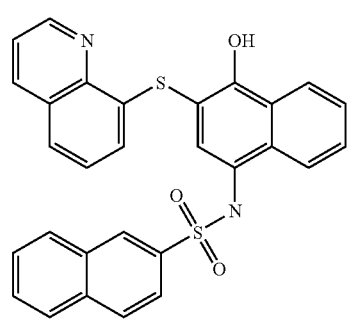 [SMILES: O=S(=O)(Nc1cc(Sc2cccc3cccnc23)c(O)c2ccccc12)c1ccc2ccccc2c1] | C29H20N2O3S2 | 508.6224 | 7.305 |
| F1566-0557 | 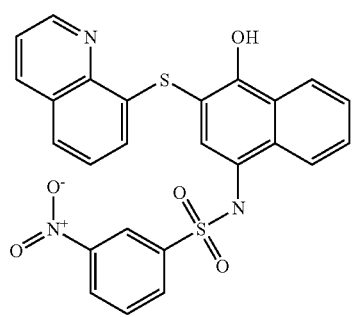 [SMILES: O=[N+]([O-])c1cccc(S(=O)(=O)Nc2cc(Sc3cccc4cccnc34)c(O)c3ccccc23)c1] | C25H17N3O5S2 | 503.5593 | 6.018 |
| F1566-0569 | 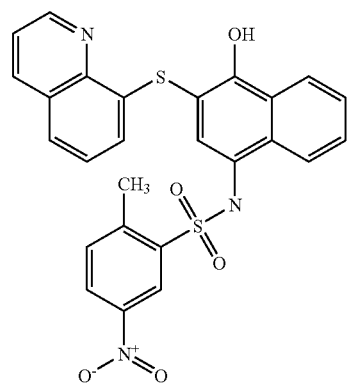 [SMILES: Cc1ccc([N+](=O)[O-])cc1S(=O)(=O)Nc1cc(Sc2cccc3cccnc23)c(O)c2ccccc12] | C26H19N3O5S2 | 517.5864 | 6.314 |

TABLE 9-continued

| IDNUMBER | Structure | Formula structure | MW | LogP |
|---|---|---|---|---|
| F1566-0617 | 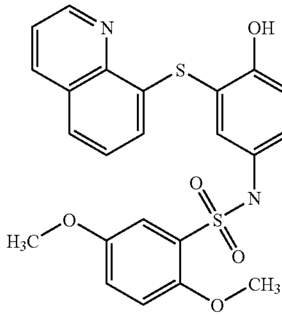 | C27H22N2O5S2 | 518.6148 | 5.993 |
| F1566-0629 | 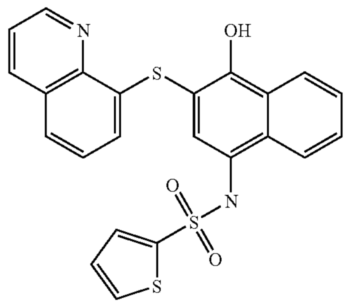 [SMILES: O=S(=O)(Nc1cc(Sc2cccc3cccnc23)c(O)c2ccccc12)c1cccs1] | C23H16N2O3S3 | 464.5876 | 5.559 |
| F1566-1608 | 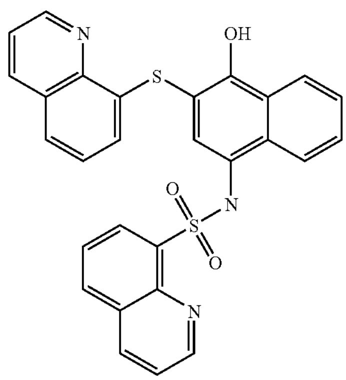 [SMILES: O=S(=O)(Nc1cc(Sc2cccc3cccnc23)c(O)c2ccccc12)c1cccc2cccnc12] | C28H19N3O3S2 | 509.6099 | 6.246 |
| F1566-1821 | 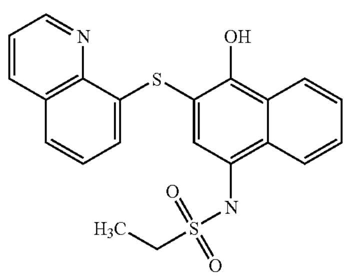 [SMILES: CCS(=O)(=O)Nc1cc(Sc2cccc3cccnc23)c(O)c2ccccc12] | C21H18N2O3S2 | 410.5172 | 4.905 |
| F1566-1835 | 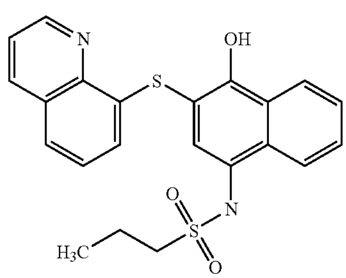 [SMILES: CCCS(=O)(=O)Nc1cc(Sc2cccc3cccnc23)c(O)c2ccccc12] | C22H20N2O3S2 | 424.5443 | 5.347 |

| IDNUMBER | Structure | Formula structure | MW | LogP |
|---|---|---|---|---|
| F1566-1849 | 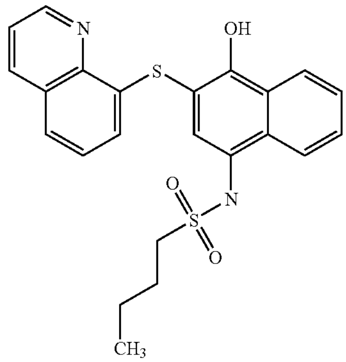 [SMILES: CCCCS(=O)(=O)Nc1cc(Sc2cccc3cccnc23)c(O)c2ccccc12] | C23H22N2O3S2 | 438.5714 | 5.789 |
| F1566-1863 | 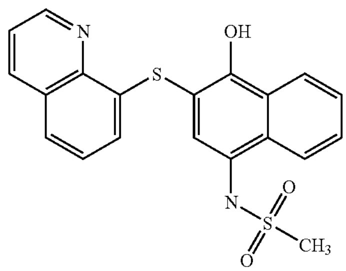 [SMILES: CS(=O)(=O)Nc1cc(Sc2cccc3cccnc23)c(O)c2ccccc12] | C20H16N2O3S2 | 396.4901 | 4.392 |
| F5749-0077 | 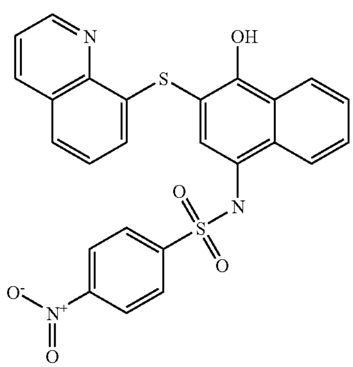 [SMILES: O=[N+]([O-])c1ccc(S(=O)(=O)Nc2cc(Sc3cccc4cccnc34)c(O)c3ccccc23)cc1] | C25H17N3O5S2 | 503.5593 | 5.981 |
| F5749-0078 | 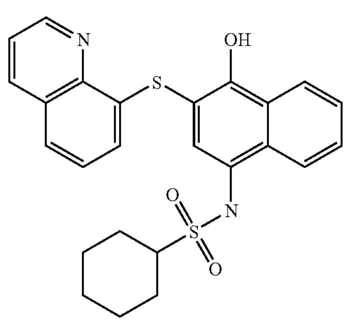 [SMILES: O=S(=O)(Nc1cc(Sc2cccc3cccnc23)c(O)c2ccccc12)C1CCCCC1] | C25H24N2O3S2 | 464.6096 | 6.371 |

TABLE 9-continued
| IDNUMBER | Structure | Formula structure | MW | LogP |
| --- | --- | --- | --- | --- |
| F5749-0079 | 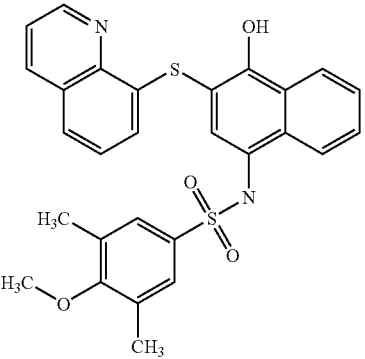 [SMILES: COc1c(C)cc(S(=O)(=O)Nc2cc(Sc3cccc4cccnc34)c(O)c3ccccc23)cc1C] | C28H24N2O4S2 | 516.6425 | 6.668 |
| F5749-0080 | 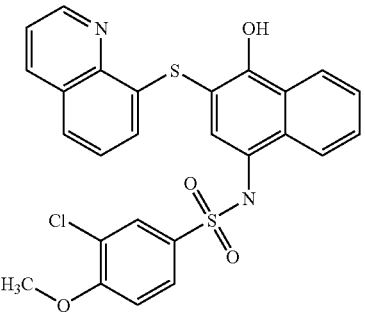 [SMILES: COc1ccc(S(=O)(=O)Nc2cc(Sc3cccc4cccnc34)c(O)c3ccccc23)cc1Cl] | C26H19ClN2O4S2 | 523.0333 | 6.629 |
| F5749-0081 | 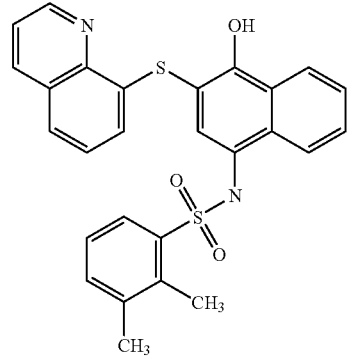 [SMILES: Cc1cccc(S(=O)(=O)Nc2cc(Sc3cccc4cccnc34)c(O)c3ccccc23)c1C] | C27H22N2O3S2 | 486.616 | 6.638 |
| F5749-0082 | 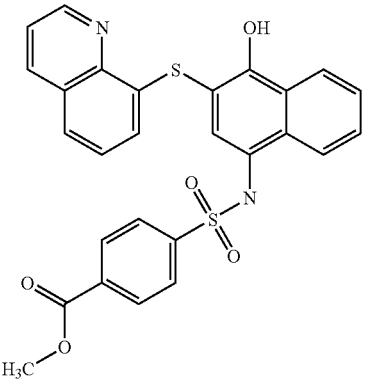 [SMILES: COC(=O)c1ccc(S(=O)(=O)Nc2cc(Sc3cccc4cccnc34)c(O)c3ccccc23)cc1] | C27H20N2O5S2 | 516.5989 | 5.987 |

TABLE 9-continued
| IDNUMBER | Structure | Formula structure | MW | LogP |
|---|---|---|---|---|
| F5749-0083 | 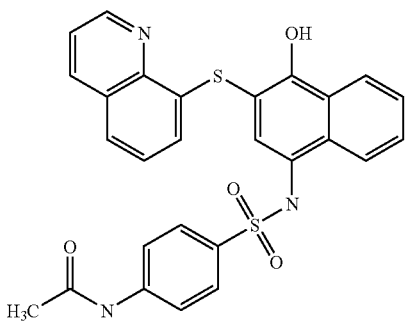 [SMILES: CC(=O)Nc1ccc(S(=O)(=O)Nc2cc(Sc3cccc4cccnc34)c(O)c3ccccc23)cc1] | C27H21N3O4S2 | 515.6141 | 5.337 |
| F5749-0084 | 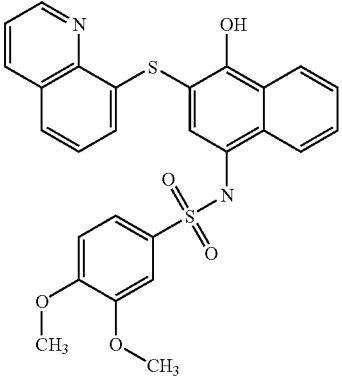 [SMILES: COc1ccc(S(=O)(=O)Nc2cc(Sc3cccc4cccnc34)c(O)c3ccccc23)cc1OC] | C27H22N2O5S2 | 518.6148 | 5.74474 |
| F5749-0085 | 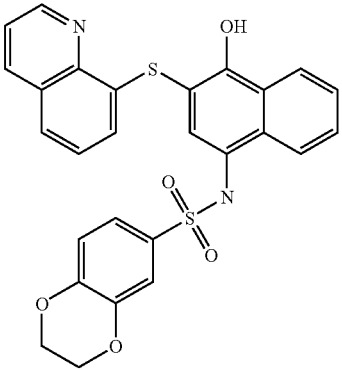 [SMILES: O=S(=O)(Nc1cc(Sc2cccc3cccnc23)c(O)c2ccccc12)c1ccc2c(c1)OCCO2] | C27H20N2O5S2 | 516.5989 | 5.641 |
| F5749-0086 | 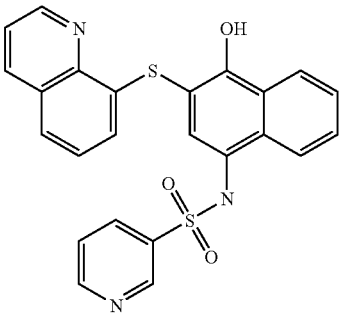 [SMILES: O=S(=O)(Nc1cc(Sc2cccc3cccnc23)c(O)c2ccccc12)c1cccnc1] | C24H17N3O3S2 | 459.5494 | 4.813 |

TABLE 9-continued

| IDNUMBER | Structure | Formula structure | MW | LogP |
|---|---|---|---|---|
| F5749-0087 | 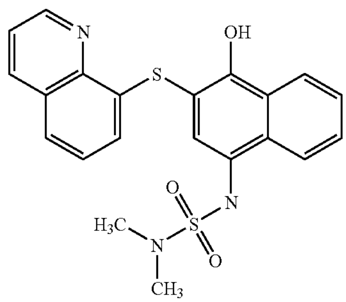 [SMILES: CN(C)S(=O)(=O)Nc1cc(Sc2cccc3cccnc23)c(O)c2ccccc12] | C21H19N3O3S2 | 425.5319 | 3.94 |
| F5749-0088 | 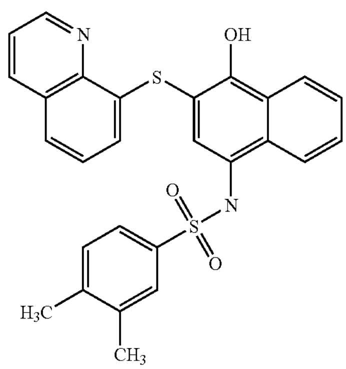 [SMILES: Cc1ccc(S(=O)(=O)Nc2cc(Sc3cccc4cccnc34)c(O)c3ccccc23)cc1C] | C27H22N2O3S2 | 486.616 | 6.677 |
| F5749-0089 | 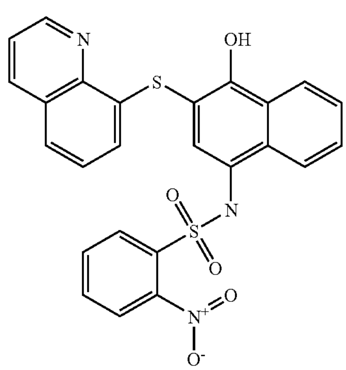 [SMILES: O=[N+]([O-])c1ccccc1S(=O)(=O)Nc1cc(Sc2cccc3cccnc23)c(O)c2ccccc12] | C25H17N3O5S2 | 503.5593 | 5.979 |
| F5749-0090 | 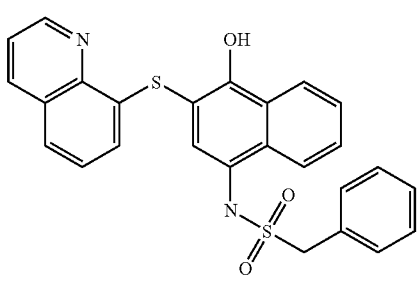 [SMILES: O=S(=O)(Cc1ccccc1)Nc1cc(Sc2cccc3cccnc23)c(O)c2ccccc12] | C26H20N2O3S2 | 472.5889 | 6.18 |

TABLE 9-continued

| IDNUMBER | Structure | Formula structure | MW | LogP |
| --- | --- | --- | --- | --- |
| F5749-0091 | 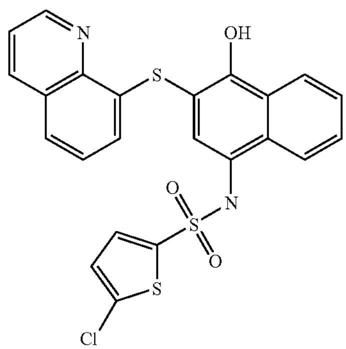 [SMILES: O=S(=O)(Nc1cc(Sc2cccc3cccnc23)c(O)c2ccccc12)c1ccc(Cl)s1] | C23H15ClN2O3S3 | 499.0326 | 6.849 |
| F5749-0092 | 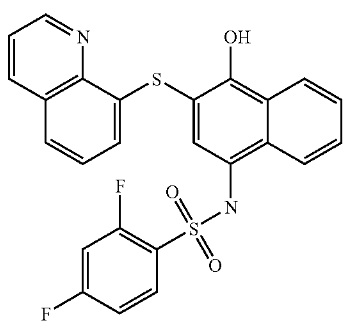 | C25H16F2N2O3S2 | 494.5427 | 6.387 |
| F5749-0093 | 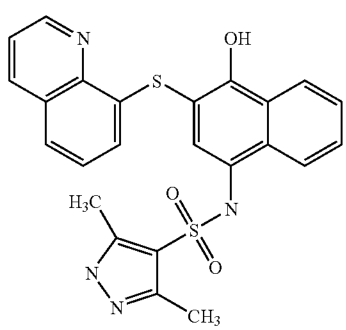 [SMILES: Cc1n[nH]c(C)c1S(=O)(=O)Nc1cc(Sc2cccc3cccnc23)c(O)c2ccccc12] | C24H20N4O3S2 | 476.58 | 5.156 |
| F5749-0094 | 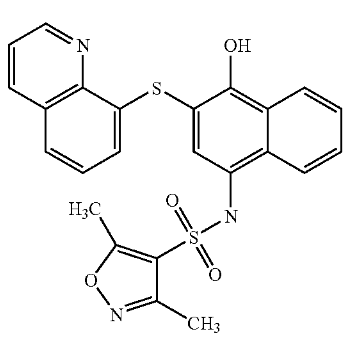 | C24H19N3O4S2 | 477.5647 | 5.19 |

TABLE 9-continued

| IDNUMBER | Structure | Formula structure | MW | LogP |
|---|---|---|---|---|
| F5749-0095 | 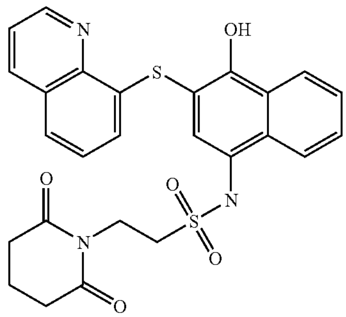 [SMILES: O=C1CCCC(=O)N1CCS(=O)(=O)Nc1cc(Sc2cccc3cccnc23)c(O)c2ccccc12] | C26H23N3O5S2 | 521.6183 | 3.833 |
| F5749-0096 | 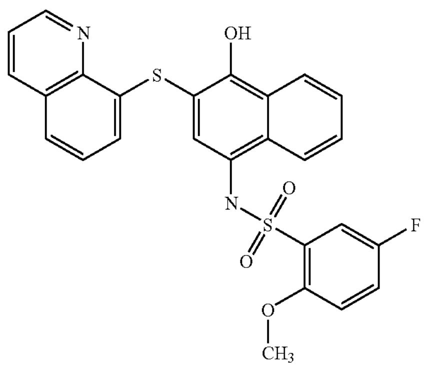 [SMILES: COc1ccc(F)cc1S(=O)(=O)Nc1cc(Sc2cccc3cccnc23)c(O)c2ccccc12] | C26H19FN2O4S2 | 506.5787 | 6.19 |
| F5749-0097 | 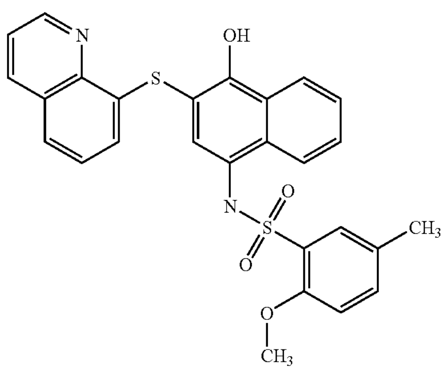 [SMILES: COc1ccc(C)cc1S(=O)(=O)Nc1cc(Sc2cccc3cccnc23)c(O)c2ccccc12] | C27H22N2O4S2 | 502.6154 | 6.335 |
| F5749-0098 | 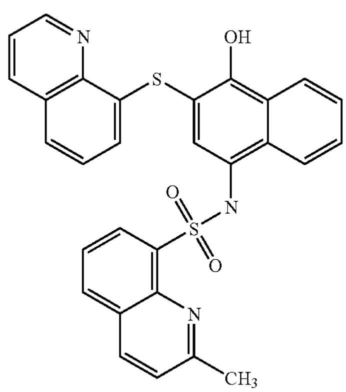 [SMILES: Cc1ccc2cccc(S(=O)(=O)Nc3cc(Sc4cccc5cccnc45)c(O)c4ccccc34)c2n1] | C29H21N3O3S2 | 523.637 | 6.505 |

TABLE 9-continued

| IDNUMBER | Structure | Formula structure | MW | LogP |
|---|---|---|---|---|
| F5749-0099 | 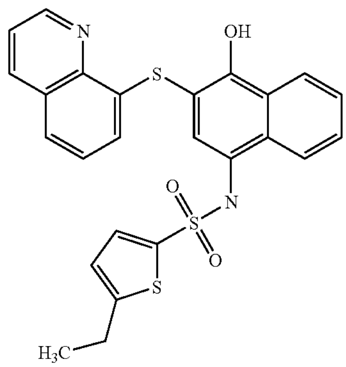 [SMILES: CCc1ccc(S(=O)(=O)Nc2cc(Sc3cccc4cccnc34)c(O)c3ccccc23)s1] | C25H20N2O3S3 | 492.6418 | 6.697 |
| F5749-0100 | 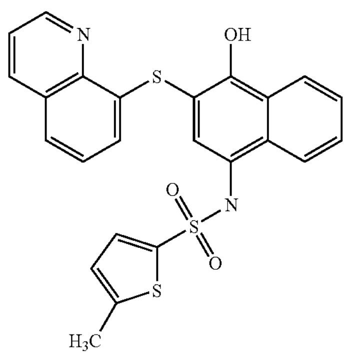 [SMILES: Cc1ccc(S(=O)(=O)Nc2cc(Sc3cccc4cccnc34)c(O)c3ccccc23)s1] | C24H18N2O3S3 | 478.6147 | 6.222 |
| F5749-0101 | 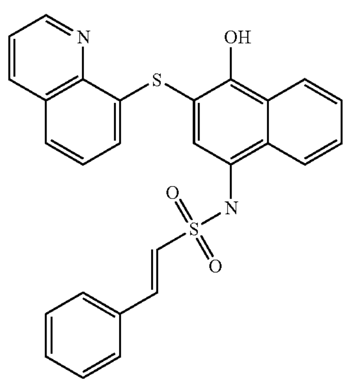 [SMILES: O=S(=O)(/C=C/c1ccccc1)Nc1cc(Sc2cccc3cccnc23)c(O)c2ccccc12] | C27H20N2O3S2 | 484.6001 | 6.404 |
| F5749-0102 | 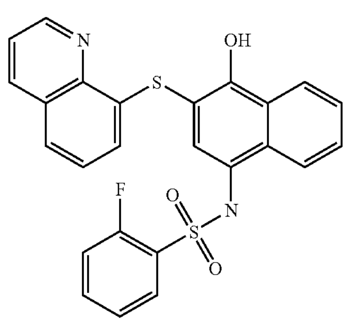 [SMILES: O=S(=O)(Nc1cc(Sc2cccc3cccnc23)c(O)c2ccccc12)c1ccccc1F] | C25H17FN2O3S2 | 476.5522 | 6.197 |

TABLE 9-continued

| IDNUMBER | Structure | Formula structure | MW | LogP |
|---|---|---|---|---|
| F5749-0103 | 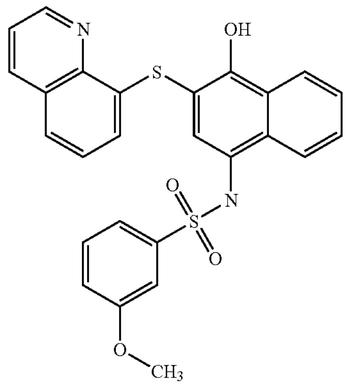 [SMILES: COc1cccc(S(=O)(=O)Nc2cc(Sc3cccc4cccnc34)c(O)c3ccccc23)c1] | C26H20N2O4S2 | 488.5883 | 6.039 |
| F5749-0104 | 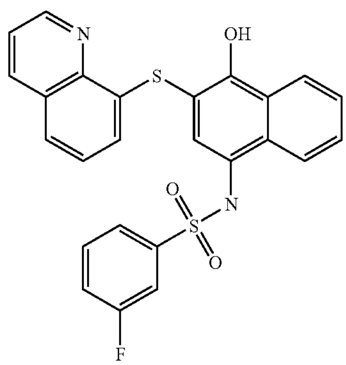 | C25H17FN2O3S2 | 476.5522 | 6.236 |
| F5749-0105 | 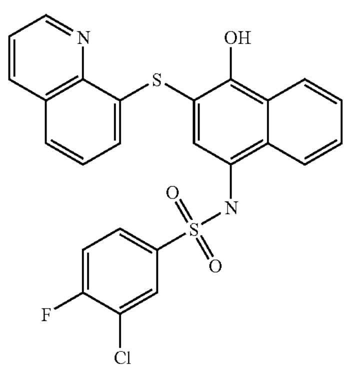 [SMILES: O=S(=O)(Nc1cc(Sc2cccc3cccnc23)c(O)c2ccccc12)c1ccc(F)c(Cl)c1] | C25H16ClFN2O3S2 | 510.9973 | 6.826 |
| F5749-0106 | 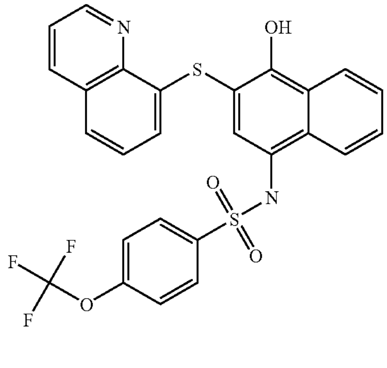 [SMILES: O=S(=O)(Nc1cc(Sc2cccc3cccnc23)c(O)c2ccccc12)c1ccc(OC(F)(F)F)cc1] | C26H17F3N2O4S2 | 542.5596 | 7.44476 |

TABLE 9-continued

| IDNUMBER | Structure | Formula structure | MW | LogP |
| --- | --- | --- | --- | --- |
| F5749-0107 | 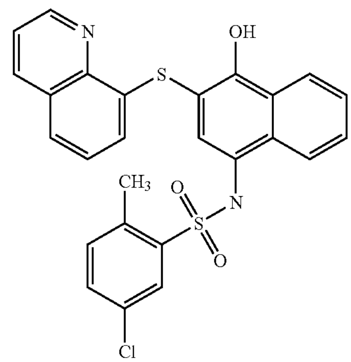 | C26H19ClN2O3S2 | 507.0339 | 6.971 |
| F5749-0108 | 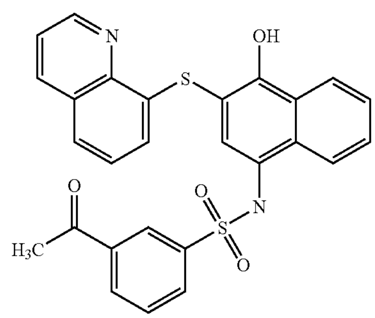 [SMILES: CC(=O)c1cccc(S(=O)(=O)Nc2cc(Sc3cccc4cccnc34)c(O)c3ccccc23)c1] | C27H20N2O4S2 | 500.5995 | 5.936 |
| F5749-0109 | 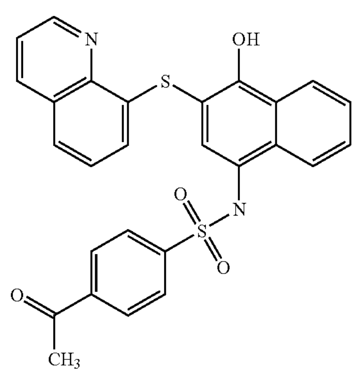 [SMILES: CC(=O)c1ccc(S(=O)(=O)Nc2cc(Sc3cccc4cccnc34)c(O)c3ccccc23)cc1] | C27H20N2O4S2 | 500.5995 | 5.899 |
| F5749-0110 | 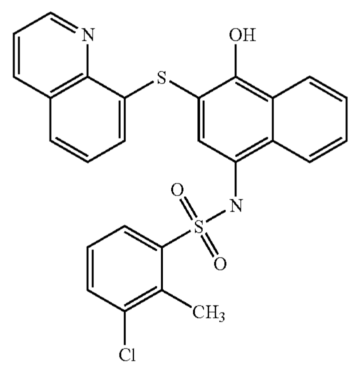 [SMILES: Cc1c(Cl)cccc1S(=O)(=O)Nc1cc(Sc2cccc3cccnc23)c(O)c2ccccc12] | C26H19ClN2O3S2 | 507.0339 | 6.932 |

TABLE 9-continued

| IDNUMBER | Structure | Formula structure | MW | LogP |
|---|---|---|---|---|
| F5749-0111 | 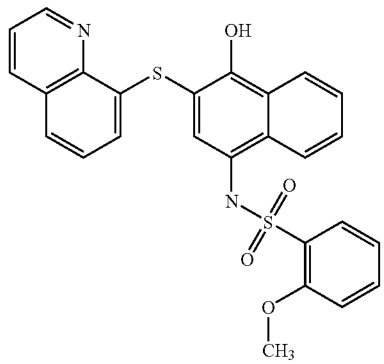 [SMILES: COc1ccccc1S(=O)(=O)Nc1cc(Sc2cccc3cccnc23)c(O)c2ccccc12] | C26H20N2O4S2 | 488.5883 | 6 |
| F5749-0112 | 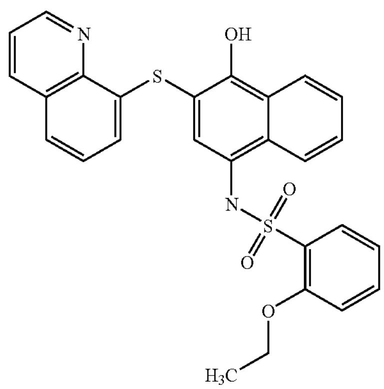 [SMILES: CCOc1ccccc1S(=O)(=O)Nc1cc(Sc2cccc3cccnc23)c(O)c2ccccc12] | C27H22N2O4S2 | 502.6154 | 6.341 |
| F5749-0113 | 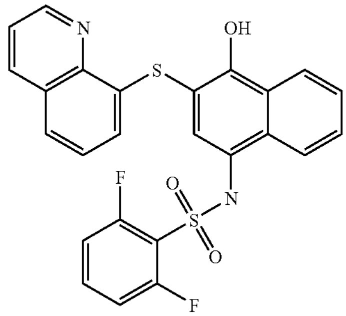 [SMILES: O=S(=O)(Nc1cc(Sc2cccc3cccnc23)c(O)c2ccccc12)c1c(F)cccc1F] | C25H16F2N2O3S2 | 494.5427 | 6.348 |
| F5749-0114 | 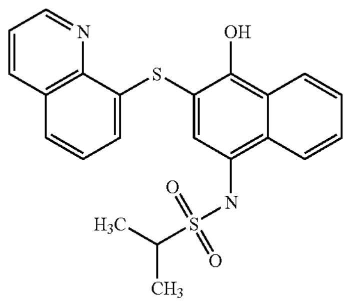 | C22H20N2O3S2 | 424.5443 | 5.539 |

TABLE 9-continued

| IDNUMBER | Structure | Formula structure | MW | LogP |
| --- | --- | --- | --- | --- |
| F5749-0115 | 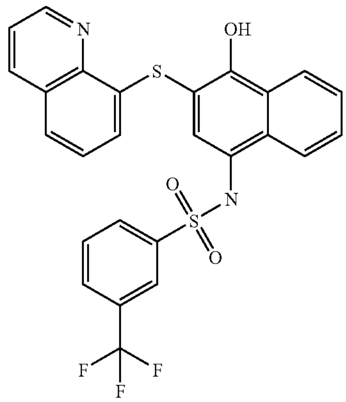 [SMILES: O=S(=O)(Nc1cc(Sc2cccc3cccnc23)c(O)c2ccccc12)c1cccc(C(F)(F)F)c1] | C26H17F3N2O3S2 | 526.5602 | 7.01776 |
| F5749-0116 | 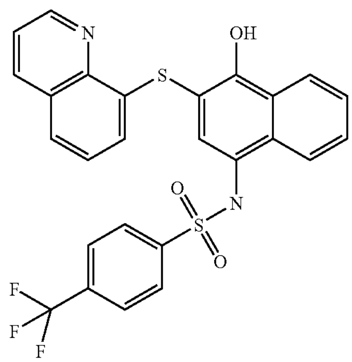 [SMILES: O=S(=O)(Nc1cc(Sc2cccc3cccnc23)c(O)c2ccccc12)c1ccc(C(F)(F)F)cc1] | C26H17F3N2O3S2 | 526.5602 | 6.98076 |
| F5749-0117 | 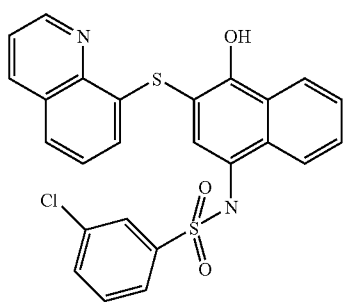 [SMILES: O=S(=O)(Nc1cc(Sc2cccc3cccnc23)c(O)c2ccccc12)c1cccc(Cl)c1] | C25H17ClN2O3S2 | 493.0068 | 6.675 |
| F5749-0118 | 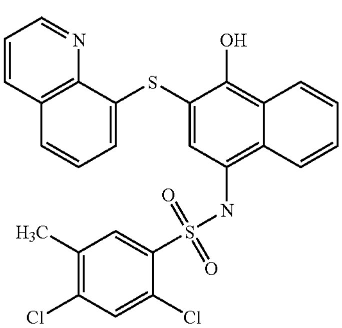 [SMILES: Cc1cc(S(=O)(=O)Nc2cc(Sc3cccc4cccnc34)c(O)c3ccccc23)c(Cl)cc1Cl] | C26H18Cl2N2O3S2 | 541.479 | 7.598 |

TABLE 9-continued

| IDNUMBER | Structure | Formula structure | MW | LogP |
|---|---|---|---|---|
| F5749-0119 | 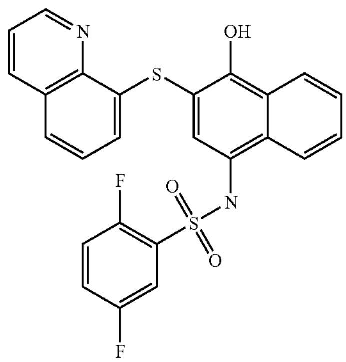 [SMILES: O=S(=O)(Nc1cc(Sc2cccc3cccnc23)c(O)c2ccccc12)c1cc(F)ccc1F] | C25H16F2N2O3S2 | 494.5427 | 6.387 |
| F5749-0120 | 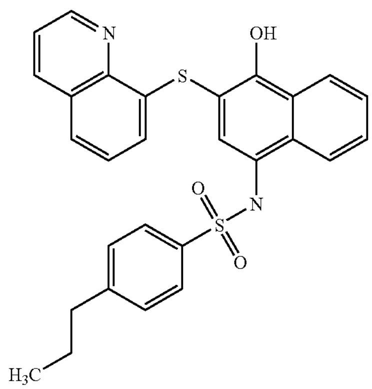 [SMILES: CCCc1ccc(S(=O)(=O)Nc2cc(Sc3cccc4cccnc34)c(O)c3ccccc23)cc1] | C28H24N2O3S2 | 500.6431 | 7.261 |
| F5749-0121 | 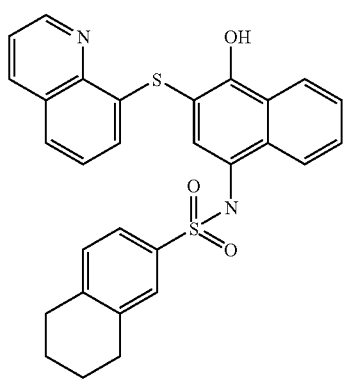 [SMILES: O=S(=O)(Nc1cc(Sc2cccc3cccnc23)c(O)c2ccccc12)c1ccc2c(c1)CCCC2] | C29H24N2O3S2 | 512.6542 | 7.133 |
| F5749-0122 | 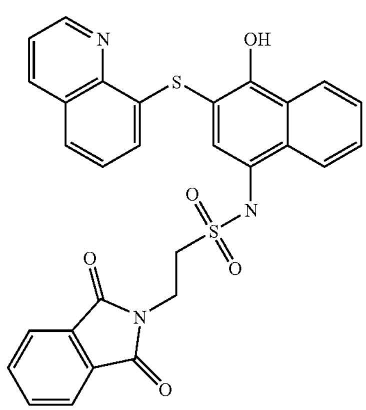 [SMILES: O=C1c2ccccc2C(=O)N1CCS(=O)(=O)Nc1cc(Sc2cccc3cccnc23)c(O)c2ccccc12] | C29H21N3O5S2 | 555.6358 | 5.173 |

TABLE 9-continued

| IDNUMBER | Structure | Formula structure | MW | LogP |
| --- | --- | --- | --- | --- |
| F5749-0123 | 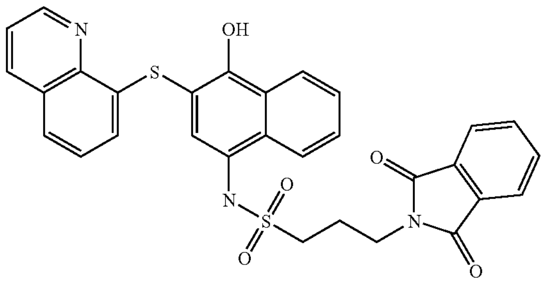 [SMILES: O=C1c2ccccc2C(=O)N1CCCS(=O)(=O)Nc1cc(Sc2cccc3cccnc23)c(O)c2ccccc12] | C30H23N3O5S2 | 569.6629 | 5.615 |
| F5749-0124 | 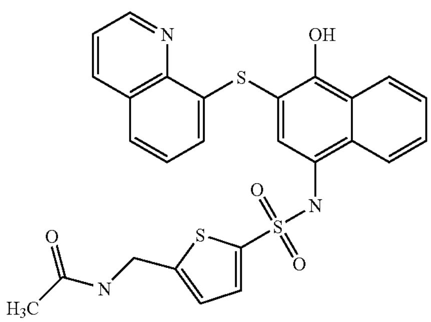 [SMILES: CC(=O)NCc1ccc(S(=O)(=O)Nc2cc(Sc3cccc4cccnc34)c(O)c3ccccc23)s1] | C26H21N3O4S3 | 535.667 | 5.349 |
| F5749-0125 | 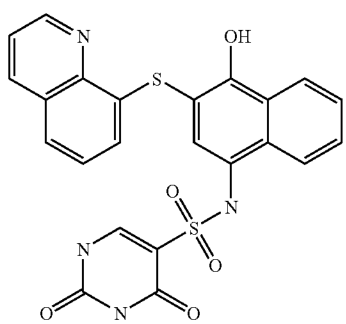 [SMILES: O=c1[nH]cc(S(=O)(=O)Nc2cc(Sc3cccc4cccnc34)c(O)c3ccccc23)c(=O)[nH]1] | C23H16N4O5S2 | 492.5358 | 3.091 |
| F5749-0126 | 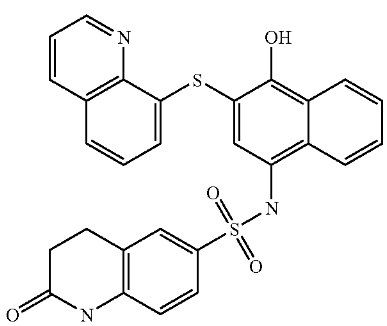 [SMILES: O=C1CCc2cc(S(=O)(=O)Nc3cc(Sc4cccc5cccnc45)c(O)c4ccccc34)ccc2N1] | C28H21N3O4S2 | 527.6253 | 5.242 |

TABLE 9-continued
| IDNUMBER | Structure | Formula structure | MW | LogP |
|---|---|---|---|---|
| F5749-0127 | 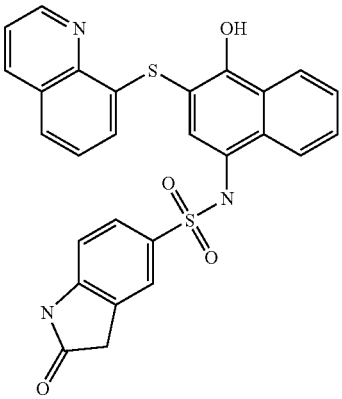 [SMILES: O=C1Cc2cc(S(=O)(=O)Nc3cc(Sc4cccc5cccnc45)c(O)c4ccccc34)ccc2N1] | C27H19N3O4S2 | 513.5982 | 5.154 |
| F5749-0128 | 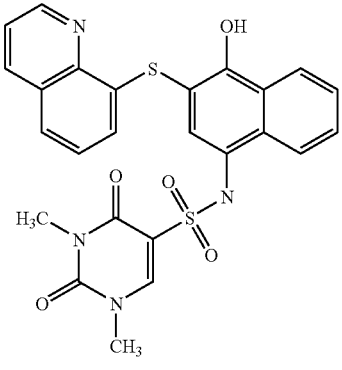 [SMILES: Cn1cc(S(=O)(=O)Nc2cc(Sc3cccc4cccnc34)c(O)c3ccccc23)c(=O)n(C)c1=O] | C25H20N4O5S2 | 520.59 | 3.155 |
| F5749-0129 | 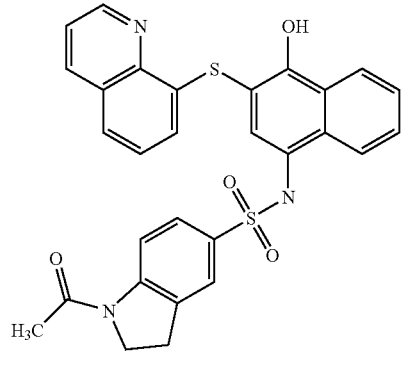 [SMILES: CC(=O)N1CCc2cc(S(=O)(=O)Nc3cc(Sc4cccc5cccnc45)c(O)c4ccccc34)ccc21] | C29H23N3O4S2 | 541.6524 | 5.477 |
| F5749-0130 | 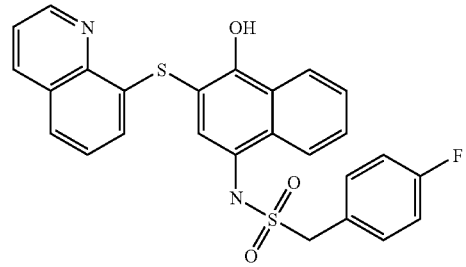 [SMILES: O=S(=O)(Cc1ccc(F)cc1)Nc1cc(Sc2cccc3cccnc23)c(O)c2ccccc12] | C26H19FN2O3S2 | 490.5793 | 6.333 |

TABLE 9-continued

| IDNUMBER | Structure | Formula structure | MW | LogP |
|---|---|---|---|---|
| F5749-0131 | 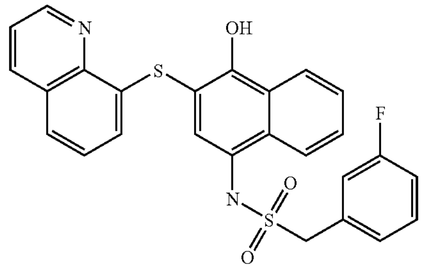 [SMILES: O=S(=O)(Cc1cccc(F)c1)Nc1cc(Sc2cccc3cccnc23)c(O)c2ccccc12] | C26H19N2O3S2 | 490.5793 | 6.37 |
| F5749-0132 | 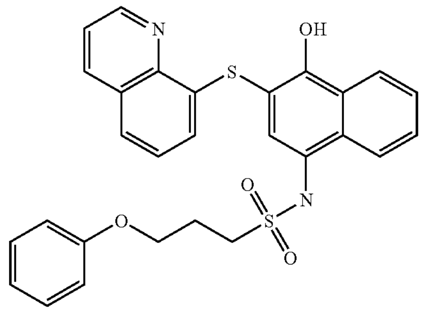 [SMILES: O=S(=O)(CCCOc1ccccc1)Nc1cc(Sc2cccc3cccnc23)c(O)c2ccccc12] | C28H24N2O4S2 | 516.6425 | 6.406 |
| F5749-0133 | 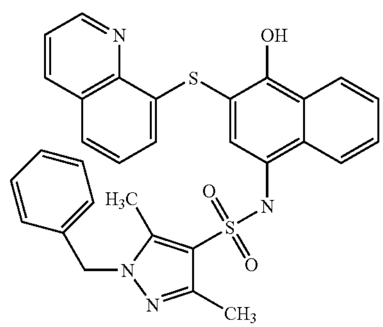 [SMILES: Cc1nn(Cc2ccccc2)c(C)c1S(=O)(=O)Nc1cc(Sc2cccc3cccnc23)c(O)c2ccccc12] | C31H26N4O3S2 | 566.7059 | 6.325 |
| F5749-0134 | 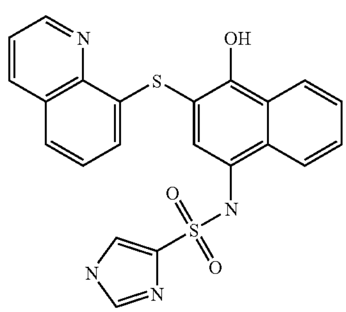 [SMILES: O=S(=O)(Nc1cc(Sc2cccc3cccnc23)c(O)c2ccccc12)c1c[nH]cn1] | C22H16N4O3S2 | 448.5258 | 4.186 |
| F5749-0135 | 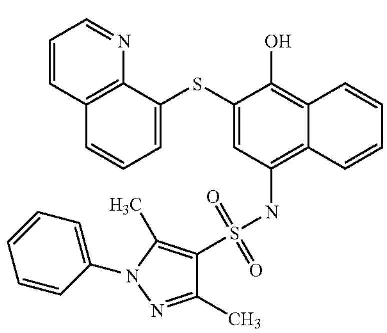 [SMILES: Cc1nn(-c2ccccc2)c(C)c1S(=O)(=O)Nc1cc(Sc2cccc3cccnc23)c(O)c2ccccc12] | C30H24N4O3S2 | 552.6788 | 6.191 |

TABLE 9-continued

| IDNUMBER | Structure | Formula structure | MW | LogP |
|---|---|---|---|---|
| F5749-0136 | 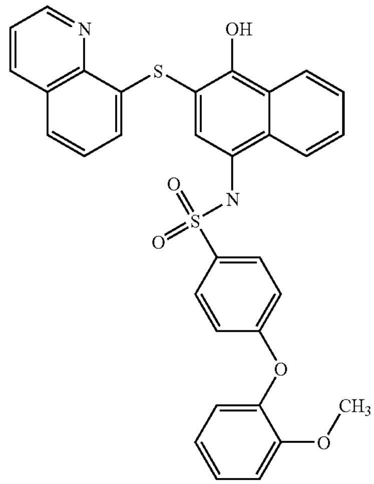 [SMILES: COc1ccccc1Oc1ccc(S(=O)(=O)Nc2cc(Sc3cccc4cccnc34)c(O)c3ccccc23)cc1] | C32H24N2O5S2 | 580.6865 | 7.36174 |
| F5749-0137 | 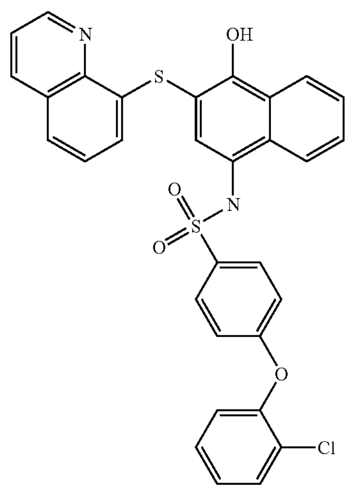 [SMILES: O=S(=O)(Nc1cc(Sc2cccc3cccnc23)c(O)c2ccccc12)c1ccc(Oc2ccccc2Cl)cc1] | C31H21ClN2O4S2 | 585.105 | 8.246 |
| F5749-0138 | 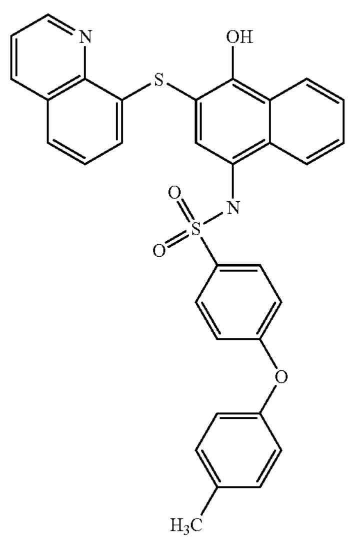 [SMILES: Cc1ccc(Oc2ccc(S(=O)(=O)Nc3cc(Sc4cccc5cccnc45)c(O)c4ccccc34)cc2)cc1] | C32H24N2O4S2 | 564.6871 | 7.954 |

TABLE 9-continued

| IDNUMBER | Structure | Formula structure | MW | LogP |
|---|---|---|---|---|
| F5749-0139 | 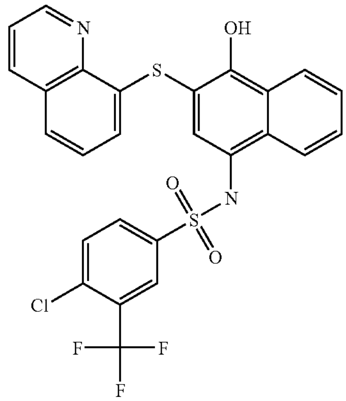 [SMILES: O=S(=O)(Nc1cc(Sc2cccc3cccnc23)c(O)c2ccccc12)c1ccc(Cl)c(C(F)(F)F)c1] | C26H16ClF3N2O3S2 | 561.0052 | 7.60776 |
| F5749-0140 | 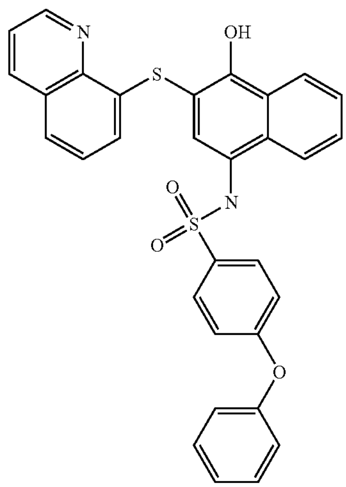 [SMILES: O=S(=O)(Nc1cc(Sc2cccc3cccnc23)c(O)c2ccccc12)c1ccc(Oc2ccccc2)cc1] | C31H22N2O4S2 | 550.66 | 7.656 |
| F5749-0141 | 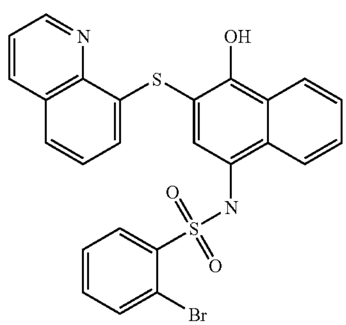 | C25H17BrN2O3S2 | 537.4578 | 6.842 |
| F5749-0142 | 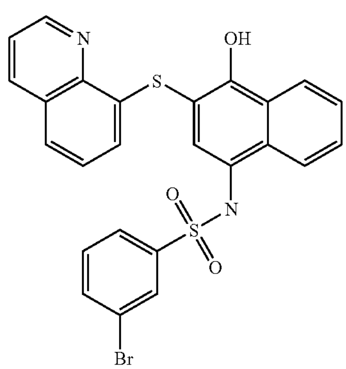 [SMILES: O=S(=O)(Nc1cc(Sc2cccc3cccnc23)c(O)c2ccccc12)c1cccc(Br)c1] | C25H17BrN2O3S2 | 537.4578 | 6.881 |

TABLE 9-continued

| IDNUMBER | Structure | Formula structure | MW | LogP |
| --- | --- | --- | --- | --- |
| F5749-0143 | 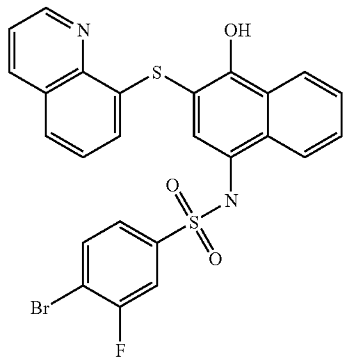 [SMILES: O=S(=O)(Nc1cc(Sc2cccc3cccnc23)c(O)c2ccccc12)c1ccc(Br)c(F)c1] | C25H16BrFN2O3S2 | 555.4483 | 7.032 |
| F5749-0144 | 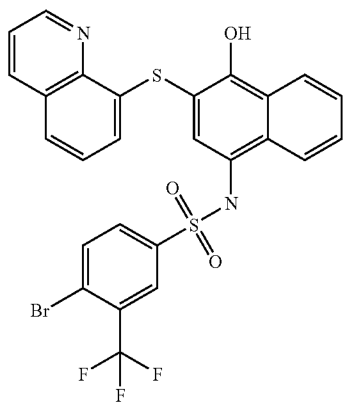 [SMILES: O=S(=O)(Nc1cc(Sc2cccc3cccnc23)c(O)c2ccccc12)c1ccc(Br)c(C(F)(F)F)c1] | C26H16BrF3N2O3S2 | 605.4562 | 7.81376 |
| F5749-0145 | 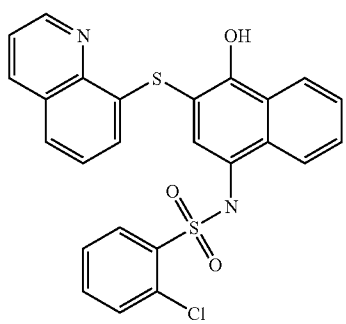 [SMILES: O=S(=O)(Nc1cc(Sc2cccc3cccnc23)c(O)c2ccccc12)c1ccccc1Cl] | C25H17ClN2O3S2 | 493.0068 | 6.636 |
| F5749-0146 | 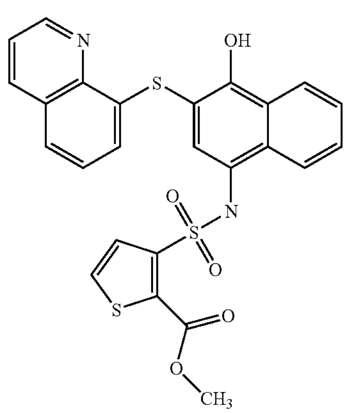 [SMILES: COC(=O)c1sccc1S(=O)(=O)Nc1cc(Sc2cccc3cccnc23)c(O)c2ccccc12] | C25H18N2O5S3 | 522.6246 | 5.246 |

TABLE 9-continued

| IDNUMBER | Structure | Formula structure | MW | LogP |
| --- | --- | --- | --- | --- |
| F5749-0147 | 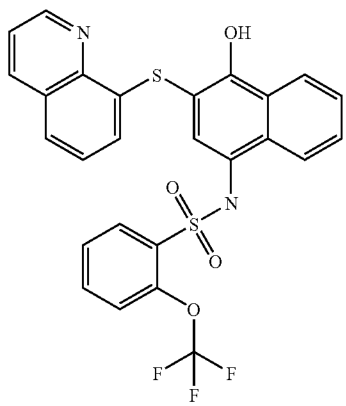 [SMILES: O=S(=O)(Nc1cc(Sc2cccc3cccnc23)c(O)c2ccccc12)c1ccccc1OC(F)(F)F] | C26H17F3N2O4S2 | 542.5596 | 7.44276 |

TABLE 10

| IDNUMBER | Structure | Formula structure | MW | LogP |
| --- | --- | --- | --- | --- |
| F1565-0253 | 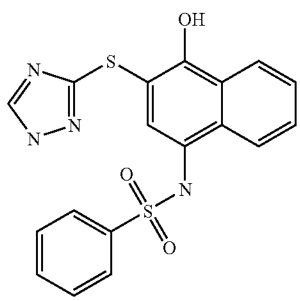 [SMILES: O=S(=O)(Nc1cc(Sc2nc[nH]n2)c(O)c2ccccc12)c1ccccc1] | C18H14N4O3S2 | 398.4653 | 3.698 |
| F1566-0328 | 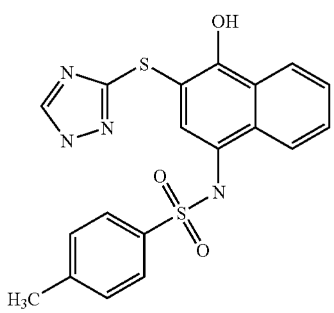 [SMILES: Cc1ccc(S(=O)(=O)Nc2cc(Sc3nc[nH]n3)c(O)c3ccccc23)cc1] | C19H16N4O3S2 | 412.4924 | 3.996 |
| F1566-0340 | 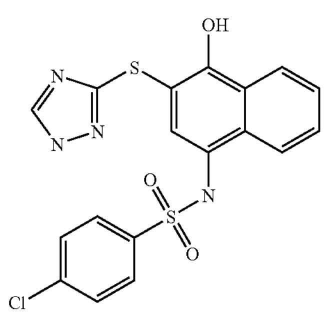 [SMILES: O=S(=O)(Nc1cc(Sc2nc[nH]n2)c(O)c2ccccc12)c1ccc(Cl)cc1] | C18H13ClN4O3S2 | 432.9103 | 4.29 |

TABLE 10-continued

| IDNUMBER | Structure | Formula structure | MW | LogP |
|---|---|---|---|---|
| F1566-0520 | 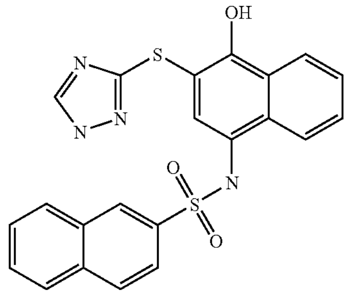 [SMILES: O=S(=O)(Nc1cc(Sc2nc[nH]n2)c(O)c2ccccc12)c1ccc2ccccc2c1] | C22H16N4O3S2 | 448.5258 | 4.957 |
| F1566-0556 | 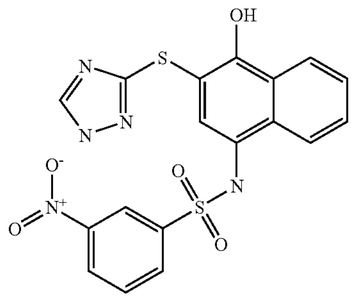 [SMILES: O=[N+]([O-])c1cccc(S(=O)(=O)Nc2cc(Sc3nc[nH]n3)c(O)c3ccccc23)c1] | C18H13N5O5S2 | 443.4628 | 3.67 |
| F1566-0568 | 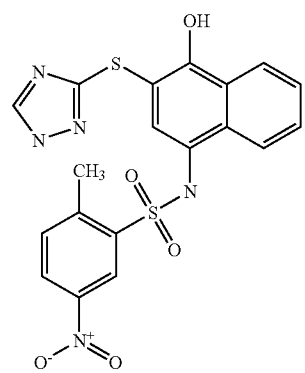 [SMILES: Cc1ccc([N+](=O)[O-])cc1S(=O)(=O)Nc1cc(Sc2nc[nH]n2)c(O)c2ccccc12] | C19H15N5O5S2 | 457.4899 | 3.966 |
| F1566-0616 | 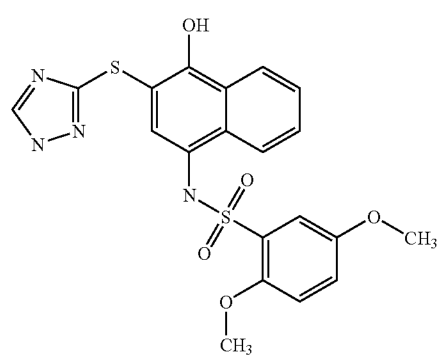 [SMILES: COc1ccc(OC)c(S(=O)(=O)Nc2cc(Sc3nc[nH]n3)c(O)c3ccccc23)c1] | C20H18N4O5S2 | 458.5183 | 3.645 |

TABLE 10-continued

| IDNUMBER | Structure | Formula structure | MW | LogP |
|---|---|---|---|---|
| F1566-0628 | 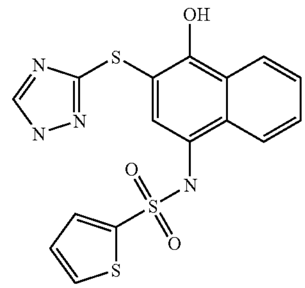 [SMILES: O=S(=O)(Nc1cc(Sc2nc[nH]n2)c(O)c2ccccc12)c1cccs1] | C16H12N4O3S3 | 404.491 | 3.211 |
| F5749-0148 | 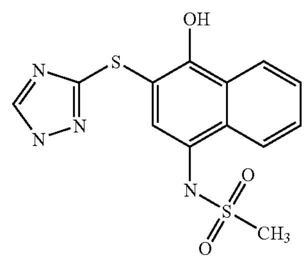 [SMILES: CS(=O)(=O)Nc1cc(Sc2nc[nH]n2)c(O)c2ccccc12] | C13H12N4O3S2 | 336.3936 | 2.044 |
| F5749-0149 | 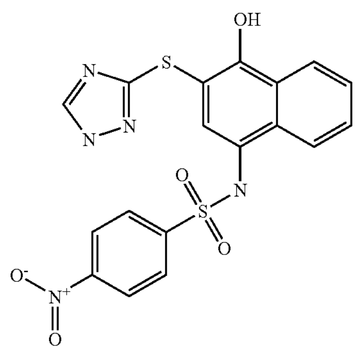 [SMILES: O=[N+]([O-])c1ccc(S(=O)(=O)Nc2cc(Sc3nc[nH]n3)c(O)c3ccccc23)cc1] | C18H13N5O5S2 | 443.4628 | 3.633 |
| F5749-0150 | 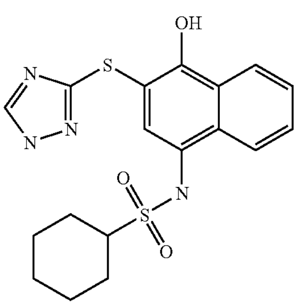 [SMILES: O=S(=O)(Nc1cc(Sc2nc[nH]n2)c(O)c2ccccc12)C1CCCCC1] | C18H20N4O3S2 | 404.5131 | 4.023 |
| F5749-0151 | 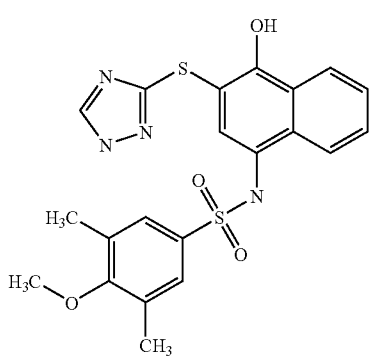 [SMILES: COc1c(C)cc(S(=O)(=O)Nc2cc(Sc3nc[nH]n3)c(O)c3ccccc23)cc1C] | C21H20N4O4S2 | 456.546 | 4.32 |

TABLE 10-continued
| IDNUMBER | Structure | Formula structure | MW | LogP |
|---|---|---|---|---|
| F5749-0152 | 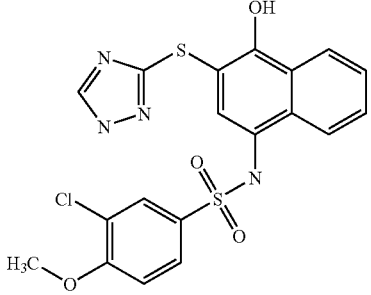 [SMILES: COc1ccc(S(=O)(=O)Nc2cc(Sc3nc[nH]n3)c(O)c3ccccc23)cc1Cl] | C19H15ClN4O4S2 | 462.9368 | 4.281 |
| F5749-0153 | 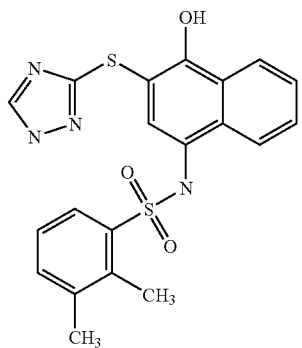 [SMILES: Cc1cccc(S(=O)(=O)Nc2cc(Sc3nc[nH]n3)c(O)c3ccccc23)c1C] | C20H18N4O3S2 | 426.5195 | 4.29 |
| F5749-0154 | 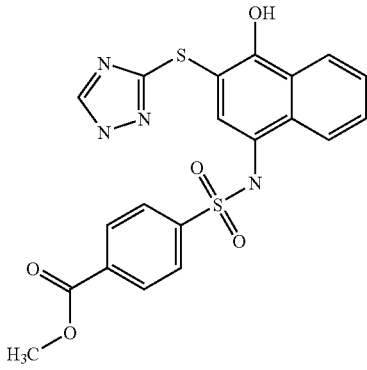 [SMILES: COC(=O)c1ccc(S(=O)(=O)Nc2cc(Sc3nc[nH]n3)c(O)c3ccccc23)cc1] | C20H16N4O5S2 | 456.5023 | 3.639 |
| F5749-0155 | 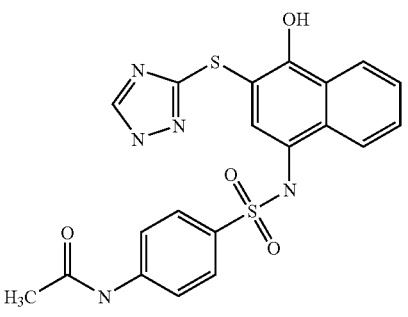 [SMILES: CC(=O)Nc1ccc(S(=O)(=O)Nc2cc(Sc3nc[nH]n3)c(O)c3ccccc23)cc1] | C20H17N5O4S2 | 455.5176 | 2.989 |

TABLE 10-continued

| IDNUMBER | Structure | Formula structure | MW | LogP |
|---|---|---|---|---|
| F5749-0156 | 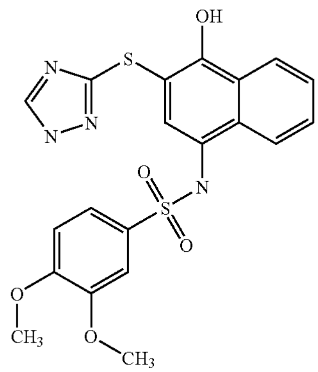 [SMILES: COc1ccc(S(=O)(=O)Nc2cc(Sc3nc[nH]n3)c(O)c3ccccc23)cc1OC] | C20H18N4O5S2 | 458.5183 | 3.39674 |
| F5749-0157 | 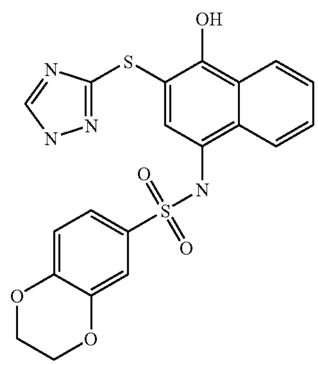 [SMILES: O=S(=O)(Nc1cc(Sc2nc[nH]n2)c(O)c2ccccc12)c1ccc2c(c1)OCCO2] | C20H16N4O5S2 | 456.5023 | 3.293 |
| F5749-0158 | 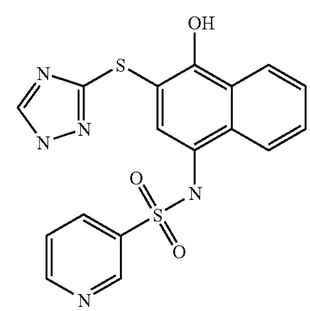 [SMILES: O=S(=O)(Nc1cc(Sc2nc[nH]n2)c(O)c2ccccc12)c1cccnc1] | C17H13N5O3S2 | 399.4529 | 2.465 |
| F5749-0159 | 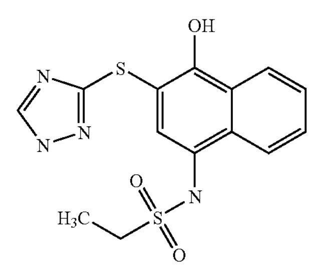 [SMILES: CCS(=O)(=O)Nc1cc(Sc2nc[nH]n2)c(O)c2ccccc12] | C14H14N4O3S2 | 350.4207 | 2.557 |
| F5749-0160 | 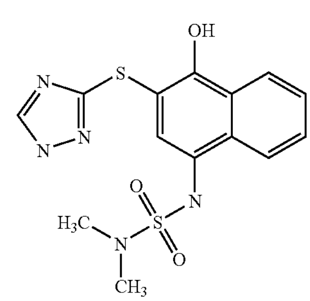 | C14H15N5O3S2 | 365.4354 | 1.592 |

TABLE 10-continued

| IDNUMBER | Structure | Formula structure | MW | LogP |
|---|---|---|---|---|
| F5749-0161 | 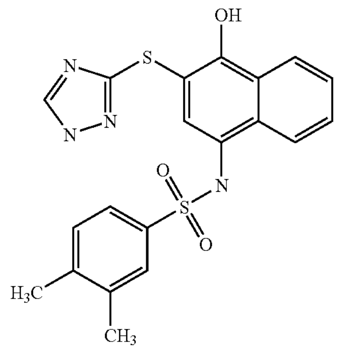 [SMILES: Cc1ccc(S(=O)(=O)Nc2cc(Sc3nc[nH]n3)c(O)c3ccccc23)cc1C] | C20H18N4O3S2 | 426.5195 | 4.329 |
| F5749-0162 | 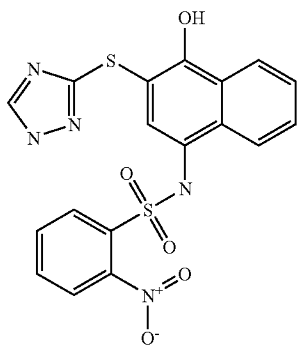 [SMILES: O=[N+]([O-])c1ccccc1S(=O)(=O)Nc1cc(Sc2nc[nH]n2)c(O)c2ccccc12] | C18H13N5O5S2 | 443.4628 | 3.631 |
| F5749-0163 | 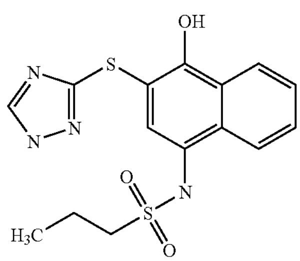 [SMILES: CCCS(=O)(=O)Nc1cc(Sc2nc[nH]n2)c(O)c2ccccc12] | C15H16N4O3S2 | 364.4478 | 2.999 |
| F5749-0164 | 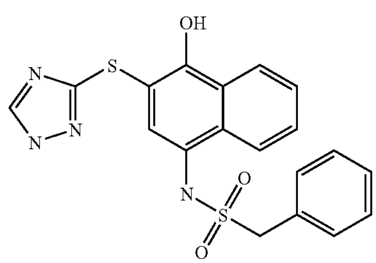 [SMILES: O=S(=O)(Cc1ccccc1)Nc1cc(Sc2nc[nH]n2)c(O)c2ccccc12] | C19H16N4O3S2 | 412.4924 | 3.832 |
| F5749-0165 | 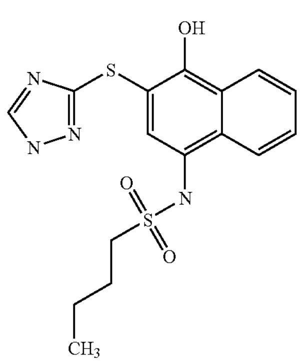 [SMILES: CCCCS(=O)(=O)Nc1cc(Sc2nc[nH]n2)c(O)c2ccccc12] | C16H18N4O3S2 | 378.4749 | 3.441 |

TABLE 10-continued

| IDNUMBER | Structure | Formula structure | MW | LogP |
|---|---|---|---|---|
| F5749-0166 | 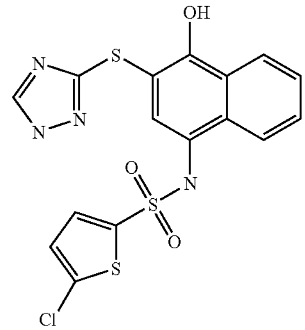 [SMILES: O=S(=O)(Nc1cc(Sc2nc[nH]n2)c(O)c2ccccc12)c1ccc(Cl)s1] | C16H11ClN4O3S3 | 438.9361 | 4.501 |
| F5749-0167 | 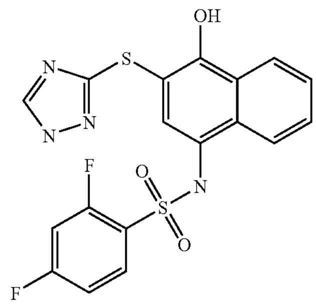 [SMILES: O=S(=O)(Nc1cc(Sc2nc[nH]n2)c(O)c2ccccc12)c1ccc(F)cc1F] | C18H12F2N4O3S2 | 434.4461 | 4.039 |
| F5749-0168 | 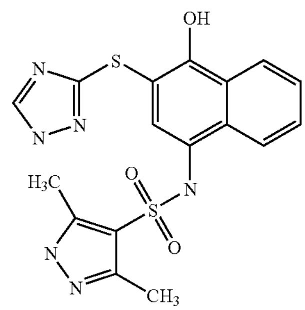 [SMILES: Cc1n[nH]c(C)c1S(=O)(=O)Nc1cc(Sc2nc[nH]n2)c(O)c2ccccc12] | C17H16N6O3S2 | 416.4835 | 2.808 |
| F5749-0169 | 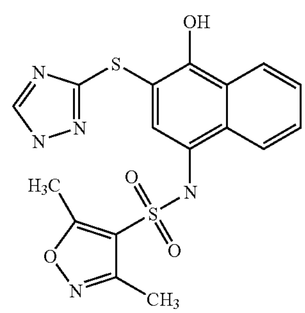 | C17H15N5O4S2 | 417.4682 | 2.842 |
| F5749-0170 | 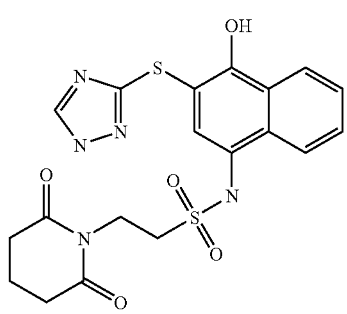 [SMILES: O=C1CCCC(=O)N1CCS(=O)(=O)Nc1cc(Sc2nc[nH]n2)c(O)c2ccccc12] | C19H19N5O5S2 | 461.5218 | 1.485 |

TABLE 10-continued
| IDNUMBER | Structure | Formula structure | MW | LogP |
| --- | --- | --- | --- | --- |
| F5749-0171 | 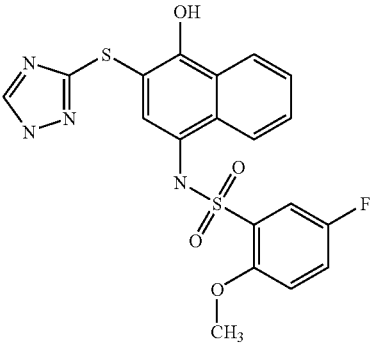 [SMILES: COc1ccc(F)cc1S(=O)(=O)Nc1cc(Sc2nc[nH]n2)c(O)c2ccccc12] | C19H15FN4O4S2 | 446.4822 | 3.842 |
| F5749-0172 | 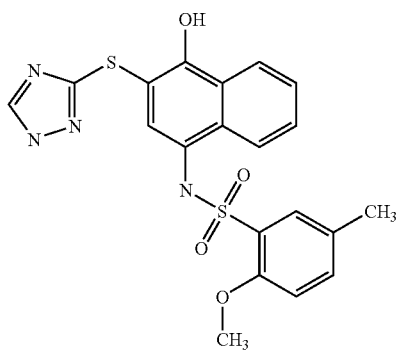 [SMILES: COc1ccc(C)cc1S(=O)(=O)Nc1cc(Sc2nc[nH]n2)c(O)c2ccccc12] | C20H18N4O4S2 | 442.5189 | 3.987 |
| F5749-0173 | 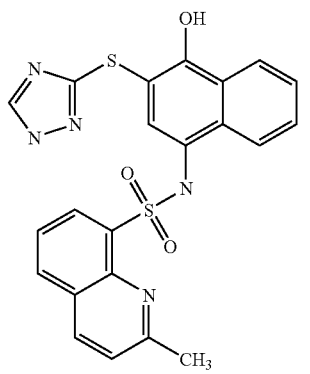 [SMILES: Cc1ccc2cccc(S(=O)(=O)Nc3cc(Sc4nc[nH]n4)c(O)c4ccccc34)c2n1] | C22H17N5O3S2 | 463.5405 | 4.157 |
| F5749-0174 | 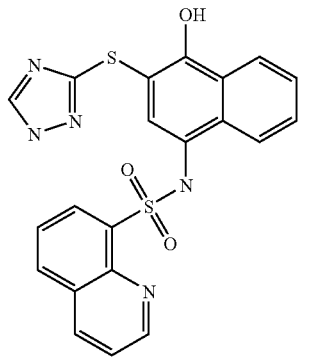 [SMILES: O=S(=O)(Nc1cc(Sc2nc[nH]n2)c(O)c2ccccc12)c1cccc2cccnc12] | C21H15N5O3S2 | 449.5134 | 3.898 |

TABLE 10-continued

| IDNUMBER | Structure | Formula structure | MW | LogP |
|---|---|---|---|---|
| F5749-0175 | 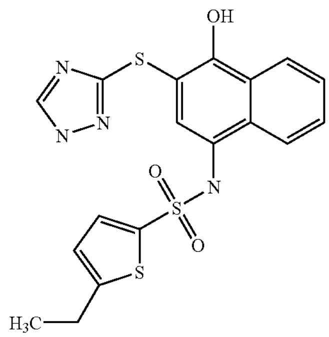 [SMILES: CCc1ccc(S(=O)(=O)Nc2cc(Sc3nc[nH]n3)c(O)c3ccccc23)s1] | C18H16N4O3S3 | 432.5452 | 4.349 |
| F5749-0176 | 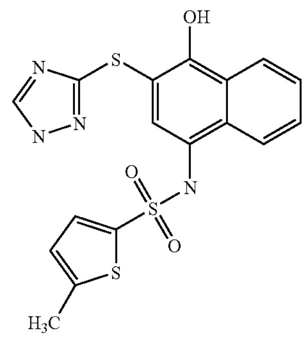 [SMILES: Cc1ccc(S(=O)(=O)Nc2cc(Sc3nc[nH]n3)c(O)c3ccccc23)s1] | C17H14N4O3S3 | 418.5181 | 3.874 |
| F5749-0177 | 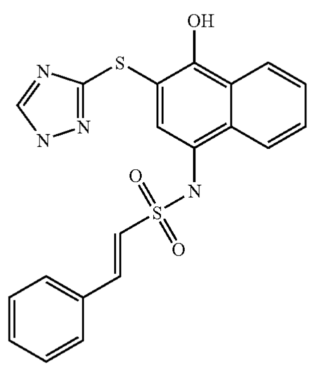 [SMILES: O=S(=O)(/C=C/c1ccccc1)Nc1cc(Sc2nc[nH]n2)c(O)c2ccccc12] | C20H16N4O3S2 | 424.5035 | 4.056 |
| F5749-0178 | 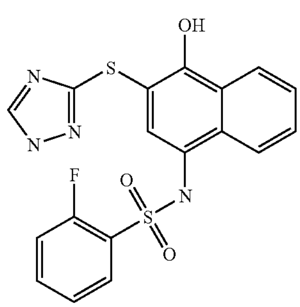 [SMILES: O=S(=O)(Nc1cc(Sc2nc[nH]n2)c(O)c2ccccc12)c1ccccc1F] | C18H13FN4O3S2 | 416.4557 | 3.849 |

TABLE 10-continued

| IDNUMBER | Structure | Formula structure | MW | LogP |
| --- | --- | --- | --- | --- |
| F5749-0179 | 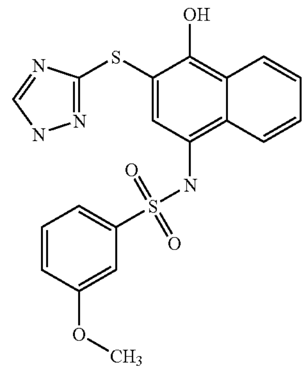 [SMILES: COc1cccc(S(=O)(=O)Nc2cc(Sc3nc[nH]n3)c(O)c3ccccc23)c1] | C19H16N4O4S2 | 428.4918 | 3.691 |
| F5749-0180 | 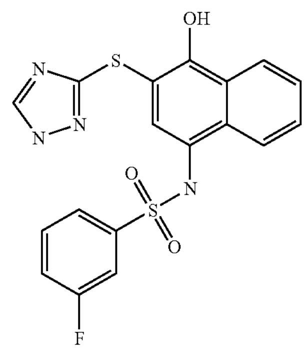 [SMILES: O=S(=O)(Nc1cc(Sc2nc[nH]n2)c(O)c2ccccc12)c1cccc(F)c1] | C18H13FN4O3S2 | 416.4557 | 3.888 |
| F5749-0181 | 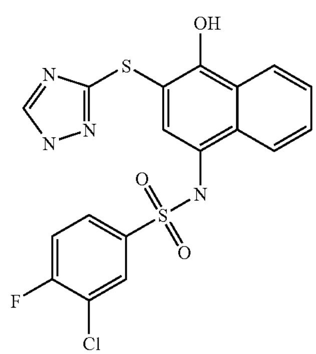 [SMILES: O=S(=O)(Nc1cc(Sc2nc[nH]n2)c(O)c2ccccc12)c1ccc(F)c(Cl)c1] | C18H12ClFN4O3S2 | 450.9007 | 4.478 |
| F5749-0182 | 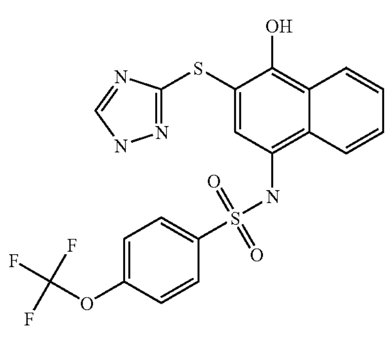 [SMILES: O=S(=O)(Nc1cc(Sc2nc[nH]n2)c(O)c2ccccc12)c1ccc(OC(F)(F)F)cc1] | C19H13F3N4O4S2 | 482.4631 | 5.09676 |

TABLE 10-continued

| IDNUMBER | Structure | Formula structure | MW | LogP |
| --- | --- | --- | --- | --- |
| F5749-0183 | 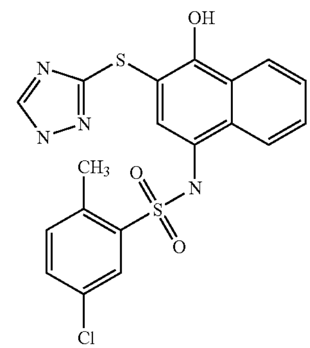 [SMILES: Cc1ccc(Cl)cc1S(=O)(=O)Nc1cc(Sc2nc[nH]n2)c(O)c2ccccc12] | C19H15ClN4O3S2 | 446.9374 | 4.623 |
| F5749-0184 | 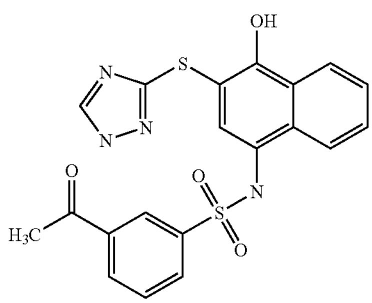 [SMILES: CC(=O)c1cccc(S(=O)(=O)Nc2cc(Sc3nc[nH]n3)c(O)c3ccccc23)c1] | C20H16N4O4S2 | 440.5029 | 3.588 |
| F5749-0185 | 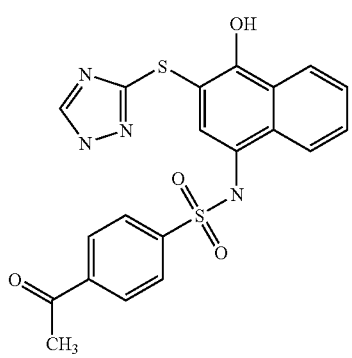 [SMILES: CC(=O)c1ccc(S(=O)(=O)Nc2cc(Sc3nc[nH]n3)c(O)c3ccccc23)cc1] | C20H16N4O4S2 | 440.5029 | 3.551 |
| F5749-0186 | 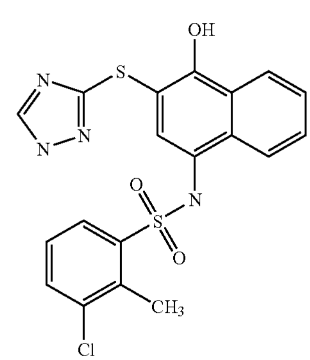 [SMILES: Cc1c(Cl)cccc1S(=O)(=O)Nc1cc(Sc2nc[nH]n2)c(O)c2ccccc12] | C19H15ClN4O3S2 | 446.9374 | 4.584 |

TABLE 10-continued

| IDNUMBER | Structure | Formula structure | MW | LogP |
|---|---|---|---|---|
| F5749-0187 | 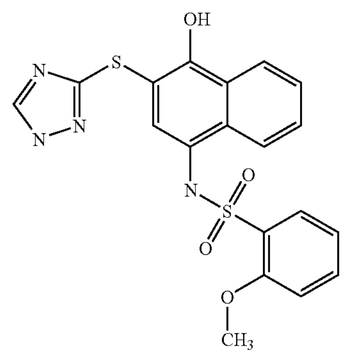 [SMILES: COc1ccccc1S(=O)(=O)Nc1cc(Sc2nc[nH]n2)c(O)c2ccccc12] | C19H16N4O4S2 | 428.4918 | 3.652 |
| F5749-0188 | 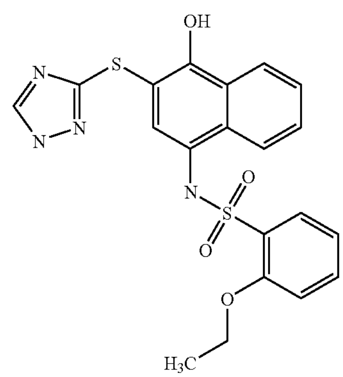 [SMILES: CCOc1ccccc1S(=O)(=O)Nc1cc(Sc2nc[nH]n2)c(O)c2ccccc12] | C20H18N4O4S2 | 442.5189 | 3.993 |
| F5749-0189 | 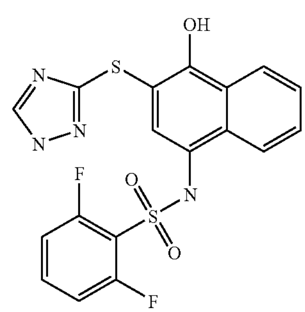 [SMILES: O=S(=O)(Nc1cc(Sc2nc[nH]n2)c(O)c2ccccc12)c1c(F)cccc1F] | C18H12F2N4O3S2 | 434.4461 | 4 |
| F5749-0190 | 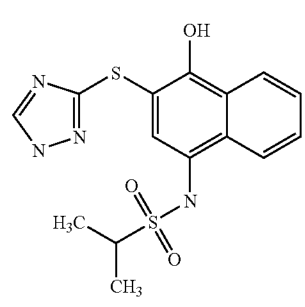 [SMILES: CC(C)S(=O)(=O)Nc1cc(Sc2nc[nH]n2)c(O)c2ccccc12] | C15H16N4O3S2 | 364.4478 | 3.191 |

TABLE 10-continued

| IDNUMBER | Structure | Formula structure | MW | LogP |
|---|---|---|---|---|
| F5749-0191 | 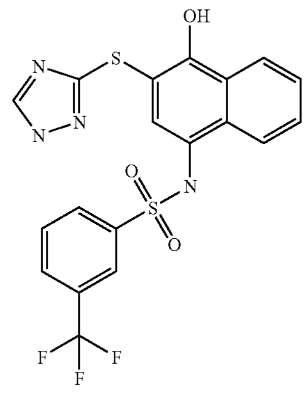 [SMILES: O=S(=O)(Nc1cc(Sc2nc[nH]n2)c(O)c2ccccc12)c1cccc(C(F)(F)F)c1] | C19H13F3N4O3S2 | 466.4637 | 4.66976 |
| F5749-0192 | 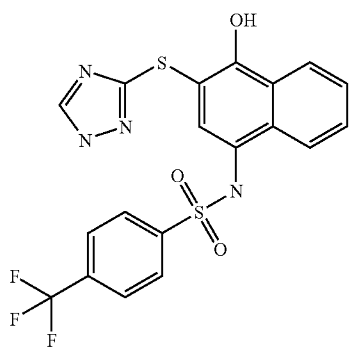 [SMILES: O=S(=O)(Nc1cc(Sc2nc[nH]n2)c(O)c2ccccc12)c1ccc(C(F)(F)F)cc1] | C19H13F3N4O3S2 | 466.4637 | 4.63276 |
| F5749-0193 | 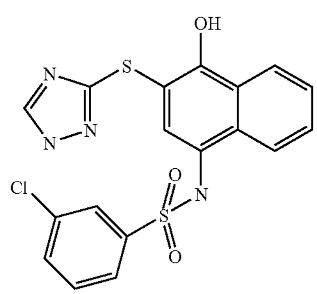 [SMILES: O=S(=O)(Nc1cc(Sc2nc[nH]n2)c(O)c2ccccc12)c1cccc(Cl)c1] | C18H13ClN4O3S2 | 432.9103 | 4.327 |
| F5749-0194 | 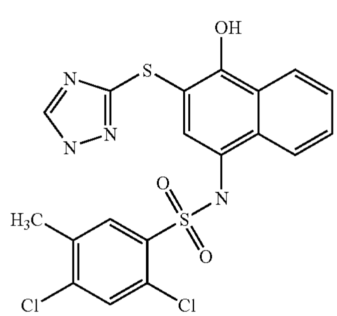 [SMILES: Cc1cc(S(=O)(=O)Nc2cc(Sc3nc[nH]n3)c(O)c3ccccc23)c(Cl)cc1Cl] | C19H14Cl2N4O3S2 | 481.3824 | 5.25 |

TABLE 10-continued

| IDNUMBER | Structure | Formula structure | MW | LogP |
|---|---|---|---|---|
| F5749-0195 | 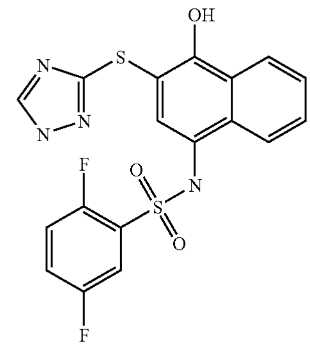 [SMILES: O=S(=O)(Nc1cc(Sc2nc[nH]n2)c(O)c2ccccc12)c1cc(F)ccc1F] | C18H12F2N4O3S2 | 434.4461 | 4.039 |
| F5749-0196 | 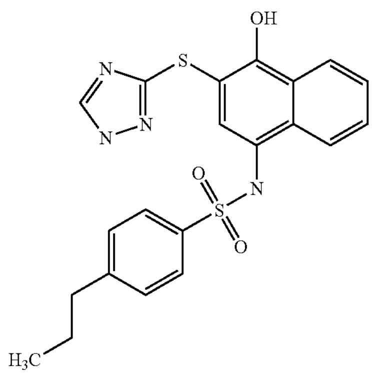 [SMILES: CCCc1ccc(S(=O)(=O)Nc2cc(Sc3nc[nH]n3)c(O)c3ccccc23)cc1] | C21H20N4O3S2 | 440.5466 | 4.913 |
| F5749-0197 | 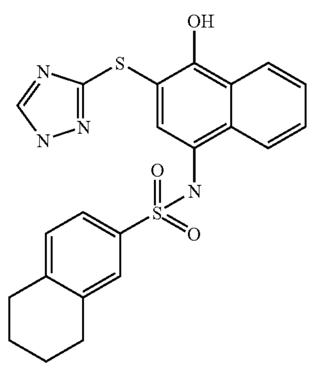 [SMILES: O=S(=O)(Nc1cc(Sc2nc[nH]n2)c(O)c2ccccc12)c1ccc2c(c1)CCCC2] | C22H20N4O3S2 | 452.5577 | 4.785 |
| F5749-0198 | 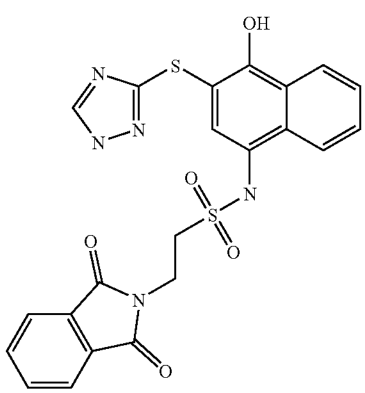 [SMILES: O=C1c2ccccc2C(=O)N1CCS(=O)(=O)Nc1cc(Sc2nc[nH]n2)c(O)c2ccccc12] | C22H17N5O5S2 | 495.5393 | 2.825 |

TABLE 10-continued

| IDNUMBER | Structure | Formula structure | MW | LogP |
|---|---|---|---|---|
| F5749-0199 | 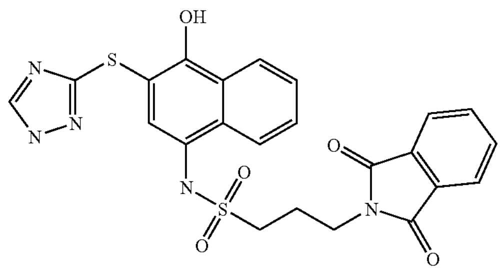 [SMILES: O=C1c2ccccc2C(=O)N1CCCS(=O)(=O)Nc1cc(Sc2nc[nH]n2)c(O)c2ccccc12] | C23H19N5O5S2 | 509.5664 | 3.267 |
| F5749-0200 | 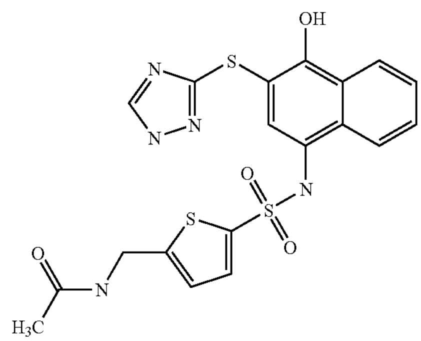 [SMILES: CC(=O)NCc1ccc(S(=O)(=O)Nc2cc(Sc3nc[nH]n3)c(O)c3ccccc23)s1] | C19H17N5O4S3 | 475.5704 | 3.001 |
| F5749-0201 | 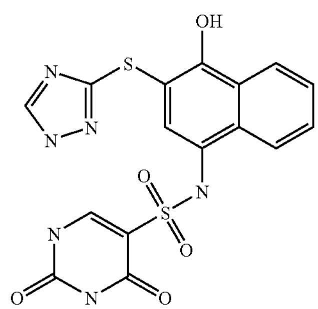 [SMILES: O=c1[nH]cc(S(=O)(=O)Nc2cc(Sc3nc[nH]n3)c(O)c3ccccc23)c(=O)[nH]1] | C16H12N6O5S2 | 432.4392 | 0.743 |
| F5749-0202 | 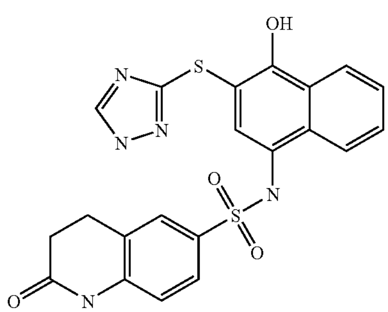 [SMILES: O=C1CCc2cc(S(=O)(=O)Nc3cc(Sc4nc[nH]n4)c(O)c4ccccc34)ccc2N1] | C21H17N5O4S2 | 467.5287 | 2.894 |
| F5749-0203 | 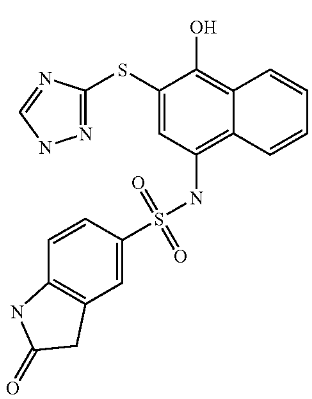 [SMILES: O=C1Cc2cc(S(=O)(=O)Nc3cc(Sc4nc[nH]n4)c(O)c4ccccc34)ccc2N1] | C20H15N5O4S2 | 453.5017 | 2.806 |

TABLE 10-continued

| IDNUMBER | Structure | Formula structure | MW | LogP |
|---|---|---|---|---|
| F5749-0204 | 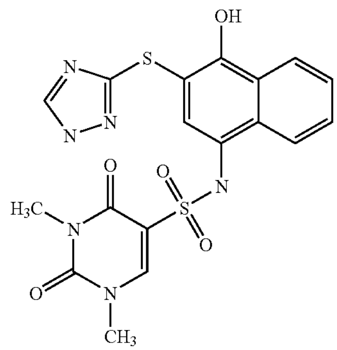 [SMILES: Cn1cc(S(=O)(=O)Nc2cc(Sc3nc[nH]n3)c(O)c3ccccc23)c(=O)n(C)c1=O] | C18H16N6O5S2 | 460.4934 | 0.807 |
| F5749-0205 | 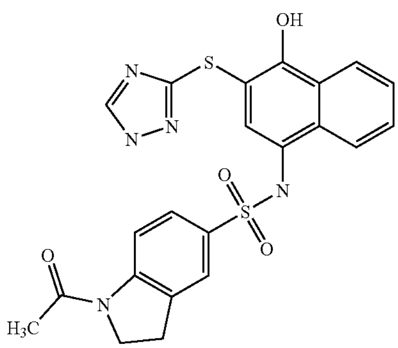 [SMILES: CC(=O)N1CCc2cc(S(=O)(=O)Nc3cc(Sc4nc[nH]n4)c(O)c4ccccc34)ccc21] | C22H19N5O4S2 | 481.5558 | 3.129 |
| F5749-0206 | 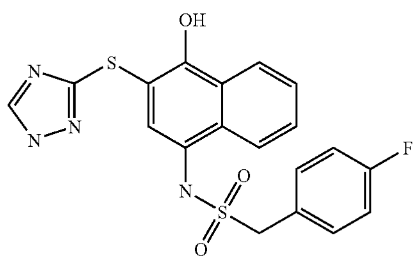 [SMILES: O=S(=O)(Cc1ccc(F)cc1)Nc1cc(Sc2nc[nH]n2)c(O)c2ccccc12] | C19H15FN4O3S2 | 430.4828 | 3.985 |
| F5749-0207 | 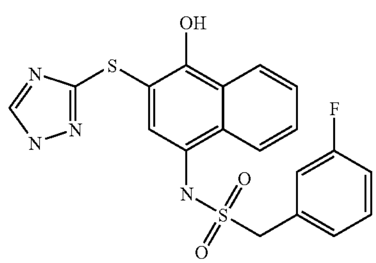 [SMILES: O=S(=O)(Cc1cccc(F)c1)Nc1cc(Sc2nc[nH]n2)c(O)c2ccccc12] | C19H15FN4O3S2 | 430.4828 | 4.022 |
| F5749-0208 | 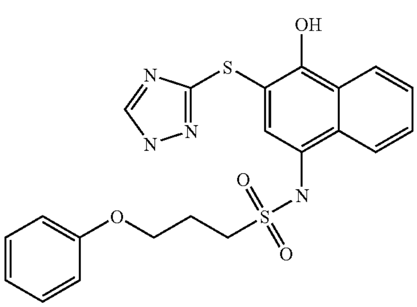 [SMILES: O=S(=O)(CCCOc1ccccc1)Nc1cc(Sc2nc[nH]n2)c(O)c2ccccc12] | C21H20N4O4S2 | 456.546 | 4.058 |

TABLE 10-continued

| IDNUMBER | Structure | Formula structure | MW | LogP |
|---|---|---|---|---|
| F5749-0209 | 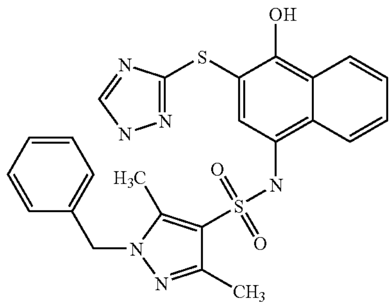 [SMILES: Cc1nn(Cc2ccccc2)c(C)c1S(=O)(=O)Nc1cc(Sc2nc[nH]n2)c(O)c2ccccc12] | C24H22N6O3S2 | 506.6093 | 3.977 |
| F5749-0210 | 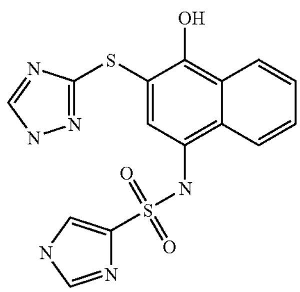 [SMILES: O=S(=O)(Nc1cc(Sc2nc[nH]n2)c(O)c2ccccc12)c1c[nH]cn1] | C15H12N6O3S2 | 388.4293 | 1.838 |
| F5749-0211 | 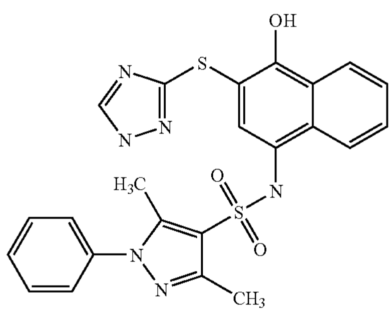 [SMILES: Cc1nn(-c2ccccc2)c(C)c1S(=O)(=O)Nc1cc(Sc2nc[nH]n2)c(O)c2ccccc12] | C23H20N6O3S2 | 492.5823 | 3.843 |
| F5749-0212 | 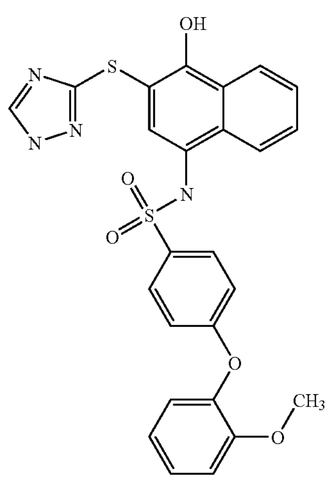 [SMILES: COc1ccccc1Oc1ccc(S(=O)(=O)Nc2cc(Sc3nc[nH]n3)c(O)c3ccccc23)cc1] | C25H20N4O5S2 | 520.59 | 5.01374 |

TABLE 10-continued

| IDNUMBER | Structure | Formula structure | MW | LogP |
|---|---|---|---|---|
| F5749-0213 | 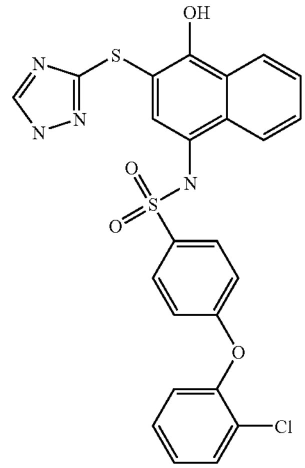 [SMILES: O=S(=O)(Nc1cc(Sc2nc[nH]n2)c(O)c2ccccc12)c1ccc(Oc2ccccc2Cl)cc1] | C24H17ClN4O4S2 | 525.0085 | 5.898 |
| F5749-0214 | 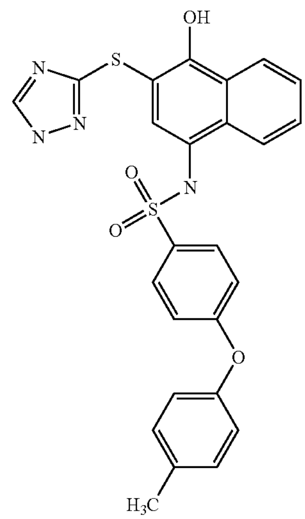 [SMILES: Cc1ccc(Oc2ccc(S(=O)(=O)Nc3cc(Sc4nc[nH]n4)c(O)c4ccccc34)cc2)cc1] | C25H20N4O4S2 | 504.5906 | 5.606 |
| F5749-0215 | 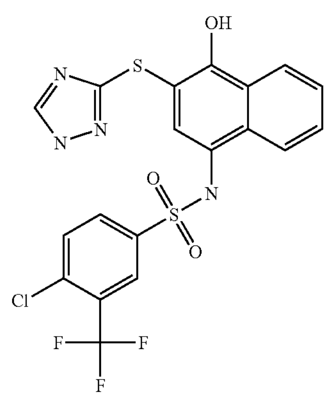 [SMILES: O=S(=O)(Nc1cc(Sc2nc[nH]n2)c(O)c2ccccc12)c1ccc(Cl)c(C(F)(F)F)c1] | C19H12ClF3N4O3S2 | 500.9087 | 5.25976 |

TABLE 10-continued

| IDNUMBER | Structure | Formula structure | MW | LogP |
| --- | --- | --- | --- | --- |
| F5749-0216 | 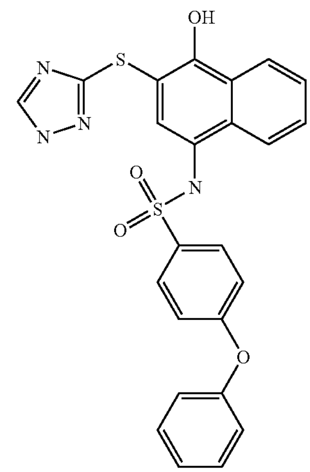 [SMILES: O=S(=O)(Nc1cc(Sc2nc[nH]n2)c(O)c2ccccc12)c1ccc(Oc2ccccc2)cc1] | C24H18N4O4S2 | 490.5635 | 5.308 |
| F5749-0217 | 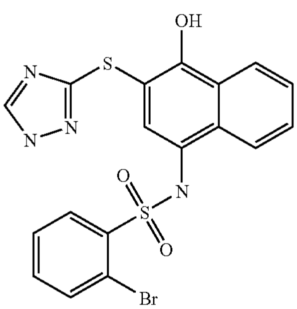 | C18H13BrN4O3S2 | 477.3613 | 4.494 |
| F5749-0218 | 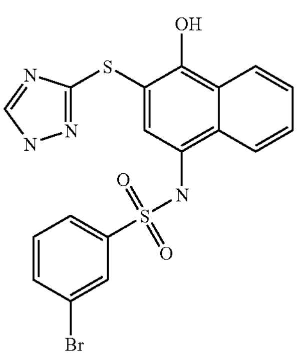 [SMILES: O=S(=O)(Nc1cc(Sc2nc[nH]n2)c(O)c2ccccc12)c1cccc(Br)c1] | C18H13BrN4O3S2 | 477.3613 | 4.533 |
| F5749-0219 | 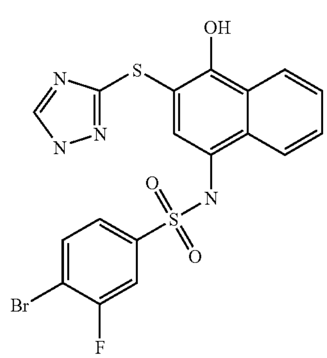 [SMILES: O=S(=O)(Nc1cc(Sc2nc[nH]n2)c(O)c2ccccc12)c1ccc(Br)c(F)c1] | C18H12BrFN4O3S2 | 495.3517 | 4.684 |

TABLE 10-continued

| IDNUMBER | Structure | Formula structure | MW | LogP |
|---|---|---|---|---|
| F5749-0220 | 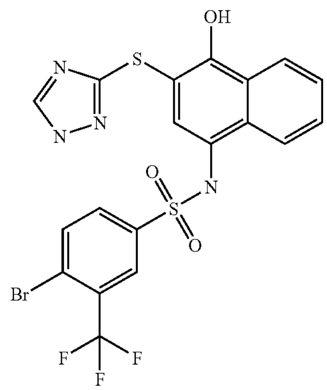 [SMILES: O=S(=O)(Nc1cc(Sc2nc[nH]n2)c(O)c2ccccc12)c1ccc(Br)c(C(F)(F)F)c1] | C19H12BrF3N4O3S2 | 545.3597 | 5.46576 |
| F5749-0221 | 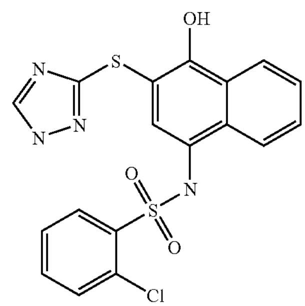 [SMILES: O=S(=O)(Nc1cc(Sc2nc[nH]n2)c(O)c2ccccc12)c1ccccc1Cl] | C18H13ClN4O3S2 | 432.9103 | 4.288 |
| F5749-0222 | 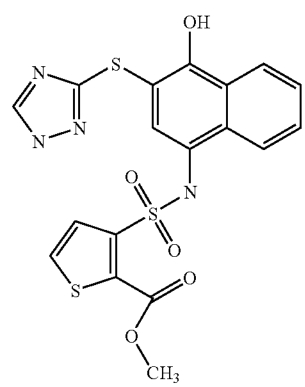 [SMILES: COC(=O)c1sccc1S(=O)(=O)Nc1cc(Sc2nc[nH]n2)c(O)c2ccccc12] | C18H14N4O5S3 | 462.5281 | 2.898 |
| F5749-0223 | 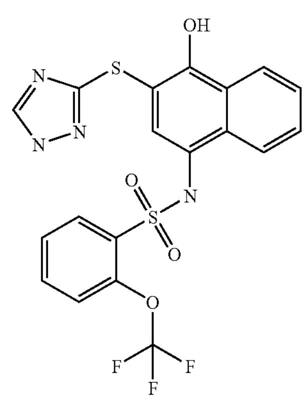 [SMILES: O=S(=O)(Nc1cc(Sc2nc[nH]n2)c(O)c2ccccc12)c1ccccc1OC(F)(F)F] | C19H13F3N4O4S2 | 482.4631 | 5.09476 |

TABLE 11

| IDNUMBER | Structure | Formula structure | MW | LogP |
| --- | --- | --- | --- | --- |
| F0808-0128 | 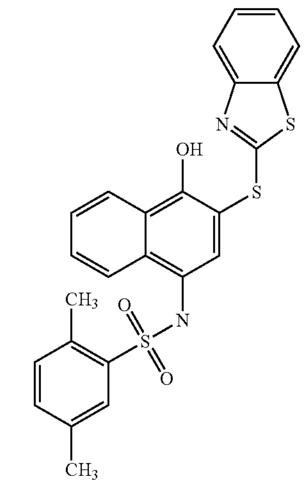 [SMILES: Cc1ccc(C)c(S(=O)(=O)Nc2cc(Sc3nc4ccccc4s3)c(O)c3ccccc23)c1] | C25H20N2O3S3 | 492.6418 | 6.892 |
| F0808-0132 | 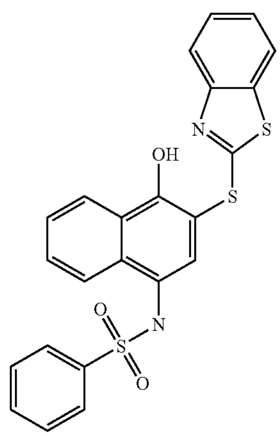 [SMILES: O=S(=O)(Nc1cc(Sc2nc3ccccc3s2)c(O)c2ccccc12)c1ccccc1] | C23H16N2O3S3 | 464.5876 | 6.261 |
| F0808-0133 | 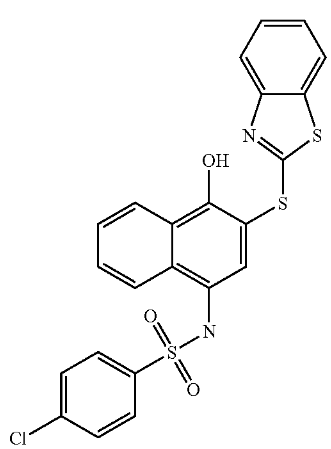 [SMILES: O=S(=O)(Nc1cc(Sc2nc3ccccc3s2)c(O)c2ccccc12)c1ccc(Cl)cc1] | C23H15ClN2O3S3 | 499.0326 | 6.853 |

TABLE 11-continued

| IDNUMBER | Structure | Formula structure | MW | LogP |
| --- | --- | --- | --- | --- |
| F0808-0134 | 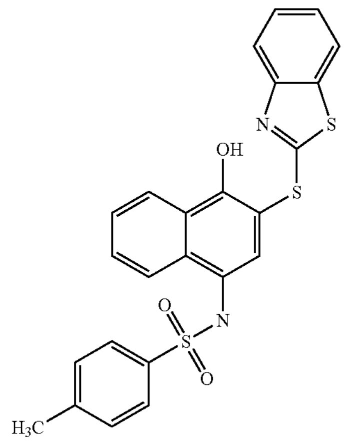 [SMILES: Cc1ccc(S(=O)(=O)Nc2cc(Sc3nc4ccccc4s3)c(O)c3ccccc23)cc1] | C24H18N2O3S3 | 478.6147 | 6.559 |
| F0808-0136 | 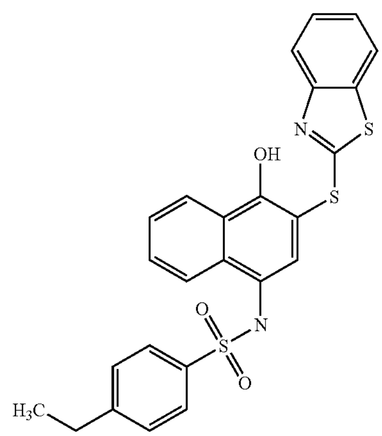 [SMILES: CCc1ccc(S(=O)(=O)Nc2cc(Sc3nc4ccccc4s3)c(O)c3ccccc23)cc1] | C25H20N2O3S3 | 492.6418 | 7.034 |
| F0808-0137 | 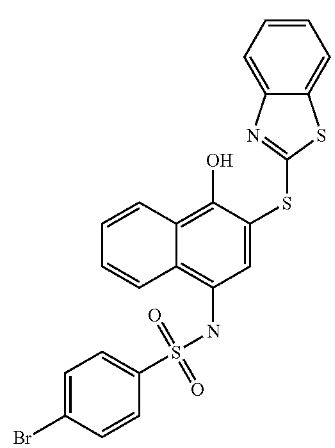 | C23H15BrN2O3S3 | 543.4836 | 7.059 |

TABLE 11-continued

| IDNUMBER | Structure | Formula structure | MW | LogP |
|---|---|---|---|---|
| F1269-0225 | 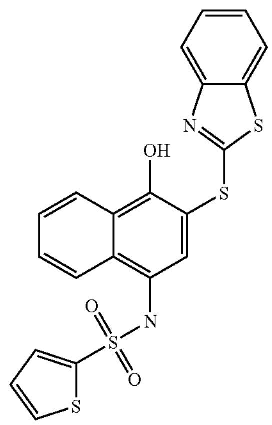 [SMILES: O=S(=O)(Nc1cc(Sc2nc3ccccc3s2)c(O)c2ccccc12)c1cccs1] | C21H14N2O3S4 | 470.6133 | 5.774 |
| F1269-1420 | 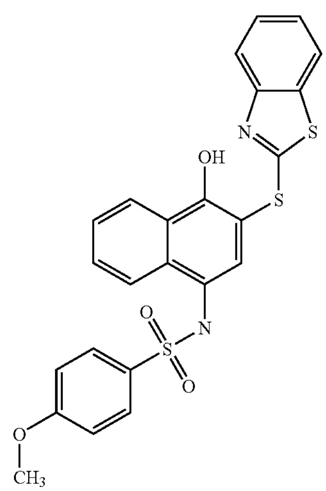 [SMILES: COc1ccc(S(=O)(=O)Nc2cc(Sc3nc4ccccc4s3)c(O)c3ccccc23)cc1] | C24H18N2O4S3 | 494.6141 | 6.217 |
| F1566-1144 | 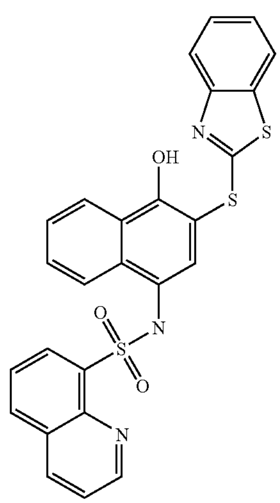 [SMILES: O=S(=O)(Nc1cc(Sc2nc3ccccc3s2)c(O)c2ccccc12)c1cccc2cccnc12] | C26H17N3O3S3 | 515.6357 | 6.461 |

TABLE 11-continued

| IDNUMBER | Structure | Formula structure | MW | LogP |
| --- | --- | --- | --- | --- |
| F1566-1584 | 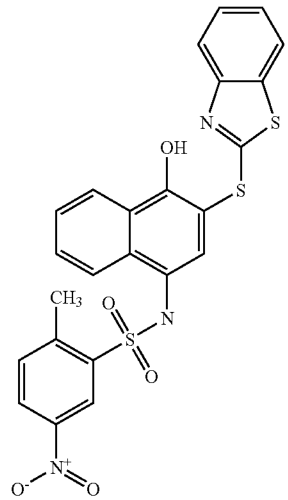 [SMILES: Cc1ccc([N+](=O)[O-])cc1S(=O)(=O)Nc1cc(Sc2nc3ccccc3s2)c(O)c2ccccc12] | C24H17N3O5S3 | 523.6122 | 6.529 |
| F1566-1596 | 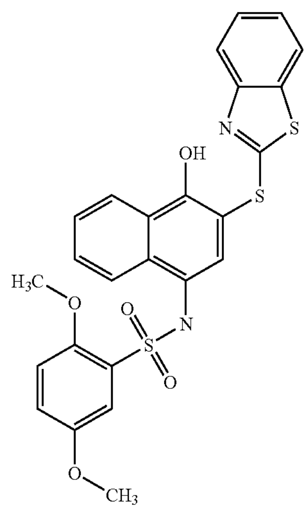 [SMILES: COc1ccc(OC)c(S(=O)(=O)Nc2cc(Sc3nc4ccccc4s3)c(O)c3ccccc23)c1] | C25H20N2O5S3 | 524.6406 | 6.208 |
| F1566-1816 | 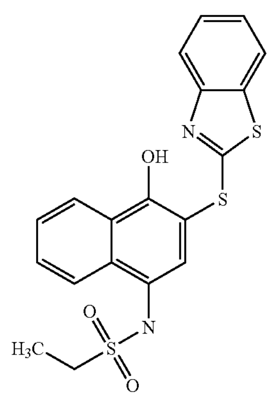 [SMILES: CCS(=O)(=O)Nc1cc(Sc2nc3ccccc3s2)c(O)c2ccccc12] | C19H16N2O3S3 | 416.543 | 5.12 |

TABLE 11-continued

| IDNUMBER | Structure | Formula structure | MW | LogP |
|---|---|---|---|---|
| F1566-1830 | 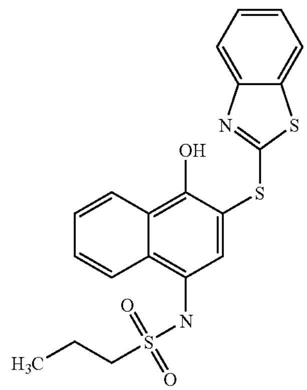 [SMILES: CCCS(=O)(=O)Nc1cc(Sc2nc3ccccc3s2)c(O)c2ccccc12] | C20H18N2O3S3 | 430.5701 | 5.562 |
| F1566-1844 | 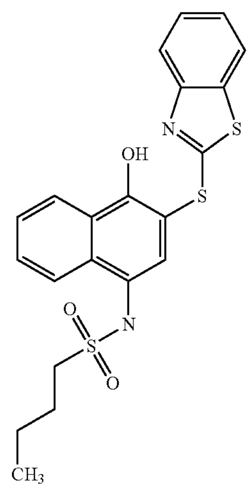 [SMILES: CCCCS(=O)(=O)Nc1cc(Sc2nc3ccccc3s2)c(O)c2ccccc12] | C21H20N2O3S3 | 444.5972 | 6.004 |
| F1566-1858 | 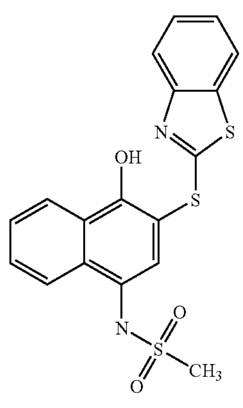 [SMILES: CS(=O)(=O)Nc1cc(Sc2nc3ccccc3s2)c(O)c2ccccc12] | C18H14N2O3S3 | 402.5159 | 4.607 |

TABLE 11-continued
| IDNUMBER | Structure | Formula structure | MW | LogP |
|---|---|---|---|---|
| F5749-0224 | 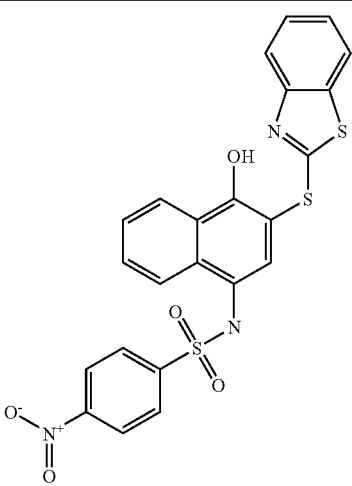 | C23H15N3O5S3 | 509.5851 | 6.196 |
| F5749-0225 | 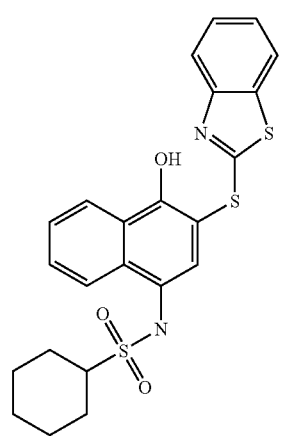 [SMILES: O=S(=O)(Nc1cc(Sc2nc3ccccc3s2)c(O)c2ccccc12)C1CCCCC1] | C23H22N2O3S3 | 470.6354 | 6.586 |
| F5749-0226 | 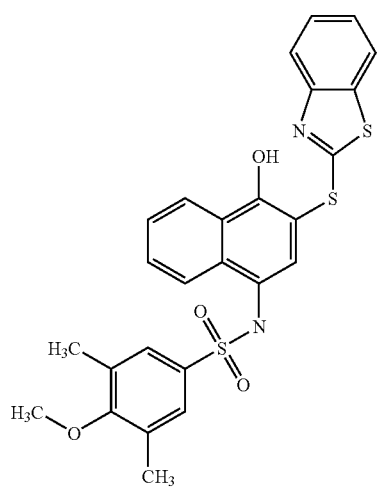 [SMILES: COc1c(C)cc(S(=O)(=O)Nc2cc(Sc3nc4ccccc4s3)c(O)c3ccccc23)cc1C] | C26H22N2O4S3 | 522.6682 | 6.883 |

TABLE 11-continued

| IDNUMBER | Structure | Formula structure | MW | LogP |
|---|---|---|---|---|
| F5749-0227 | 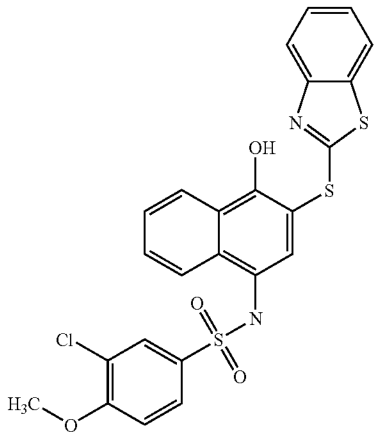 [SMILES: COc1ccc(S(=O)(=O)Nc2cc(Sc3nc4ccccc4s3)c(O)c3ccccc23)cc1Cl] | C24H17ClN2O4S3 | 529.0591 | 6.844 |
| F5749-0228 | 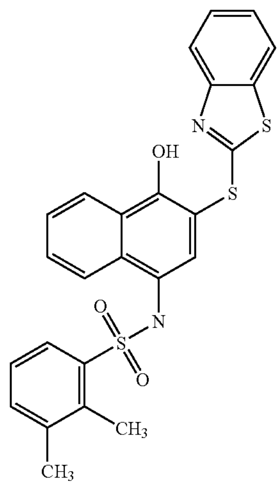 [SMILES: Cc1cccc(S(=O)(=O)Nc2cc(Sc3nc4ccccc4s3)c(O)c3ccccc23)c1C] | C25H20N2O3S3 | 492.6418 | 6.853 |
| F5749-0229 | 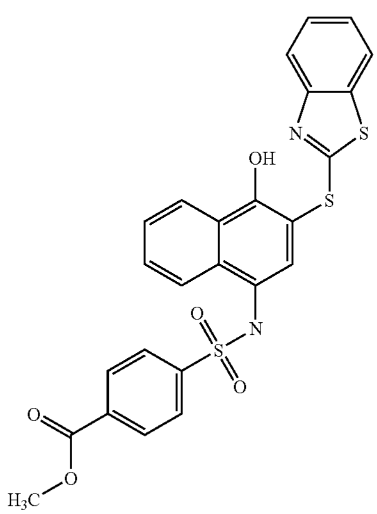 [SMILES: COC(=O)c1ccc(S(=O)(=O)Nc2cc(Sc3nc4ccccc4s3)c(O)c3ccccc23)cc1] | C25H18N2O5S3 | 522.6246 | 6.202 |

TABLE 11-continued

| IDNUMBER | Structure | Formula structure | MW | LogP |
|---|---|---|---|---|
| F5749-0230 | 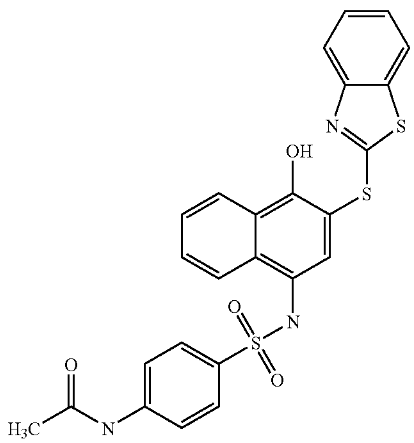 [SMILES: CC(=O)Nc1ccc(S(=O)(=O)Nc2cc(Sc3nc4ccccc4s3)c(O)c3ccccc23)cc1] | C25H19N3O4S3 | 521.6399 | 5.552 |
| F5749-0231 | 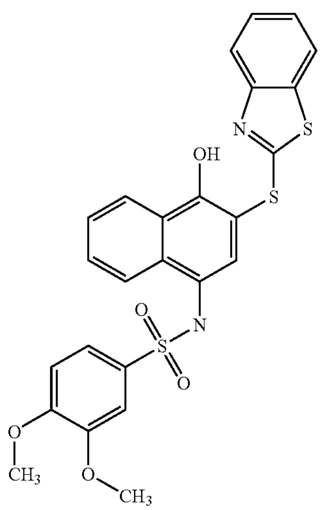 [SMILES: COc1ccc(S(=O)(=O)Nc2cc(Sc3nc4ccccc4s3)c(O)c3ccccc23)cc1OC] | C25H20N2O5S3 | 524.6406 | 5.95974 |
| F5749-0232 | 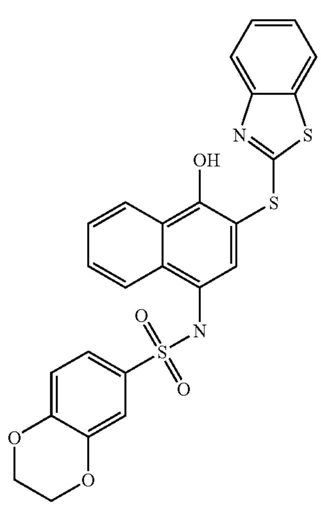 [SMILES: O=S(=O)(Nc1cc(Sc2nc3ccccc3s2)c(O)c2ccccc12)c1ccc2c(c1)OCCO2] | C25H18N2O5S3 | 522.6246 | 5.856 |

TABLE 11-continued

| IDNUMBER | Structure | Formula structure | MW | LogP |
|---|---|---|---|---|
| F5749-0233 | 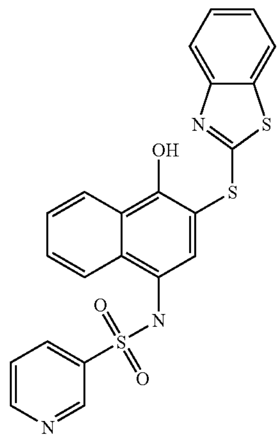 [SMILES: O=S(=O)(Nc1cc(Sc2nc3ccccc3s2)c(O)c2ccccc12)c1cccnc1] | C22H15N3O3S3 | 465.5752 | 5.028 |
| F5749-0234 | 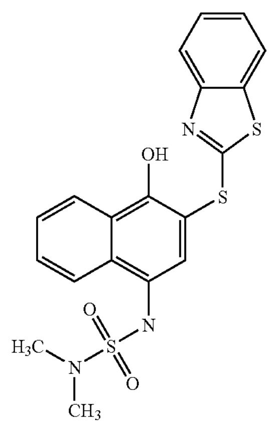 [SMILES: CN(C)S(=O)(=O)Nc1cc(Sc2nc3ccccc3s2)c(O)c2ccccc12] | C19H17N3O3S3 | 431.5576 | 4.155 |
| F5749-0235 | 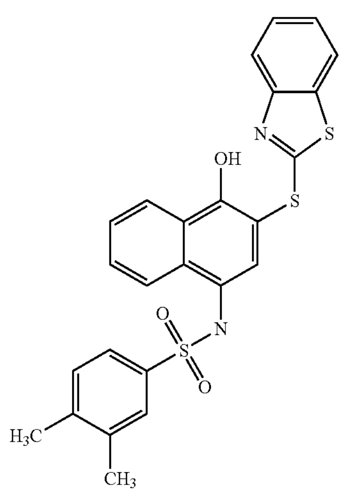 [SMILES: Cc1ccc(S(=O)(=O)Nc2cc(Sc3nc4ccccc4s3)c(O)c3ccccc23)cc1C] | C25H20N2O3S3 | 492.6418 | 6.892 |

TABLE 11-continued

| IDNUMBER | Structure | Formula structure | MW | LogP |
|---|---|---|---|---|
| F5749-0236 | 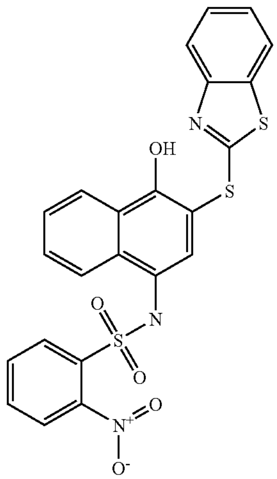 [SMILES: O=[N+]([O-])c1ccccc1S(=O)(=O)Nc1cc(Sc2nc3ccccc3s2)c(O)c2ccccc12] | C23H15N3O5S3 | 509.5851 | 6.194 |
| F5749-0237 | 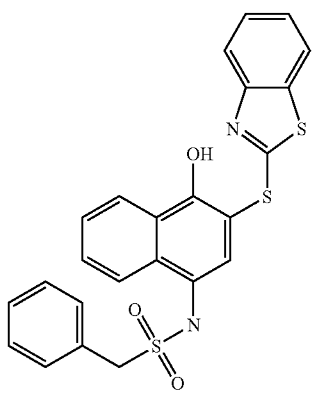 [SMILES: O=S(=O)(Cc1ccccc1)Nc1cc(Sc2nc3ccccc3s2)c(O)c2ccccc12] | C24H18N2O3S3 | 478.6147 | 6.395 |
| F5749-0238 | 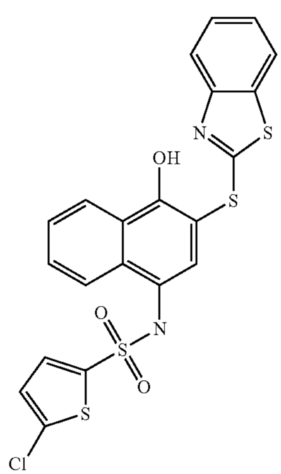 [SMILES: O=S(=O)(Nc1cc(Sc2nc3ccccc3s2)c(O)c2ccccc12)c1ccc(Cl)s1] | C21H13ClN2O3S4 | 505.0584 | 7.064 |

TABLE 11-continued

| IDNUMBER | Structure | Formula structure | MW | LogP |
|---|---|---|---|---|
| F5749-0239 | 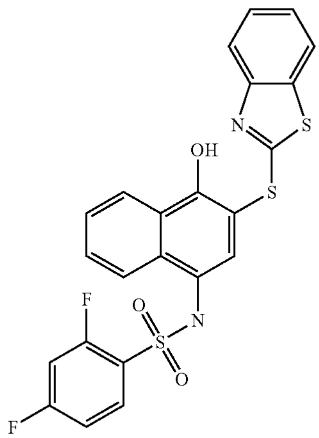 [SMILES: O=S(=O)(Nc1cc(Sc2nc3ccccc3s2)c(O)c2ccccc12)c1ccc(F)cc1F] | C23H14F2N2O3S3 | 500.5684 | 6.602 |
| F5749-0240 | 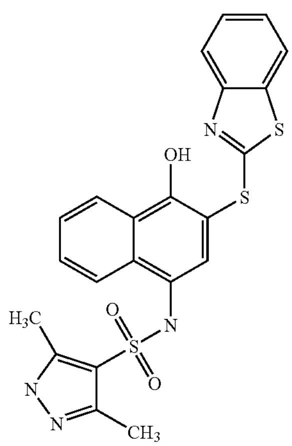 | C22H18N4O3S3 | 482.6058 | 5.371 |
| F5749-0241 | 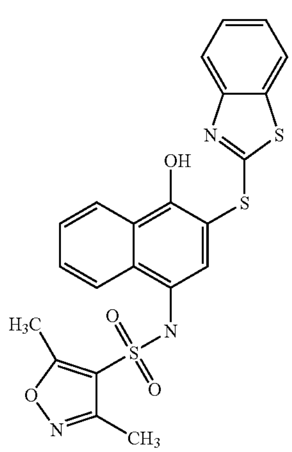 [SMILES: Cc1noc(C)c1S(=O)(=O)Nc1cc(Sc2nc3ccccc3s2)c(O)c2ccccc12] | C22H17N3O4S3 | 483.5905 | 5.405 |

TABLE 11-continued

| IDNUMBER | Structure | Formula structure | MW | LogP |
| --- | --- | --- | --- | --- |
| F5749-0242 | 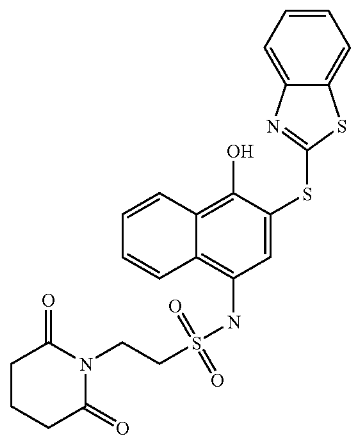 [SMILES: O=C1CCCC(=O)N1CCS(=O)(=O)Nc1cc(Sc2nc3ccccc3s2)c(O)c2ccccc12] | C24H21N3O5S3 | 527.6441 | 4.048 |
| F5749-0243 | 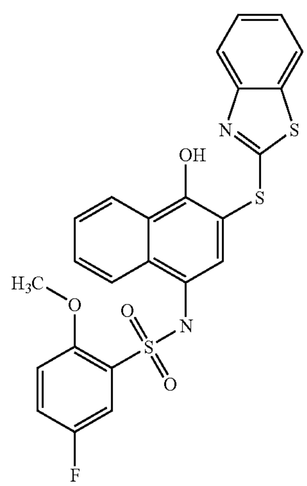 [SMILES: COc1ccc(F)cc1S(=O)(=O)Nc1cc(Sc2nc3ccccc3s2)c(O)c2ccccc12] | C24H17FN2O4S3 | 512.6045 | 6.405 |
| F5749-0244 | 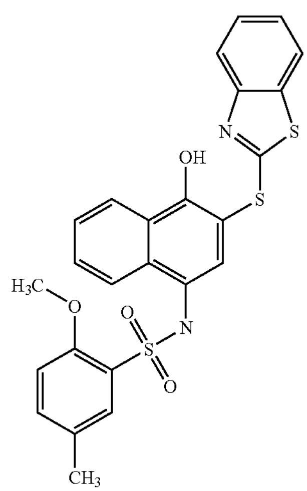 [SMILES: COc1ccc(C)cc1S(=O)(=O)Nc1cc(Sc2nc3ccccc3s2)c(O)c2ccccc12] | C25H20N2O4S3 | 508.6412 | 6.55 |

TABLE 11-continued

| IDNUMBER | Structure | Formula structure | MW | LogP |
|---|---|---|---|---|
| F5749-0245 | 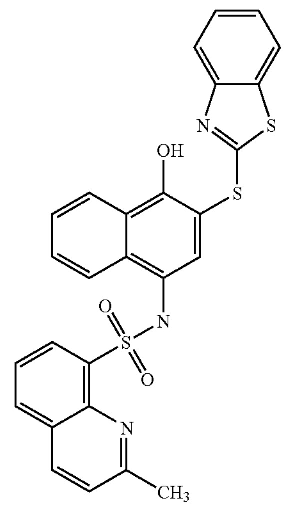 [SMILES: Cc1ccc2cccc(S(=O)(=O)Nc3cc(Sc4nc5ccccc5s4)c(O)c4ccccc34)c2n1] | C27H19N3O3S3 | 529.6628 | 6.72 |
| F5749-0246 | 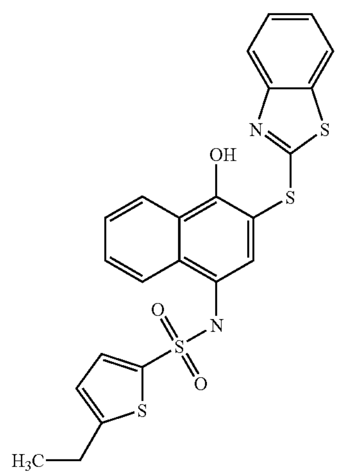 [SMILES: CCc1ccc(S(=O)(=O)Nc2cc(Sc3nc4ccccc4s3)c(O)c3ccccc23)s1] | C23H18N2O3S4 | 498.6675 | 6.912 |
| F5749-0247 | 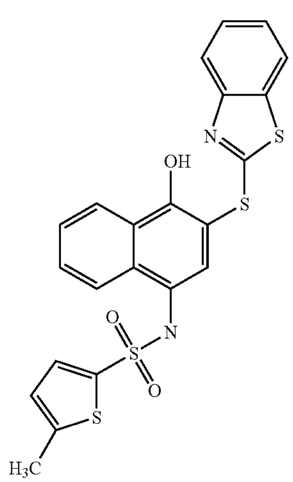 [SMILES: Cc1ccc(S(=O)(=O)Nc2cc(Sc3nc4ccccc4s3)c(O)c3ccccc23)s1] | C22H16N2O3S4 | 484.6404 | 6.437 |

TABLE 11-continued

| IDNUMBER | Structure | Formula structure | MW | LogP |
| --- | --- | --- | --- | --- |
| F5749-0248 | 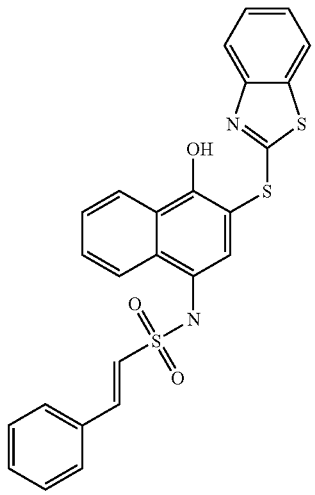 [SMILES: O=S(=O)(/C=C/c1ccccc1)Nc1cc(Sc2nc3ccccc3s2)c(O)c2ccccc12] | C25H18N2O3S3 | 490.6258 | 6.619 |
| F5749-0249 | 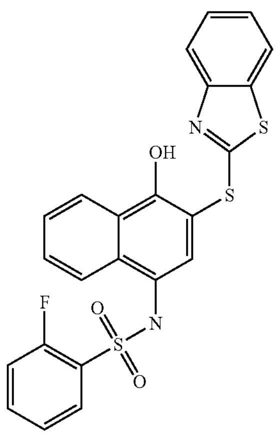 [SMILES: O=S(=O)(Nc1cc(Sc2nc3ccccc3s2)c(O)c2ccccc12)c1ccccc1F] | C23H15FN2O3S3 | 482.578 | 6.412 |
| F5749-0250 | 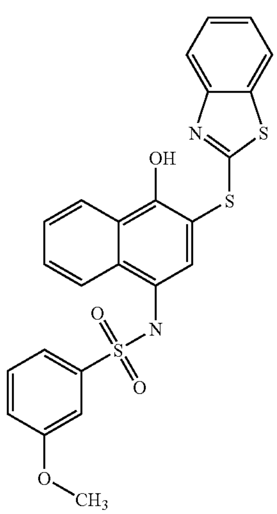 [SMILES: COc1cccc(S(=O)(=O)Nc2cc(Sc3nc4ccccc4s3)c(O)c3ccccc23)c1] | C24H18N2O4S3 | 494.6141 | 6.254 |

TABLE 11-continued

| IDNUMBER | Structure | Formula structure | MW | LogP |
|---|---|---|---|---|
| F5749-0251 | 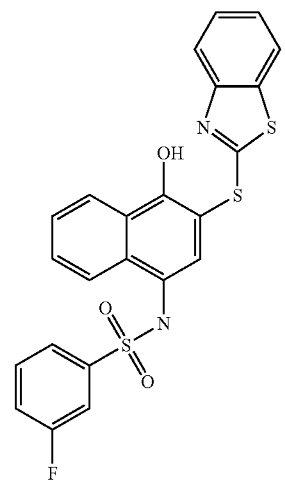 | C23H15FN2O3S3 | 482.578 | 6.451 |
| F5749-0252 | 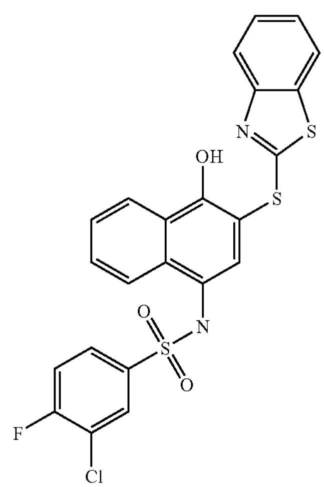 [SMILES: O=S(=O)(Nc1cc(Sc2nc3ccccc3s2)c(O)c2ccccc12)c1ccc(F)c(Cl)c1] | C23H14ClFN2O3S3 | 517.023 | 7.041 |
| F5749-0253 | 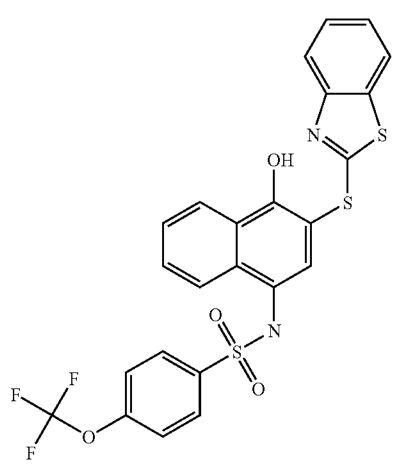 [SMILES: O=S(=O)(Nc1cc(Sc2nc3ccccc3s2)c(O)c2ccccc12)c1ccc(OC(F)(F)F)cc1] | C24H15F3N2O4S3 | 548.5854 | 7.65976 |

TABLE 11-continued

| IDNUMBER | Structure | Formula structure | MW | LogP |
|---|---|---|---|---|
| F5749-0254 | 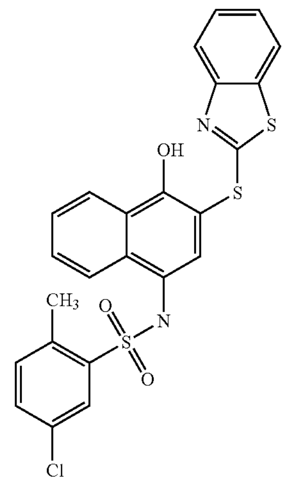 [SMILES: Cc1ccc(Cl)cc1S(=O)(=O)Nc1cc(Sc2nc3ccccc3s2)c(O)c2ccccc12] | C24H17ClN2O3S3 | 513.0597 | 7.186 |
| F5749-0255 | 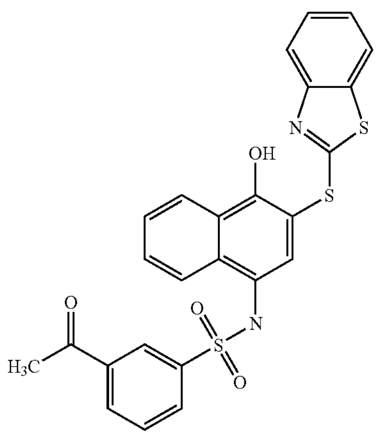 [SMILES: CC(=O)c1cccc(S(=O)(=O)Nc2cc(Sc3nc4ccccc4s3)c(O)c3ccccc23)c1] | C25H18N2O4S3 | 506.6252 | 6.151 |
| F5749-0256 | 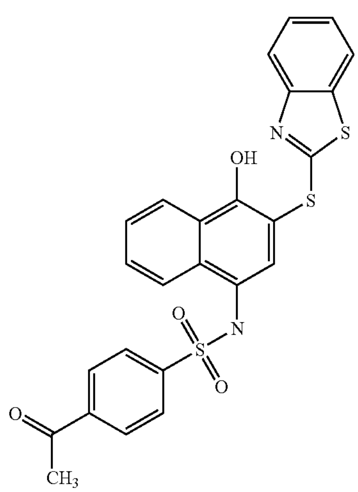 [SMILES: CC(=O)c1ccc(S(=O)(=O)Nc2cc(Sc3nc4ccccc4s3)c(O)c3ccccc23)cc1] | C25H18N2O4S3 | 506.6252 | 6.114 |

TABLE 11-continued

| IDNUMBER | Structure | Formula structure | MW | LogP |
| --- | --- | --- | --- | --- |
| F5749-0257 | 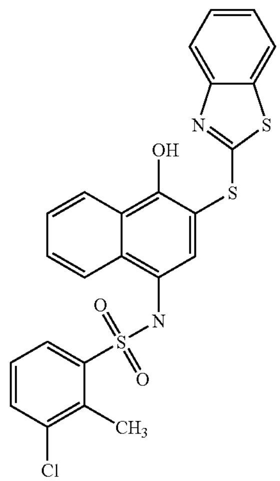 [SMILES: Cc1c(Cl)cccc1S(=O)(=O)Nc1cc(Sc2nc3ccccc3s2)c(O)c2ccccc12] | C24H17ClN2O3S3 | 513.0597 | 7.147 |
| F5749-0258 | 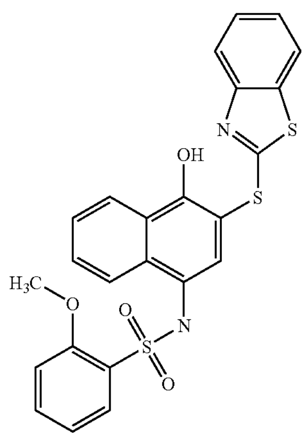 [SMILES: COc1ccccc1S(=O)(=O)Nc1cc(Sc2nc3ccccc3s2)c(O)c2ccccc12] | C24H18N2O4S3 | 494.6141 | 6.215 |
| F5749-0259 | 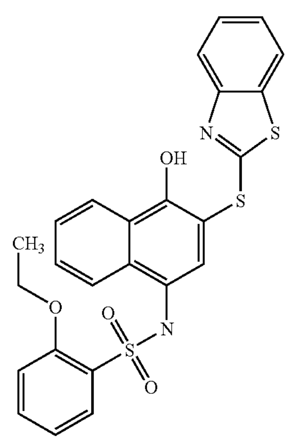 [SMILES: CCOc1ccccc1S(=O)(=O)Nc1cc(Sc2nc3ccccc3s2)c(O)c2ccccc12] | C25H20N2O4S3 | 508.6412 | 6.556 |

TABLE 11-continued

| IDNUMBER | Structure | Formula structure | MW | LogP |
|---|---|---|---|---|
| F5749-0260 | 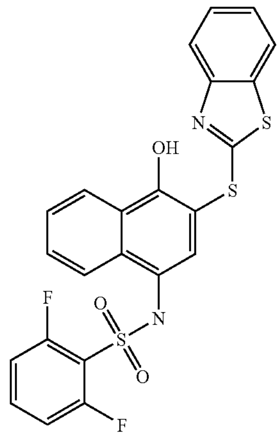 [SMILES: O=S(=O)(Nc1cc(Sc2nc3ccccc3s2)c(O)c2ccccc12)c1c(F)cccc1F] | C23H14F2N2O3S3 | 500.5684 | 6.563 |
| F5749-0261 | 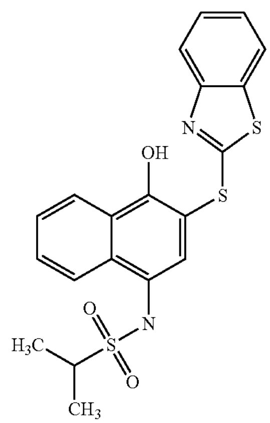 | C20H18N2O3S3 | 430.5701 | 5.754 |
| F5749-0262 | 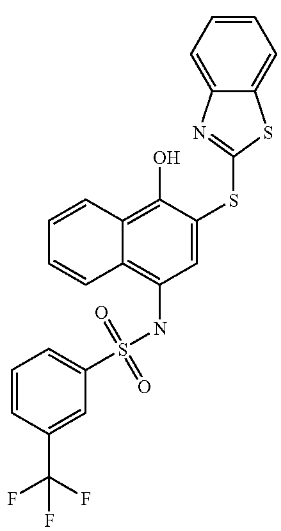 [SMILES: O=S(=O)(Nc1cc(Sc2nc3ccccc3s2)c(O)c2ccccc12)c1cccc(C(F)(F)F)c1] | C24H15F3N2O3S3 | 532.586 | 7.23276 |

TABLE 11-continued

| IDNUMBER | Structure | Formula structure | MW | LogP |
|---|---|---|---|---|
| F5749-0263 | 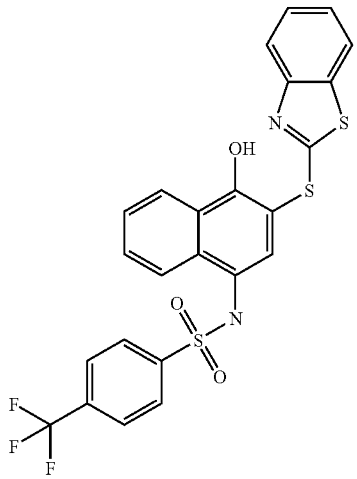 [SMILES: O=S(=O)(Nc1cc(Sc2nc3ccccc3s2)c(O)c2ccccc12)c1ccc(C(F)(F)F)cc1] | C24H15F3N2O3S3 | 532.586 | 7.19576 |
| F5749-0264 | 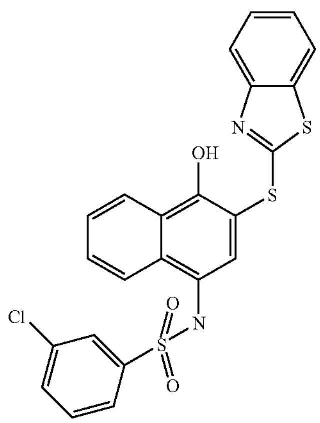 [SMILES: O=S(=O)(Nc1cc(Sc2nc3ccccc3s2)c(O)c2ccccc12)c1cccc(Cl)c1] | C23H15ClN2O3S3 | 499.0326 | 6.89 |
| F5749-0265 | 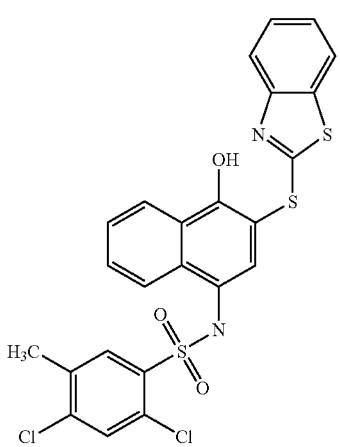 [SMILES: Cc1cc(S(=O)(=O)Nc2cc(Sc3nc4ccccc4s3)c(O)c3ccccc23)c(Cl)cc1Cl] | C24H16Cl2N2O3S3 | 547.5047 | 7.813 |

TABLE 11-continued

| IDNUMBER | Structure | Formula structure | MW | LogP |
| --- | --- | --- | --- | --- |
| F5749-0266 | 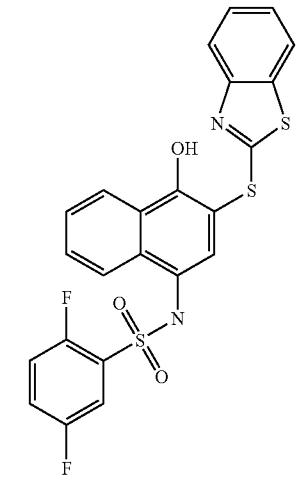 [SMILES: O=S(=O)(Nc1cc(Sc2nc3ccccc3s2)c(O)c2ccccc12)c1cc(F)ccc1F] | C23H14F2N2O3S3 | 500.5684 | 6.602 |
| F5749-0267 | 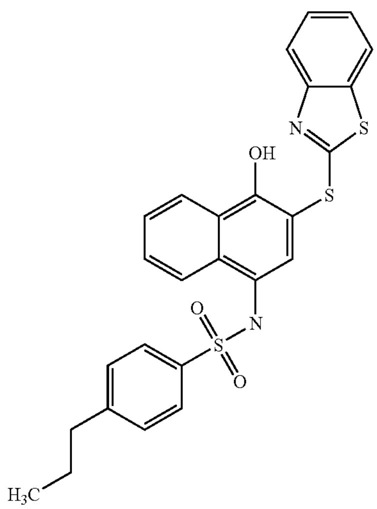 [SMILES: CCCc1ccc(S(=O)(=O)Nc2cc(Sc3nc4ccccc4s3)c(O)c3ccccc23)cc1] | C26H22N2O3S3 | 506.6688 | 7.476 |
| F5749-0268 | 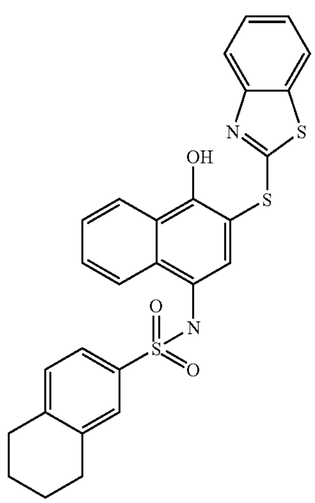 [SMILES: O=S(=O)(Nc1cc(Sc2nc3ccccc3s2)c(O)c2ccccc12)c1ccc2c(c1)CCCC2] | C27H22N2O3S3 | 518.68 | 7.348 |

TABLE 11-continued

| IDNUMBER | Structure | Formula structure | MW | LogP |
|---|---|---|---|---|
| F5749-0269 | 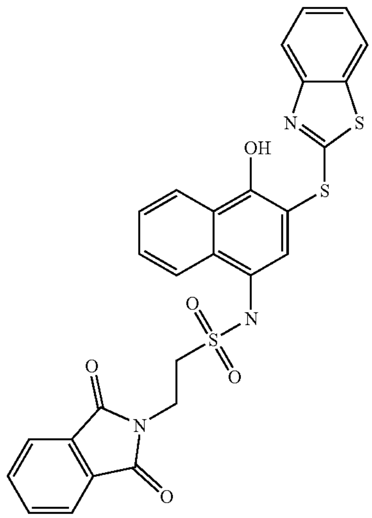 [SMILES: O=C1c2ccccc2C(=O)N1CCS(=O)(=O)Nc1cc(Sc2nc3ccccc3s2)c(O)c2ccccc12] | C27H19N3O5S3 | 561.6616 | 5.388 |
| F5749-0270 | 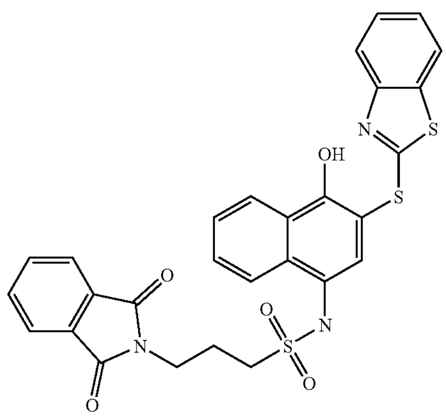 [SMILES: O=C1c2ccccc2C(=O)N1CCCS(=O)(=O)Nc1cc(Sc2nc3ccccc3s2)c(O)c2ccccc12] | C28H21N3O5S3 | 575.6887 | 5.83 |
| F5749-0271 | 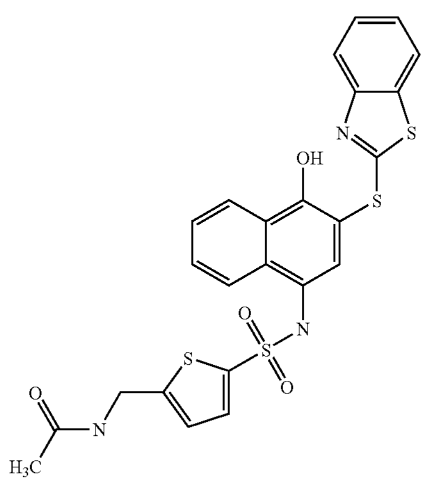 [SMILES: CC(=O)NCc1ccc(S(=O)(=O)Nc2cc(Sc3nc4ccccc4s3)c(O)c3ccccc23)s1] | C24H19N3O4S4 | 541.6927 | 5.564 |

TABLE 11-continued

| IDNUMBER | Structure | Formula structure | MW | LogP |
|---|---|---|---|---|
| F5749-0272 | 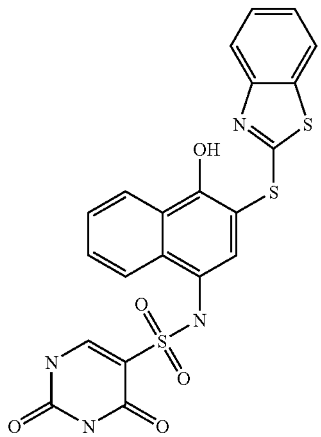 [SMILES: O=c1[nH]cc(S(=O)(=O)Nc2cc(Sc3nc4ccccc4s3)c(O)c3ccccc23)c(=O)[nH]1] | C21H14N4O5S3 | 498.5615 | 3.306 |
| F5749-0273 | 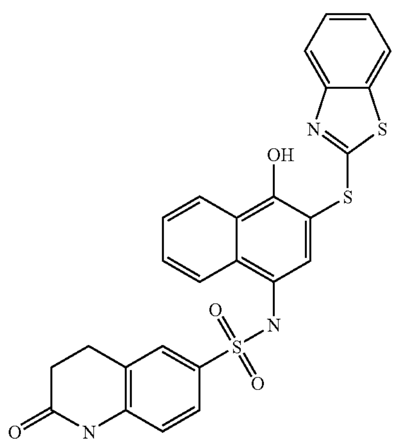 [SMILES: O=C1CCc2cc(S(=O)(=O)Nc3cc(Sc4nc5ccccc5s4)c(O)c4ccccc34)ccc2N1] | C26H19N3O4S3 | 533.651 | 5.457 |
| F5749-0274 | 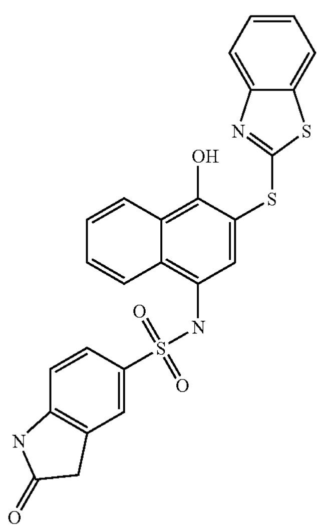 [SMILES: O=C1Cc2cc(S(=O)(=O)Nc3cc(Sc4nc5ccccc5s4)c(O)c4ccccc34)ccc2N1] | C25H17N3O4S3 | 519.6239 | 5.369 |

TABLE 11-continued

| IDNUMBER | Structure | Formula structure | MW | LogP |
|---|---|---|---|---|
| F5749-0275 | 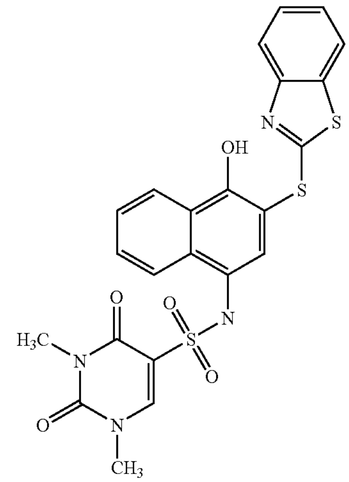 [SMILES: Cn1cc(S(=O)(=O)Nc2cc(Sc3nc4ccccc4s3)c(O)c3ccccc23)c(=O)n(C)c1=O] | C23H18N4O5S3 | 526.6157 | 3.37 |
| F5749-0276 | 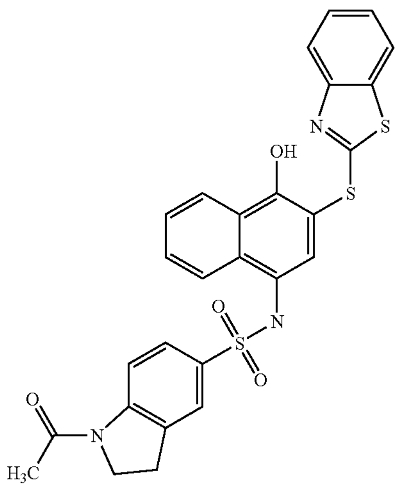 [SMILES: CC(=O)N1CCc2cc(S(=O)(=O)Nc3cc(Sc4nc5ccccc5s4)c(O)c4ccccc34)ccc21] | C27H21N3O4S3 | 547.6781 | 5.692 |
| F5749-0277 | 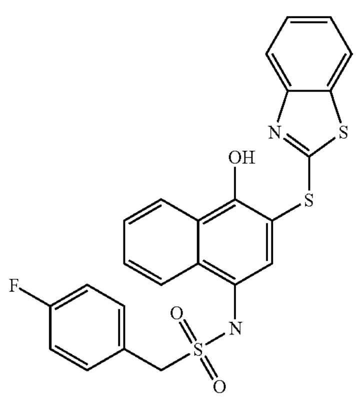 [SMILES: O=S(=O)(Cc1ccc(F)cc1)Nc1cc(Sc2nc3ccccc3s2)c(O)c2ccccc12] | C24H17FN2O3S3 | 496.6051 | 6.548 |

TABLE 11-continued

| IDNUMBER | Structure | Formula structure | MW | LogP |
|---|---|---|---|---|
| F5749-0278 | 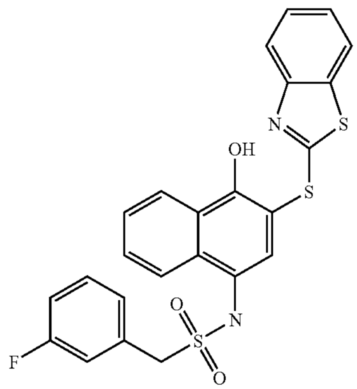 [SMILES: O=S(=O)(Cc1cccc(F)c1)Nc1cc(Sc2nc3ccccc3s2)c(O)c2ccccc12] | C24H17FN2O3S3 | 496.6051 | 6.585 |
| F5749-0279 | 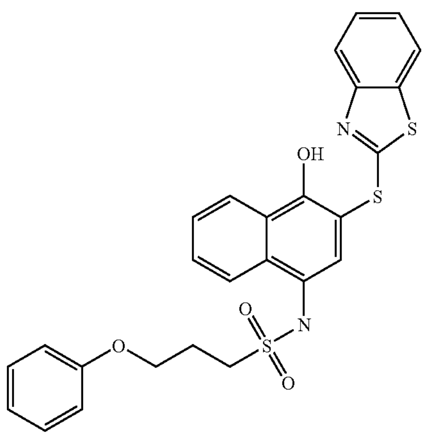 [SMILES: O=S(=O)(CCCOc1ccccc1)Nc1cc(Sc2nc3ccccc3s2)c(O)c2ccccc12] | C26H22N2O4S3 | 522.6682 | 6.621 |
| F5749-0280 | 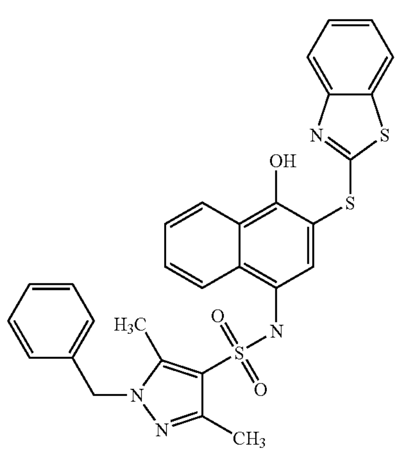 [SMILES: Cc1nn(Cc2ccccc2)c(C)c1S(=O)(=O)Nc1cc(Sc2nc3ccccc3s2)c(O)c2ccccc12] | C29H24N4O3S3 | 572.7316 | 6.54 |

| IDNUMBER | Structure | Formula structure | MW | LogP |
| --- | --- | --- | --- | --- |
| F5749-0281 | 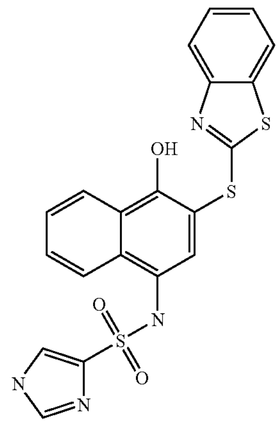 [SMILES: O=S(=O)(Nc1cc(Sc2nc3ccccc3s2)c(O)c2ccccc12)c1c[nH]cn1] | C20H14N4O3S3 | 454.5516 | 4.401 |
| F5749-0282 | 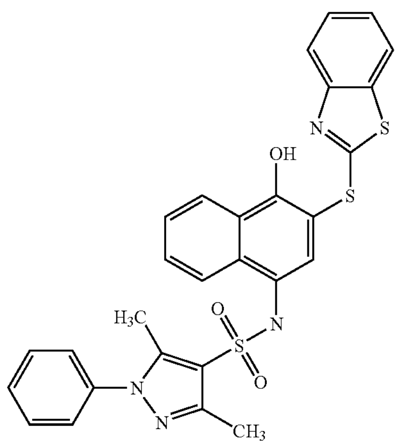 [SMILES: Cc1nn(-c2ccccc2)c(C)c1S(=O)(=O)Nc1cc(Sc2nc3ccccc3s2)c(O)c2ccccc12] | C28H22N4O3S3 | 558.7045 | 6.406 |
| F5749-0283 | 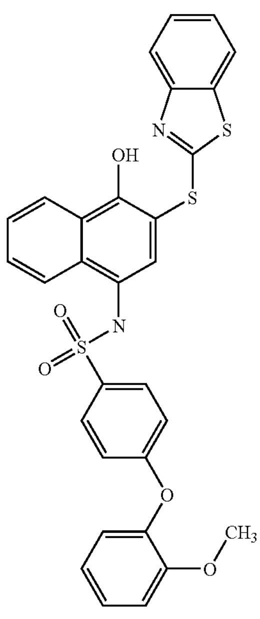 [SMILES: COc1ccccc1Oc1ccc(S(=O)(=O)Nc2cc(Sc3nc4ccccc4s3)c(O)c3ccccc23)cc1] | C30H22N2O5S3 | 586.7122 | 7.57674 |

TABLE 11-continued

| IDNUMBER | Structure | Formula structure | MW | LogP |
|---|---|---|---|---|
| F5749-0284 | 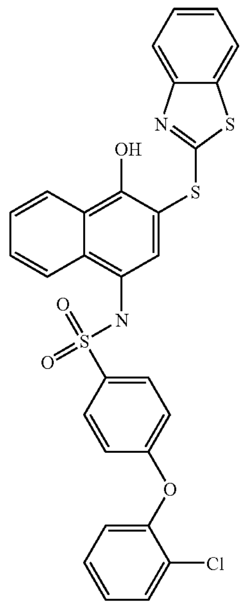 [SMILES: O=S(=O)(Nc1cc(Sc2nc3ccccc3s2)c(O)c2ccccc12)c1ccc(Oc2ccccc2Cl)cc1] | C29H19ClN2O4S3 | 591.1308 | 8.461 |
| F5749-0285 | 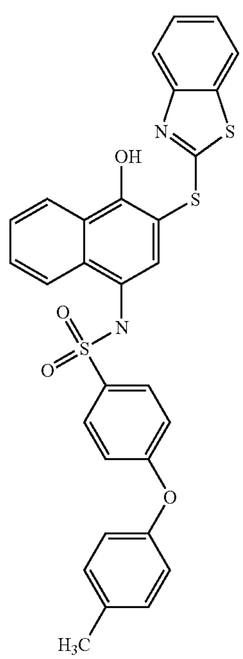 [SMILES: Cc1ccc(Oc2ccc(S(=O)(=O)Nc3cc(Sc4nc5ccccc5s4)c(O)c4ccccc34)cc2)cc1] | C30H22N2O4S3 | 570.7128 | 8.169 |

TABLE 11-continued

| IDNUMBER | Structure | Formula structure | MW | LogP |
| --- | --- | --- | --- | --- |
| F5749-0286 | 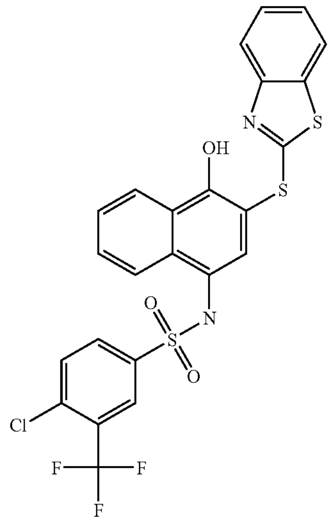 [SMILES: O=S(=O)(Nc1cc(Sc2nc3ccccc3s2)c(O)c2ccccc12)c1ccc(Cl)c(C(F)(F)F)c1] | C24H14ClF3N2O3S3 | 567.031 | 7.82276 |
| F5749-0287 | 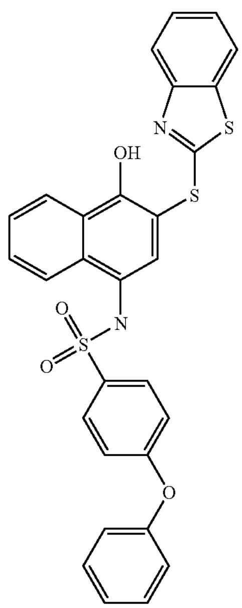 [SMILES: O=S(=O)(Nc1cc(Sc2nc3ccccc3s2)c(O)c2ccccc12)c1ccc(Oc2ccccc2)cc1] | C29H20N2O4S3 | 556.6858 | 7.871 |
| F5749-0288 | 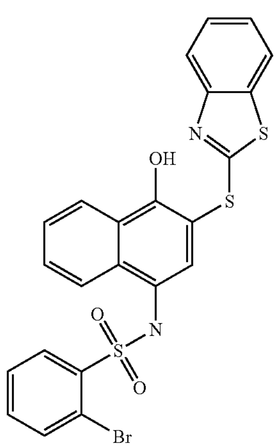 [SMILES: O=S(=O)(Nc1cc(Sc2nc3ccccc3s2)c(O)c2ccccc12)c1ccccc1Br] | C23H15BrN2O3S3 | 543.4836 | 7.057 |

TABLE 11-continued

| IDNUMBER | Structure | Formula structure | MW | LogP |
|---|---|---|---|---|
| F5749-0289 | 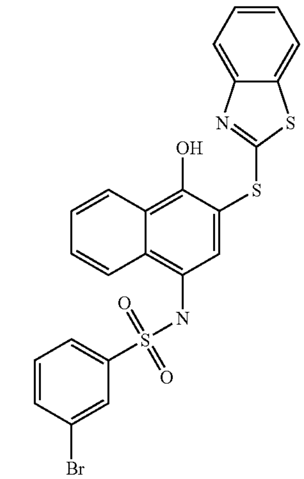 [SMILES: O=S(=O)(Nc1cc(Sc2nc3ccccc3s2)c(O)c2ccccc12)c1cccc(Br)c1] | C23H15BrN2O3S3 | 543.4836 | 7.096 |
| F5749-0290 | 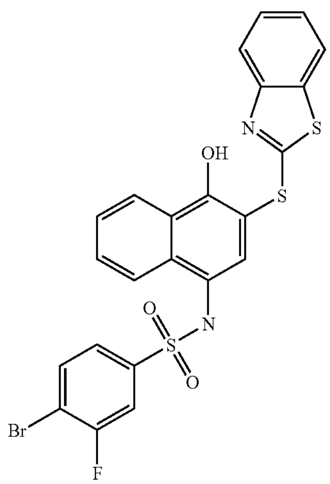 [SMILES: O=S(=O)(Nc1cc(Sc2nc3ccccc3s2)c(O)c2ccccc12)c1ccc(Br)c(F)c1] | C23H14BrFN2O3S3 | 561.474 | 7.247 |
| F5749-0291 | 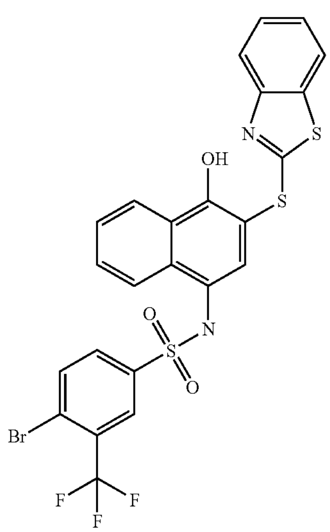 [SMILES: O=S(=O)(Nc1cc(Sc2nc3ccccc3s2)c(O)c2ccccc12)c1ccc(Br)c(C(F)(F)F)c1] | C24H14BrFN2O3S3 | 611.482 | 8.02876 |

TABLE 11-continued

| IDNUMBER | Structure | Formula structure | MW | LogP |
|---|---|---|---|---|
| F5749-0292 | 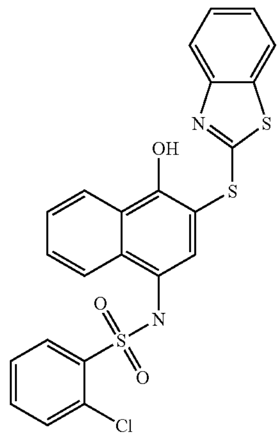 | C23H15ClN2O3S3 | 499.0326 | 6.851 |
| F5749-0293 | 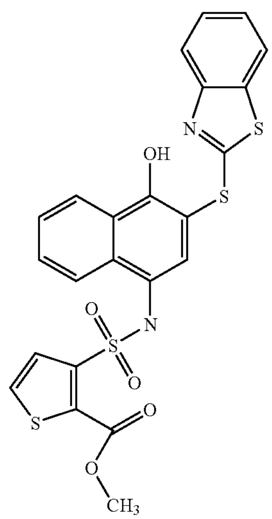 [SMILES: COC(=O)c1sccc1S(=O)(=O)Nc1cc(Sc2nc3ccccc3s2)c(O)c2ccccc12] | C23H16N2O5S4 | 528.6504 | 5.461 |
| F5749-0294 | 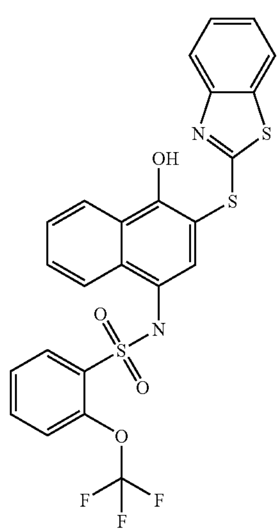 [SMILES: O=S(=O)(Nc1cc(Sc2nc3ccccc3s2)c(O)c2ccccc12)c1ccccc1OC(F)(F)F] | C24H15F3N2O4S3 | 548.5854 | 7.65776 |

TABLE 12

| IDNUMBER | Structure | Formula structure | MW | LogP |
|---|---|---|---|---|
| F0433-0038 | 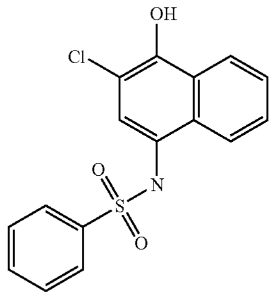 [SMILES: O=S(=O)(Nc1cc(Cl)c(O)c2ccccc12)c1ccccc1] | C16H12ClNO3S | 333.7959 | 4.192 |
| F0433-0041 | 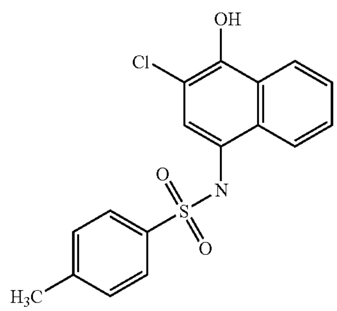 [SMILES: Cc1ccc(S(=O)(=O)Nc2cc(Cl)c(O)c3ccccc23)cc1] | C17H14ClNO3S | 347.823 | 4.49 |
| F0433-0044 | 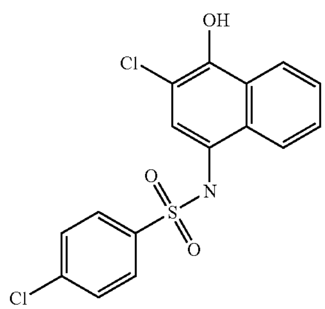 [SMILES: O=S(=O)(Nc1cc(Cl)c(O)c2ccccc12)c1ccc(Cl)cc1] | C16H11Cl2NO3S | 368.241 | 4.784 |
| F0433-0047 | 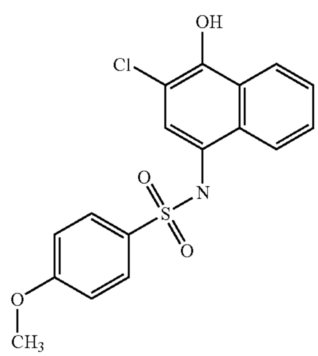 [SMILES: COc1ccc(S(=O)(=O)Nc2cc(Cl)c(O)c3ccccc23)cc1] | C17H14ClNO4S | 363.8224 | 4.148 |
| F-0433-0050 | 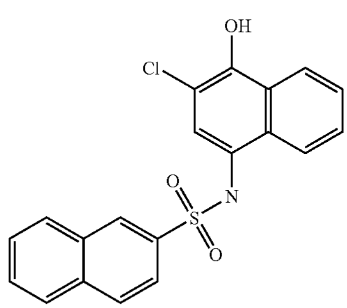 [SMILES: O=S(=O)(Nc1cc(Cl)c(O)c2ccccc12)c1ccc2ccccc2c1] | C20H14ClNO3S | 383.8565 | 5.451 |

TABLE 12-continued
| IDNUMBER | Structure | Formula structure | MW | LogP |
|---|---|---|---|---|
| F0808-1895 | 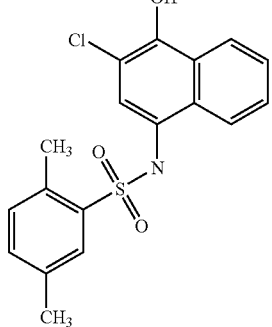 | C18H16ClNO3S | 361.8501 | 4.823 |
| F0808-1902 | 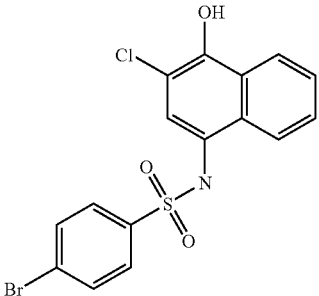 | C16H11BrClNO3S | 412.692 | 4.99 |
| F0808-1909 | 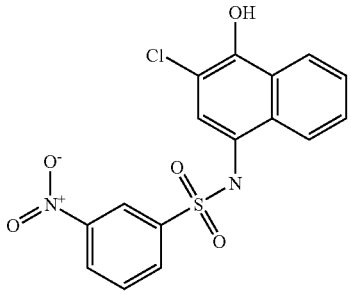 [SMILES: O=[N+]([O-])c1cccc(S(=O)(=O)Nc2cc(Cl)c(O)c3ccccc23)c1] | C16H11ClN2O5S | 378.7935 | 4.164 |
| F0808-1913 | 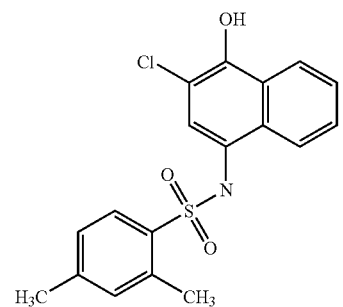 [SMILES: Cc1ccc(S(=O)(=O)Nc2cc(Cl)c(O)c3ccccc23)c(C)c1] | C18H16ClNO3S | 361.8501 | 4.823 |

TABLE 12-continued
| IDNUMBER | Structure | Formula structure | MW | LogP |
|---|---|---|---|---|
| F0808-1914 | 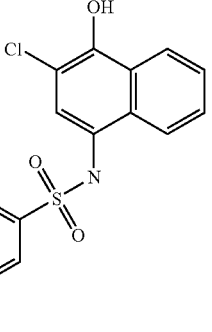 | C20H20ClNO3S | 389.9043 | 5.691 |
| F1269-0272 | 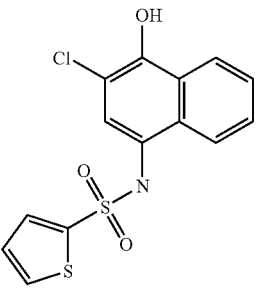 [SMILES: O=S(=O)(Nc1cc(Cl)c(O)c2ccccc12)c1cccs1] | C14H10ClNO3S2 | 339.8217 | 3.705 |
| F1269-1995 | 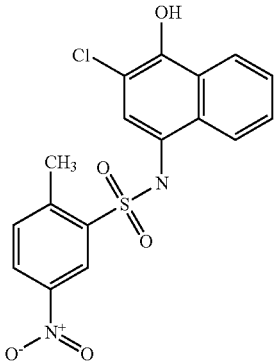 [SMILES: Cc1ccc([N+](=O)[O-])cc1S(=O)(=O)Nc1cc(Cl)c(O)c2ccccc12] | C17H13ClN2O5S | 392.8206 | 4.46 |
| F1566-1223 | 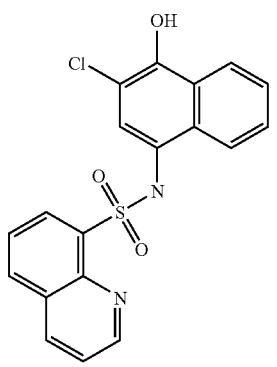 [SMILES: O=S(=O)(Nc1cc(Cl)c(O)c2ccccc12)c1cccc2cccnc12] | C19H13ClN2O3S | 384.8441 | 4.392 |

TABLE 12-continued

| IDNUMBER | Structure | Formula structure | MW | LogP |
|---|---|---|---|---|
| F5749-0295 | 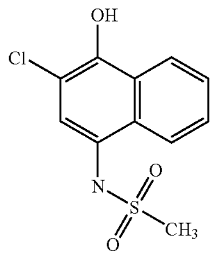 [SMILES: CS(=O)(=O)Nc1cc(Cl)c(O)c2ccccc12] | C11H10ClNO3S | 271.7243 | 2.538 |
| F5749-0296 | 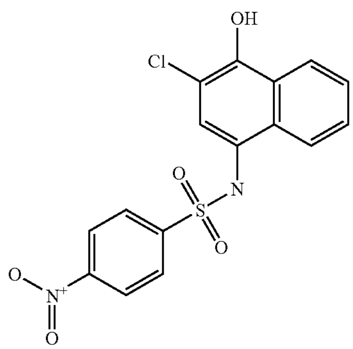 | C16H11ClN2O5S | 378.7935 | 4.127 |
| F5749-0297 | 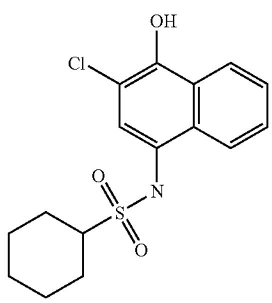 [SMILES: O=S(=O)(Nc1cc(Cl)c(O)c2ccccc12)C1CCCCC1] | C16H18ClNO3S | 339.8438 | 4.517 |
| F5749-0298 | 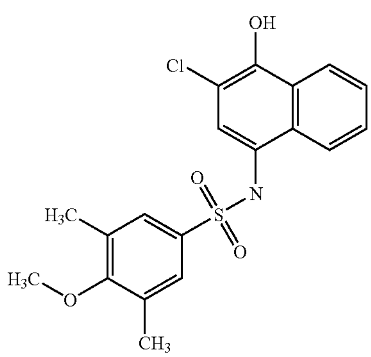 [SMILES: COc1c(C)cc(S(=O)(=O)Nc2cc(Cl)c(O)c3ccccc23)cc1C] | C19H18ClNO4S | 391.8766 | 4.814 |
| F5749-0299 | 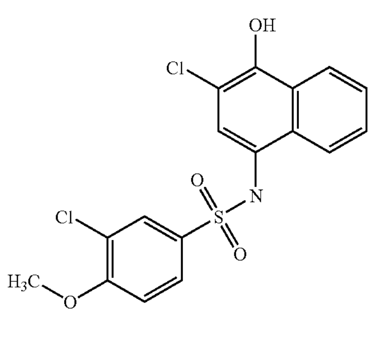 [SMILES: COc1ccc(S(=O)(=O)Nc2cc(Cl)c(O)c3ccccc23)cc1Cl] | C17H13Cl2NO4S | 398.2675 | 4.775 |

TABLE 12-continued
| IDNUMBER | Structure | Formula structure | MW | LogP |
| --- | --- | --- | --- | --- |
| F5749-0300 | 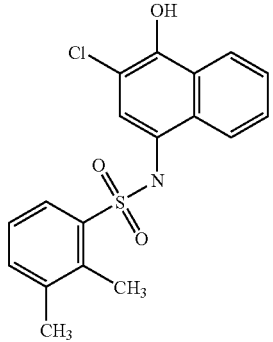 [SMILES: Cc1cccc(S(=O)(=O)Nc2cc(Cl)c(O)c3ccccc23)c1C] | C18H16ClNO3S | 361.8501 | 4.784 |
| F5749-0301 | 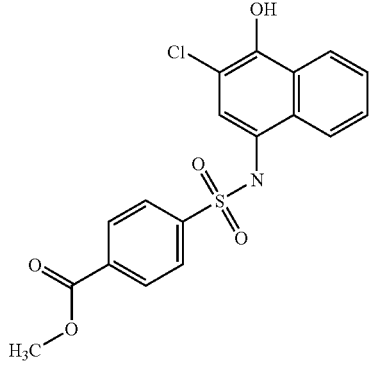 [SMILES: COC(=O)c1ccc(S(=O)(=O)Nc2cc(Cl)c(O)c3ccccc23)cc1] | C18H14ClNO5S | 391.833 | 4.133 |
| F5749-0302 | 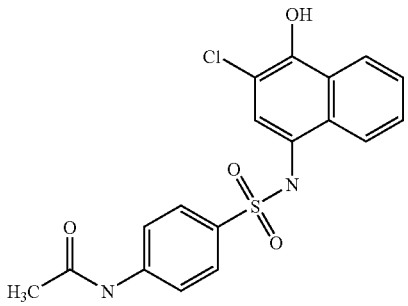 [SMILES: CC(=O)Nc1ccc(S(=O)(=O)Nc2cc(Cl)c(O)c3ccccc23)cc1] | C18H15ClN2O4S | 390.8483 | 3.483 |
| F5749-0303 | 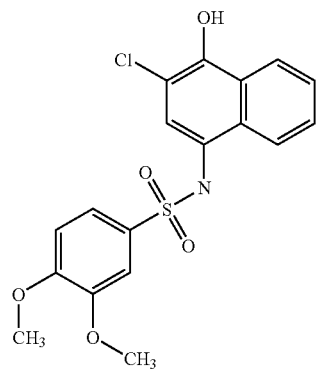 [SMILES: COc1ccc(S(=O)(=O)Nc2cc(Cl)c(O)c3ccccc23)cc1OC] | C18H16ClNO5S | 393.8489 | 3.89074 |

TABLE 12-continued

| IDNUMBER | Structure | Formula structure | MW | LogP |
|---|---|---|---|---|
| F5749-0304 | 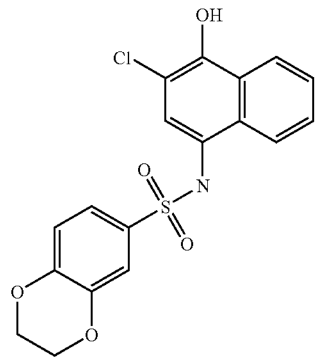 [SMILES: O=S(=O)(Nc1cc(Cl)c(O)c2ccccc12)c1ccc2c(c1)OCCO2] | C18H14ClNO5S | 391.833 | 3.787 |
| F5749-0305 | 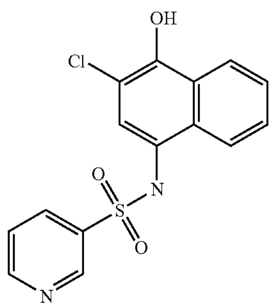 [SMILES: O=S(=O)(Nc1cc(Cl)c(O)c2ccccc12)c1cccnc1] | C15H11ClN2O3S | 334.7835 | 2.959 |
| F5749-0306 | 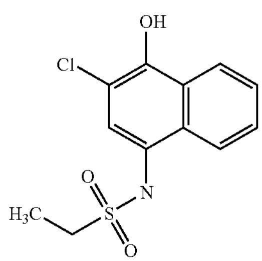 [SMILES: CCS(=O)(=O)Nc1cc(Cl)c(O)c2ccccc12] | C12H12ClNO3S | 285.7513 | 3.051 |
| F5749-0307 | 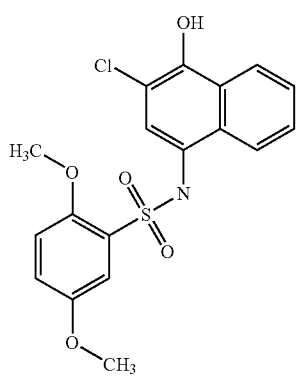 [SMILES: COc1ccc(OC)c(S(=O)(=O)Nc2cc(Cl)c(O)c3ccccc23)c1] | C18H16ClNO5S | 393.8489 | 4.139 |
| F5749-0308 | 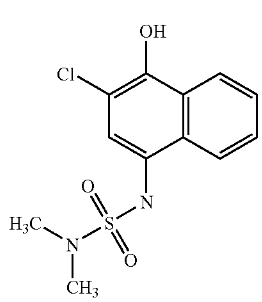 [SMILES: CN(C)S(=O)(=O)Nc1cc(Cl)c(O)c2ccccc12] | C12H13ClN2O3S | 300.766 | 2.086 |

TABLE 12-continued

| IDNUMBER | Structure | Formula structure | MW | LogP |
|---|---|---|---|---|
| F5749-0309 | 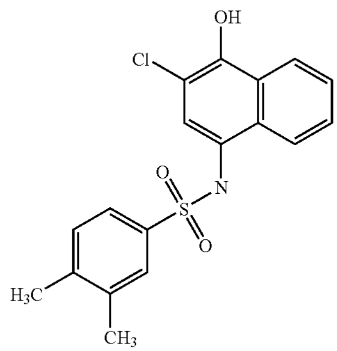 [SMILES: Cc1ccc(S(=O)(=O)Nc2cc(Cl)c(O)c3ccccc23)cc1C] | C18H16ClNO3S | 361.8501 | 4.823 |
| F5749-0310 | 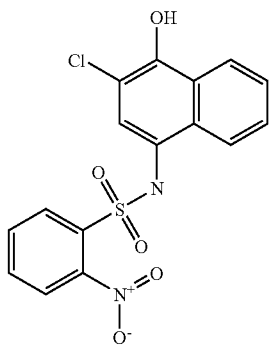 [SMILES: O=[N+]([O-])c1ccccc1S(=O)(=O)Nc1cc(Cl)c(O)c2ccccc12] | C16H11ClN2O5S | 378.7935 | 4.125 |
| F5749-0311 | 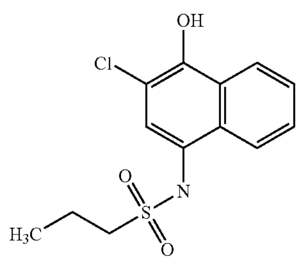 [SMILES: CCCS(=O)(=O)Nc1cc(Cl)c(O)c2ccccc12] | C13H14ClNO3S | 299.7784 | 3.493 |
| F5749-0312 | 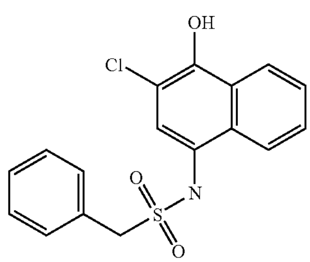 [SMILES: O=S(=O)(Cc1ccccc1)Nc1cc(Cl)c(O)c2ccccc12] | C17H14ClNO3S | 347.823 | 4.326 |
| F5749-0313 | 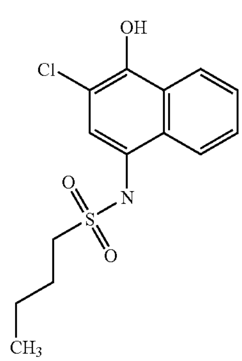 [SMILES: CCCCS(=O)(=O)Nc1cc(Cl)c(O)c2ccccc12] | C14H16ClNO3S | 313.8055 | 3.935 |

TABLE 12-continued
| IDNUMBER | Structure | Formula structure | MW | LogP |
|---|---|---|---|---|
| F5749-0314 | 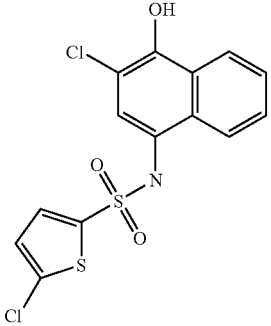 [SMILES: O=S(=O)(Nc1cc(Cl)c(O)c2ccccc12)c1ccc(Cl)s1] | C14H9Cl2NO3S2 | 374.2667 | 4.995 |
| F5749-0315 | 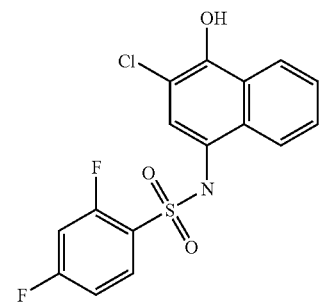 [SMILES: O=S(=O)(Nc1cc(Cl)c(O)c2ccccc12)c1ccc(F)cc1F] | C16H10ClF2NO3S | 369.7768 | 4.533 |
| F5749-0316 | 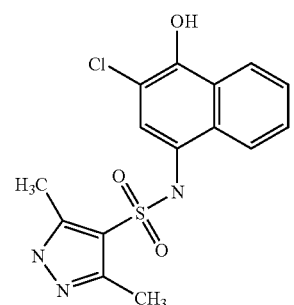 | C15H14ClN3O3S | 351.8141 | 3.302 |
| F5749-0317 | 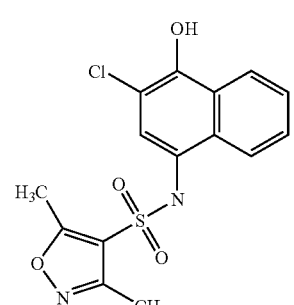 | C15H13ClN2O4S | 352.7989 | 3.336 |
| F5749-0318 | 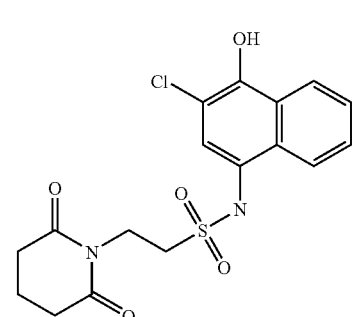 | C17H17ClN2O5S | 396.8524 | 1.979 |

TABLE 12-continued
| IDNUMBER | Structure | Formula structure | MW | LogP |
|---|---|---|---|---|
| F5749-0319 | 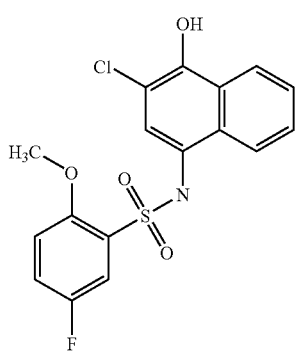 [SMILES: COc1ccc(F)cc1S(=O)(=O)Nc1cc(Cl)c(O)c2ccccc12] | C17H13ClFNO4S | 381.8129 | 4.336 |
| F5749-0320 | 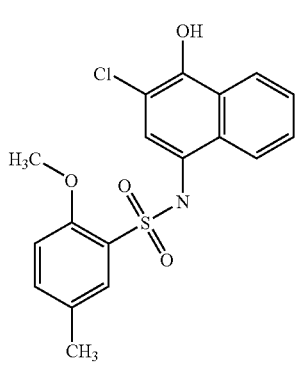 [SMILES: COc1ccc(C)cc1S(=O)(=O)Nc1cc(Cl)c(O)c2ccccc12] | C18H16ClNO4S | 377.8495 | 4.481 |
| F5749-0321 | 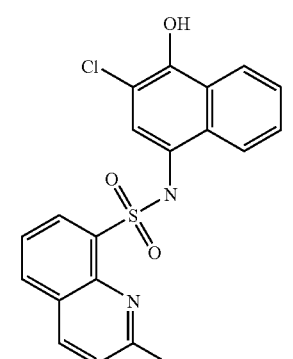 | C20H15ClN2O3S | 398.8712 | 4.651 |
| F5749-0322 | 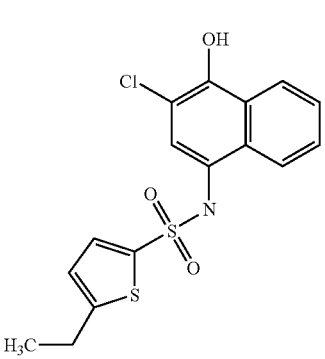 [SMILES: CCc1ccc(S(=O)(=O)Nc2cc(Cl)c(O)c3ccccc23)s1] | C16H14ClNO3S2 | 367.8759 | 4.843 |

TABLE 12-continued

| IDNUMBER | Structure | Formula structure | MW | LogP |
| --- | --- | --- | --- | --- |
| F5749-0323 | 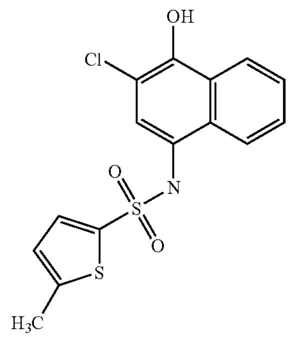 [SMILES: Cc1ccc(S(=O)(=O)Nc2cc(Cl)c(O)c3ccccc23)s1] | C15H12ClNO3S2 | 353.8488 | 4.368 |
| F5749-0324 | 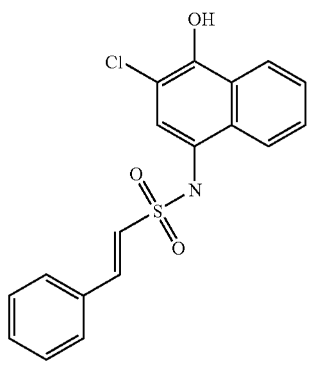 [SMILES: O=S(=O)(/C=C/c1ccccc1)Nc1cc(Cl)c(O)c2ccccc12] | C18H14ClNO3S | 359.8342 | 4.55 |
| F5749-0325 | 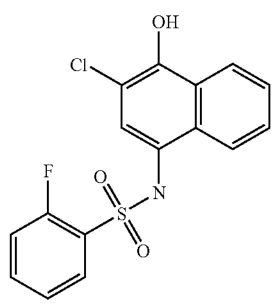 [SMILES: O=S(=O)(Nc1cc(Cl)c(O)c2ccccc12)c1ccccc1F] | C16H11ClFNO3S | 351.7864 | 4.343 |
| F5749-0326 | 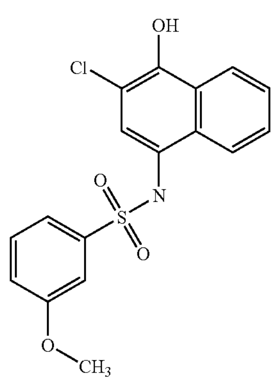 [SMILES: COc1cccc(S(=O)(=O)Nc2cc(Cl)c(O)c3ccccc23)c1] | C17H14ClNO4S | 363.8224 | 4.185 |

TABLE 12-continued
| IDNUMBER | Structure | Formula structure | MW | LogP |
|---|---|---|---|---|
| F5749-0327 | 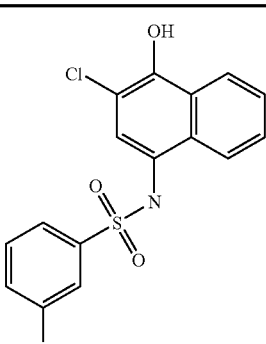 | C16H11ClFNO3S | 351.7864 | 4.382 |
| F5749-0328 | 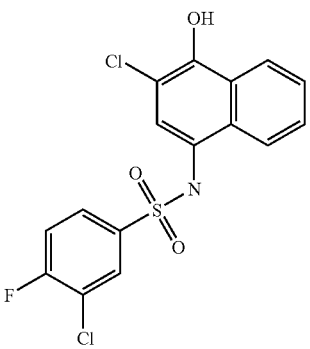 [SMILES: O=S(=O)(Nc1cc(Cl)c(O)c2ccccc12)c1ccc(F)c(Cl)c1] | C16H10Cl2FNO3S | 386.2314 | 4.972 |
| F5749-0329 | 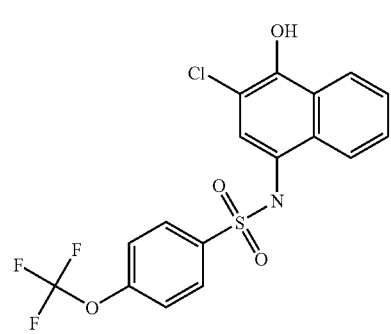 [SMILES: O=S(=O)(Nc1cc(Cl)c(O)c2ccccc12)c1ccc(OC(F)(F)F)cc1] | C17H11ClF3NO4S | 417.7937 | 5.59076 |
| F5749-0330 | 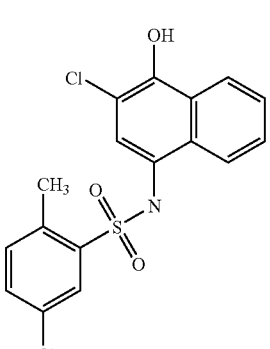 | C17H13Cl2NO3S | 382.2681 | 5.117 |

TABLE 12-continued

| IDNUMBER | Structure | Formula structure | MW | LogP |
|---|---|---|---|---|
| F5749-0331 | 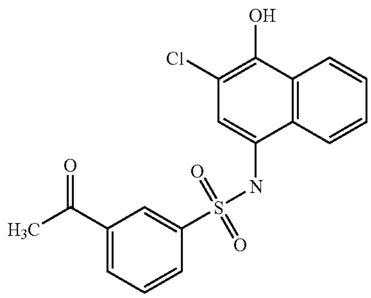 [SMILES: CC(=O)c1cccc(S(=O)(=O)Nc2cc(Cl)c(O)c3ccccc23)c1] | C18H14ClNO4S | 375.8336 | 4.082 |
| F5749-0332 | 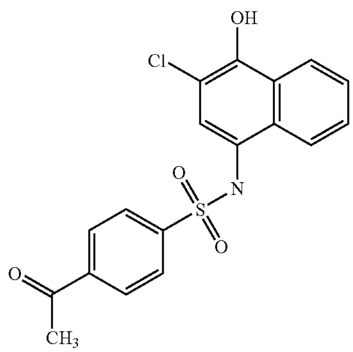 [SMILES: CC(=O)c1ccc(S(=O)(=O)Nc2cc(Cl)c(O)c3ccccc23)cc1] | C18H14ClNO4S | 375.8336 | 4.045 |
| F5749-0333 | 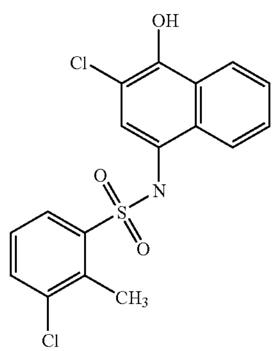 [SMILES: Cc1c(Cl)cccc1S(=O)(=O)Nc1cc(Cl)c(O)c2ccccc12] | C17H13Cl2NO3S | 382.2681 | 5.078 |
| F5749-0334 | 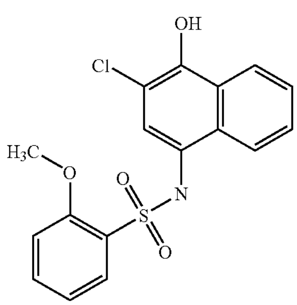 [SMILES: COc1ccccc1S(=O)(=O)Nc1cc(Cl)c(O)c2ccccc12] | C17H14ClNO4S | 363.8224 | 4.146 |
| F5749-0335 | 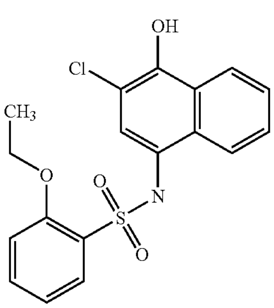 [SMILES: CCOc1ccccc1S(=O)(=O)Nc1cc(Cl)c(O)c2ccccc12] | C18H16ClNO4S | 377.8495 | 4.487 |

TABLE 12-continued
| IDNUMBER | Structure | Formula structure | MW | LogP |
|---|---|---|---|---|
| F5749-0336 | 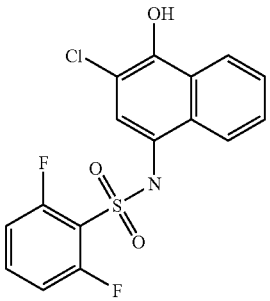 [SMILES: O=S(=O)(Nc1cc(Cl)c(O)c2ccccc12)c1c(F)cccc1F] | C16H10ClF2NO3S | 369.7768 | 4.494 |
| F5749-0337 | 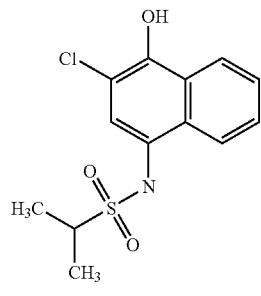 [SMILES: CC(C)S(=O)(=O)Nc1cc(Cl)c(O)c2ccccc12] | C13H14ClNO3S | 299.7784 | 3.685 |
| F5749-0338 | 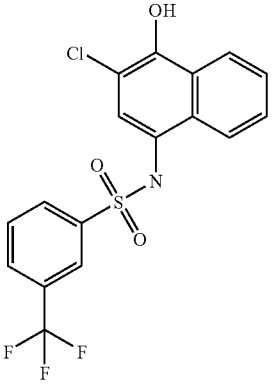 [SMILES: O=S(=O)(Nc1cc(Cl)c(O)c2ccccc12)c1cccc(C(F)(F)F)c1] | C17H11ClF3NO3S | 401.7943 | 5.16376 |
| F5749-0339 | 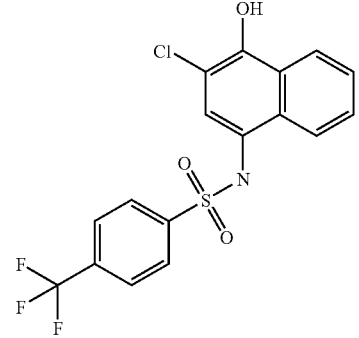 [SMILES: O=S(=O)(Nc1cc(Cl)c(O)c2ccccc12)c1ccc(C(F)(F)F)cc1] | C17H11ClF3NO3S | 401.7943 | 5.12676 |

TABLE 12-continued

| IDNUMBER | Structure | Formula structure | MW | LogP |
| --- | --- | --- | --- | --- |
| F5749-0340 | 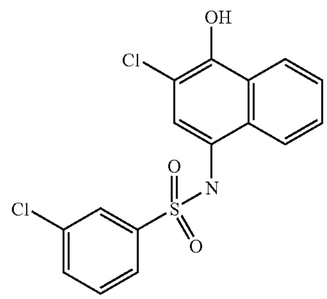 [SMILES: O=S(=O)(Nc1cc(Cl)c(O)c2ccccc12)c1cccc(Cl)c1] | C16H11Cl2NO3S | 368.241 | 4.821 |
| F5749-0341 | 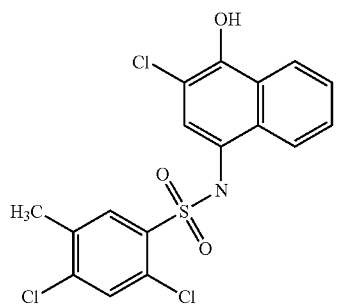 [SMILES: Cc1cc(S(=O)(=O)Nc2cc(Cl)c(O)c3ccccc23)c(Cl)cc1Cl] | C17H12Cl3NO3S | 416.7131 | 5.744 |
| F5749-0342 | 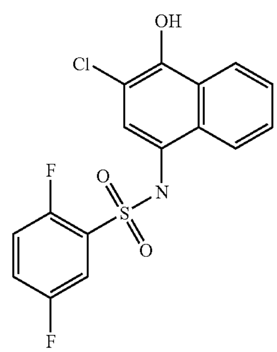 [SMILES: O=S(=O)(Nc1cc(Cl)c(O)c2ccccc12)c1cc(F)ccc1F] | C16H10ClF2NO3S | 369.7768 | 4.533 |
| F5749-0343 | 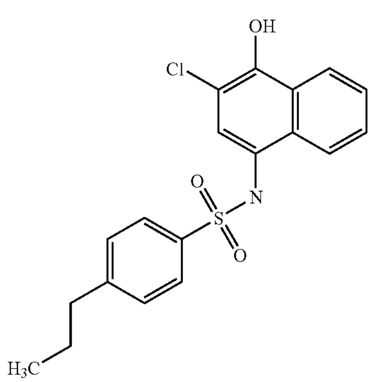 [SMILES: CCCc1ccc(S(=O)(=O)Nc2cc(Cl)c(O)c3ccccc23)cc1] | C19H18ClNO3S | 375.8772 | 5.407 |

TABLE 12-continued

| IDNUMBER | Structure | Formula structure | MW | LogP |
|---|---|---|---|---|
| F5749-0344 | 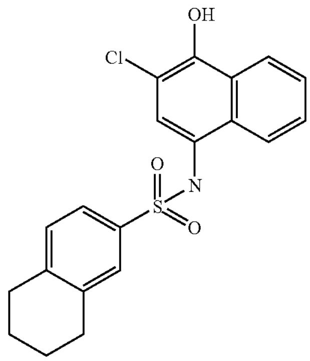 [SMILES: O=S(=O)(Nc1cc(Cl)c(O)c2ccccc12)c1ccc2c(c1)CCCC2] | C20H18ClNO3S | 387.8884 | 5.279 |
| F5749-0345 | 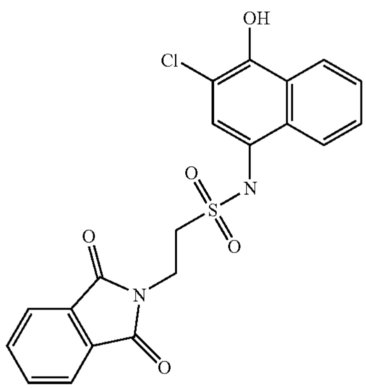 [SMILES: O=C1c2ccccc2C(=O)N1CCS(=O)(=O)Nc1cc(Cl)c(O)c2ccccc12] | C20H15ClN2O5S | 430.87 | 3.319 |
| F5749-0346 | 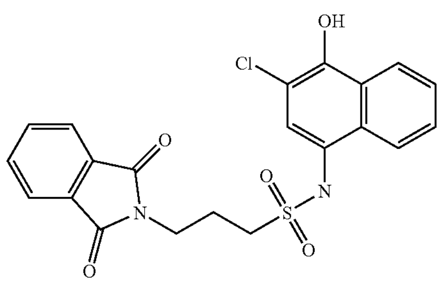 [SMILES: O=C1c2ccccc2C(=O)N1CCCS(=O)(=O)Nc1cc(Cl)c(O)c2ccccc12] | C21H17ClN2O5S | 444.897 | 3.761 |
| F5749-0347 | 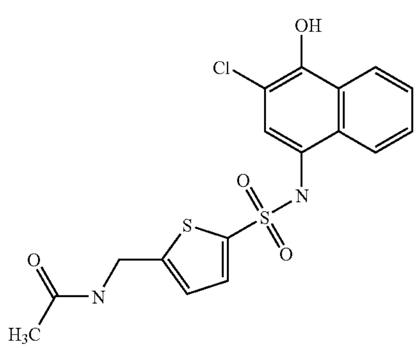 [SMILES: CC(=O)NCc1ccc(S(=O)(=O)Nc2cc(Cl)c(O)c3ccccc23)s1] | C17H15ClN2O4S2 | 410.9011 | 3.495 |

TABLE 12-continued

| IDNUMBER | Structure | Formula structure | MW | LogP |
|---|---|---|---|---|
| F5749-0348 | 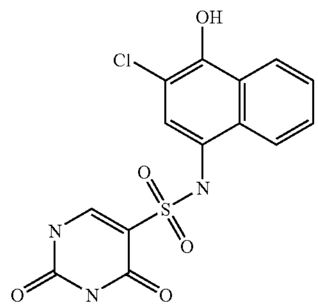 [SMILES: O=c1[nH]cc(S(=O)(=O)Nc2cc(Cl)c(O)c3ccccc23)c(=O)[nH]1] | C14H10ClN3O5S | 367.7699 | 1.237 |
| F5749-0349 | 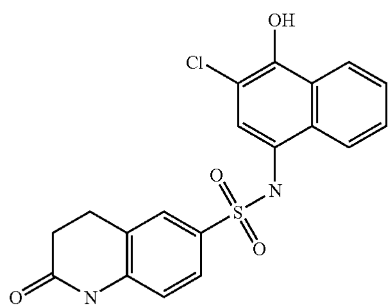 [SMILES: O=C1CCc2cc(S(=O)(=O)Nc3cc(Cl)c(O)c4ccccc34)ccc2N1] | C19H15ClN2O4S | 402.8594 | 3.388 |
| F5749-0350 | 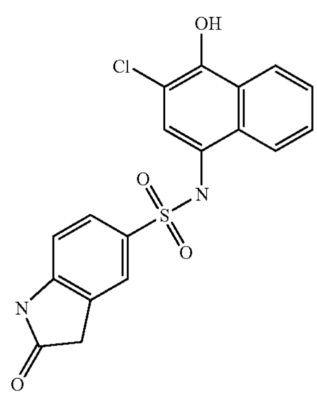 [SMILES: O=C1Cc2cc(S(=O)(=O)Nc3cc(Cl)c(O)c4ccccc34)ccc2N1] | C18H13ClN2O4S | 388.8323 | 3.3 |
| F5749-0351 | 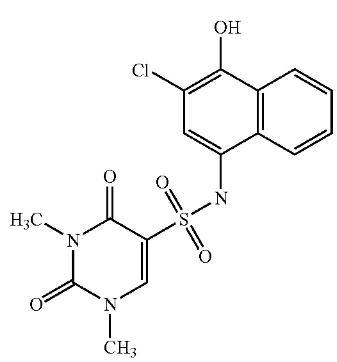 [SMILES: Cn1cc(S(=O)(=O)Nc2cc(Cl)c(O)c3ccccc23)c(=O)n(C)c1=O] | C16H14ClN3O5S | 395.8241 | 1.301 |

TABLE 12-continued

| IDNUMBER | Structure | Formula structure | MW | LogP |
|---|---|---|---|---|
| F5749-0352 | 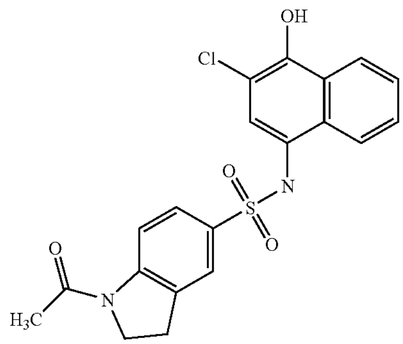 [SMILES: CC(=O)N1CCc2cc(S(=O)(=O)Nc3cc(Cl)c(O)c4ccccc34)ccc21] | C20H17ClN2O4S | 416.8865 | 3.623 |
| F5749-0353 | 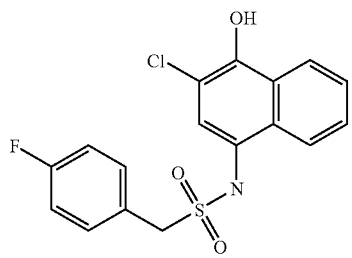 [SMILES: O=S(=O)(Cc1ccc(F)cc1)Nc1cc(Cl)c(O)c2ccccc12] | C17H13ClFNO3S | 365.8135 | 4.479 |
| F5749-0354 | 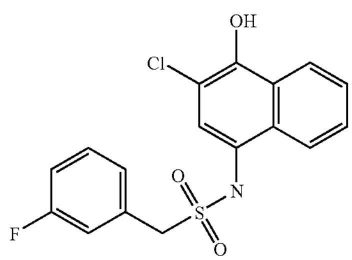 [SMILES: O=S(=O)(Cc1cccc(F)c1)Nc1cc(Cl)c(O)c2ccccc12] | C17H13ClFNO3S | 365.8135 | 4.516 |
| F5749-0355 | 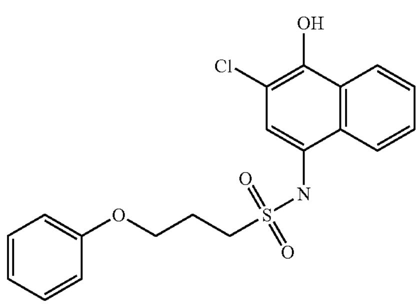 [SMILES: O=S(=O)(CCCOc1ccccc1)Nc1cc(Cl)c(O)c2ccccc12] | C19H18ClNO4S | 391.8766 | 4.552 |
| F5749-0356 | 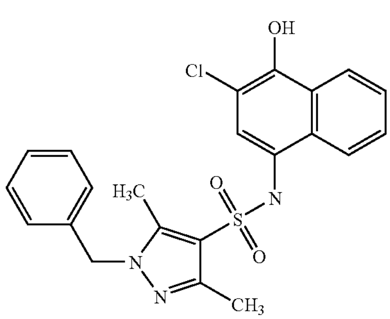 [SMILES: Cc1nn(Cc2ccccc2)c(C)c1S(=O)(=O)Nc1cc(Cl)c(O)c2ccccc12] | C22H20ClN3O3S | 441.94 | 4.471 |

TABLE 12-continued
| IDNUMBER | Structure | Formula structure | MW | LogP |
|---|---|---|---|---|
| F5749-0357 | 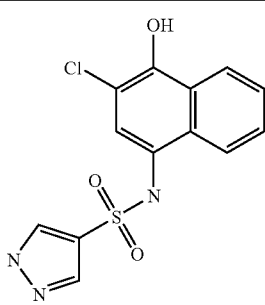 | C13H10ClN3O3S | 323.76 | 2.332 |
| F5749-0358 | 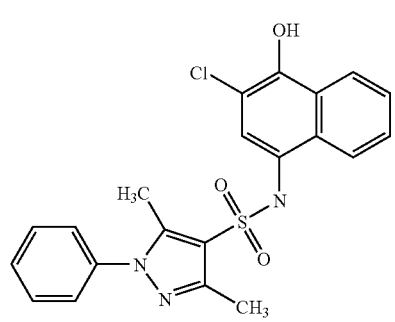 [SMILES: Cc1nn(-c2ccccc2)c(C)c1S(=O)(=O)Nc1cc(Cl)c(O)c2ccccc12] | C21H18ClN3O3S | 427.9129 | 4.337 |
| F5749-0359 | 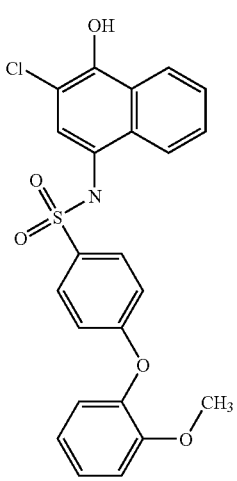 [SMILES: COc1ccccc1Oc1ccc(S(=O)(=O)Nc2cc(Cl)c(O)c3ccccc23)cc1] | C23H18ClNO5S | 455.9206 | 5.50774 |
| F5749-0360 | 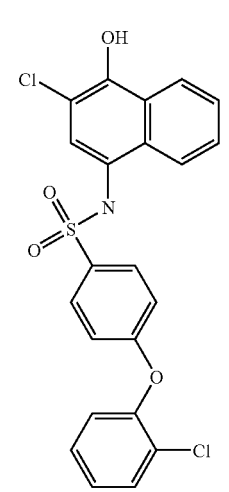 [SMILES: O=S(=O)(Nc1cc(Cl)c(O)c2ccccc12)c1ccc(Oc2ccccc2Cl)cc1] | C22H15Cl2NO4S | 460.3392 | 6.392 |

TABLE 12-continued
| IDNUMBER | Structure | Formula structure | MW | LogP |
|---|---|---|---|---|
| F5749-0361 | 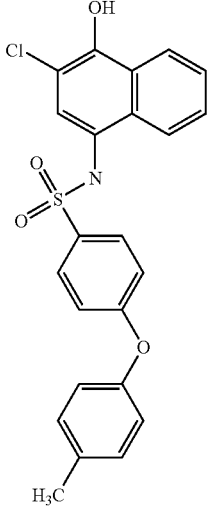 [SMILES: Cc1ccc(Oc2ccc(S(=O)(=O)Nc3cc(Cl)c(O)c4ccccc34)cc2)cc1] | C23H18ClNO4S | 439.9212 | 6.1 |
| F5749-0362 | 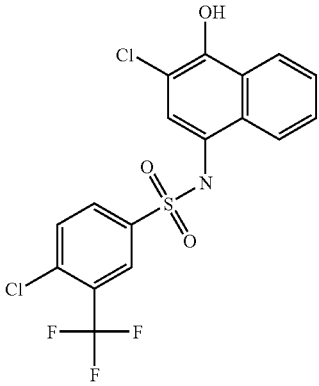 [SMILES: O=S(=O)(Nc1cc(Cl)c(O)c2ccccc12)c1ccc(Cl)c(C(F)(F)F)c1] | C17H10Cl2F3NO3S | 436.2394 | 5.75376 |
| F5749-0363 | 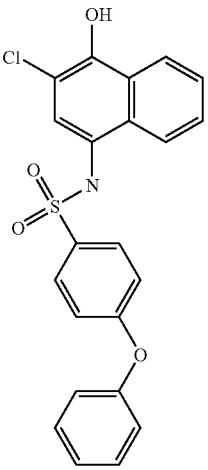 [SMILES: O=S(=O)(Nc1cc(Cl)c(O)c2ccccc12)c1ccc(Oc2ccccc2)cc1] | C22H16ClNO4S | 425.8941 | 5.802 |

TABLE 12-continued
| IDNUMBER | Structure | Formula structure | MW | LogP |
|---|---|---|---|---|
| F5749-0364 | 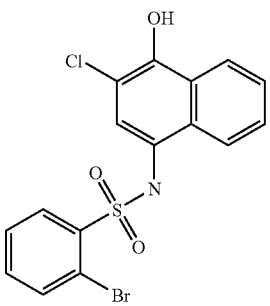 [SMILES: O=S(=O)(Nc1cc(Cl)c(O)c2ccccc12)c1ccccc1Br] | C16H11BrClNO3S | 412.692 | 4.988 |
| F5749-0365 | 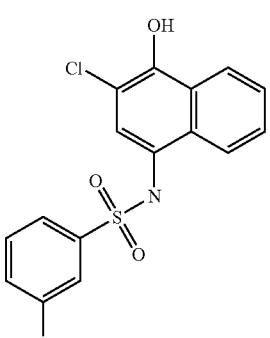 | C16H11BrClNO3S | 412.692 | 5.027 |
| F5749-0366 | 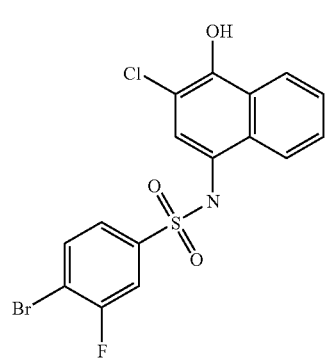 [SMILES: O=S(=O)(Nc1cc(Cl)c(O)c2ccccc12)c1ccc(Br)c(F)c1] | C16H10BrClFNO3S | 430.6824 | 5.178 |
| F5749-0367 | 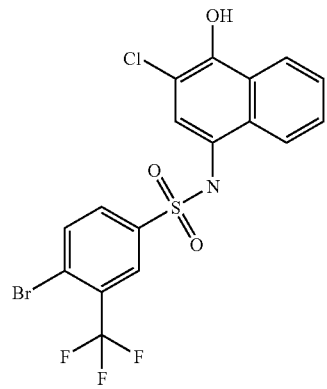 [SMILES: O=S(=O)(Nc1cc(Cl)c(O)c2ccccc12)c1ccc(Br)c(C(F)(F)F)c1] | C17H10BrClF3NO3S | 480.6904 | 5.95976 |

TABLE 12-continued

| IDNUMBER | Structure | Formula structure | MW | LogP |
|---|---|---|---|---|
| F5749-0368 | 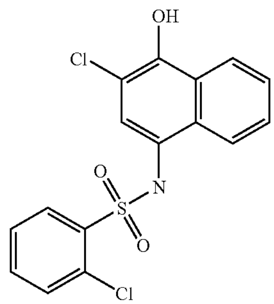 [SMILES: O=S(=O)(Nc1cc(Cl)c(O)c2ccccc12)c1ccccc1Cl] | C16H11Cl2NO3S | 368.241 | 4.782 |
| F5749-0369 | 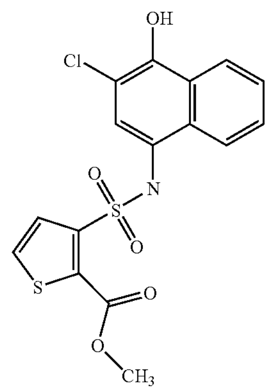 [SMILES: COC(=O)c1sccc1S(=O)(=O)Nc1cc(Cl)c(O)c2ccccc12] | C16H12ClNO5S2 | 397.8587 | 3.392 |
| F5749-0370 | 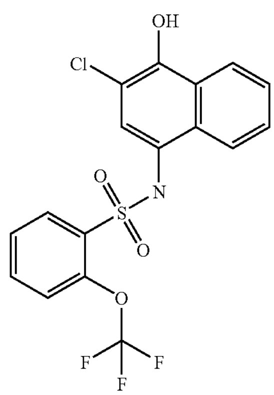 [SMILES: O=S(=O)(Nc1cc(Cl)c(O)c2ccccc12)c1ccccc1OC(F)(F)F] | C17H11ClF3NO4S | 417.7937 | 5.58876 |

REFERENCES

All patents and publications cited herein are hereby incorporated by reference in their entirety herein. Full citations for the references cited herein are provided in the following list.

PUBLICATIONS

Akira, S., 2000. Roles of STAT3 defined by tissue-specific gene targeting. Oncogene 19:2607-2611.

Akira, S. 1997, IL-6-regulated transcription factors. Int J Biochem Cell Biol 29:1401-1418.

Al-Hajj, M., Wicha, M. S., Benito-Hernandez, A., Morrison, S. J., and Clarke, M. F. 2003. Prospective identification of tumorigenic breast cancer cells. Proc Natl Acad Sci USA 100:3983-3988.

Becker, S., Groner B, Muller C W (1998) Three-dimensional structure of the Stat3-[beta]homodimer bound to DNA. Nature 394(6689): 145-151.

Bhasin, D., Cisek K, Pandharkar T, Regan N, Li C et al. (207) Design, synthesis, and studies of small molecule STAT3 inhibitors. Bioorganic & Medicinal Chemistry Letters In Press, Corrected Proof.

Brinkley, B R, Beall P T, Wible L J, Mace M L, Turner D S et al. (1980) Variations in Cell Form and Cytoskeleton in Human Breast Carcinoma Cells in Vitro. Cancer Res 40(9): 3118-3129.

Bromberg, J., 2002. Stat proteins and oncogenesis. J Clin Invest 109:1139-1142.

Bromberg, J., and Darnell, J. E., Jr. 2000. The role of STATs in transcriptional control and their impact on cellular function. Oncogene 19:2468-2473.

Bromberg, J. F., Horvath, C. M., Besser, D., Lathem, W. W., and Darnell, J. E., Jr. 1998. Stat3 activation is required for cellular transformation by v-src. Mol Cell Biol 18:2553-2558.

Bromberg, J. F., Wrzeszczynska, M. H., Devgan, G., Zhao, Y., Pestell, R. G., Albanese, C., and Darnell, J. E., Jr. 1999.

Stat3 as an oncogene [published erratum appears in Cell 1999 Oct. 15; 99(2):239]. Cell 98:295-303.

Cailleau R O M, Crueiger Q V J. (1978) Long term human breast carcinoma cell lines of metastatic origin: preliminary characterization. In Vitro 14: 911-915.

Caldenhoven, E., van, D. T. B., Solari, R., Armstrong, J., Raaijmakers, J. A. M., Lammers, J. W. J., Koenderman, L., and de, G. R. P. 1996. STAT3beta, a splice variant of transcription factor STAT3, is a dominant negative regulator of transcription. Journal of Biological Chemistry 271: 13221-13227.

Catlett-Falcone, R., Landowski, T. H., Oshiro, M. M., Turkson, J., Levitzki, A., Savino, R., Ciliberto, G., Moscinski, L., Fernandez-Luna, J. L., Nunez, G., et al. 1999. Constitutive activation of Stat3 signaling confers resistance to apoptosis in human U266 myeloma cells. Immunity 10:105-115.

Chakraborty, A., Dyer K F, Cascio M, Mietzner T A, Tweardy D J (1999) Identification of a Novel Stat3 Recruitment and Activation Motif Within the Granulocyte Colony-Stimulating Factor Receptor. Blood 93(1): 15-24.

Chakraborty, A., White, S. M., Schaefer, T. S., Ball, E. D., Dyer, K. F., and Tweardy, D. J. 1996. Granulocyte colony-stimulating factor activation of Stat3 alpha and Stat3 beta in immature normal and leukemic human myeloid cells. Blood 88:2442-2449.

Chapman, R. S., Lourenco, P. C., Tonner, E., Flint, D. J., Seibert, S., Takeda, K., Akira, S., Clarke, A. R., and Watson, C. J. 1999. Suppression of epithelial apoptosis and delayed mammary gland involution in mice with a conditional knockout of Stat3. Genes Dev 13:2604-2616.

Chen, X., Vinkemeier U, Zhao Y, Jeruzalmi D, Darnell J E et al. (1998) Crystal Structure of a Tyrosine Phosphorylated STAT-1 Dimer Bound to DNA. Cell 93(5): 827-839.

Cohen, M S, Zhang C, Shokat K M, Taunton J (2005) Structural Bioinformatics-Based Design of Selective, Irreversible Kinase Inhibitors. Science 308(5726): 1318-1321.

Coleman, D R, Ren Z, Mandal P K, Cameron A G, Dyer G A et al. (2005) Investigation of the Binding Determinants of Phosphopeptides Targeted to the Src Homology 2 Domain of the Signal Transducer and Activator of Transcription 3. Development of a High-Affinity Peptide Inhibitor. J Med Chem 48(21): 6661-6670.

Costa-Pereira, A. P., Tininini, S., Strobl, B., Alonzi, T., Schlaak, J. F., Is'harc, H., Gesualdo, I., Newman, S. J., Kerr, I. M., and Poli, V. 2002. Mutational switch of an IL-6 response to an interferon-gamma-like response. Proc Natl Acad Sci USA 99:8043-8047.

Daling, J. R., and Malone, K. E. 2003. Incidence of invasive breast cancer by hormone receptor status from 1992 to 1998. J Clin Oncol 21:28-34.

Darnell J E (2005), Validating Stat3 in cancer therapy. Nat Med 11(6): 595-596.

Dave, B., and Chang, J. 2009. Treatment resistance in stem cells and breast cancer. J Mammary Gland Biol Neoplasia 14:79-82.

Diaz, N., Minton, S., Cox, C., Bowman, T., Gritsko, T., Garcia, R., Eweis, I., Wloch, M., Livingston, S., Seijo, E., et al. 2006. Activation of stat3 in primary tumors from high-risk breast cancer patients is associated with elevated levels of activated SRC and survivin expression. Clin Cancer Res 12:20-28.

Dong, S., Chen S-J, Tweardy DJ (2003) Cross-talk between Retinoic Acid and Stat3 Signaling Pathways in Acute Promyelocytic Leukemia. Leuk Lymphoma 44: 2023-2029.

Dong, S., Cheng, Z., and Tweardy, D. J. 2003. Cross-talk between retinoic acid and Stat3 signaling pathways in acute promyelocytic leukemia. Leukemia and Lymphoma In press.

Dunn, G P, Bruce A T, Ikeda H, Old L J, Schreiber R D (2002) Cancer immunoediting: from immunosurveillance to tumor escape. Nat Immunol 3(11): 991-998.

Durbin, J. E., Hackenmiller, R., Simon, M. C., and Levy, D. E. 1996. Targeted disruption of the mouse Stat1 gene results in compromised innate immunity to viral disease. Cell 84:443-450.

Eckert, H., Bajorath J (2007) Molecular similarity analysis in virtual screening: foundations, limitations and novel approaches. Drug discovery today 12(5-6): 225-233.

Epling-Burnette, P. K., Liu, J. H., Catlett-Falcone, R., Turkson, J., Oshiro, M., Kothapalli, R., Li, Y., Wang, J. M., Yang-Yen, H. F., Karras, J., et al. 2001. Inhibition of STAT3 signaling leads to apoptosis of leukemic large granular lymphocytes and decreased Mcl-1 expression. J Clin Invest 107:351-362.

Fiala, S., 1968. The cancer cell as a stem cell unable to differentiate. A theory of carcinogenesis. Neoplasma 15:607-622.

Fu, X.-Y., Schindler, C, Improta, T., Aebersold, R., and Darnell, J. E., Jr. 1992. The proteins of ISGF-3, the interferon alpha-induced transcriptional activator, define a gene family involved in signal transduction. Proceedings of the National Academy of Sciences of the United States of America 89:7840-7843.

Garcia R, Yu C L, Hudnall A, Catlett R, Nelson K L et al. (1997) Constitutive activation of Stat3 in fibroblasts transformed by diverse oncoproteins and in breast carcinoma cells. Cell Growth Differ 8(12): 1267-1276.

Garcia R, Bowman T L, Niu G, Yu H, Minton S et al. (2001) Constitutive activation of Stat3 by the Src and Jak tyrosine kinases participates in growth regulation of human breast carcinoma cells. Oncogene 20: 2499-2513.

Garcia, R., and, Jove, R. 1998. Activation of STAT transcription factors in oncogenic tyrosine kinase signaling. Journal of Biomedical Science In press.

Grandis, J. R., Drenning, S. D., Zeng, Q., Watkins, S. C., Melhem, M. F., Endo, S., Johnson, D. E., Huang, L., He, Y., and Kim, J. D. 2000. Constitutive activation of Stat3 signaling abrogates apoptosis in squamous cell carcinogenesis in vivo. Proc Natl Acad Sci USA 97:4227-4232.

Gritsko, T., Williams, A., Turkson, J., Kaneko, S., Bowman, T., Huang, M., Nam, S., Eweis, I., Diaz, N., Sullivan, D., et al. 2006. Persistent activation of stat3 signaling induces survivin gene expression and confers resistance to apoptosis in human breast cancer cells. Clin Cancer Res 12:11-19.

Haan, S., Hemmann, U., Hassiepen, U., Schaper, F., Schneider-Mergener, J., Wollmer, A., Heinrich, P. C., and Grotzinger, J. 1999. Characterization and binding specificity of the monomeric STAT3-SH2 domain. J Biol Chem 274:1342-1348.

Huang, Y., Qiu J, Dong S, Redell M S, Poli V et al. (2007) Stat3 Isoforms, {alpha} and, Demonstrate Distinct Intracellular Dynamics with Prolonged Nuclear Retention of Stat3 Mapping to Its Unique C-terminal End. J Biol Chem 282(48): 34958-34967.

Jemal, A., Siegel, R., Ward, E., Murray, T., Xu, J., Smigal, C., and Thun, M. J. 2006. Cancer statistics, 2006. CA Cancer J Clin 56:106-130.

Jing, N., Tweardy DJ (2005) Targeting Stat3 in cancer therapy. anticancer Drugs 16(6): 601-607.

Jing, N., Zhu Q, Yuan P, Li Y, Mao L et al. (2006) Targeting signal transducer and activator of transcription 3 with G-quartet oligonucleotides: a potential novel therapy for head and neck cancer. Mol Cancer Ther 5(2): 279-286.

Jing, N., Li Y, Xu X, Sha W, Li P et al. (2003) Targeting Stat3 with G-quartet oligodeoxynucleotides in human cancer cells. DNA Cell Biol 22(11): 685-696.

Jing, N., Li, Y., Xiong, W., Sha, W., Jing, L., and Tweardy, D. J. 2004. G-quartet oligonucleotides: a new class of signal transducer and activator of transcription 3 inhibitors that suppresses growth of prostate and breast tumors through induction of apoptosis. Cancer Res 64:6603-6609.

Kaplan, D. H., Shankaran, V., Dighe, A. S., Stocked, E., Aguet, M., Old, L. J., and Schreiber, R. D. 1998. Demonstration of an interferon gamma-dependent tumor surveillance system in immunocompetent mice. Proc Natl Acad Sci USA 95:7556-7561.

Kato, T., Sakamoto E, Kutsuna H, Kimura-Eto A, Hato F et al. (2004) Proteolytic Conversion of STAT3 {alpha} to STAT3 {gamma} in Human Neutrophils: ROLE OF GRANULE-DERIVED SERINE PROTEASES. J Biol Chem 279(30): 31076-31080.

Kim, J. K., Xu Y, Xu X, Keene D R, Gurusiddappa S et al. (2005) A Novel Binding Site in Collagen Type III for Integrins {alpha}1{beta}1 and {alpha}2{beta}1. J Biol Chem 280(37): 32512-32520.

Kortylewski, M., Kujawski M, Wang T, Wei S, Zhang S et al. (2005) Inhibiting Stat3 signaling in the hematopoietic system elicits multicomponent antitumor immunity. Nat Med 11(12): 1314-1321.

Leong, P. L., Andrews, G. A., Johnson, D. E., Dyer, K. F., Xi, S., Mai, J. C., Robbins, P. D., Gadiparthi, S., Burke, N. A., Watkins, S. F., et al. 2003. Targeted inhibition of Stat3 with a decoy oligonucleotide abrogates head and neck cancer cell growth. Proc Natl Acad Sci USA 100:4138-4143.

Li, C. I., Daling, J. R., and Malone, K. E. 2003. Incidence of invasive breast cancer by hormone receptor status from 1992 to 1998. J Clin Oncol 21:28-34.

Li, L., and Shaw, P. E. 2002. Autocrine-mediated activation of STAT3 correlates with cell proliferation in breast carcinoma lines. J Biol Chem 277:17397-17405.

Li, X., Lewis, M. T., Huang, J., Gutierrez, C., Osborne, C. K., Wu, M. F., Hilsenbeck, S. G., Pavlick, A., Zhang, X., Chamness, G. C., et al. 2008. Intrinsic resistance of tumorigenic breast cancer cells to chemotherapy. J Natl Cancer Inst 100:672-679.

Lin, Q., Lai R, Chirieac L R, Li C, Thomazy V A et al. (2005) Constitutive Activation of JAK3/STAT3 in Colon Carcinoma Tumors and Cell Lines: Inhibition of JAK3/STAT3 Signaling Induces Apoptosis and Cell Cycle Arrest of Colon Carcinoma Cells. Am J Pathol 167(4): 969-980.

Maritano, D., Sugrue, M. L., Tininini, S., Dewilde, S., Strobl, B., Fu, X., Murray-Tait, V., Chiarle, R., and Poli, V. 2004. The STAT3 isoforms alpha and beta have unique and specific functions. Nat Immunol 5:401-409.

McMurray J S (2006), A New Small-Molecule Stat3 Inhibitor. Chemistry & Biology 13(11): 1123-1124.

Meraz, M. A., White, J. M., Sheehan, K. C., Bach, E. A., Rodig, S. J., Dighe, A. S., Kaplan, D. H., Riley, J. K., Greenlund, A. C., Campbell, D., et al. 1996. Targeted disruption of the Stat1 gene in mice reveals unexpected physiologic specificity in the JAK-STAT signaling pathway. Cell 84:431-442.

Minino, A. M., Heron, M. P., Murphy, S. L., and Kochanek, K. D. 2007. Deaths: final data for 2004. Natl Vital Stat Rep 55:1-119.

Mora, L. B., Buettner, R., Seigne, J., Diaz, J., Ahmad, N., Garcia, R., Bowman, T., Falcone, R., Fairclough, R., Cantor, A., et al. 2002. Constitutive activation of Stat3 in human prostate tumors and cell lines: direct inhibition of Stat3 signaling induces apoptosis of prostate cancer cells. Cancer Res 62:6659-6666.

Neculai, D., Neculai A M, Verrier S, Straub K, Klumpp K et al. (2005) Structure of the Unphosphorylated STAT5a Dimer. J Biol Chem 280(49): 40782-40787.

Nemethy, G., Gibson K D, Palmer K A, Yoon C N, Paterlini G et al. (1992) Energy Parameters in Polypeptides. 10. Improved Geometrical Parameters and Nonbonded Interactions for Use in the ECEPP/3 Algorithm, with Application to Proline-Containing Peptides. JPhys Chem 96: 6472-6484.

Park, O. K., Schaefer, T. S., and Nathans, D. 1996. In vitro activation of Stat3 by epidermal growth factor receptor kinase. Proceedings of the National Academy of Sciences of the United States of America 93:13704-13708.

Park, O. K., Schaefer, L. K., Wang, W., and Schaefer, T. S. 2000. Dimer stability as a determinant of differential DNA binding activity of Stat3 isoforms. J Biol Chem 275:32244-32249.

Qing, Y., and Stark, G. R. 2004. Alternative activation of STAT1 and STAT3 in response to interferon-gamma. J Biol Chem 279:41679-41685.

Ramana, C., Chatterjee-Kishore M, Nguyen H, Stark G (2000) Complex roles of Stat1 in regulating gene expression. Oncogene 19(21): 2619-2627.

Real, P. J., Sierra, A., De Juan, A., Segovia, J. C., Lopez-Vega, J. M., and Fernandez-Luna, J. L. 2002. Resistance to chemotherapy via Stat3-dependent overexpression of Bcl-2 in metastatic breast cancer cells. Oncogene 21:7611-7618.

Redell, M S, Tweardy D J (2006) Targeting transcription factors in cancer: Challenges and evolving strategies. Drug Discovery Today: Technologies 3(3): 261-267.

Redell, M. S., and Tweardy, D. J. 2005. Targeting transcription factors for cancer therapy. Curr Pharm Des 11:2873-2887.

Ren, Z., Cabell, L. A., Schaefer, T. S., and McMurray, J. S. 2003. Identification of a high-affinity phosphopeptide inhibitor of stat3. Bioorg Med Chem Lett 13:633-636.

Ryan, J. J., McReynolds, L. J., Huang, H., Nelms, K., and Paul, W. E. 1998. Characterization of a mobile Stat6 activation motif in the human IL-4 receptor. J Immunol 161: 1811-1821.

Satya-Prakash K L P S, Hsu T C, Olive M, Cailleau R (1981) Cytogenetic analysis on eight human breast tumor cell lines: high frequencies of 1q, 11q, and HeLa-like marker chromosomes. Cancer GenetCytogenet 3: 61-73.

Schaefer, T. S., Sanders, L. K., and Nathans, D. 1995. Cooperative transcriptional activity of Jun and Stat3 beta, a short form of Stat3. Proceedings of the National Academy of Sciences of the United States of America 92:9097-9101.

Schindler, C., and Darnell, J. E., Jr. 1995. Transcriptional responses to polypeptide ligands: the JAK-STAT pathway. [Review]. Annual Review of Biochemistry 64:621-651.

Schindler, C., Fu, X. Y., Improta, T., Aebersold, R., and Darnell, J. E., Jr. 1992. Proteins of transcription factor ISGF-3: one gene encodes the 91- and 84-kDa ISGF-3 proteins that are activated by interferon alpha. Proceedings of the National Academy of Sciences of the United States of America 89:7836-7839.

Schust, J., Sperl, B., Hollis, A., Mayer, T. U., and Berg, T. 2006. Stattic: a small-molecule inhibitor of STAT3 activation and dimerization. Chem Biol 13:1235-1242.

Shao, H., Cheng H Y, Cook R G, Tweardy D J (2003) Identification and Characterization of Signal Transducer and Activator of Transcription 3 Recruitment Sites within the Epidermal Growth Factor Receptor. Cancer Res 63(14): 3923-3930.

Shao, H., Xu X, Jing N, Tweardy D J (2006) Unique Structural Determinants for Stat3 Recruitment and Activation by the Granulocyte Colony-Stimulating Factor Receptor at Phosphotyrosine Ligands 704 and 744. J Immunol 176(5): 2933-2941.

Shao, H., Xu X, Mastrangelo M-A A, Jing N, Cook R G et al. (2004) Structural Requirements for Signal Transducer and Activator of Transcription 3 Binding to Phosphotyrosine Ligands Containing the YXXQ Motif. J Biol Chem 279 (18): 18967-18973.

Sharp, Z. D., Mancini M G, Hinojos C A, Dai F, Berno V et al. (2006) Estrogen-receptor-{alpha} exchange and chromatin dynamics are ligand- and domain-dependent. J Cell Sci 119(19): 4101-4116.

Siddiquee, K., Zhang S, Guida W C, Blaskovich M A, Greedy B et al. (2007) Selective chemical probe inhibitor of Stat3, identified through structure-based virtual screening, induces antitumor activity. Proceedings of the National Academy of Sciences 104(18): 7391-7396.

Song, H., Wang R, Wang S, Lin J (2005) A low-molecular-weight compound discovered through virtual database screening inhibits Stat3 function in breast cancer cells. Proceedings of the National Academy of Sciences 102(13): 4700-4705.

Strecker, T. E., Shen, Q., Zhang, Y., Hill, J. L., Li, Y., Wang, C., Kim, H. T., Gilmer, T. M., Sexton, K. R., Hilsenbeck, S. G., et al. 2009. Effect of lapatinib on the development of estrogen receptor-negative mammary tumors in mice. J Natl Cancer Inst 101:107-113.

Takeda, K., Noguchi, K., Shi, W., Tanaka, T., Matsumoto, M., Yoshida, N., Kishimoto, T., and Akira, S. 1997. Targeted disruption of the mouse Stat3 gene leads to early embryonic lethality. Proc Natl Acad Sci USA 94:3801-3804.

Totrov, M., Abagyan R (1997) Proteins 1: 215-220.

Turkson, J., 2004. STAT proteins as novel targets for cancer drug discovery. Expert Opin Ther Targets 8:409-422.

Turkson, J., Bowman, T., Garcia, R., Caldenhoven, E., De Groot, R. P., and Jove, R. 1998. Stat3 activation by Src induces specific gene regulation and is required for cell transformation. Mol Cell Biol 18:2545-2552.

Turkson, J., Jove R (2000) STAT proteins: novel molecular targets for cancer drug discovery. Oncogene 19: 6613-6626.

Turkson, J., Ryan, D., Kim, J. S., Zhang, Y., Chen, Z., Haura, E., Laudano, A., Sebti, S., Hamilton, A. D., and Jove, R. 2001. Phosphotyrosyl peptides block Stat3-mediated DNA binding activity, gene regulation, and cell transformation. J Biol Chem 276:45443-45455.

Turkson, J., Zhang, S., Palmer, J., Kay, H., Stanko, J., Mora, L. B., Sebti, S., Yu, H., and Jove, R. 2004. Inhibition of constitutive signal transducer and activator of transcription 3 activation by novel platinum complexes with potent antitumor activity. Mol Cancer Ther 3:1533-1542.

Tweardy, D J, Redell M S (2005) Targeting Transcription Factors for Cancer Therapy. Curr Pharm Des 11: 2873-2887.

Tweardy, D J, Wright T M, Ziegler S F, Baumann H, Chakraborty A et al. (1995) Granulocyte colony-stimulating factor rapidly activates a distinct STAT-like protein in normal myeloid cells. Blood 86(12): 4409-4416.

Uddin, S., Hussain, A. R., Manogaran, P. S., Al-Hussein, K., Platanias, L. C., Gutierrez, M. I., and Bhatia, K. G. 2005. Curcumin suppresses growth and induces apoptosis in primary effusion lymphoma. Oncogene 24:7022-7030.

Wiederkehr-Adam, M., Ernst, P., Muller, K., Bieck, E., Gombert, F. O., Ottl, J., Graff, P., Grossmuller, F., and Heim, M. H. 2003. Characterization of phosphopeptide motifs specific for the Src homology 2 domains of signal transducer and activator of transcription 1 (STAT1) and STAT3. J Biol Chem 278:16117-16128.

Xu, X., Kasembeli, M. M., Jiang, X., Tweardy, B. J., and Tweardy, D. J. 2009. Chemical probes that competitively and selectively inhibit Stat3 activation. PLoS ONE 4:e4783.

Yoo, J. Y., Huso, D. L., Nathans, D., and Desiderio, S. 2002. Specific ablation of Stat3beta distorts the pattern of Stat3-responsive gene expression and impairs recovery from endotoxic shock. Cell 108:331-344.

Yoshikawa, H., Matsubara, K., Qian, G. S., Jackson, P., Groopman, J. D., Manning, J. E., Harris, C. C., and Herman, J. G. 2001. SOCS-1, a negative regulator of the JAK/STAT pathway, is silenced by methylation in human hepatocellular carcinoma and shows growth-suppression activity. Nat Genet. 28:29-35.

Yu, C. L., Meyer, D. J., Campbell, G. S., Lamer, A. C., Carter-Su, C., Schwartz, J., and Jove, R. 1995. Enhanced DNA-binding activity of a Stat3-related protein in cells transformed by the Src oncoprotein. Science 269:81-83.

Yu, H., Jove R (2004) The STATs of cancer-new molecular targets come of age. Nature Reviews Cancer 4(2): 97-105.

Zhang R D F I, Price J E (1991) Relative malignant potential of human breast carcinoma cell lines established from pleural effusions and brain metastasis. Invasion Metastasis 11: 204-215.

Zhu, Q., Jing N (2007) Computational study on mechanism of G-quartet oligonucleotide T40214 selectively targeting Stat3. Journal of Computer-Aided Molecular Design 21(10): 641-648.

---

What is claimed is:

1. A method of inhibiting Stat3 in a cell, comprising delivering to the cell an effective amount of a compound as follows:

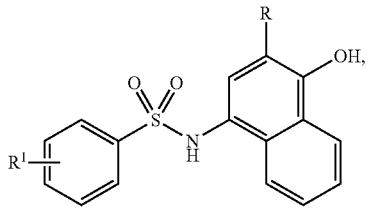

wherein R is selected from the group consisting of hydrogen, phenylsulfanyl, 2-hydroxy-naphthalen-1-yl, quinolin-8-ylsulfanyl, triazol-3-yl sulfanyl, and benzothiazol-2-ylsulfanyl, wherein $R^1$ is selected from the group consisting of hydrogen, methyl, chloro, bromo, methoxy, ethoxy, tert-butyl, nitro, methyl ester, acetamide, 1,4 dioxine, fluoro, trifluoro methoxy, acetyl, trifluoro methyl, propyl, cyclohexene, methoxy-phenoxy, chloro phenoxy, tolyloxy, and phenoxy.

2. The method of claim 1, wherein the cell is in vivo in a mammal.

3. The method of claim 2, wherein the mammal is a human.

4. The method of claim 3, wherein the human is known, suspected, or at risk for developing cancer, a hyperproliferative disease, a chronic viral infection, pulmonary fibrosis, myelofibrosis, or myelodysplastic syndrome, asthma, psoriasis, inflammatory bowel disease, uveitis, scleritis, multiple sclerosis, graft-versus-host diseases, pancreatitis, pulmonary lymphangioleiomyomatosis, age-related macular degeneration or amyloidosis.

5. The method of claim 4, wherein the human is known to have cancer and is receiving an additional therapy.

6. The method of claim 5, wherein the additional therapy is chemotherapy, surgery, radiation, or a combination thereof.

7. The method of claim 1, wherein Stat1 is not inhibited by the compound.

8. The method of claim 1, wherein the cell is a cancer stem cell.

9. The method of claim 8, wherein the cancer stem cell is a leukemic stem cell.

10. The method of claim 8, wherein the cancer stem cell is a breast cancer stem cell.

11. A method of ameliorating head and neck cancer, breast cancer, or leukemia in an individual, comprising administering to the individual a compound as follows:

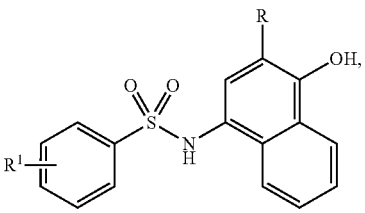

wherein R is selected from the group consisting of hydrogen, phenylsulfanyl, 2-Hydroxy-naphthalen-1-yl, quinolin-8-ylsulfanyl, triazol-3-yl sulfanyl, and benzothiazol-2-ylsulfanyl, wherein $R^1$ is selected from the group consisting of hydrogen, methyl, chloro, bromo, methoxy, ethoxy, tert-butyl, nitro, methyl ester, acetamide, 1,4 dioxine, fluoro, trifluoro methoxy, acetyl, trifluoro methyl, propyl, cyclohexene, methoxy-phenoxy, chloro phenoxy, tolyloxy, and phenoxy.

12. The method of claim 11, wherein the individual is a human.

13. The method of claim 12, wherein the human is receiving an additional cancer therapy.

14. The method of claim 13, wherein the additional therapy is chemotherapy, surgery, radiation, or a combination thereof.

15. A kit for the treatment of cancer, comprising a compound as follows, said compound housed in a suitable container:

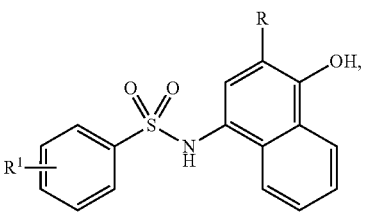

wherein R is selected from the group consisting of hydrogen, phenylsulfanyl, 2-Hydroxy-naphthalen-1-yl, quinolin-8-ylsulfanyl, triazol-3-yl sulfanyl, and benzothiazol-2-ylsulfanyl, wherein $R^1$ is selected from the group consisting of hydrogen, methyl, chloro, bromo, methoxy, ethoxy, tert-butyl, nitro, methyl ester, acetamide, 1,4 dioxine, fluoro, trifluoro methoxy, acetyl, trifluoro methyl, propyl, cyclohexene, methoxy-phenoxy, chloro phenoxy, tolyloxy, and phenoxy.

16. The kit of claim 15, further comprising an additional cancer treatment.

* * * * *

UNITED STATES PATENT AND TRADEMARK OFFICE
CERTIFICATE OF CORRECTION

| | | |
|---|---|---|
| PATENT NO. | : 8,779,001 B2 | Page 1 of 1 |
| APPLICATION NO. | : 12/477583 | |
| DATED | : July 15, 2014 | |
| INVENTOR(S) | : David J. Tweardy et al. | |

It is certified that error appears in the above-identified patent and that said Letters Patent is hereby corrected as shown below:

Title page, item (73) should read as follows:

Assignee Baylor College of Medicine, Houston, TX (US)

Signed and Sealed this
Fifth Day of May, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,779,001 B2 | Page 1 of 1 |
| APPLICATION NO. | : 12/477583 | |
| DATED | : July 15, 2014 | |
| INVENTOR(S) | : Tweardy et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 528 days.

Signed and Sealed this
Third Day of November, 2015

Michelle K. Lee
*Director of the United States Patent and Trademark Office*